US008440393B2

(12) United States Patent
Birrer et al.

(10) Patent No.: US 8,440,393 B2
(45) Date of Patent: May 14, 2013

(54) PRO-ANGIOGENIC GENES IN OVARIAN TUMOR ENDOTHELIAL CELL ISOLATES

(75) Inventors: Michael J. Birrer, Mt. Airy, MD (US); Tomas A. Bonome, Washington, DC (US); Anil Sood, Pearland, TX (US); Chunhua Lu, Missouri City, TX (US)

(73) Assignees: The United States of America as Represented by the Secretary of the Department of Health and Human Services, Washington, DC (US); The University of MD Anderson Cancer Center, Houston, TX (US)

( * ) Notice: Subject to any disclaimer, the term of this patent is extended or adjusted under 35 U.S.C. 154(b) by 194 days.

(21) Appl. No.: 12/541,729

(22) Filed: Aug. 14, 2009
(Under 37 CFR 1.47)

(65) Prior Publication Data
US 2010/0286237 A1 Nov. 11, 2010

Related U.S. Application Data

(63) Continuation-in-part of application No. PCT/US2008/054014, filed on Feb. 14, 2008.

(60) Provisional application No. 60/901,455, filed on Feb. 14, 2007.

(51) Int. Cl.
*C12Q 1/00* (2006.01)
*C12Q 1/68* (2006.01)
*G01N 33/53* (2006.01)
*G01N 33/567* (2006.01)
*G01N 33/574* (2006.01)
*C12N 15/11* (2006.01)

(52) U.S. Cl.
USPC ............... 435/4; 435/6.1; 435/6.14; 435/7.1; 435/7.21; 435/7.23; 514/44 A

(58) Field of Classification Search .................. None
See application file for complete search history.

(56) References Cited

U.S. PATENT DOCUMENTS

| | | | |
|---|---|---|---|
| 2003/0186909 A1 | 10/2003 | McSwiggen | |
| 2005/0037389 A1 | 2/2005 | Santin | |
| 2005/0059682 A1* | 3/2005 | Rubinfeld | 514/263.1 |
| 2006/0094046 A1 | 5/2006 | Abo et al. | |
| 2006/0104981 A1* | 5/2006 | Hikichi et al. | 424/155.1 |

FOREIGN PATENT DOCUMENTS

| | | |
|---|---|---|
| WO | WO 02083874 | 10/2002 |
| WO | WO 03080800 | 10/2003 |
| WO | WO 2004005883 | 1/2004 |
| WO | WO 2004015396 | 2/2004 |
| WO | WO 2004108896 | 12/2004 |
| WO | WO 2006085746 | 8/2006 |
| WO | WO 2006138275 | 12/2006 |
| WO | WO 2007016367 | 2/2007 |

OTHER PUBLICATIONS

Boyd (The Basic Science of Oncology, 1992, McGraw-Hill, Inc., p. 379).*
Tockman et al. (Cancer Res., 1992, 52:2711s-2718s).*
Pritzker (Clinical Chemistry, 2002, 48:1147-1150).*
Benedict et al. (J. Exp. Medicine, 2001, 193(1) 89-99).*
Jiang et al. (J. Biol. Chem., 2003, 278(7) 4763-4769).*
Matsushita et al. (FEBS Letters, 1999, vol. 443, pp. 348-352).*
Singh et al. (Glycobiology, 2001, vol. 11, pp. 587-592).*
Abbosh et al. (Cancer Res. Jun. 1, 2006 66:5582-5591 and Supplemental Figs. S1-S7).*
Zhai et al. (Chinese General Practice Aug. 2008, 11(8A): 1366-1367).*
Lu et al. (Cancer Res. Feb. 15, 2007, 64(4): 1757-1768).*
Bagnato et al., "Activation of Mitogenic Signaling by Endothelin 1 in Ovarian Carcinoma Cells", *Cancer Research*, vol. 57, pp. 1306-1311, 1997.
Bouras et al., "*Stanniocalcin 2* is an Estrogen-responsive Gene Coexpressed with the Estrogen Receptor in Human Breast Cancer", *Cancer Research*, vol. 62, pp. 1289-1295, 2002.
Bryant et al., "EZH2 promotes proliferation and invasiveness of prostate cancer cells", *Prostate*, vol. 67, No. 5, pp. 547-556, 2007.
Bumgardner et al., "Chitosan: potential use as a bioactive coating for orthopaedic and craniofacial / dental implants", *J. Biomater. Sci. Polymer Edn*, vol. 14, No. 5, pp. 423-438, 2003.
Carson-Walter et al., "Cell surface tumor endothelial markers are conserved in mice and humans", *Cancer Res.*, vol. 61, No. 18, pp. 6649-6655, 2001.
Chang et al., "The Murine Stanniocalcin 1 Gene Is Not Essential for Growth and Development", *Molecular and Cellular Biology*, vol. 25, No. 23, pp. 10604-10610, 2005.
Conejo-Garcia et al., "Vascular leukocytes contribute to tumor vascularization", *Blood*, vol. 105, No. 2, pp. 679-681, 2005.
Donninger et al., "Whole genome expression profiling of advance stage papillary serous ovarian cancer reveals activated pathways", *Oncogene*, vol. 23, No. 49, pp. 8065-8077, 2004.
Dupraz et al., "Characterization of silane-treated hydroxyapatite powders for use as filler in biodegradable composites", *Journal of Biomedical Materials Research*, vol. 30, pp. 231-238, 1996.

(Continued)

*Primary Examiner* — Peter J Reddig
(74) *Attorney, Agent, or Firm* — Klarquist Sparkman, LLP

(57) ABSTRACT

A gene profiling signature for ovarian tumor endothelial cells is disclosed herein. The gene signature can be used to diagnosis or prognosis an ovarian tumor, identify agents to treat an ovarian tumor, to predict the metastatic potential of an ovarian tumor and to determine the effectiveness of ovarian tumor treatments. Thus, methods are provided for identifying agents that can be used to treat ovarian cancer, for determining the effectiveness of an ovarian tumor treatment, or to diagnose or prognose an ovarian tumor. Methods of treatment are also disclosed which include administering a composition that includes a specific binding agent that specifically binds to one of the disclosed ovarian endothelial cell tumor-associated molecules and inhibits ovarian tumor in the subject.

7 Claims, 20 Drawing Sheets

OTHER PUBLICATIONS

Garcia et al., "2-Methoxyestradiol Inhibits Prostate Tumor Development in Transgenic Adenocarcinoma of Mouse Prostate: Role of Tumor Necrosis Factor-α-Stimulated Gene 6", *Clin Cancer Res*, vol. 12, No. 3, pp. 980-988, 2006.

Halder et al., "Focal Adhesion Kinase Targeting Using In vivo Short Interfering RNA Delivery in Neutral Liposomes for Ovarian Carcinoma Therapy", *Clin Cancer Res*, vol. 12, No. 16, pp. 4916-4924, 2006.

Kleer et al., "EZH2 is a marker of aggressive breast cancer and promotes neoplastic transformation of breast epithelial cells", *PNAS*, vol. 100, No. 20, pp. 11606-11611, 2003.

Lemaire et al., "Loss of HOP tumour suppressor expression in head and neck squamous cell carcinoma", *British Journal of Cancer*, vol. 91, pp. 258-261, 2004.

Lu et al., "Selection of Potential Markers for Epithelial Ovarian Cancer with Gene Expression Arrays and Recursive Descent Partition Analysis", *Clinical Cancer Research*, vol. 10, pp. 3291-3300, 2004.

Mok et al., "Biomarker Discovery in Epithelial Ovarian Cancer by Genomic approaches", *Advances in Cancer Research*, vol. 96, pp. 1-22, 2006.

Nanda et al., "Identification of a Binding Partner for the Endothelial Cell Surface Proteins TEM7 and TEM7R", *Cancer Research*, vol. 64, pp. 8507-8511, 2004.

Nanjundan et al., "Identification of a novel splice variant of AML1b in ovarian cancer patients conferring loss of wild-type tumor suppressive functions", *Oncogene*, vol. 26, No. 18, pp. 2574-2584, E-published 2006.

Narita et al., "Analysis of Heat Shock Related Gene Expression in Head-And-Neck Cancer Using cDNA Arrays", *Int. J. Radiation Oncology Biol. Phys*, vol. 53, No. 1, pp. 190-196, 2002.

Reedijk et al., "High-level Coexpression of JAG1 and NOTCH1 is Observed in Human Breast Cancer and is Associated with Poor Overall Survival", *Cancer Research*, vol. 65, No. 18, pp. 8530-8537, 2005.

Voutilainen et al., "Versican in Epithelial Ovarian Cancer: Relation to Hyaluronan, Clinicopathologic Factors and Prognosis", *Int. J. Cancer*, vol. 107, pp. 359-364, 2003.

Wang et al., "Identification of a novel function of TWIST, a bHLH protein, in the development of acquired taxol resistance in human cancer cells", *Oncogene*, vol. 23, No. 2, pp. 474-482, 2004.

Weiner et al., "Decreased Src Tyrosine Kinase Activity Inhibits Malignant Human Ovarian Cancer Tumor Growth in a Nude Mouse Model", *Clinical Cancer Research*, vol. 5, pp. 2164-2170, 1999.

Yeung et al., "Cloning of a novel epidermal growth factor repeat containing gene EGFL6: expressed in tumor and fetal tissues", *Genomics*, vol. 62, No. 2, pp. 304-307, 1999.

Yeung et al., "Hypoxia-Inducible Factor-1-Mediated Activation of Stanniocalcin-1 in Human Cancer Cells", *Endocrinology*, vol. 146, No. 11, pp. 4951-4960, 2005.

Zhang et al., "Down-regulation of Jagged-1 induces cell growth inhibition and S phase arrest in prostate cancer cells", *Int. J. Cancer*, vol. 119, pp. 2071-2077, 2006.

\* cited by examiner

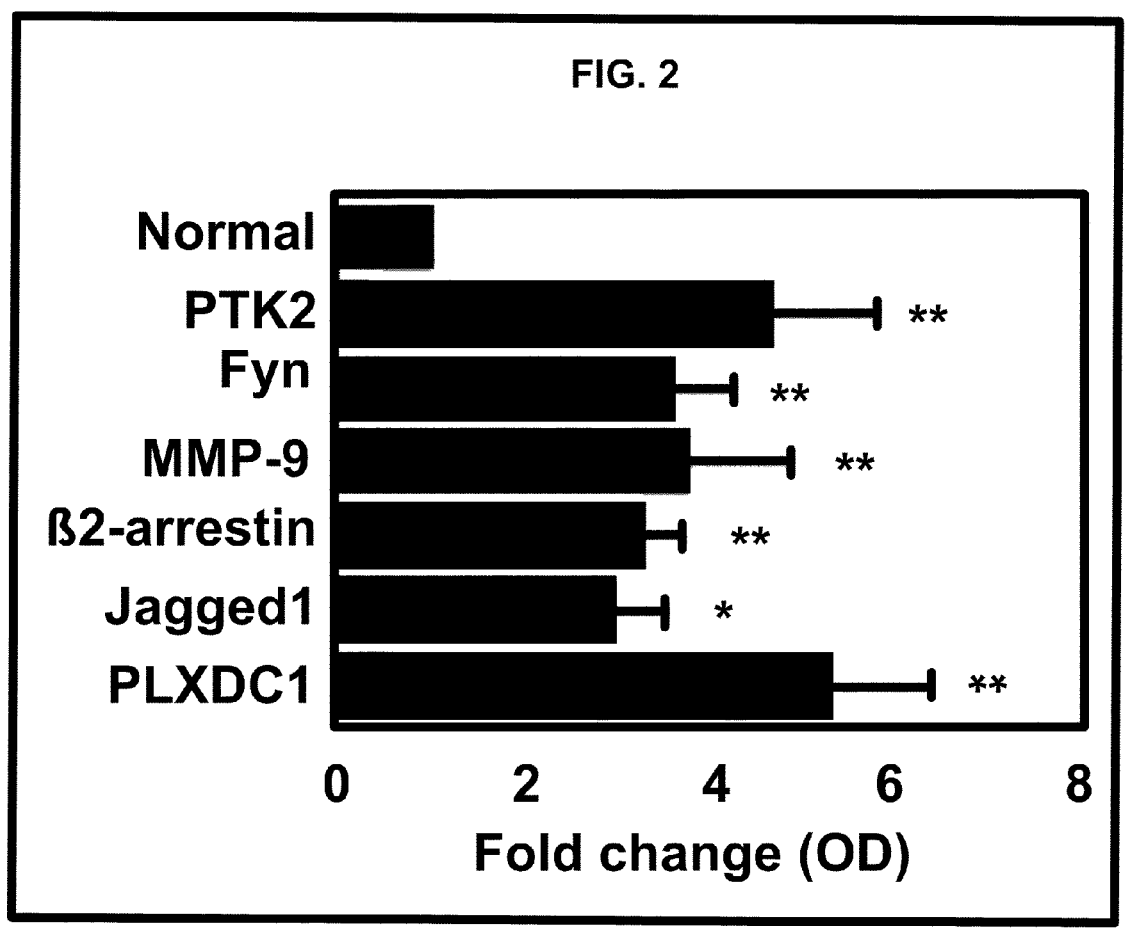

*$p<0.05$
**$p<0.01$
***$p<0.001$

FIG. 10
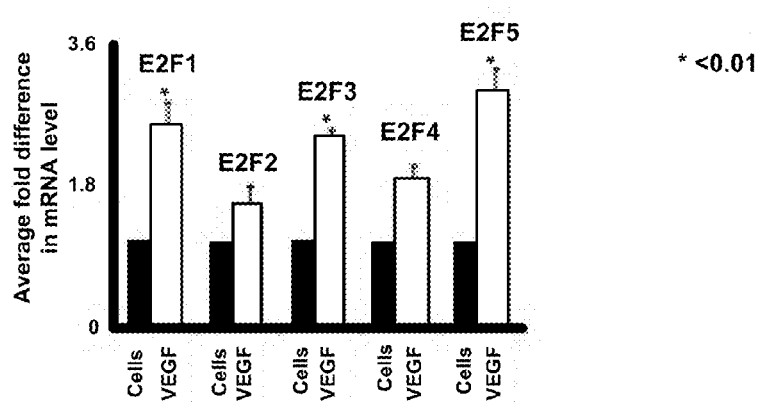
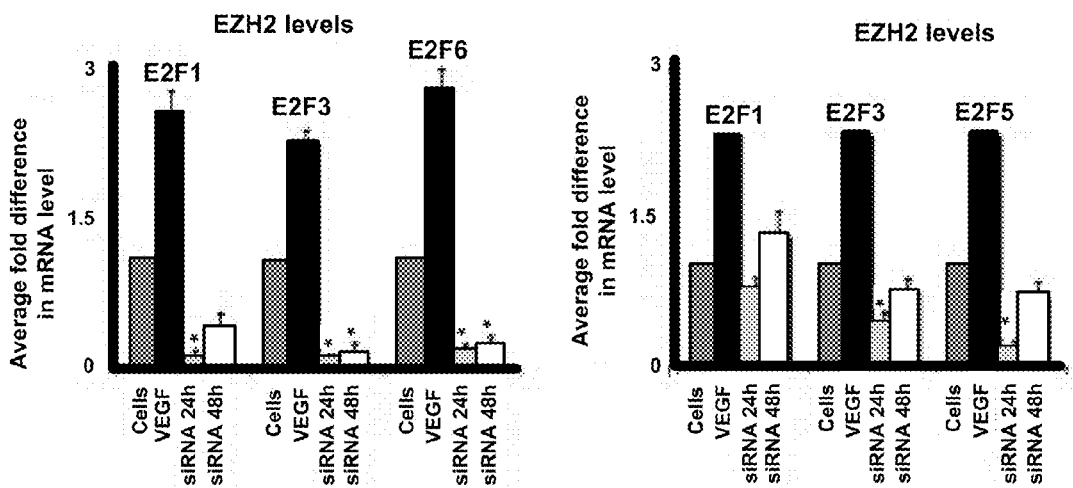
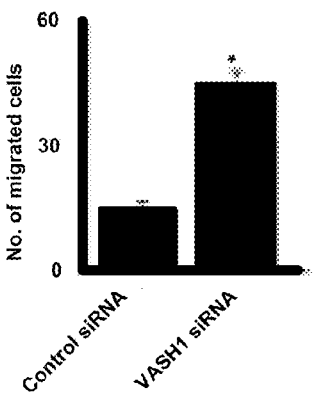

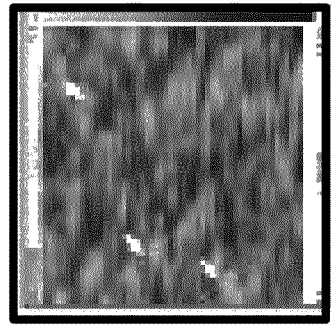
FIG. 11A
| CH particles | Weight ratio (Chitosan TPP) | CH (mg) | TPP (mg) | siRNA (ug) |
|---|---|---|---|---|
| siRNA-CH3 | 3.1 | 1.05 | 0.35 | 35 |
| siRNA-CH5 | 5.1 | 1.75 | 0.35 | 35 |
| siRNA-CH7 | 7.1 | 2.45 | 0.35 | 35 |
| siRNA-CH9 | 9.1 | 3.15 | 0.35 | 35 |
| siRNA-CH10 | 11.1 | 3.85 | 0.35 | 35 |
| siRNA-CH13 | 13.1 | 4.55 | 0.35 | 35 |
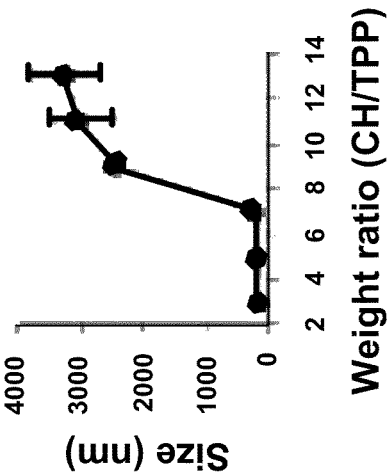
FIG. 11B
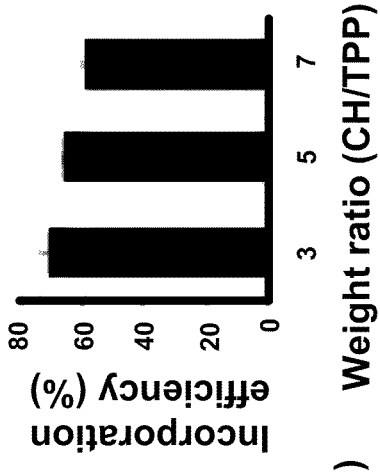
FIG. 11C
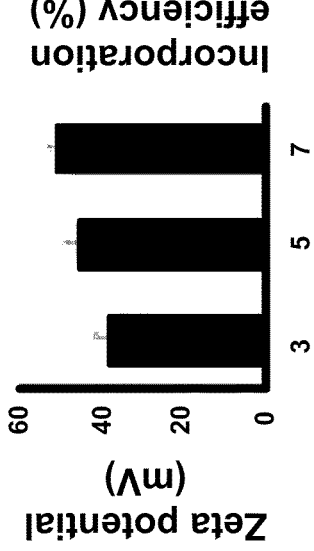
FIG. 11D
FIG. 11E

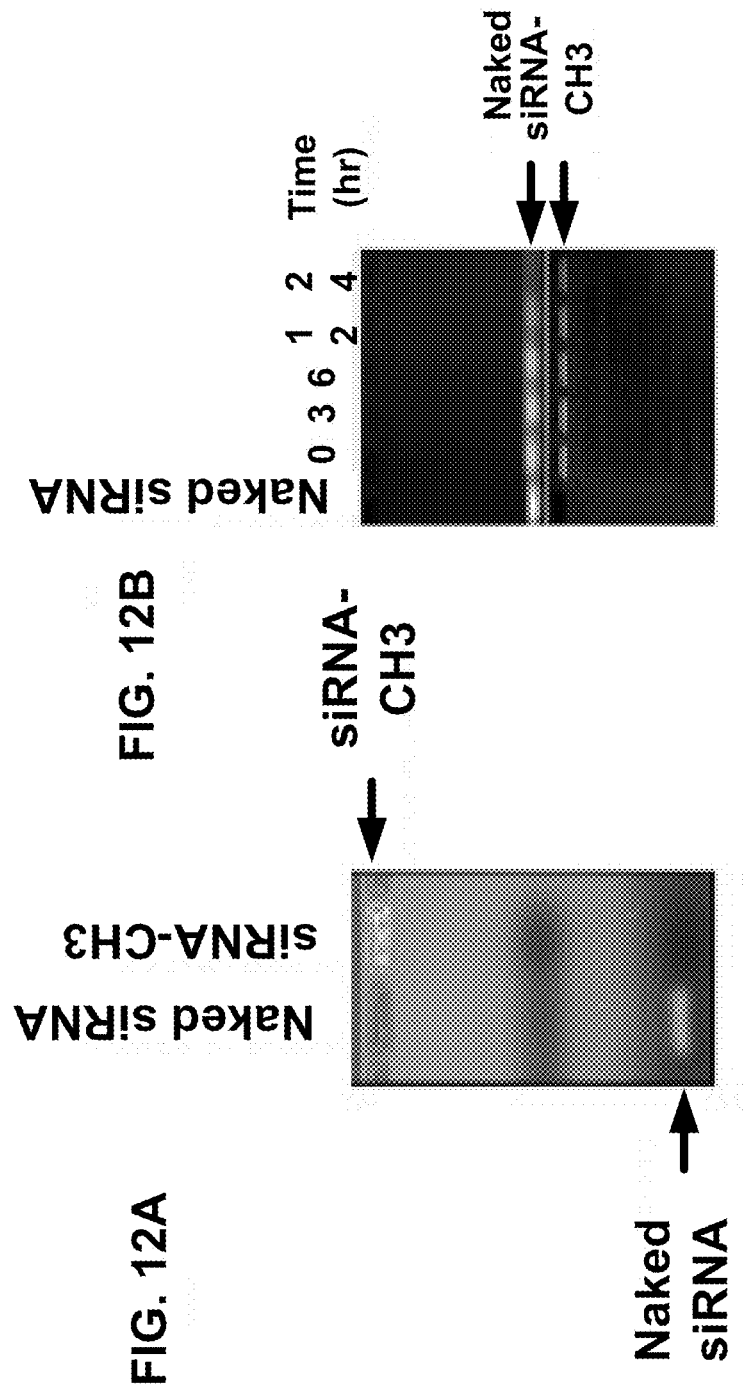

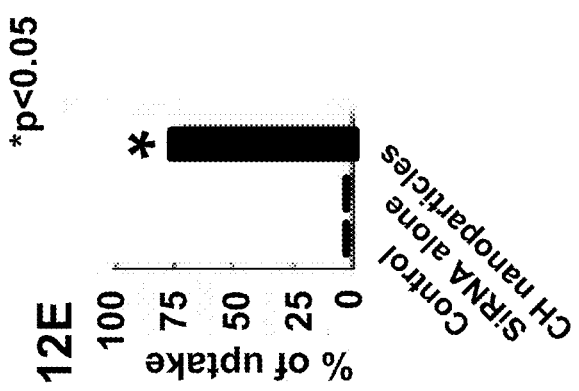
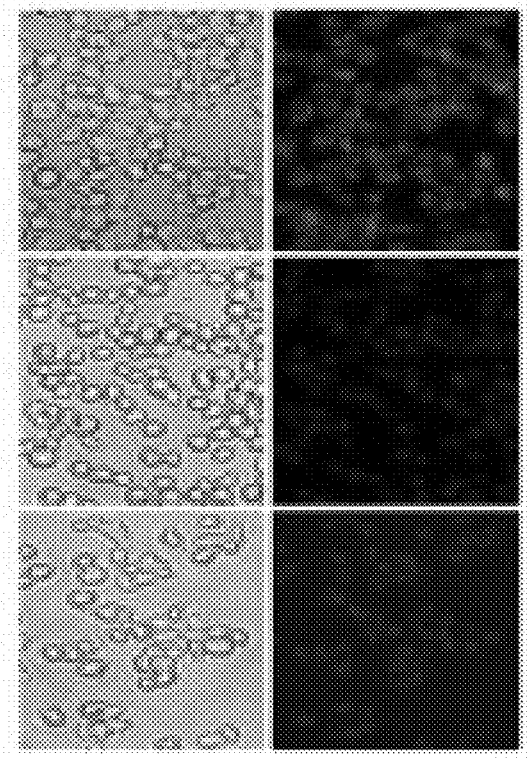
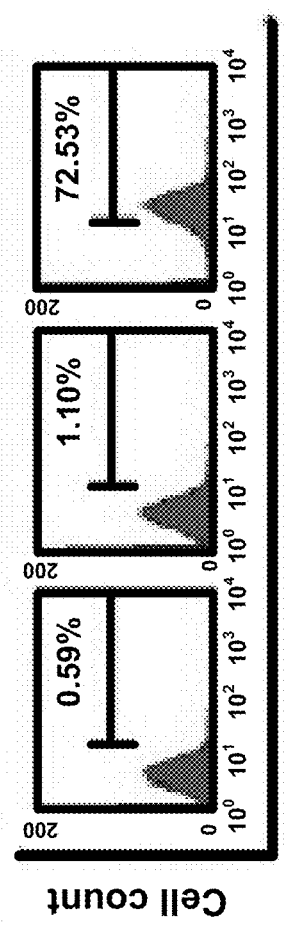
FIG. 12C
FIG. 12D
FIG. 12E

US 8,440,393 B2

PRO-ANGIOGENIC GENES IN OVARIAN TUMOR ENDOTHELIAL CELL ISOLATES

CROSS REFERENCE TO RELATED APPLICATION

This is a continuation-in-part application of International Patent Application PCT/US2008/054014, filed Feb. 14, 2008, designating the United States and published in English as WO 2008/101118, which claims the benefit of U.S. Provisional Application No. 60/901,455, filed on Feb. 14, 2007. The entire contents of these prior applications are incorporated herein by reference.

ACKNOWLEDGMENT OF GOVERNMENT SUPPORT

This invention was made with government support under contract CA083639 awarded by the National Institutes of Health. The government has certain rights in the invention.

FIELD OF THE DISCLOSURE

This disclosure relates to the field of ovarian cancer and in particular, to methods for treating ovarian cancer by targeting ovarian endothelial cell tumor-associated molecules identified by an ovarian tumor endothelial cell gene expression profile and methods for identifying therapeutic agents.

BACKGROUND

Ovarian cancer is the fifth most common form of cancer in women in the United States, accounting for three percent of the total number of cancer cases and twenty-six percent of those occurring in the female genital tract. The American Cancer Society estimated that 15,310 deaths would be caused in women living in the United States in 2006. A large majority of women who die of ovarian cancer will have had serous carcinoma of the ovarian epithelium, a condition which occurs in sixty percent of all cases of ovarian cancer (Boring et al., *Cancer J. Clin.* 44: 7-26, 1994).

Women with ovarian cancer are typically asymptomatic until the cancer has metastasized. As a result, most women with ovarian cancer are not diagnosed until the cancer has progressed to an advanced and usually incurable stage (Boente et al., *Curr. Probl. Cancer* 20: 83-137, 1996). Survival rates are much better in women diagnosed with early-stage ovarian cancers, about ninety percent of these women are still alive five years after diagnosis.

Treatment of ovarian cancer typically involves a variety of treatment modalities. Generally, surgical intervention serves as the basis for treatment (Dennis S Chi & William J. Hoskins, *Primary Surgical Management of Advanced Epithelial Ovarian Cancer*, in *Ovarian Cancer* 241, Stephen C. Rubin & Gregory P. Sutton eds., 2d ed. 2001). Treatment of serous carcinoma often involves cytoreductive surgery (hysterectomy, bilateral salpingo-oophorectomy, omentectomy, and lymphadenectomy) followed by adjuvant chemotherapy with paclitaxel and either cisplatin or carboplatin (Eltabbakh, G. H. & Awtrey, C. S., *Expert Op. Pharmacother.* 2(10): 109-24, 2001).

Despite a clinical response rate of 80% to primary treatment with surgery and chemotherapy, most subjects experience tumor recurrence within two years of treatment. The overwhelming majority of subjects will eventually develop chemoresistance and die as a result of their cancer. Thus, a need exists to identify alternative treatments for ovarian cancer.

SUMMARY OF THE DISCLOSURE

A gene profiling signature is disclosed herein that can be used to predict clinical outcome and develop therapeutics for treating ovarian cancer in a subject. For example, the ovarian endothelial cell tumor-associated molecules identified by the gene profile signature can serve as prognostic indicators as well as targets for specific therapeutic molecules that can reduce or eliminate ovarian cancer. Thus, methods of identifying an agent for treating an ovarian tumor are provided. In some examples, the methods include contacting a cell, such as an ovarian tumor cell or an ovarian tumor endothelial cell, with one or more test agents under conditions sufficient for the one or more test agents to alter the activity of at least one ovarian endothelial cell tumor-associated molecule listed in any of Tables 1-5. The method includes detecting the activity of the at least one ovarian endothelial cell tumor-associated molecule in the presence and absence of the one or more test agents. The activity of the at least one ovarian endothelial cell tumor-associated molecule in the presence of the one or more test agents is then compared to the activity in the absence of such agents to determine if there is differential expression of the at least one ovarian endothelial cell tumor associated molecule. Differential expression of the ovarian endothelial cell tumor-associated molecule in the presence of the test agent(s) indicates that the one or more test agents can be used to treat an ovarian tumor.

Methods are also provided for treating an ovarian tumor. In some examples, the method includes administering to the subject a therapeutically effective treatment to inhibit ovarian tumor growth. In an example, the treatment includes administering a therapeutically effective amount of a specific binding agent that binds with high specificity to one of the ovarian endothelial cell tumor-associated molecules listed in Tables 1, 2, 4 or 5 and alters expression or activity of the molecules, thereby treating the ovarian tumor in the subject (for example, by decreasing tumor vascular growth, tumor growth or tumor volume). In particular examples, the specific binding agent preferentially binds to and inhibits expression or activity of one of the ovarian endothelial cell tumor-associated molecules that is upregulated in an ovarian tumor endothelial cell, such as Zeste homologue 2 (EZH2), EGF-like domain, multiple 6 (EGFL6), tumor necrosis factor, alpha-induced protein 6 (TNFAIP6), Twist homologue 1 (TWIST1), stanniocalcin 1 (STC1), homeodomain-only protein (HOP), chondroitin sulfate proteoglycan 2 (CSPG2), and plexin domain containing 1 (PLXDC1). In other particular examples, ovarian tumor growth is inhibited by the specific binding agent preferentially binding to and inhibiting expression of one of the ovarian endothelial cell tumor-associated molecules listed in any of Tables 1, 2, 4 or 5 which are involved in angiogenesis, such as molecules involved in cell proliferation, tube formation or cell motility and are upregulated in ovarian tumor endothelial cells.

Methods are also provided for determining the effectiveness of an agent for the treatment of an ovarian tumor in a subject with the ovarian tumor. In an example, the method includes detecting expression of an ovarian endothelial cell tumor-associated molecule in a sample from the subject following administration of the agent. The expression of the ovarian endothelial cell tumor-associated molecule following administration is compared to a control, such as specific binding agents that bind to and inhibit one of the ovarian endothelial cell tumor-associated molecules listed in any of Tables 1, 2, 4 or 5 that is upregulated in ovarian endothelial tumor cells. An alteration in the expression of the ovarian endothelial cell tumor-associated molecule (such as a decrease in expression of a molecule upregulated in ovarian tumor endothelial cells or an increase in expression of a molecule downregulated in such cells) following treatment indicates that the agent is effective for the treatment of the ovarian cancer in the subject. In a specific example, the method includes detecting and comparing the protein expression levels of the ovarian endothelial cell tumor-associated molecules. In other examples, the method includes detecting and comparing the mRNA expression levels of the ovarian endothelial cell tumor-associated molecules.

Methods of diagnosing and prognosing an ovarian tumor (such as a tumor that overexpresses at least one of the disclosed ovarian endothelial cell tumor-associated molecules) are provided. In some examples, such methods are performed prior to the treatment methods described herein. However, such methods can also be used independently of the disclosed treatment methods. In particular examples, the method includes determining the metastatic potential of an ovarian tumor in a subject by detecting expression of at least one ovarian endothelial cell tumor-associated molecule in a sample obtained from a subject with an ovarian tumor. The at least one ovarian endothelial cell tumor-associated molecule is involved in promoting angiogenesis, such as cell proliferation, cell motility or tube formation, such as EZH2. The method further includes comparing expression of the at least one ovarian endothelial cell tumor-associated molecule in the sample obtained from the subject with the ovarian tumor to a control. An alteration in the expression of the at least one ovarian endothelial cell tumor-associated molecule involved in promoting angiogenesis indicates that the subject has an ovarian tumor with increased metastatic potential.

In additional examples, methods are disclosed for predicting a clinical outcome in a subject with an ovarian tumor, such as advanced stage epithelial ovarian cancer. In an example, the methods include detecting expression of at least one ovarian endothelial cell tumor-associated molecules listed in Tables 1-5 or combinations thereof (such as at least 1, at least 3, at least 5 or at least 10 of such molecules) in a sample obtained from the subject with the ovarian tumor. The methods also can include comparing expression of the at least one ovarian endothelial cell tumor-associated molecule in the sample obtained from the subject with the ovarian tumor to a control (such as a normal sample or value representing such expression expected in a normal sample), wherein an alteration in the expression of the at least one ovarian endothelial cell tumor-associated molecule indicates that the subject has a decreased chance of survival. For example, an alteration in the expression, such as an increase in the expression of EZH2 indicates a poor prognosis, such as a decreased chance of survival. In one example, a decreased chance of survival includes a survival time of equal to or less than a year. Alterations in the expression can be measured using methods known in the art, and this disclosure is not limited to particular methods. For example, expression can be measured at the nucleic acid level (such as by real time quantitative polymerase chain reaction or microarray analysis) or at the protein level (such as by Western blot analysis).

The foregoing and other features of the disclosure will become more apparent from the following detailed description of several embodiments which proceeds with reference to the accompanying figures.

BRIEF DESCRIPTION OF THE FIGURES

FIG. 2 is a graph illustrating protein expression in ovarian endothelial cells for a subset of the proteins detected following staining of samples with immunofluorescently-labeled PTK2, Fyn, MMP-9, β2-arrestin, Jagged1 and PLXDC1.

FIG. 7A provides digital images representative of human tumors with low and high EZH2 expression based on immunohistochemical staining. FIG. 7B provides Kaplan-Meier curves of disease-specific mortality for patients whose ovarian tumors expressed high and low levels of EZH2 (EZH2-T). The log-rank test (two-sided) was used to compare differences between the two groups. Increased EZH2-T was significantly associated with decreased overall survival ($p<0.001$). FIG. 7C provides digital images representative of human ovarian tumor vasculature (arrowheads point to endothelial cells) with low and high immunohistochemical staining for EZH2. FIG. 7D provides Kaplan-Meier curves of disease-specific mortality of patients whose ovarian vasculature expressed low versus high EZH2 (EZH2-Endo) EZH2-Endo was predictive of poor overall survival. FIG. 7E provides digital images representative of human ovarian tumors with low or high immunohistochemical staining for VEGF. FIG. 7F provides a bar graph VEGF expression was strongly associated with high EZH2-Endo (*$p<0.01$). FIG. 7G provides digital images representative of human ovarian tumors with low or high immunohistochemical staining for microvessel density (MVD). FIG. 7H provides a bar graph illustrating high MVD counts in a tumor were significantly associated with high EZH2-Endo expression (*$p<0.001$). Images in panels A, C, and E were taken at original magnification ×200, and in panel g at original magnification ×200.

FIG. 8A illustrates that EZH2 promoter activity is increased in an endothelial cell line in response to EGF, VEGF, and conditioned media from ovarian cancer cell lines. EAhy926 hybridoma endothelial cell line was cotransfected with the *Renilla* luciferase plasmid and firefly luciferase plasmid either with or without the EZH2 promoter construct followed by treatment with EGF, VEGF and conditioned medium and promoter activity was determined. FIG. 8B illustrates that EZH2 mRNA levels are increased in HUVEC in response to EGF, VEGF, and conditioned media from ovarian cancer cell lines. Cells were treated as indicated and purified RNA was used in real-time quantitative RT-PCR. Control values were normalized using 3 housekeeping genes. FIG. 8C Pearson's analysis shows significant correlation between EZH2 and VEGF expression values ($Log_2$) from 29 microdissected high-grade serous papillary ovarian adenocarcinomas.

FIG. 9A is a digital image of a polyacrylamide gel illustrating PCR products generated by as ChIP assay of EZH2 binding to human VASH1 promoter in response to VEGF in HUVEC. Cross-linked chromatin from HUVEC was treated with (+) or without (−) VEGF and immunoprecipitated (IP) using EZH2 or mouse IgG antibodies. The input and immunoprecipitated DNA were subjected to PCR using primers corresponding to the 3800 to 3584 base pairs upstream of VASH1 transcription start site. PCR products were examined on ethidium bromide-stained agarose gel. FIG. 9B is a bar graph illustrating EZH2 mRNA levels in cells transfected with control or mouse EZH2 siRNA and harvested after 72 hours. RNA was isolated and subjected to real-time quantitative RT-PCR. The fold difference in levels of EZH2 mRNA represents the mean of triplicate experiments compared to control siRNA treated cells. Error bars represent s.e.m. *$p<0.05$. FIG. 9C is a bar graph illustrating the fold difference in levels of VASH1 mRNA as compared to control siRNA treated cells. Error bars represent s.e.m. *$p<0.01$. FIG. 9D illustrates the effect of EZH2 gene silencing on methylation status of VASH1 in VEGF-treated MOECs as detected by methylation specific PCR. The inhibitory units of methylated VASH1 were normalized by that of the un-methylated VASH1 and represent the mean of triplicate experiments. FIG. 9E is a digital image of a Western blot of lysate collected 48 hours after transfection of MOEC with control, VEGF treated and mouse EZH2 siRNA treated cells.

FIGS. 10A-10C show E2F transcription factors increases upon VEGF treatment in MOEC. FIG. 10A is a bar graph illustrating expression levels of E2F transcription factors in MOEC. Cells were treated with VEGF for 6 hours and subjected to Q-RT-PCR. FIG. 10B provides a pair of bar graphs illustrating silencing of E2F1, E2F3 and E2F5 transcription factors by targeted siRNA in MOEC. Cells were transfected with corresponding siRNAs. After 24 hours and 48 hours, cells were collected; RNA was isolated and was subjected to real-time Q-RT-PCR. E2F3 and E2F5 gene silencing decreases EZH2 expression levels. EZH2 expression levels were analyzed in E2F1, E2F3 and E2F5 silenced samples using Q-RT-PCR. The fold difference in levels of mRNA expression represents the mean of triplicate experiments compared to cells (A) and VEGF treated cells (B). Error bars represent s.e.m. *$p<0.01$. FIG. 10C is a bar graph illustrating the effect of VASH1 gene silencing on tube formation in endothelial cells. HUVECs were plated on Matrigel after transfecting the cells with either control or human VASH1 siRNA. Vascular tube formation was evaluated by microscopic observation.

FIGS. 11A-11E illustrate the physical characteristics of siRNA/CH nanoparticles. FIG. 11A is a table providing the composition of CH/TPP/siRNAs. FIG. 11B is a graph illustrating the mean particle size of siRNA/CH particles as measured using light scattering with a particle analyzer, showing that nanoparticles maintained 100-200 nm size up to 7:1 ratio (CH:TPP). FIG. 11C is a graph illustrating that zeta potential of siRNA/CH nanoparticles showed slight positive charge. FIG. 11D is a graph illustrating incorporation efficiency of siRNA into CH nanoparticles with 3:1 ratio of CH:TPP resulting in >75% incorporation efficiency. FIG. 11E is a digital image following atomic force microscopy (AFM) demonstrating that siRNA/CH nanoparticles were spherical and <150 nm in size.

FIGS. 12A-12E illustrate incorporation, stability and intracellular uptake of siRNA/CH nanoparticles. FIG. 12A is a digital image illustrating electrophoretic migration of naked siRNA and siRNA/CH nanoparticles. SiRNA/CH nanoparticles (open arrow) remained at top of the gel compared to naked siRNA (solid arrow), which migrated downward. FIG. 12B is a digital image illustrating electrophoretic migration of siRNA/CH nanoparticles in the presence of 50% serum. SiRNA/CH nanoparticles were collected at different time points of incubation at 37° C. (Lane 1; naked siRNA, Lanes 2 to 5; siRNA/CH nanoparticles). Naked siRNA (solid arrow) was degraded over 12 to 24 hours in serum containing media; whereas CH nanoparticles (open arrow) protected the siRNA from degradation in serum. Increased binding efficiency of siRNA/CH nanoparticles was noted compared to naked siRNA. FIG. 12C is a fluorescence microscopy digital image of HeyA8 cells after incubating either with siRNA alone or with siRNA/CH nanoparticles at 4° C. for 20 minutes in PBS. FIG. 12D is a series of tracings from a flow cytometry analysis demonstrating that uptake efficiency of nanoparticles into cells was increased by 72-fold after incubating cells in PBS at 4° C. for 20 minutes. FIG. 12E is graphical representation of percentage of uptake of Alexa-555 siRNA by cells by flow cytometry analysis.

FIG. 13A provides a pair of digital images illustrating fluorescent siRNA distribution in tumor tissue of hematoxylin and eosin, original magnification ×200 (left); stained with anti-CD31 (green) antibody to detect endothelial cells (right). FIG. 13B provides a pair of digital images of 50-µm sections stained with Cytox Green and examined with confocal microscopy (original magnification ×400) (left); lateral view (right) Images taken every 1 µm were stacked and examined from the lateral view. Nuclei were labeled green and fluorescent siRNA (red) was seen throughout the section. At all time points, punctated emissions of the siRNA were noted in the perinuclear regions of individual cells, and siRNA was seen in >80% of fields examined. (c) Western blot of lysates from orthotopic tumors collected 24, 48, 72 and 96 hours after a single injection of control siRNA/CH or human (EZH2 Hs siRNA/CH). FIG. 13D provides multiple digital images illustrating EZH2 gene silencing in HeyA8 tumor as well as tumor endothelial cells. Tumors were collected after 48 hours of single injection of control siRNA/CH, or EZH2 Hs siRNA/CH, or EZH2 Mm siRNA/CH and stained for EZH2 (green) and CD31 (red). Images were taken at original magnification, ×200. FIG. 13E is a pair of graphs illustrating the effects of EZH2 Hs siRNA/CH or EZH2 Mm siRNA/CH on tumor weight in mouse orthotopic tumor models. Nude mice were injected with HeyA8 or SKOV3ip1 ovarian cancer cells and 1 week later, were randomly assigned (10 mice per group) to receive therapy: (1) control siRNA/CH, (2) EZH2 Hs siRNA/CH, (3) EZH2 Mm siRNA/CH, and (4) combination of EZH2 Hs siRNA/CH plus EZH2 Mm siRNA/CH. Mice were sacrificed when any animals in control or a treatment group became moribund (after 3 to 4 weeks of therapy) and mouse weight, tumor weight and tumor location were recorded. Error bars represent s.e.m. *p<0.05; **p<0.001.

FIG. 16B is a bar graph illustrating the number of cells that migrated in the presence and absence of VASH1 siRNA. Mice were sacrificed when any animals in control or a treatment group became moribund (after 3 to 4 weeks of therapy) and mouse weight, tumor weight and tumor location were recorded. Error bars represent s.e.m. *p<0.05.

SEQUENCE LISTING

Figure 1:
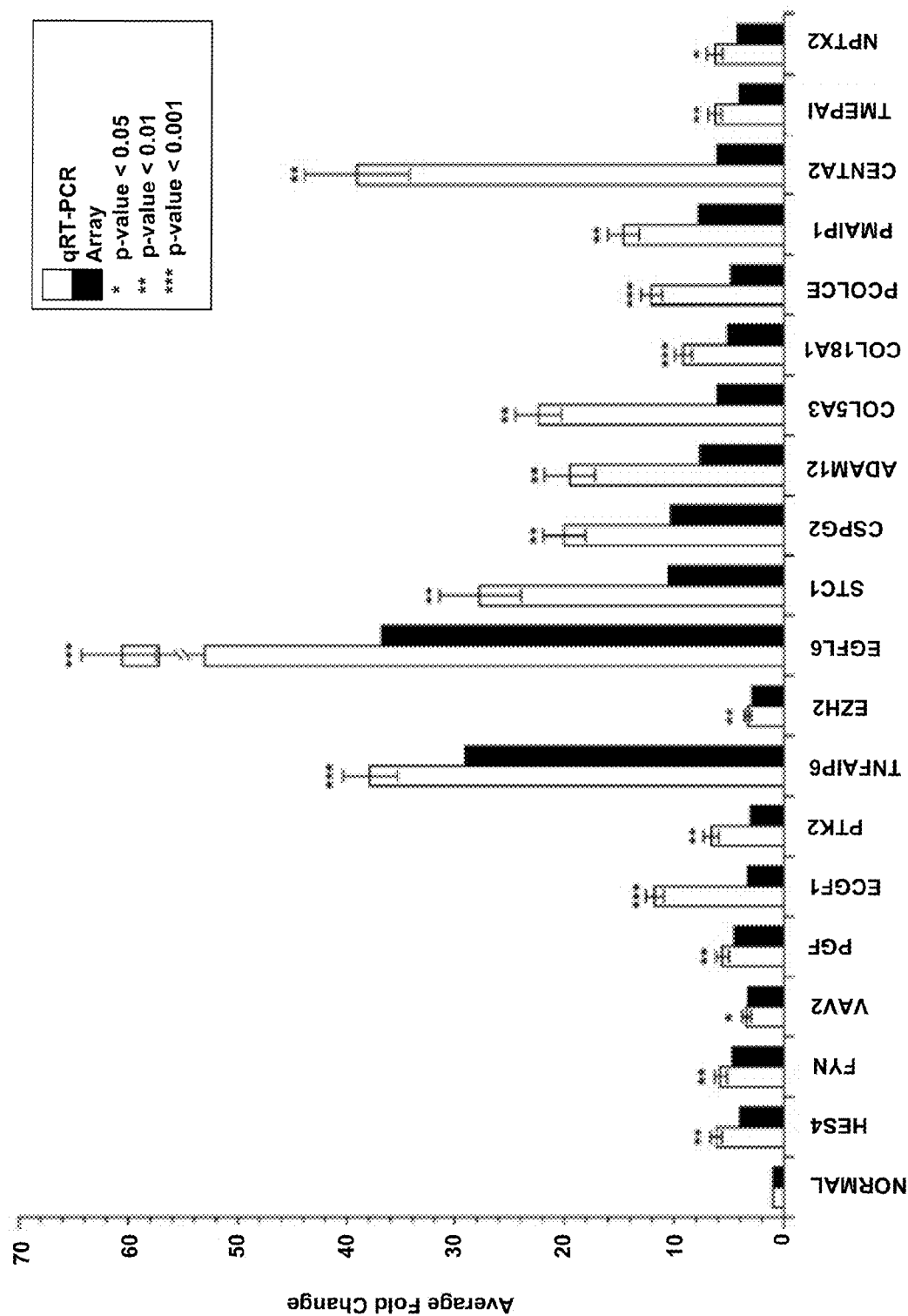
FIG. 1 is a graph illustrating the comparative fold change in relative expression levels between microarray data and real-time quantitative RT-PCR data of selected genes from the pro-angiogenic gene signature provided in Table 1.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NOS: 1, 6-27, and 44-47 are nucleic acid sequences of exemplary primers.

SEQ ID NOS: 2-5 and 28-43 are nucleic acid sequences of exemplary siRNAs.

DETAILED DESCRIPTION OF SEVERAL EMBODIMENTS

Despite improvements in surgery and chemotherapy, mortality rates in women with advanced ovarian carcinoma have remained largely unchanged (Cannistra, *N. Engl. J. Med.* 329: 1550-1559, 1993). Therefore, novel therapeutic strategies are needed. Growth of tumors, both at the primary and metastatic sites, requires a blood supply for expansion beyond 1-2 mm (Folkman, *J. Nat. Canc. Inst.* 82: 4-6, 1990). Targeting tumor angiogenesis by inhibiting endothelial cells that support tumor growth is particularly promising because of their presumed genetic stability. The recent success of a humanized monoclonal antibody bevacizumab (trade name Avastin®) against vascular endothelial growth factor in prolonging the lives of patients with advanced colon and breast carcinoma demonstrates the promise of such approaches (Hurwitz et al., *N. Engl. J. Med.* 350: 2335-2342, 2004 and Jain et al., *Nat. Clin. Pract. Oncol.* 3: 24-40, 2006). However, the full spectrum of differences in the tumor vasculature compared to its normal counterpart is not known. Identification of additional targets on tumor endothelium may allow opportunities for developing new therapeutic approaches to inhibit angiogenesis in a tumor-specific manner.

In recent years, whole genome expression profiling of cancer using methods such as microarray and serial analysis of gene expression (SAGE) have provided insight into the molecular pathways involved in cancer onset and progression. While selected genes in ovarian cancer vasculature have been characterized, there is little information regarding global gene expression alterations in ovarian cancer endothelium.

Disclosed herein is a gene expression signature identifying endothelial cell tumor-associated molecules in ovarian tumor endothelial cell isolates. Endothelial cells were purified from human ovarian tissues and invasive ovarian epithelial cancers, and a gene expression profile was established for ovarian tumor endothelial cells using microarray analyses. The gene expression profile disclosed herein identifies genes whose expression is differentially regulated in tumor versus normal endothelial cells. This profile reveals distinct expression profiles for tumor endothelial cell isolates as compared to non-tumor endothelial isolates.

The disclosed gene expression profile also reveals genes and collections or sets of genes that serve as effective molecular markers for angiogenesis in ovarian cancer, predict clinical outcome as well as such genes or gene sets that can provide clinically effective therapeutic targets for ovarian cancer. This has significant implications for the treatment of ovarian cancer. For example, methods are disclosed for treating ovarian cancer (for example, reducing or inhibiting ovarian cancer growth by targeting ovarian endothelial cell tumor-associated molecules, such as molecules believed to be involved in angiogenesis). For example, molecules involved in cell motility, tube formation or cell proliferation can be identified by the gene profile signature. In an example, a therapeutically effective amount of a specific binding agent is administered to a subject. For example, the specific binding agent preferentially binds to one or more of the identified ovarian endothelial cell tumor-associated molecules listed in any of Tables 1, 2, 4, 5 or a combination thereof to alter the expression or activity of such molecule (e.g., increase expression or activity of a molecule that is downregulated in ovarian endothelial tumor cells or decrease expression or activity of a molecule that is upregulated in such cells). In one example, the specific binding agent preferentially binds to one or more of the identified ovarian endothelial cell tumor-associated molecules listed in any of Tables 1, 2, 4, 5 or a combination thereof that are upregulated in ovarian endothelial tumor cells (as indicated by a positive fold change in Table 1) to decrease expression or activity of the one or more molecules. As a result, ovarian cancer in the subject is thereby reduced or eliminated. In a particular example, the specific binding agent is an inhibitor, such as a siRNA, of one or more of the disclosed ovarian endothelial cell tumor-associated molecules described in any of Table 1, 2, 4 or 5 whose expression is upregulated in ovarian endothelial tumor cells, such as EZH2. In some examples, the specific binding agent preferentially binds to one or more of the identified ovarian endothelial cell tumor-associated molecules listed in any of Tables 1, 2, 4, 5 or a combination thereof that are downregulated in ovarian endothelial tumor cells (as indicated by a negative fold change in Table 1) to increase expression or activity of the one or more molecules. As a result, ovarian cancer in the subject is thereby reduced or eliminated.

Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a nucleic acid molecule" includes single or plural nucleic acid molecules and is considered equivalent to the phrase "comprising at least one nucleic acid molecule." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

Administration:

To provide or give a subject an agent, such as a chemotherapeutic agent, by any effective route. Exemplary routes of administration include, but are not limited to, injection (such as subcutaneous, intramuscular, intradermal, intraperitoneal, and intravenous), oral, sublingual, rectal, transdermal, intranasal, vaginal and inhalation routes.

Agent:

Any protein, nucleic acid molecule, compound, small molecule, organic compound, inorganic compound, or other molecule of interest. Agent can include a therapeutic agent, a diagnostic agent or a pharmaceutical agent. A therapeutic or pharmaceutical agent is one that alone or together with an additional compound induces the desired response (such as inducing a therapeutic or prophylactic effect when administered to a subject). In a particular example, a pharmaceutical agent (such as a siRNA to any of the genes listed in Tables 2 and Table 4) significantly reduces angiogenesis. A test agent is any substance, including, but not limited to, a protein (such as an antibody), nucleic acid molecule (such as a siRNA), organic compound, inorganic compound, or other molecule of interest. In particular examples, a test agent can permeate a cell membrane (alone or in the presence of a carrier).

Amplifying a Nucleic Acid Molecule:

To increase the number of copies of a nucleic acid molecule, such as a gene or fragment of a gene, for example a region of an ovarian endothelial cell tumor-associated gene. The resulting products are called amplification products.

An example of in vitro amplification is the polymerase chain reaction (PCR), in which a biological sample obtained from a subject (such as a sample containing ovarian cancer cells) is contacted with a pair of oligonucleotide primers, under conditions that allow for hybridization of the primers to a nucleic acid molecule in the sample. The primers are extended under suitable conditions, dissociated from the template, and then re-annealed, extended, and dissociated to amplify the number of copies of the nucleic acid molecule. Other examples of in vitro amplification techniques include quantitative real-time PCR, strand displacement amplification (see U.S. Pat. No. 5,744,311); transcription-free isothermal amplification (see U.S. Pat. No. 6,033,881); repair chain reaction amplification (see WO 90/01069); ligase chain reaction amplification (see EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134).

A commonly used method for real-time quantitative polymerase chain reaction involves the use of a double stranded DNA dye (such as SYBR Green I dye). For example, as the amount of PCR product increases, more SYBR Green I dye binds to DNA, resulting in a steady increase in fluorescence. Another commonly used method is real-time quantitative TaqMan PCR (Applied Biosystems). The 5' nuclease assay provides a real-time method for detecting only specific amplification products. The use of fluorogenic probes makes it possible to eliminate post-PCR processing for the analysis of probe degradation. The probe is an oligonucleotide with both a reporter fluorescent dye and a quencher dye attached. While the probe is intact, the proximity of the quencher greatly reduces the fluorescence emitted by the reporter dye by Förster resonance energy transfer (FRET) through space. Probe design and synthesis has been simplified by the finding that adequate quenching is observed for probes with the reporter at the 5' end and the quencher at the 3' end.

Angiogenesis:

A physiological process involving the growth of new blood vessels from pre-existing vessels. Angiogenesis can occur under normal physiological conditions such as during growth and development or wound healing (known as physiological angiogenesis) as well as pathological conditions such as in the transition of tumors from a dormant state to a malignant state (known as pathological angiogenesis). As used herein, pro-angiogenic genes are genes that facilitate angiogenesis, such as angiogenesis in an ovarian tumor.

The complex phenomenon of angiogenesis begins with degradation of the basement membrane by cellular proteases. This allows endothelial cells to penetrate and migrate (process known as cell motility) into the extracellular matrix and then proliferate. In the final stages of this process, the endothelial cells align themselves to form capillary or tubelike structures (process known as tube formation). These new structures then form a network that undergoes significant remodeling and rearrangement before fully functioning capillaries exist. Therefore, angiogenesis can be studied or identified by monitoring tube formation, cell motility, and/or cell proliferation.

Antibody:

A polypeptide ligand including at least a light chain or heavy chain immunoglobulin variable region which specifically recognizes and binds an epitope of an antigen, such as an ovarian endothelial cell tumor-associated molecule or a fragment thereof. Antibodies are composed of a heavy and a light chain, each of which has a variable region, termed the variable heavy ($V_H$) region and the variable light ($V_L$) region. Together, the $V_H$ region and the $V_L$ region are responsible for binding the antigen recognized by the antibody. In one example, an antibody specifically binds to one of the proteins listed in Tables 8 and 9.

This includes intact immunoglobulins and the variants and portions of them well known in the art, such as Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook,* 1994-1995 (Pierce Chemical Co., Rockford, Ill.); Kuby, *J., Immunology,* 3$^{rd}$ Ed., W.H. Freeman & Co., New York, 1997.

Typically, a naturally occurring immunoglobulin has heavy (H) chains and light (L) chains interconnected by disulfide bonds. There are two types of light chain, lambda and kappa. There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs". The extent of the framework region and CDRs have been defined (see, Kabat et al., *Sequences of Proteins of Immunological Interest,* U.S. Department of Health and Human Services, 1991, which is hereby incorporated by reference). The Kabat database is now maintained online. The sequences of the framework regions of different light or heavy chains are relatively conserved within a species. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. An antibody that binds RET will have a specific $V_H$ region and the $V_L$ region sequence, and thus specific CDR sequences. Antibodies with different specificities (such as different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" is an antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells. Monoclonal antibodies include humanized monoclonal antibodies.

A "polyclonal antibody" is an antibody that is derived from different B-cell lines. Polyclonal antibodies are a mixture of immunoglobulin molecules secreted against a specific antigen, each recognizing a different epitope. These antibodies are produced by methods known to those of skill in the art, for instance, by injection of an antigen into a suitable mammal (such as a mouse, rabbit or goat) that induces the B-lymphocytes to produce IgG immunoglobulins specific for the antigen which are then purified from the mammal's serum.

A "chimeric antibody" has framework residues from one species, such as human, and CDRs (which generally confer antigen binding) from another species, such as a murine antibody that specifically binds an ovarian endothelial cell tumor-associated molecule.

A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, e.g., at least about 85-90%, such as about 95% or more identical. Hence, all parts of a humanized immunoglobulin, except possibly the CDRs, are substantially identical to corresponding parts of natural human immunoglobulin sequences. Humanized immunoglobulins can be constructed by means of genetic engineering (see for example, U.S. Pat. No. 5,585, 089).

Array:

An arrangement of molecules, such as biological macromolecules (such as peptides or nucleic acid molecules) or biological samples (such as tissue sections), in addressable locations on or in a substrate. A "microarray" is an array that is miniaturized so as to require or be aided by microscopic examination for evaluation or analysis.

The array of molecules ("features") makes it possible to carry out a very large number of analyses on a sample at one time. In certain example arrays, one or more molecules (such as an oligonucleotide probe) will occur on the array a plurality of times (such as twice), for instance to provide internal controls. The number of addressable locations on the array can vary, for example from at least one, to at least 2, to at least 5, to at least 10, at least 20, at least 30, at least 50, at least 75, at least 100, at least 150, at least 200, at least 300, at least 500, least 550, at least 600, at least 800, at least 1000, at least 10,000, or more. In particular examples, an array includes nucleic acid molecules, such as oligonucleotide sequences that are at least 15 nucleotides in length, such as about 15-40 nucleotides in length. In particular examples, an array includes oligonucleotide probes or primers which can be used to detect sensitive to ovarian endothelial cell tumor-associated molecule sequences, such as at least one of those listed in Table 1, such as at least 5, at least 7, at least 10, at least 20, at least 30, at least 40, at least 50, at least 60, at least 70, at least 80, at least 90, at least 100, at least 150, at least 200, at least 250, at least 300, at least 400, at least 500, at least 600, at least 700, at least 800, at least 900, at least 1000, or at least 1100 sequences listed in Table 1 (for example, 2, 6, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 120, 130, 140, 150, 175, 225, 275, 325, 350, 375, 450, 550, 650, 750, 850, 950, 1050 or 1149 of those listed). In an example, the array is a commercially available such as a U133 Plus 2.0 oligonucleotide array from Affymetrix (Affymetrix, Santa Clara, Calif.).

Within an array, each arrayed sample is addressable, in that its location can be reliably and consistently determined within at least two dimensions of the array. The feature application location on an array can assume different shapes. For example, the array can be regular (such as arranged in uniform rows and columns) or irregular. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (such as in radially distributed lines, spiral lines, or ordered clusters). Addressable arrays usually are computer readable, in that a computer can be programmed to correlate a particular address on the array with information about the sample at that position (such as hybridization or binding data, including for instance signal intensity). In some examples of computer readable formats, the individual features in the array are arranged regularly, for instance in a Cartesian grid pattern, which can be correlated to address information by a computer.

Protein-based arrays include probe molecules that are or include proteins, or where the target molecules are or include proteins, and arrays including nucleic acids to which proteins are bound, or vice versa. In some examples, an array contains antibodies to ovarian endothelial cell tumor-associated proteins, such as any combination of those listed in Table 1, such as at least 2, least 5, at least 7, at least 10, at least 20, at least 30, at least 40, at least 50, at least 60, at least 70, at least 80, at least 90, at least 100, at least 150, at least 200, at least 250, at least 300, at least 400, at least 500, at least 600, at least 700, at least 800, at least 900, at least 1000, or at least 1100 sequences listed in Table 1 (for example, 2, 6, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 120, 130, 140, 150, 175, 225, 275, 325, 350, 375, 450, 550, 650, 750, 850, 950, 1050 or 1149 of those listed).

Binding or Stable Binding:

An association between two substances or molecules, such as the hybridization of one nucleic acid molecule to another (or itself), the association of an antibody with a peptide, or the association of a protein with another protein or nucleic acid molecule. An oligonucleotide molecule binds or stably binds to a target nucleic acid molecule if a sufficient amount of the oligonucleotide molecule forms base pairs or is hybridized to its target nucleic acid molecule, to permit detection of that binding. "Preferentially binds" indicates that one molecule binds to another with high affinity, and binds to heterologous molecules at a low affinity.

Binding can be detected by any procedure known to one skilled in the art, such as by physical or functional properties of a target:oligonucleotide complex or a protein:antibody complex. For example, binding can be detected functionally by determining whether binding has an observable effect upon a biosynthetic process such as expression of a gene, DNA replication, transcription, translation, and the like.

Physical methods of detecting the binding of complementary strands of nucleic acid molecules, include but are not limited to, such methods as DNase I or chemical footprinting, gel shift and affinity cleavage assays, Northern blotting, dot blotting and light absorption detection procedures. For example, one method involves observing a change in light absorption of a solution containing an oligonucleotide (or an analog) and a target nucleic acid at 220 to 300 nm as the temperature is slowly increased. If the oligonucleotide or analog has bound to its target, there is a sudden increase in absorption at a characteristic temperature as the oligonucleotide (or analog) and target disassociate from each other, or melt. In another example, the method involves detecting a signal, such as a detectable label, present on one or both nucleic acid molecules (or antibody or protein as appropriate).

The binding between an oligomer and its target nucleic acid is frequently characterized by the temperature ($T_m$) at which 50% of the oligomer is melted from its target. A higher ($T_m$) means a stronger or more stable complex relative to a complex with a lower ($T_m$).

Biological Activity:

An expression describing the beneficial or adverse effects of an agent on living matter. When the agent is a complex chemical mixture, this activity is exerted by the substance's active ingredient or pharmacophore, but can be modified by the other constituents. Activity is generally dosage-dependent and it is not uncommon to have effects ranging from beneficial to adverse for one substance when going from low to high doses. In one example, a specific binding agent significantly reduces the biological activity of the one or more ovarian endothelial cell tumor-associated molecules that is upregulated in ovarian endothelial tumor cells (such as those listed in Tables 2 and 4) which reduces or eliminates ovarian cancer, such as by reducing or inhibiting angiogenesis. In some examples, a specific binding agent significantly increases the biological activity of one or more ovarian endothelial cell tumor-associated molecules that is downregulated in ovarian endothelial tumor cells (such as those listed in Table 3).

Cancer:

The "pathology" of cancer includes all phenomena that compromise the well-being of the subject. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc. "Metastatic disease" refers to cancer cells that have left the original tumor site and migrate to other parts of the body for example via the bloodstream or lymph system.

Chemotherapeutic Agent or Chemotherapy:

Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating ovarian cancer, such as papillary serous ovarian cancer. In one example, a chemotherapeutic agent is a radioactive compound. One of skill in the art can readily identify a chemotherapeutic agent of use (see for example, Slapak and Kufe, Principles of Cancer Therapy, Chapter 86 in Harrison's Principles of Internal Medicine, 14th edition; Perry et al., Chemotherapy, Ch. 17 in Abeloff, Clinical Oncology 2nd ed., 2000 Churchill Livingstone, Inc; Baltzer and Berkery. (eds): Oncology Pocket Guide to Chemotherapy, 2nd ed. St. Louis, Mosby-Year Book, 1995; Fischer Knobf, and Durivage (eds): The Cancer Chemotherapy Handbook, 4th ed. St. Louis, Mosby-Year Book, 1993). Chemotherapeutic agents used for treating ovarian cancer include, but are not limited to, carboplatin, cisplatin, paclitaxel, docetaxel, doxorubicin, epirubicin, topotecan, irinotecan, gemcitabine, iazofurine, gemcitabine, etoposide, vinorelbine, tamoxifen, valspodar, cyclophosphamide, methotrexate, fluorouracil, mitoxantrone and vinorelbine. Combination chemotherapy is the administration of more than one agent (such as more than one chemotherapeutic agent) to treat cancer.

Chrondroitin Sulfate Proteoglycan 2 (CSPG2):

An extracellular matrix component of the vitreous gel that has been reported to be an anti-cell adhesive. In particular examples, expression of CSPG2 is increased in ovarian cancer endothelial cells. The term CSPG2 includes any CSPG2 gene, cDNA, mRNA, or protein from any organism and that is CSPG2 and is expressed and in some examples overexpressed in ovarian cancer endothelial cells.

Nucleic acid and protein sequences for CSPG2 are publicly available. For example, GenBank Accession Nos.: NM_004385 and BC096495 disclose CSPG2 nucleic acid sequences, and GenBank Accession Nos.: AAH50524, NP_004376, and AAH96495 disclose CSPG2 protein sequences, all of which are incorporated by reference as provided by GenBank on Feb. 14, 2007.

In one example, CSPG2 includes a full-length wild-type (or native) sequence, as well as CSPG2 allelic variants that retain the ability to be expressed in ovarian tumor endothelial cells and/or modulate ovarian tumor endothelial cells, such as increase vascular growth. In certain examples, CSPG2 has at least 80% sequence identity, for example at least 85%, 90%, 95%, or 98% sequence identity to GenBank Accession No. AAH50524, NP_004376, or AAH96495. In other examples, CSPG2 has a sequence that hybridizes to AFFYMETRIX® Probe ID No. 204619_s_at and 221731_x_a and retains CSPG2 activity (such as the capability to be expressed in ovarian tumor endothelial cells and/or modulate tumor and/or vascular growth).

Complementarity and Percentage Complementarity:

Molecules with complementary nucleic acids form a stable duplex or triplex when the strands bind, (hybridize), to each other by forming Watson-Crick, Hoogsteen or reverse Hoogsteen base pairs. Stable binding occurs when an oligonucleotide molecule remains detectably bound to a target nucleic acid sequence (such as an ovarian endothelial cell tumor-associated molecule) under the required conditions.

Complementarity is the degree to which bases in one nucleic acid strand base pair with the bases in a second nucleic acid strand. Complementarity is conveniently described by percentage, that is, the proportion of nucleotides that form base pairs between two strands or within a specific region or domain of two strands. For example, if 10 nucleotides of a 15-nucleotide oligonucleotide form base pairs with a targeted region of a DNA molecule, that oligonucleotide is said to have 66.67% complementarity to the region of DNA targeted.

In the present disclosure, "sufficient complementarity" means that a sufficient number of base pairs exist between an oligonucleotide molecule and a target nucleic acid sequence (such as a ovarian endothelial cell tumor-associated molecule, for example any of the genes listed in Table 1) to achieve detectable binding. When expressed or measured by percentage of base pairs formed, the percentage complementarity that fulfills this goal can range from as little as about 50% complementarity to full (100%) complementary. In general, sufficient complementarity is at least about 50%, for example at least about 75% complementarity, at least about 90% complementarity, at least about 95% complementarity, at least about 98% complementarity, or even at least about 100% complementarity.

A thorough treatment of the qualitative and quantitative considerations involved in establishing binding conditions that allow one skilled in the art to design appropriate oligonucleotides for use under the desired conditions is provided by Beltz et al. *Methods Enzymol.* 100:266-285, 1983, and by Sambrook et al. (ed.), *Molecular Cloning: A Laboratory Manual*, 2nd ed., vol. 1-3, Cold Spring Harbor Laboratory Press, Cold Spring Harbor, N.Y., 1989.

Contacting:

Placement in direct physical association, including both a solid and liquid form. Contacting can occur in vitro, for example, with isolated cells or in vivo by administering to a subject.

Decrease:

To reduce the quality, amount, or strength of something. In one example, a therapy decreases a tumor (such as the size of a tumor, the growth of a tumor, number of tumors, the metastasis of a tumor, or combinations thereof), or one or more symptoms associated with a tumor, for example as compared to the response in the absence of the therapy (such as a therapy administered to affect tumor size by inhibiting angiogenesis via administration of a binding agent capable of binding to one or more of the ovarian endothelial cell tumor-associated markers listed in Tables 1 through 5 that is involved in promoting angiogenesis, such as by inhibiting an ovarian endothelial cell tumor-associated marker that is upregulated in ovarian endothelial tumor cells or by increasing activity of an ovarian endothelial cell tumor-associated marker that is downregulated in ovarian endothelial tumor cells). In a particular example, a therapy decreases the size of a tumor, the growth of a tumor, the number of tumors, the metastasis of a tumor, or combinations thereof, subsequent to the therapy, such as a decrease of at least 10%, at least 20%, at least 50%, or even at least 90%. Such decreases can be measured using the methods disclosed herein.

Determining Expression of a Gene Product:

Detection of a level expression in either a qualitative or quantitative manner.

Diagnosis:

The process of identifying a disease by its signs, symptoms and results of various tests. The conclusion reached through that process is also called "a diagnosis." Forms of testing commonly performed include blood tests, medical imaging, urinalysis, and biopsy.

DNA (Deoxyribonucleic Acid):

A long chain polymer which includes the genetic material of most living organisms (some viruses have genes including ribonucleic acid, RNA). The repeating units in DNA polymers are four different nucleotides, each of which includes one of the four bases, adenine, guanine, cytosine and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

Differential Expression:

A difference, such as an increase or decrease, in the conversion of the information encoded in a gene (such as an ovarian endothelial cell tumor-associated molecule) into messenger RNA, the conversion of mRNA to a protein, or both. In some examples, the difference is relative to a control or reference value, such as an amount of gene expression that is expected in a subject who does not have ovarian cancer or in a normal (non-cancerous) endothelial cell sample. Detecting differential expression can include measuring a change in gene expression.

Downregulated or Inactivation:

When used in reference to the expression of a nucleic acid molecule, such as a gene, refers to any process which results in a decrease in production of a gene product. A gene product can be RNA (such as mRNA, rRNA, tRNA, and structural RNA) or protein. Therefore, gene downregulation or deactivation includes processes that decrease transcription of a gene or translation of mRNA. Examples of genes whose expression is downregulated in ovarian tumor endothelial cells can be found in Table 1 (indicated by a negative fold change, such as TLOC1 and HS6ST2) and Table 3 (such as PLN, SELE, GREB1, OGN and LCXD3).

Examples of processes that decrease transcription include those that facilitate degradation of a transcription initiation complex, those that decrease transcription initiation rate, those that decrease transcription elongation rate, those that decrease processivity of transcription and those that increase transcriptional repression. Gene downregulation can include reduction of expression above an existing level. Examples of processes that decrease translation include those that decrease translational initiation, those that decrease translational elongation and those that decrease mRNA stability.

Gene downregulation includes any detectable decrease in the production of a gene product. In certain examples, production of a gene product decreases by at least 2-fold, for example at least 3-fold or at least 4-fold, as compared to a control (such an amount of gene expression in a normal endothelial cell). In one example, a control is a relative amount of gene expression or protein expression in a biological sample taken from a subject who does not have ovarian cancer.

Endothelial Cell:

Cells that line the interior surface of blood vessels, forming an interface between circulating blood in the lumen and the rest of the vessel wall. For example, endothelial cells line the entire circulatory system. Further, both blood and lymphatic capillaries are composed of a single layer of endothelial cells.

Epidermal Growth Factor-like Domain Multiple 6 (EGFL6):

A member of the epidermal growth factor (EGF) repeat superfamily of genes known to encode proteins that govern cellular proliferative responses. EGFL6 has been identified as a possible regulator of cell cycle and oncogenesis.

In particular examples, expression of EGFL6 is increased in ovarian cancer endothelial cells. The term EGFL6 includes any EGFL6 gene, cDNA, mRNA, or protein from any organism and that is EGFL6 and is expressed and in some examples overexpressed in ovarian cancer endothelial cells.

Nucleic acid and protein sequences for EGFL6 are publicly available. For example, GenBank Accession Nos.: NM_015507, NM_019397 and BC038587 disclose EGFL6 nucleic acid sequences, and GenBank Accession Nos.: AAQ88699, CAM23572, and AAF27812 disclose EGFL6 protein sequences, all of which are incorporated by reference as provided by GenBank on Feb. 14, 2007.

In one example, EGFL6 includes a full-length wild-type (or native) sequence, as well as EGFL6 allelic variants that retain the ability to be expressed in ovarian tumor endothelial cells and/or modulate ovarian tumor endothelial cells, such as increase vascular growth. In certain examples, EGFL6 has at least 80% sequence identity, for example at least 85%, 90%, 95%, or 98% sequence identity to GenBank Accession No. AAQ88699, CAM23572, or AAF27812. In other examples, EGFL6 has a sequence that hybridizes to Affymetrix Probe ID No. 219454_at and retains EGFL6 activity (such as the capability to be expressed in ovarian tumor endothelial cells and/or modulate tumor and/or vascular growth).

Expression:

The process by which the coded information of a gene is converted into an operational, non-operational, or structural part of a cell, such as the synthesis of a protein. Gene expression can be influenced by external signals. For instance, exposure of a cell to a hormone may stimulate expression of a hormone-induced gene. Different types of cells can respond differently to an identical signal. Expression of a gene also can be regulated anywhere in the pathway from DNA to RNA to protein. Regulation can include controls on transcription, translation, RNA transport and processing, degradation of intermediary molecules such as mRNA, or through activation, inactivation, compartmentalization or degradation of specific protein molecules after they are produced.

The expression of a nucleic acid molecule can be altered relative to a normal (wild type) nucleic acid molecule. Alterations in gene expression, such as differential expression, include but are not limited to: (1) overexpression; (2) underexpression; or (3) suppression of expression. Alternations in the expression of a nucleic acid molecule can be associated with, and in fact cause, a change in expression of the corresponding protein. Specific examples of ovarian endothelial cell tumor-associated molecules that are up-regulated in ovarian tumor endothelial cells are provided in Tables 2 and 4. Specific examples of ovarian endothelial cell tumor-associated molecules that are down-regulated in ovarian tumor endothelial cells are listed in Table 3. For example, EZH2, EGFL6, TNFAIP6, TWIST1, STC1, HOP, CSPG2, and PLXDC1 are upregulated or increased in expression in ovarian tumor endothelial cells, while TLOC1 and HS6ST2 are downregulated or decreased in expression in such cells.

Protein expression can also be altered in some manner to be different from the expression of the protein in a normal (wild type) situation. This includes but is not necessarily limited to: (1) a mutation in the protein such that one or more of the amino acid residues is different; (2) a short deletion or addition of one or a few (such as no more than 10-20) amino acid residues to the sequence of the protein; (3) a longer deletion or addition of amino acid residues (such as at least 20 residues), such that an entire protein domain or sub-domain is removed or added; (4) expression of an increased amount of the protein compared to a control or standard amount; (5) expression of a decreased amount of the protein compared to a control or standard amount; (6) alteration of the subcellular localization or targeting of the protein; (7) alteration of the temporally regulated expression of the protein (such that the protein is expressed when it normally would not be, or alternatively is not expressed when it normally would be); (8) alteration in stability of a protein through increased longevity in the time that the protein remains localized in a cell; and (9) alteration of the localized (such as organ or tissue specific or subcellular localization) expression of the protein (such that the protein is not expressed where it would normally be expressed or is expressed where it normally would not be expressed), each compared to a control or standard.

Controls or standards for comparison to a sample, for the determination of differential expression, include samples believed to be normal (in that they are not altered for the desired characteristic, for example a sample from a subject who does not have cancer, such as ovarian cancer) as well as laboratory values, even though possibly arbitrarily set, keeping in mind that such values can vary from laboratory to laboratory.

Laboratory standards and values may be set based on a known or determined population value and can be supplied in the format of a graph or table that permits comparison of measured, experimentally determined values.

Gene Expression Profile (or Fingerprint):

Differential or altered gene expression can be detected by changes in the detectable amount of gene expression (such as cDNA or mRNA) or by changes in the detectable amount of proteins expressed by those genes. A distinct or identifiable pattern of gene expression, for instance a pattern of high and low expression of a defined set of genes or gene-indicative nucleic acids such as ESTs; in some examples, as few as one or two genes provides a profile, but more genes can be used in a profile, for example at least 3, at least 4, at least 5, at least 6, at least 10, at least 20, at least 25, at least 30, at least 50, at least 80, at least 100, at least 190, at least 200, at least 300, at least 400, at least 500, at least 550, at least 600, at least 700, at least 800, at least 900, at least 1000, at least 1100 or more of those listed in any of Tables 1-5. A gene expression profile (also referred to as a fingerprint) can be linked to a tissue or cell type (such as ovarian cancer cell), to a particular stage of normal tissue growth or disease progression (such as advanced ovarian cancer), or to any other distinct or identifiable condition that influences gene expression in a predictable way. Gene expression profiles can include relative as well as absolute expression levels of specific genes, and can be viewed in the context of a test sample compared to a baseline or control sample profile (such as a sample from a subject who does not have ovarian cancer or normal endothelial cells). In one example, a gene expression profile in a subject is read on an array (such as a nucleic acid or protein array). For example, a gene expression profile is performed using a commercially available array such as a Human Genome U133 2.0 Plus Microarray from AFFYMETRIX® (AFFYMETRIX®, Santa Clara, Calif.).

Homeodomain-Only Protein, Transcript Variant 2 (HOP):

A transcriptional repressor that modulates serum response factor-dependent cardiac-specific gene expression and cardiac development. In particular examples, expression of HOP is increased in ovarian cancer endothelial cells. The term HOP includes any HOP gene, cDNA, mRNA, or protein from any organism and that is HOP and is expressed and in some examples overexpressed in ovarian cancer endothelial cells.

Nucleic acid and protein sequences for HOP are publicly available. For example, GenBank Accession Nos.: NM_139211, XM_001083738, and XM_001137349 disclose HOP nucleic acid sequences, and GenBank Accession Nos.: AAH14225, NP_631958, and NP_631957 disclose HOP protein sequences, all of which are incorporated by reference as provided by GenBank on Feb. 14, 2007.

In one example, HOP includes a full-length wild-type (or native) sequence, as well as HOP allelic variants that retain the ability to be expressed in ovarian tumor endothelial cells and/or modulate ovarian tumor endothelial cells, such as increase vascular growth. In certain examples, HOP has at least 80% sequence identity, for example at least 85%, 90%, 95%, or 98% sequence identity to GenBank Accession No.: AAH14225, NP_631958, or NP_631957. In other examples, HOP has a sequence that hybridizes to AFFYMETRIX® Probe ID No. 211597_s_at and retains HOP activity (such as the capability to be expressed in ovarian tumor endothelial cells and/or modulate tumor and/or vascular growth).

Hybridization:

To form base pairs between complementary regions of two strands of DNA, RNA, or between DNA and RNA, thereby forming a duplex molecule. Hybridization conditions resulting in particular degrees of stringency will vary depending upon the nature of the hybridization method and the composition and length of the hybridizing nucleic acid sequences. Generally, the temperature of hybridization and the ionic strength (such as the $Na^+$ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11). The following is an exemplary set of hybridization conditions and is not limiting:

Very High Stringency (Detects Sequences that Share at Least 90% Identity)
Hybridization: 5×SSC at 65° C. for 16 hours
Wash twice: 2×SSC at room temperature (RT) for 15 minutes each
Wash twice: 0.5×SSC at 65° C. for 20 minutes each
High Stringency (Detects Sequences that Share at Least 80% Identity)
Hybridization: 5×-6×SSC at 65° C.-70° C. for 16-20 hours
Wash twice: 2×SSC at RT for 5-20 minutes each
Wash twice: 1×SSC at 55° C.-70° C. for 30 minutes each
Low Stringency (Detects Sequences that Share Greater than 50% Identity)
Hybridization: 6×SSC at RT to 55° C. for 16-20 hours
Wash at least twice: 2×-3×SSC at RT to 55° C. for 20-30 minutes each.

Inhibitor:

Any chemical compound, nucleic acid molecule, peptide or polypeptide such as an antibody or RNAi that can reduce activity of a gene product or interfere with expression of a gene, respectively. In some examples, an inhibitor can reduce or inhibit the activity of a protein that is encoded by a gene either directly or indirectly. Direct inhibition can be accomplished, for example, by binding to a protein and thereby preventing the protein from binding an intended target, such as a receptor. Indirect inhibition can be accomplished, for example, by binding to a protein's intended target, such as a receptor or binding partner, thereby blocking or reducing activity of the protein. In some examples, an inhibitor of the disclosure can inhibit a gene by reducing or inhibiting expression of the gene, inter alia by interfering with gene expression (transcription, processing, translation, post-translational modification), for example, by interfering with the gene's mRNA and blocking translation of the gene product or by post-translational modification of a gene product, or by causing changes in intracellular localization.

Isolated:

An "isolated" biological component (such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" include nucleic acid molecules and proteins purified by standard purification methods. The term also embraces nucleic acid molecules and proteins prepared by recombinant expression in a host cell as well as chemically synthesized nucleic acid molecules and proteins. For example, an isolated serous papillary ovarian cancer cell is one that is substantially separated from other ovarian cell subtypes, such as endometrioid, clear cell or mucinous subtypes.

Label:

An agent capable of detection, for example by ELISA, spectrophotometry, flow cytometry, or microscopy. For example, a label can be attached to a nucleic acid molecule or protein, thereby permitting detection of the nucleic acid molecule or protein. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al.

(Molecular Cloning: A Laboratory Manual, Cold Spring Harbor, N.Y., 1989) and Ausubel et al. (In Current Protocols in Molecular Biology, John Wiley & Sons, New York, 1998). In a particular example, a label is conjugated to a binding agent that specifically binds to one or more of the ovarian endothelial cell tumor-associated molecules disclosed in Tables 1 through 5 to allow for the detection/screening for angiogenesis and/or the presence of a tumor in a subject.

Malignant:

Cells that have the properties of anaplasia invasion and metastasis.

Mammal:

This term includes both human and non-human mammals. Examples of mammals include, but are not limited to: humans and veterinary and laboratory animals, such as pigs, cows, goats, cats, dogs, rabbits and mice.

Neoplasm:

Abnormal growth of cells.

Normal Cell:

Non-tumor cell, non-malignant, uninfected cell.

Nucleic Acid Array:

An arrangement of nucleic acids (such as DNA or RNA) in assigned locations on a matrix, such as that found in cDNA arrays, or oligonucleotide arrays, such as those listed in Tables 1-5.

Nucleic Acid Molecules Representing Genes:

Any nucleic acid, for example DNA (intron or exon or both), cDNA, or RNA (such as mRNA), of any length suitable for use as a probe or other indicator molecule, and that is informative about the corresponding gene.

Nucleic Acid Molecules:

A deoxyribonucleotide or ribonucleotide polymer including, without limitation, cDNA, mRNA, genomic DNA, and synthetic (such as chemically synthesized) DNA. The nucleic acid molecule can be double-stranded or single-stranded. Where single-stranded, the nucleic acid molecule can be the sense strand or the antisense strand. In addition, nucleic acid molecule can be circular or linear.

The disclosure includes isolated nucleic acid molecules that include specified lengths of an ovarian endothelial cell tumor-associated molecule nucleotide sequence, for sequences for genes listed in Tables 1 through 4. Such molecules can include at least 10, at least 15, at least 20, at least 25, at least 30, at least 35, at least 40, at least 45 or at least 50 consecutive nucleotides of these sequences or more, and can be obtained from any region of a ovarian endothelial cell tumor-associated molecule.

Oligonucleotide:

A plurality of joined nucleotides joined by native phosphodiester bonds, between about 6 and about 300 nucleotides in length. An oligonucleotide analog refers to moieties that function similarly to oligonucleotides but have non-naturally occurring portions. For example, oligonucleotide analogs can contain non-naturally occurring portions, such as altered sugar moieties or inter-sugar linkages, such as a phosphorothioate oligodeoxynucleotide.

Particular oligonucleotides and oligonucleotide analogs can include linear sequences up to about 200 nucleotides in length, for example a sequence (such as DNA or RNA) that is at least 6 nucleotides, for example at least 8, at least 10, at least 15, at least 20, at least 21, at least 25, at least 30, at least 35, at least 40, at least 45, at least 50, at least 100 or even at least 200 nucleotides long, or from about 6 to about 50 nucleotides, for example about 10-25 nucleotides, such as 12, 15 or 20 nucleotides.

Oligonucleotide Probe:

A short sequence of nucleotides, such as at least 8, at least 10, at least 15, at least 20, at least 21, at least 25, or at least 30 nucleotides in length, used to detect the presence of a complementary sequence by molecular hybridization. In particular examples, oligonucleotide probes include a label that permits detection of oligonucleotide probe:target sequence hybridization complexes, such as with an ovarian endothelial cell tumor-associated molecule listed in Tables 1-5.

Ovarian Cancer: A malignant ovarian neoplasm (an abnormal growth located on the ovaries). Cancer of the ovaries includes ovarian carcinoma, papillary serous cystadenocarcinoma, mucinous cystadenocarcinoma, endometrioid tumors, celioblastoma, clear cell carcinoma, unclassified carcinoma, granulosa-thecal cell tumors, Sertoli-Leydig cell tumors, dysgerminoma, and malignant teratoma. The most common type of ovarian cancer is papillary serous carcinoma.

Surgery is an exemplary treatment for ovarian cancer and can be necessary for diagnosis. The type of surgery depends upon how widespread the cancer is when diagnosed (the cancer stage), as well as the type and grade of cancer. The surgeon may remove one (unilateral oophorectomy) or both ovaries (bilateral oophorectomy), the fallopian tubes (salpingectomy), and the uterus (hysterectomy). For some very early tumors (stage 1, low grade or low-risk disease), only the involved ovary and fallopian tube will be removed (called a "unilateral salpingo-oophorectomy," USO), especially in young females who wish to preserve their fertility. In advanced disease as much tumor as possible is removed (debulking surgery). In cases where this type of surgery is successful, the prognosis is improved compared to subjects where large tumor masses (more than 1 cm in diameter) are left behind.

Chemotherapy is often used after surgery to treat any residual disease. At present systemic chemotherapy often includes a platinum derivative with a taxane as a method of treating advanced ovarian cancer. Chemotherapy is also used to treat subjects who have a recurrence.

Ovarian Endothelial Cell Tumor-Associated (or Related) Molecule:

A molecule whose expression is altered in ovarian tumor endothelial cells. Such molecules include, for instance, nucleic acid sequences (such as DNA, cDNA, or mRNAs) and proteins. Specific genes include those listed in Tables 1 through 5. Thus, the presence of the respective ovarian endothelial cell tumor-associated molecules can be used to diagnose, or determine the prognosis of, an ovarian tumor in a subject.

In an example, an ovarian endothelial cell tumor-associated molecule is any molecule listed in Tables 1 through 5. Specific examples of ovarian endothelial cell tumor-associated molecules that are up-regulated in ovarian tumor endothelial cells are provided in Tables 2 and 4. Specific examples of ovarian endothelial cell tumor-associated molecules that are down-regulated in ovarian tumor endothelial cells are listed in Table 3. As illustrated in Table 4, a number of the identified ovarian cell tumor-associated molecules are related to cell proliferation, tube formation and cell motility.

Ovarian endothelial cell tumor-associated molecules can be involved in or influenced by cancer in different ways, including causative (in that a change in a ovarian endothelial cell tumor-associated molecule leads to development of or progression of ovarian cancer) or resultive (in that development of or progression of ovarian cancer causes or results in a change in the ovarian endothelial cell tumor-associated molecule).

Pharmaceutically Acceptable Carriers:

The pharmaceutically acceptable carriers (vehicles) useful in this disclosure are conventional. Remington's Pharmaceutical Sciences, by E. W. Martin, Mack Publishing Co., Easton, Pa., 15th Edition (1975), describes compositions and formulations suitable for pharmaceutical delivery of one or more therapeutic agents, such as one or more compositions that include a binding agent that specifically binds to at least one of the disclosed ovarian endothelial cell tumor-associated molecules.

In general, the nature of the carrier will depend on the particular mode of administration being employed. For instance, parenteral formulations can include injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate, sodium lactate, potassium chloride, calcium chloride, and triethanolamine oleate.

Plexin Domain Containing 1 (PLXDC1):

A large transmembrane receptor. In vitro, plexin-C1 has been shown to bind the GPI-anchored semaphorin Sema7A and the soluble viral semaphorins SemaVA (A39R) and SemaVB (AHV). Plexin C1 engagement by SemaVA inhibits integrin-mediated dendritic cell adhesion and chemotaxis in vitro, suggesting a role for plexin C1 in dendritic cell migration.

In an example, expression of PLXDL1 is increased in ovarian tumor endothelial cells. The term PLXDC1 includes any plexin C1 gene, cDNA, mRNA, or protein from any organism and that is a PLXDC1 and is expressed and in some examples overexpressed in ovarian tumor endothelial cells.

Exemplary nucleic acid and protein sequences for PLXDC1 are publicly available. For example, GenBank Accession Nos.: NM_018797, XM_622776, AB208934, and NM_005761 disclose PLXDC1 nucleic acid sequences and GenBank Accession Nos.: NP_061267, XP_622776, BAD92171, and NP_005752 disclose PLXDC1 protein sequences, all of which are incorporated by reference as provided by GenBank on Feb. 14, 2007.

In one example, a PLXDC1 sequence includes a full-length wild-type (or native) sequence, as well as PLXDC1 allelic variants, fragments, homologs or fusion sequences that retain the ability to be expressed in ovarian tumor endothelial cells and/or modulate ovarian tumor endothelial cells, such as increase vascular growth. In certain examples, PLXDC1 has at least 80% sequence identity, for example at least 85%, 90%, 95%, or 98% sequence identity to GenBank Accession No.: NP_061267, XP_622776, BAD92171, or NP_005752. In other examples, a PLXDC1 has a sequence that hybridizes to AFFYMETRIX® Probe ID No. 214081_at and retains PLXDC1 activity (such as the capability to be expressed in ovarian tumor endothelial cells and/or modulate tumor and/or vascular growth).

Polymerase Chain Reaction (PCR):

An in vitro amplification technique that increases the number of copies of a nucleic acid molecule (for example, a nucleic acid molecule in a sample or specimen). In an example, a biological sample collected from a subject (e.g., with ovarian cancer) is contacted with a pair of oligonucleotide primers, under conditions that allow for the hybridization of the primers to nucleic acid template in the sample. The primers are extended under suitable conditions, dissociated from the template, and then re-annealed, extended, and dissociated to amplify the number of copies of the nucleic acid. The product of a PCR can be characterized by methods known in the art such as electrophoresis, restriction endonuclease cleavage patterns, oligonucleotide hybridization or ligation, and/or nucleic acid sequencing, using standard techniques.

Primers:

Short nucleic acid molecules, for instance DNA oligonucleotides 10-100 nucleotides in length, such as about 15, 20, 25, 30 or 50 nucleotides or more in length. Primers can be annealed to a complementary target DNA strand (such as a gene listed in Table 1) by nucleic acid hybridization to form a hybrid between the primer and the target DNA strand. Primer pairs can be used for amplification of a nucleic acid sequence, such as by PCR or other nucleic acid amplification methods known in the art.

Methods for preparing and using nucleic acid primers are described, for example, in Sambrook et al. (In *Molecular Cloning: A Laboratory Manual*, CSHL, New York, 1989), Ausubel et al. (ed.) (In *Current Protocols in Molecular Biology*, John Wiley & Sons, New York, 1998), and Innis et al. (*PCR Protocols, A Guide to Methods and Applications*, Academic Press, Inc., San Diego, Calif., 1990). PCR primer pairs can be derived from a known sequence, for example, by using computer programs intended for that purpose such as Primer (Version 0.5, © 1991, Whitehead Institute for Biomedical Research, Cambridge, Mass.). One of ordinary skill in the art will appreciate that the specificity of a particular primer increases with its length. Thus, for example, a primer including 30 consecutive nucleotides of an ovarian endothelial cell tumor-associated molecule will anneal to a target sequence, such as another homolog of the designated endothelial cell tumor-associated protein, with a higher specificity than a corresponding primer of only 15 nucleotides. Thus, in order to obtain greater specificity, primers can be selected that include at least 20, at least 25, at least 30, at least 35, at least 40, at least 45, at least 50 or more consecutive nucleotides of an ovarian endothelial cell tumor-associated nucleotide sequence.

Prognosis:

A prediction of the course of a disease, such as ovarian cancer. The prediction can include determining the likelihood of a subject to develop aggressive, recurrent disease, to survive a particular amount of time (e.g., determine the likelihood that a subject will survive 1, 2, 3 or 5 years), to respond to a particular therapy (e.g., chemotherapy), or combinations thereof.

Purified:

The term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation. Similarly, a purified oligonucleotide preparation is one in which the oligonucleotide is more pure than in an environment including a complex mixture of oligonucleotides.

Recombinant:

A recombinant nucleic acid molecule is one that has a sequence that is not naturally occurring or has a sequence that is made by an artificial combination of two otherwise separated segments of sequence. This artificial combination can be accomplished for example, by chemical synthesis or by the artificial manipulation of isolated segments of nucleic acid molecules, such as by genetic engineering techniques.

Sample (or Biological Sample):

A biological specimen containing genomic DNA, RNA (including mRNA), protein, or combinations thereof, obtained from a subject. Examples include, but are not limited to, peripheral blood, urine, saliva, tissue biopsy, surgical specimen, amniocentesis samples and autopsy material. In one example, a sample includes an ovarian cancer tissue biopsy.

Sensitivity:

A measurement of activity, such as biological activity, of a molecule or a collection of molecules in a given condition. In an example, sensitivity refers to the activity of an agent, such as a binding agent that preferentially binds to one or more ovarian endothelial cell tumor-associated molecules, to alter the growth, development or progression of a disease, such as ovarian cancer. In certain examples, sensitivity or responsiveness can be assessed using any endpoint indicating a benefit to the subject, including, without limitation, (1) inhibition, to some extent, of tumor growth, including slowing down and complete growth arrest; (2) reduction in the number of tumor cells; (3) reduction in tumor size; (4) inhibition (such as reduction, slowing down or complete stopping) of tumor cell infiltration into adjacent peripheral organs and/or tissues; (5) inhibition (such as reduction, slowing down or complete stopping) of metastasis; (6) enhancement of anti-tumor immune response, which may, but does not have to, result in the regression or rejection of the tumor; (7) relief, to some extent, of one or more symptoms associated with the tumor; (8) increase in the length of survival following treatment; (9) decreased mortality at a given point of time following treatment; and/or (10) reducing or inhibiting angiogenesis.

Sequence Identity/Similarity:

The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Sequence similarity can be measured in terms of percentage similarity (which takes into account conservative amino acid substitutions); the higher the percentage, the more similar the sequences are. Homologs or orthologs of nucleic acid or amino acid sequences possess a relatively high degree of sequence identity/similarity when aligned using standard methods. This homology is more significant when the orthologous proteins or cDNAs are derived from species which are more closely related (such as human and mouse sequences), compared to species more distantly related (such as human and *C. elegans* sequences).

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, *CABIOS* 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn and tblastx. Additional information can be found at the NCBI web site.

BLASTN is used to compare nucleic acid sequences, while BLASTP is used to compare amino acid sequences. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide or amino acid residue is presented in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1154 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that identified sequence (that is, 15÷20*100=75).

For comparisons of amino acid sequences of greater than about 30 amino acids, the Blast 2 sequences function is employed using the default BLOSUM62 matrix set to default parameters, (gap existence cost of 11, and a per residue gap cost of 1). Homologs are typically characterized by possession of at least 70% sequence identity counted over the full-length alignment with an amino acid sequence using the NCBI Basic Blast 2.0, gapped blastp with databases such as the nr or swissprot database. Queries searched with the blastn program are filtered with DUST (Hancock and Armstrong, 1994, *Comput. Appl. Biosci.* 10:67-70). Other programs use SEG. In addition, a manual alignment can be performed. Proteins with even greater similarity will show increasing percentage identities when assessed by this method, such as at least about 75%, 80%, 85%, 90%, 95%, 98%, or 99% sequence identity with the proteins listed in Table 1.

When aligning short peptides (fewer than around 30 amino acids), the alignment is be performed using the Blast 2 sequences function, employing the PAM30 matrix set to default parameters (open gap 9, extension gap 1 penalties). Proteins with even greater similarity to the reference sequence will show increasing percentage identities when assessed by this method, such as at least about 60%, 70%, 75%, 80%, 85%, 90%, 95%, 98%, 99% sequence identity with the proteins listed in Table 1. When less than the entire sequence is being compared for sequence identity, homologs will typically possess at least 75% sequence identity over short windows of 10-20 amino acids, and can possess sequence identities of at least 85%, 90%, 95% or 98% depending on their identity to the reference sequence. Methods for determining sequence identity over such short windows are described at the NCBI web site.

One indication that two nucleic acid molecules are closely related is that the two molecules hybridize to each other under stringent conditions, as described above. Nucleic acid sequences that do not show a high degree of identity may nevertheless encode identical or similar (conserved) amino acid sequences, due to the degeneracy of the genetic code. Changes in a nucleic acid sequence can be made using this degeneracy to produce multiple nucleic acid molecules that all encode substantially the same protein. Such homologous nucleic acid sequences can, for example, possess at least about 60%, 70%, 80%, 90%, 95%, 98%, or 99% sequence identity with the genes listed in Table 1 as determined by this method. An alternative (and not necessarily cumulative) indication that two nucleic acid sequences are substantially identical is that the polypeptide which the first nucleic acid encodes is immunologically cross reactive with the polypeptide encoded by the second nucleic acid.

One of skill in the art will appreciate that the particular sequence identity ranges are provided for guidance only; it is possible that strongly significant homologs could be obtained that fall outside the ranges provided.

Short interfering RNA (siRNA):

A double stranded nucleic acid molecule capable of RNA interference or "RNAi." (See, for example, Bass *Nature* 411: 428-429, 2001; Elbashir et al., *Nature* 411: 494-498, 2001; and Kreutzer et al., International PCT Publication No. WO 00/44895; Zernicka-Goetz et al., International PCT Publication No. WO 01/36646; Fire, International PCT Publication No. WO 99/32619; Plaetinck et al., International PCT Publication No. WO 00/01846; Mello and Fire, International PCT Publication No. WO 01/29058; Deschamps-Depaillette, International PCT Publication No. WO 99/07409; and Li et al., International PCT Publication No. WO 00/44914.) As used herein, siRNA molecules need not be limited to those molecules containing only RNA, but further encompasses chemically modified nucleotides and non-nucleotides having RNAi capacity or activity. In an example, an siRNA molecule is one that reduces or inhibits the biological activity or expression of one or more ovarian endothelial cell tumor-associated molecules disclosed in Tables 1, 2, 4 or 5 that are upregulated in ovarian tumor endothelial cells, such as EGFL6, TNFAIP6, TWIST1, STC1, HOP, CSPG2, PLXDC1, EZH2, the Notch ligand Jagged1 or PTK2.

Specific Binding Agent:

An agent that binds substantially or preferentially only to a defined target (for example, those listed in Table 1), such as a protein, enzyme, polysaccharide, oligonucleotide, DNA, RNA, recombinant vector or a small molecule. In an example, a "specific binding agent" is capable of binding to at least one of the disclosed ovarian endothelial cell tumor-associated molecules. Thus, a RNA-specific binding agent binds substantially only to the defined RNA, or to a specific region within the RNA. For example, a "specific binding agent" includes a siRNA that binds substantially to a specified RNA.

A protein-specific binding agent binds substantially only the defined protein, or to a specific region within the protein. For example, a "specific binding agent" includes antibodies and other agents that bind substantially to a specified polypeptide. The antibodies can be monoclonal or polyclonal antibodies that are specific for the polypeptide, as well as immunologically effective portions ("fragments") thereof. The determination that a particular agent binds substantially only to a specific polypeptide may readily be made by using or adapting routine procedures. One suitable in vitro assay makes use of the Western blotting procedure (described in many standard texts, including Harlow and Lane, Using Antibodies: A Laboratory Manual, CSHL, New York, 1999).

Stanniocalcin 1 (STC1):

A hormone that plays a role in calcium regulation, phosphate homeostasis and cell metabolism. In particular examples, expression of STC1 is increased in ovarian tumor endothelial cells. The term STC1 includes any STC1 gene, cDNA, mRNA, or protein from any organism and that is STC1 and is expressed or overexpressed in some examples in ovarian tumor endothelial cells.

Nucleic acid and protein sequences for STC1 are publicly available. For example, GenBank Accession Nos.: NM_009285, NM_00003155, and NM_031123 disclose STC1 nucleic acid sequences, and GenBank Accession Nos.: AAH21425, NP_112385, and NP_033311 disclose STC1 protein sequences, all of which are incorporated by reference as provided by GenBank on Feb. 14, 2007.

In one example, STC1 includes a full-length wild-type (or native) sequence, as well as STC1 allelic variants that retain the ability to be expressed in ovarian tumor endothelial cells and/or modulate ovarian tumor endothelial cells, such as increase vascular growth. In certain examples, STC1 has at least 80% sequence identity, for example at least 85%, 90%, 95%, or 98% sequence identity to GenBank Accession No.: AAH21425, NP_112385, or NP_033311. In other examples, STC1 has a sequence that hybridizes to AFFYMETRIX® Probe ID No. 230746_s_at, 204595_s_at, and 204597_x_at and retains STC1 activity (such as the capability to be expressed in ovarian tumor endothelial cells and/or modulate tumor and/or vascular growth).

Subject:

Living multi-cellular vertebrate organisms, a category that includes human and non-human mammals.

Target Sequence:

A sequence of nucleotides located in a particular region in the human genome that corresponds to a desired sequence, such as an ovarian endothelial cell tumor-associated sequence. The target can be for instance a coding sequence; it can also be the non-coding strand that corresponds to a coding sequence. Examples of target sequences include those sequences associated with ovarian tumor endothelial cells, such as any of those listed in Tables 1 through 5.

Therapeutically Effective Amount:

An amount of a composition that alone, or together with an additional therapeutic agent(s) (for example a chemotherapeutic agent), induces the desired response (e.g., treatment of a tumor). The preparations disclosed herein are administered in therapeutically effective amounts.

In one example, a desired response is to decrease ovarian tumor size or metastasis in a subject to whom the therapy is administered. Tumor metastasis does not need to be completely eliminated for the composition to be effective. For example, a composition can decrease metastasis by a desired amount, for example by at least 20%, at least 50%, at least 60%, at least 70%, at least 80%, at least 90%, at least 95%, at least 98%, or even at least 100% (elimination of the tumor), as compared to metastasis in the absence of the composition.

In particular examples, it is an amount of the therapeutic agent conjugated to the specific binding agent effective to decrease a number of ovarian cancer cells, such as in a subject to whom it is administered, for example a subject having one or more ovarian carcinomas. The cancer cells do not need to be completely eliminated for the composition to be effective. For example, a composition can decrease the number of cancer cells or growth of such cells by a desired amount, for example by at least 20%, at least 50%, at least 60%, at least 70%, at least 80%, at least 90%, at least 95%, at least 98%, or even at least 100% (elimination of detectable cancer cells), as compared to the number of cancer cells in the absence of the composition.

In other examples, it is an amount of the specific binding agent for one or more of the disclosed ovarian endothelial cell tumor-associated molecules capable of reducing angiogenesis by least 20%, at least 50%, at least 60%, at least 70%, at least 80%, at least 90%, at least 95%, at least 98%, or even at least 100% (elimination of detectable angiogenesis) by the specific binding agent, or both, effective to decrease the metastasis of a tumor.

A therapeutically effective amount of a specific binding agent for at least one of the disclosed ovarian endothelial cell tumor-associated molecules, or cancer cells lysed by a therapeutic molecule conjugated to the agent, can be administered in a single dose, or in several doses, for example daily, during a course of treatment. However, the therapeutically effective amount can depend on the subject being treated, the severity and type of the condition being treated, and the manner of administration. For example, a therapeutically effective amount of such agent can vary from about 1 μg-10 mg per 70 kg body weight if administered intravenously and about 10 μg-100 mg per 70 kg body weight if administered intratumorally.

Tissue:

A plurality of functionally related cells. A tissue can be a suspension, a semi-solid, or solid. Tissue includes cells collected from a subject such as the ovaries.

Treating a Disease:

"Treatment" refers to a therapeutic intervention that ameliorates a sign or symptom of a disease or pathological condition, such as a sign or symptom of ovarian cancer. Treatment can also induce remission or cure of a condition, such as ovarian cancer. In particular examples, treatment includes preventing a disease, for example by inhibiting the full development of a disease. Prevention of a disease does not require a total absence of disease. For example, a decrease of at least 50% can be sufficient.

Tumor:

All neoplastic cell growth and proliferation, whether malignant or benign, and all pre-cancerous and cancerous cells and tissues. In an example, a tumor is an ovarian tumor.

Tumor-Necrosis Factor, Alpha-Induced Protein 6 (TN-FAIP6):

A protein capable of regulating the expression of various molecules involved in the control of inflammation. In particular examples, expression of TNFAIP6 is increased in ovarian cancer endothelial cells. The term TNFAIP6 includes any TNFAIP6 gene, cDNA, mRNA, or protein from any organism and that is TNFAIP6 and is expressed or overexpressed in some examples in ovarian cancer endothelial cells.

Nucleic acid and protein sequences for TNFAIP6 are publicly available. For example, GenBank Accession Nos.: NM_007115, BC021155 and NM_009398 disclose TNFAIP6 nucleic acid sequences, and GenBank Accession Nos.: AAH21155, NP_009046 and NP_033424 disclose TNFAIP6 protein sequences, all of which are incorporated by reference as provided by GenBank on Feb. 14, 2007.

In one example, TNFAIP6 includes a full-length wild-type (or native) sequence, as well as TNFAIP6 allelic variants that retain the ability to be expressed in ovarian tumor endothelial cells and/or modulate ovarian tumor endothelial cells, such as suppression of vascular growth. In certain examples, TNFAIP6 has at least 80% sequence identity, for example, at least 85%, 90%, 95%, or 98% sequence identity to GenBank Accession No.: AAH21155, NP_009046 or NP_033424. In other examples, TNFAIP6 has a sequence that hybridizes to AFFYMETRIX® Probe ID No. 206026_s_at and retains TNFAIP6 activity (such as the capability to be expressed in ovarian tumor endothelial cells and/or modulate tumor and/or vascular growth).

Twist Homologue 1 (TWIST1):

Overexpression of TWIST1 has been reported to play a role in destabilizing the genome, thus promoting chromosomal instability. For example, TWIST1 is capable of inhibiting chrondrogenesis. TWIST1 protein has also been noted to be involved in the regulation of tumor necrosis factor alpha production by antiinflammatory factors and pathways. In particular examples, expression of TWIST1 is increased in ovarian cancer endothelial cells. The term TWIST1 includes any TWIST1 gene, cDNA, mRNA, or protein from any organism and that is TWIST1 and is expressed or overexpressed in some examples in ovarian cancer endothelial cells.

Nucleic acid and protein sequences for TWIST1 are publicly available. For example, GenBank Accession Nos.: NM_000474, NM_053530 and XM_001076553 and disclose TWIST1 nucleic acid sequences, and GenBank Accession Nos.: NP_000465 and ABM87769 disclose TWIST1 protein sequences, all of which are incorporated by reference as provided by GenBank on Feb. 14, 2007.

In one example, TWIST1 includes a full-length wild-type (or native) sequence, as well as TWIST1 allelic variants that retain the ability to be expressed in ovarian tumor endothelial cells and/or modulate ovarian tumor endothelial cells, such as increase vascular growth. In certain examples, TWIST1 has at least 80% sequence identity, for example at least 85%, 90%, 95%, or 98% sequence identity to GenBank Accession No.: NP_000465 or ABM87769. In other examples, TWIST1 has a sequence that hybridizes to AFFYMETRIX® Probe ID No. 206026_s_at and retains TWIST1 activity (such as the capability to be expressed in ovarian tumor endothelial cells and/or modulate tumor and/or vascular growth).

Under Conditions Sufficient for:

A phrase that is used to describe any environment that permits the desired activity. In one example, includes administering a test agent to an ovarian cancer cell or a subject sufficient to allow the desired activity. In particular examples, the desired activity is altering the activity (such as the expression) of an ovarian endothelial cell tumor-associated molecule.

Unit Dose:

A physically discrete unit containing a predetermined quantity of an active material calculated to individually or collectively produce a desired effect, such as a therapeutic effect. A single unit dose or a plurality of unit doses can be used to provide the desired effect, such as treatment of a tumor, for example a metastatic tumor. In one example, a unit dose includes a desired amount of an agent that decreases or inhibits angiogenesis.

Upregulated or Activation:

When used in reference to the expression of a nucleic acid molecule, such as a gene, refers to any process which results in an increase in production of a gene product. A gene product can be RNA (such as mRNA, rRNA, tRNA, and structural RNA) or protein. Therefore, gene upregulation or activation includes processes that increase transcription of a gene or translation of mRNA. Specific examples of ovarian endothelial cell tumor-associated molecules that are up-regulated in ovarian tumor endothelial cells are provided in Tables 2 and 4. For example, EZH2, EGFL6, TNFAIP6, TWIST1, STC1, HOP, CSPG2, and PLXDC1 are upregulated or increased in expression in ovarian tumor endothelial cells.

Examples of processes that increase transcription include those that facilitate formation of a transcription initiation complex, those that increase transcription initiation rate, those that increase transcription elongation rate, those that increase processivity of transcription and those that relieve transcriptional repression (for example by blocking the binding of a transcriptional repressor). Gene upregulation can include inhibition of repression as well as stimulation of expression above an existing level. Examples of processes that increase translation include those that increase translational initiation, those that increase translational elongation and those that increase mRNA stability.

Gene upregulation includes any detectable increase in the production of a gene product. In certain examples, production of a gene product increases by at least 2-fold, for example at least 3-fold or at least 4-fold, as compared to a control (such an amount of gene expression in a normal endothelial cell). In one example, a control is a relative amount of gene expression in a biological sample, such as in an ovarian tissue biopsy obtained from a subject that does not have ovarian cancer.

Vasohibin 1 (VASH1):

a protein that is expressed in a variety of tissues and inhibits functions relevant to neovascularization (migration, proliferation, and network formation by endothelial cells). Vasohibin also inhibits angiogenesis in vivo. The unglycosylated protein (42 kDa) does not contain a classical secretory secretion sequence and appears in the medium as a protein of 30 kDa, suggesting proteolytic processing during secretion. In particular examples, VASH1 is regulated by EZH2 wherein EZH2 binds to the VASH1 promoter and decreases or inhibits VASH1 anti-angiogenesis activity. The term VASH1 includes any VASH1 gene, cDNA, mRNA, or protein from any organism and that is VASH1 and is expressed or overexpressed in some examples in ovarian cancer endothelial cells.

Nucleic acid and protein sequences for VASH1 are publicly available. For example, GenBank Accession Nos.: NP_055724 (human); NP_796328 (mouse); and NP_659128 disclose VASH1 amino acid sequences which are incorporated by reference as provided by GenBank on Aug. 14, 2009. Further, GenBank Accession Nos.: NM_014909 (human) and NM_177354 (mouse) disclose nucleic acid sequences which are incorporated by reference as provided by GenBank on Aug. 14, 2009.

In one example, vasohibin includes a full-length wild-type (or native) sequence, as well as VASH1 allelic variants that retain the ability to be expressed in ovarian tumor endothelial cells and/or modulate ovarian tumor endothelial cells, such as increase vascular growth. In certain examples, VASH1 has at least 80% sequence identity, for example at least 85%, 90%, 95%, or 98% sequence identity to GenBank Accession No.: NP_055724; NP_796328 or NP_659128 and retains VASH1 activity (such as the capability to be expressed in ovarian tumor endothelial cells and/or modulate tumor and/or vascular growth).

Zeste Homologue 2 (EZH2):

A member of the polycomb group of genes that has been reported to be involved in cell cycle regulation EZH2, a component of the polycomb repressive complex 2 (PRC2), has intrinsic histone methyl transferase (HMTase) activity and has been implicated in the progression and metastasis of several cancers. EZH2 is also a transcriptional repressor that has multiple targets, including anti-angiogenic, pro-apoptotic, and tumor suppressor genes. In particular examples, expression of EZH2 is increased in ovarian cancer endothelial cells. In one example, expression of EZH2 is an indicator of poor prognosis. The term EZH2 includes any EZH2 gene, cDNA, mRNA, or protein from any organism and that is EZH2 and is expressed or overexpressed in some examples in ovarian cancer endothelial cells.

Nucleic acid and protein sequences for EZH2 are publicly available. For example, GenBank Accession Nos.: NM_004456 and AY519465.1 disclose EZH2 nucleic acid sequences, and GenBank Accession No. AAS09975 discloses a EZH2 protein sequence, which are incorporated by reference as provided by GenBank on Feb. 14, 2007.

In one example, EZH2 includes a full-length wild-type (or native) sequence, as well as EZH2 allelic variants, fragments, homologs or fusion sequences that retain the ability to be expressed in ovarian tumor endothelial cells and/or modulate ovarian tumor endothelial cells, such as increase vascular growth. In certain examples, EZH2 has at least 80% sequence identity, for example at least 85%, 90%, 95%, or 98% sequence identity to AAS09975. In other examples, EZH2 has a sequence that hybridizes to AFFYMETRIX® Probe ID No. 203358_s_at and retains EZH2 activity (such as the capability to be expressed in ovarian tumor endothelial cells and/or modulate tumor and/or vascular growth).

Additional terms commonly used in molecular genetics can be found in Benjamin Lewin, Genes V published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

Methods of Treatment

It is shown herein that ovarian cancer is associated with differential expression of ovarian endothelial cell tumor-associated molecules. For example, the disclosed gene expression profile has identified ovarian endothelial cell tumor-associated molecules. Based on these observations, methods of treatment to reduce or eliminate ovarian cancer are disclosed. For example, the method can include inhibiting the expression or biological activity of at least one of the ovarian endothelial cell tumor associated molecules from Tables 1, 2, 4, and/or 5 that are upregulated in ovarian tumor cells or increasing the expression or biological activity of at least one of the ovarian endothelial cell tumor associated molecules from Tables 1, 3 and/or 5 that are downregulated in ovarian tumor cells or combinations thereof. As used herein, "inhibit" does not require 100% inhibition of expression or activity. For example, a substantial reduction may be adequate, such as reduction in expression or activity of at least 20%, at least 30%, at least 50%, at least 75%, or at least 95% may be sufficient to obtain desired therapeutic results. In some examples, an "increase" in expression or activity is an increase of at least 20%, at least 30%, at least 50%, at least 75%, or at least 95%. In some embodiments, the subject is a human, but the subject can alternatively be a veterinary or laboratory subject. In some embodiments, the ovarian cancer is papillary serous ovarian cancer.

Methods are disclosed herein for treating an ovarian tumor, such as ovarian cancer. In one example, the method includes administering a therapeutically effective amount of a composition to a subject. The composition can include a binding agent that is specific for one of the ovarian endothelial cell tumor-associated molecules listed in any of Tables 1, 2, 4 or 5 that are upregulated in ovarian tumor cells. Administration of such compounds decreases the expression or activity of the molecule that is undesirably upregulated in ovarian cancer cells. The molecules in Tables 1, 2, 4, or 5 include, for instance, nucleic acid sequences (such as DNA, cDNA, or mRNAs) and proteins. Specific genes include those listed in Tables 1, 2, 4 or 5 as well as fragments of the full-length genes, cDNAs, or mRNAs (and proteins encoded thereby) whose expression is upregulated in response to an ovarian tumor, such as ovarian cancer.

In particular examples, the specific binding agent is an inhibitor such as a siRNA or an antibody to one of the disclosed ovarian endothelial cell tumor-associated molecules that is upregulated in ovarian tumor cells. For example, the specific binding agent can be a siRNA that interferes with mRNA expression of one of the disclosed ovarian endothelial cell tumor-associated molecules that are involved in angiogenesis, such as a molecule involved in regulating cell motility, cell proliferation or tube formation, thereby inhibiting cell motility, cell proliferation or tube formation. For example, the specific binding agent can be a siRNA that inhibits the expression of PTK2, EZH2 or Jagged1. In other particular examples, ovarian tumor growth is reduced or inhibited by administering a specific binding agent to inhibit or reduce the expression or production of EZH2, EGFL6, TNFAIP6, TWIST1, STC1, HOP, CSPG2, and PLXDC1. In additional examples, a composition includes at least two specific binding agents such as two specific siRNAs that each bind to their respective ovarian endothelial cell tumor-associated nucleotide sequences and inhibit ovarian tumor growth in a subject. In some examples, the composition includes at least 2, 3, 4, 5, 5, 8 or 10 different siRNA molecules. For example, the composition can include PTK2, EZH2 and Jagged1 siRNAs.

Treating Ovarian Cancer by Altering Activity of an Ovarian Endothelial Cell Tumor-Associated Molecule Methods are provided to inhibit ovarian endothelial cell tumor-associated molecule activity or expression to treat an ovarian tumor. Treatment of tumors by reducing the number of ovarian endothelial cell tumor-associated molecules can include delaying the development of the tumor in a subject (such as preventing metastasis of a tumor). Treatment of a tumor also includes reducing signs or symptoms associated with the presence of such a tumor (for example by reducing the size, growth or volume of the tumor or a metastasis thereof). Such reduced growth can in some examples decrease or slow metastasis of the tumor, or reduce the size or volume of the tumor by at least 10%, at least 20%, at least 50%, or at least 75%, such as by inhibiting angiogenesis by at least 10%, at least 20%, at least 50%, or at least 75%. For example, ovarian endothelial cell tumor-associated molecules involved in angiogenesis, such as molecules involved in promoting cell proliferation, cell motility or tube formation can be inhibited to treat an ovarian tumor, such as those provided in any of Tables 1, 2, 4 or 5 that are upregulated in ovarian endothelial tumor cells. In other examples, ovarian tumor growth is reduced or inhibited by inhibiting the expression or biological activity ovarian endothelial cell tumor-associated molecules provided in any of Tables 1, 2, 4 or 5 that are upregulated in ovarian tumor endothelial cells. In further examples, inhibition of ovarian endothelial cell tumor-associated molecules includes reducing the invasive activity of the tumor in the subject. In some examples, treatment using the methods disclosed herein prolongs the time of survival of the subject.

Specific Binding Agents

Specific binding agents are agents that selectively bind with higher affinity to a molecule of interest, than to other molecules. For example, a specific binding agent can be one that binds with high affinity to one of the genes or gene products of the ovarian endothelial cell tumor-associated molecules listed in any of Tables 1, 2, 4 or 5 that are upregulated in ovarian tumor endothelial cells, but does not substantially bind to another gene or gene product. In a specific example, a specific binding agent binds to one gene listed in Tables 1, 2, 4 or 5 that is upregulated in ovarian tumor endothelial cells thereby reducing or inhibiting expression of the gene, but does not bind to the other genes (or gene product) listed in such Tables under similar conditions. For example, the agent can interfere with gene expression (transcription, processing, translation, post-translational modification), such as, by interfering with the gene's mRNA and blocking translation of the gene product or by post-translational modification of a gene product, or by causing changes in intracellular localization. In another specific example, a specific binding agent binds to a protein encoded by of one of the genes listed in Table 1, 2, 4 or 5 that is upregulated in ovarian tumor endothelial cells with a binding affinity in the range of 0.1 to 20 nM and reduces or inhibits the activity of such protein.

Examples of specific binding agents include, but are not limited to, siRNAs, antibodies, ligands, recombinant proteins, peptide mimetics, and soluble receptor fragments. One example of a specific binding agent is a siRNA. Methods of making siRNA that can be used clinically are known in the art. Particular siRNAs and methods that can be used to produce and administer them are described in detail below. In some examples, the siRNA is incorporated into a chitosan (CH) nanoparticle, such as chitosan obtained from shellfish or fungi.

Another specific example of a specific binding agent is an antibody, such as a monoclonal or polyclonal antibody. Methods of making antibodies that can be used clinically are known in the art. Particular antibodies and methods that can be used to produce them are described in detail below.

In a further example, small molecular weight inhibitors or antagonists of the receptor protein can be used to regulate activity such as the expression or production of ovarian endothelial cell tumor-associated molecules. In a particular example, small molecular weight inhibitors or antagonists of the proteins encoded by the genes listed in Tables 2 and/or 4 are employed.

Specific binding agents can be therapeutic, for example by reducing or inhibiting the biological activity of a nucleic acid or protein. Complete inhibition is not required. For example, a reduction by at least 10%, at least 20%, at least 30%, at least 50%, at least 70%, or even at least 90% can be sufficient. For example, a specific binding agent that binds with high affinity to a gene listed in Tables 1, 2, 4 and/or 5 that are upregulated in ovarian tumor endothelial cells, may substantially reduce the biological function of the gene or gene product (for example, the ability of the gene or gene product to facilitate angiogenesis). In other examples, a specific binding agent that binds with high affinity to one of the proteins encoded by the genes listed in Tables 1, 2, 4 and/or 5 that are upregulated in ovarian tumor endothelial cells, may substantially reduce the biological function of the protein (for example, the ability of the protein to promote angiogenesis). Such agents can be administered in therapeutically effective amounts to subjects in need thereof, such as a subject having ovarian cancer, such as papillary serous ovarian cancer.

Pre-Screening Subjects

In some examples, subjects are initially screened to determine if they have ovarian cancer. In an example, subjects are initially screened for ovarian cancer by using one of the disclosed gene expression profiles (as discussed in detail below). In some examples, if one or more of the disclosed endothelial cell tumor-associated molecules upregulated in ovarian endothelial cells (such as those listed in Tables 2 and 4) is detected, a specific binding agent capable of reducing or inhibiting ovarian cancer is adminstered.

Pre-Screening Specific Binding Agents

In some examples, specific binding agents are initially screened for treating ovarian cancer by use of the disclosed gene expression profile (see below). For example, the disclosed gene expression profile can be used to identify specific binding agents capable of reducing or inhibiting ovarian cancer. In an example, the disclosed gene expression profile is used to identify compositions that can be employed to reduce or inhibit angiogenesis in ovarian tumors.

Exemplary Tumors

A tumor is an abnormal growth of tissue that results from excessive cell division. A particular example of a tumor is cancer. For example, the current application provides methods for the treatment (such as the prevention or reduction of metastasis) of tumors (such as cancers) by altering the expression/production of one or more disclosed ovarian endothelial cell tumor-associated molecules. In some examples, the tumor is treated in vivo, for example in a mammalian subject, such as a human subject. Exemplary tumors that can be treated using the disclosed methods include, but are not limited to ovarian cancer, including metastases of such tumors to other organs. Generally, the tumor is an ovarian cancer, such as papillary serous ovarian cancer.

Administration

Methods of administrating the disclosed compositions are routine, and can be determined by a skilled clinician. For example, the disclosed therapies (such as those that include a binding agent specific for one of the disclosed ovarian endothelial cell tumor-associated molecules listed in Tables 1, 2, 4 or 5 whose expression is increased in ovarian endothelial tumor-associated cells) can be administered via injection, intratumorally, orally, topically, transdermally, parenterally, or via inhalation or spray. In a particular example, a composition is administered intravenously to a mammalian subject, such as a human.

The therapeutically effective amount of the agents administered can vary depending upon the desired effects and the subject to be treated. In one example, the method includes daily administration of at least 1 µg of the composition to the subject (such as a human subject). For example, a human can be administered at least 1 µg or at least 1 mg of the composition daily, such as 10 µg to 100 µg daily, 100 µg to 1000 µg daily, for example 10 µg daily, 100 µg daily, or 1000 µg daily. In one example, the subject is administered at least 1 µg (such as 1-100 µg) intravenously of the composition including a binding agent that specifically binds to one of the disclosed ovarian endothelial cell tumor-associated molecules provided herein. In one example, the subject is administered at least 1 mg intramuscularly (for example in an extremity) of such composition. In a specific example, the dose is 50 to 350 µg/kg twice weekly, such as 150 µg/kg twice weekly (for example via iv injection). The dosage can be administered in divided doses (such as 2, 3, or 4 divided doses per day), or in a single dosage daily.

In particular examples, the subject is administered the therapeutic composition that includes a binding agent specific for one of the disclosed ovarian endothelial cell tumor-associated molecules on a multiple daily dosing schedule, such as at least two consecutive days, 10 consecutive days, and so forth, for example for a period of weeks, months, or years. In one example, the subject is administered the therapeutic composition that a binding agent specific for one of the disclosed ovarian endothelial cell tumor-associated molecules daily for a period of at least 30 days, such as at least 2 months, at least 4 months, at least 6 months, at least 12 months, at least 24 months, or at least 36 months.

The therapeutic compositions, such as those that include a binding agent specific for one of the ovarian endothelial cell tumor-associated molecules, can further include one or more biologically active or inactive compounds (or both), such as anti-neoplastic agents and conventional non-toxic pharmaceutically acceptable carriers, respectively.

In a particular example, a therapeutic composition that includes a therapeutically effective amount of a binding agent specific for one of the disclosed ovarian endothelial cell tumor-associated molecules further includes one or more biologically inactive compounds. Examples of such biologically inactive compounds include, but are not limited to: carriers, thickeners, diluents, buffers, preservatives, and carriers. The pharmaceutically acceptable carriers useful for these formulations are conventional (see Remington's Pharmaceutical Sciences, by E. W. Martin, Mack Publishing Co., Easton, Pa., 19th Edition (1995)). For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can include minor amounts of non-toxic auxiliary substances, such as wetting or emulsifying agents, preservatives, and pH buffering agents and the like, for example sodium acetate or sorbitan monolaurate.

Additional Treatments

In particular examples, prior to, during, or following administration of a therapeutic amount of an agent that reduces or inhibits ovarian cancer due to the interaction of a binding agent with one of the disclosed ovarian endothelial cell tumor-associated molecules, the subject can receive one or more other therapies. In one example, the subject receives one or more treatments to remove or reduce the tumor prior to administration of a therapeutic amount of a composition including a binding agent specific for one of the disclosed ovarian endothelial cell tumor-associated molecules.

Examples of such therapies include, but are not limited to, surgical treatment for removal or reduction of the tumor (such as surgical resection, cryotherapy, or chemoembolization), as well as anti-tumor pharmaceutical treatments which can include radiotherapeutic agents, anti-neoplastic chemotherapeutic agents, antibiotics, alkylating agents and antioxidants, kinase inhibitors, and other agents. Particular examples of additional therapeutic agents that can be used include microtubule binding agents, DNA intercalators or cross-linkers, DNA synthesis inhibitors, DNA and/or RNA transcription inhibitors, antibodies, enzymes, enzyme inhibitors, and gene regulators. These agents (which are administered at a therapeutically effective amount) and treatments can be used alone or in combination. Methods and therapeutic dosages of such agents are known to those skilled in the art, and can be determined by a skilled clinician.

"Microtubule binding agent" refers to an agent that interacts with tubulin to stabilize or destabilize microtubule formation thereby inhibiting cell division. Examples of microtubule binding agents that can be used in conjunction with the disclosed therapy include, without limitation, paclitaxel, docetaxel, vinblastine, vindesine, vinorelbine (navelbine), the epothilones, colchicine, dolastatin 15, nocodazole, podophyllotoxin and rhizoxin. Analogs and derivatives of such compounds also can be used and are known to those of ordinary skill in the art. For example, suitable epothilones and epothilone analogs are described in International Publication No. WO 2004/018478. Taxoids, such as paclitaxel and docetaxel, as well as the analogs of paclitaxel taught by U.S. Pat. Nos. 6,610,860; 5,530,020; and 5,912,264 can be used.

The following classes of compounds are of use in the methods disclosed herein: Suitable DNA and/or RNA transcription regulators, including, without limitation, actinomycin D, daunorubicin, doxorubicin and derivatives and analogs thereof also are suitable for use in combination with the disclosed therapies. DNA intercalators and cross-linking agents that can be administered to a subject include, without limitation, cisplatin, carboplatin, oxaliplatin, mitomycins, such as mitomycin C, bleomycin, chlorambucil, cyclophosphamide and derivatives and analogs thereof. DNA synthesis inhibitors suitable for use as therapeutic agents include, without limitation, methotrexate, 5-fluoro-5'-deoxyuridine, 5-fluorouracil and analogs thereof. Examples of suitable enzyme inhibitors include, without limitation, camptothecin, etoposide, formestane, trichostatin and derivatives and analogs thereof. Suitable compounds that affect gene regulation include agents that result in increased or decreased expression of one or more genes, such as raloxifene, 5-azacytidine, 5-aza-2'-deoxycytidine, tamoxifen, 4-hydroxytamoxifen, mifepristone and derivatives and analogs thereof. Kinase inhibitors include Gleevac, Iressa, and Tarceva that prevent phosphorylation and activation of growth factors.

Other therapeutic agents, for example anti-tumor agents, that may or may not fall under one or more of the classifications above, also are suitable for administration in combination with the disclosed therapies. By way of example, such agents include adriamycin, apigenin, rapamycin, zebularine, cimetidine, and derivatives and analogs thereof.

In one example, the therapeutic composition (such as one including a binding agent specific for one or more of the disclosed ovarian endothelial cell tumor-associated molecules) is injected into the subject in the presence of an adjuvant. An adjuvant is an agent that when used in combination with an immunogenic agent augments or otherwise alters or modifies a resultant immune response. In some examples, an adjuvant increases the titer of antibodies induced in a subject by the immunogenic agent. In one example, the one or more peptides are administered to the subject as an emulsion with an adjuvant and sterile water for injection (for example an intravenous or intramuscular injection). Incomplete Freund's Adjuvant (Seppic, Inc.) can be used as the Freund's Incomplete Adjuvant (IFA) (Fairfield, N.J.). In some examples, IFA is provided in 3 ml of a mineral oil solution based on mannide oleate (Montanide ISA-51). At the time of injection, the peptide(s) is mixed with the Montanide ISA.51 and then administered to the subject. Other adjuvants can be used, for example, Freund's complete adjuvant, B30-MDP, LA-15-PH, montanide, saponin, aluminum hydroxide, alum, lipids, keyhole lympet protein, hemocyanin, a mycobacterial antigen, and combinations thereof.

In some examples, the subject receiving the therapeutic peptide composition (such as one including a binding agent specific for one of the disclosed ovarian endothelial cell tumor-associated molecules) is also administered interleukin-2 (IL-2), for example via intravenous administration. In particular examples, IL-2 (Chiron Corp., Emeryville, Calif.) is administered at a dose of at least 500,000 IU/kg as an intravenous bolus over a 15 minute period every eight hours beginning on the day after administration of the peptides and continuing for up to 5 days. Doses can be skipped depending on subject tolerance.

In some examples, the disclosed compositions can be co-administered with a fully human antibody to cytotoxic T-lymphocyte antigen-4 (anti-CTLA-4). In some example subjects receive at least 1 mg/kg anti-CTLA-4 (such as 3 mg/kg every 3 weeks or 3 mg/kg as the initial dose with subsequent doses reduced to 1 mg/kg every 3 weeks).

In one example, at least a portion of the ovarian tumor (such as a metastatic tumor) is surgically removed (for example via cryotherapy), irradiated, chemically treated (for example via chemoembolization) or combinations thereof, prior to administration of the disclosed therapies (such as administration of a binding agent specific for one of the disclosed ovarian endothelial cell tumor-associated molecules). For example, a subject having a metastatic tumor can have all or part of the tumor surgically excised prior to administration of the disclosed therapies (such as one including a binding agent specific for one of the disclosed ovarian endothelial cell tumor-associated molecules). In an example, one or more chemotherapeutic agents is administered following treatment with a binding agent specific for one of the disclosed ovarian endothelial cell tumor-associated molecules. In another particular example, the subject has a metastatic tumor and is administered radiation therapy, chemoembolization therapy, or both concurrently with the administration of the disclosed therapies (such as one including a binding agent specific for one of the disclosed ovarian endothelial cell tumor-associated molecules).

Generation and Administration of siRNA

In an example, certain inhibitors provided by this disclosure are species of siRNAs. One of ordinary skill in the art can readily generate siRNAs which specifically bind to one of the disclosed ovarian endothelial cell tumor-associated molecules that are upregulated in ovarian endothelial cell tumor cells. In an example, commercially available kits, such as siRNA molecule synthesizing kits from PROMEGA® (Madison, Wis.) or AMBION® (Austin, Tex.) may be used to synthesize siRNA molecules. In another example, siRNAs are obtained from commercial sources, such as from QIAGEN® Inc (Germantown, Md.), INVITROGEN® (Carlsbad, Calif.), AMBION (Austin, Tex.), DHARMACON® (Lafayette, Colo.) or OPENBIOSYSTEMS® (Huntsville, Ala.).

In certain examples, expression vectors are employed to express the at least one siRNA molecule. For example, an expression vector can include a nucleic acid sequence encoding at least one siRNA molecule corresponding to at least one of the disclosed ovarian endothelial cell tumor-associated molecules listed in Tables 1, 2, 4 and/or Table 5 that are upregulated in ovarian endothelial cell tumor cells. For example, siRNA specific for EZH2 can be generated using publicly available EZH2 nucleic acid sequences, such as those described above. In a particular example, the vector contains a sequence(s) encoding both strands of a siRNA molecule comprising a duplex. In another example, the vector also contains sequence(s) encoding a single nucleic acid molecule that is self-complementary and thus forms a siRNA molecule. Non-limiting examples of such expression vectors are described in Paul et al., *Nature Biotechnology* 19:505, 2002; Miyagishi and Taira, *Nature Biotechnology* 19:497, 2002; Lee et al., *Nature Biotechnology* 19:500, 2002; and Novina et al., *Nature Medicine*, online publication Jun. 3, 2003.

In other examples, siRNA molecules include a delivery vehicle, including inter alia liposomes, for administration to a subject, carriers and diluents and their salts, and can be present in pharmaceutical compositions. Nucleic acid molecules can be administered to cells by a variety of methods known to those of skill in the art, including, but not restricted to, encapsulation in liposomes, by iontophoresis, or by incorporation into other delivery vehicles, such as hydrogels, cyclodextrins, biodegradable nanocapsules, and bioadhesive microspheres, or by proteinaceous vectors (see, for example, O'Hare and Normand, International PCT Publication No. WO 00/53722). In one specific example, siRNAs are administered at according to the teachings of Soutschek et al. (Nature Vol. 432: 173-178, 2004) or Karpilow et al. (Pharma Genomics 32-40, 2004) both of which are herein incorporated by reference in their entireties.

In some examples, siRNAs are incorporated into neutral liposomes, such as DOPC or chitosan, and injected intraperitoneal or intravenously. For example, a siRNA can be administered at least 1 µg/kg twice weekly, such as at least 50 µg/kg twice weekly, at least 100 µg/kg twice weekly, at least 125 µg/kg twice weekly, at least 150 µg/kg twice weekly, at least 200 µg/kg twice weekly for at least 1 week, such as at least 2 weeks, at least 3 weeks, at least 4 weeks, at least 6 weeks, at least 12 weeks, or at least 24 weeks. In one example, about at least 1-500 µg/kg, such 10-250 µg/kg, is adminstered at least twice weekly for at least 1 week, such as at least 2 weeks, at least 3 weeks, at least 4 weeks, at least 6 weeks, at least 12 weeks, or at least 24 weeks. In a certain example, approximately 150 µg/kg is administered twice weekly, for 2 to 3 weeks. In other examples, approximately 1 ug/kg daily for 3 weeks or 50 ug/kg every other day for 3 weeks is administered.

Alternatively, the nucleic acid/vehicle combination can be locally delivered by direct injection or by use of an infusion pump. Direct injection of the nucleic acid molecules of the disclosure, whether subcutaneous, intramuscular, or intradermal, can take place using standard needle and syringe methodologies, or by needle-free technologies such as those described by Barry et al., International PCT Publication No. WO 99/31262. Other delivery routes, but are not limited to, oral delivery (such as in tablet or pill form), intrathecal or intraperitoneal delivery. For example, intraperitoneal delivery can take place by injecting the treatment into the peritoneal cavity of the subject in order to directly deliver the molecules to the tumor site. More detailed descriptions of nucleic acid delivery and administration are provided in Sullivan et al., PCT WO 94/02595, Draper et al., PCT WO93/23569, Beigelman et al., PCT WO99/05094, and Klimuk et al., PCT WO99/04819, all of which are incorporated by reference herein.

Alternatively, certain siRNA molecules can be expressed within cells from eukaryotic promoters. Those skilled in the art will recognize that any nucleic acid can be expressed in eukaryotic cells using the appropriate DNA/RNA vector. The activity of such nucleic acids can be augmented by their release from the primary transcript by an enzymatic nucleic acid (Draper et al., PCT WO 93/23569, and Sullivan et al., PCT WO 94/02595).

In other examples, siRNA molecules can be expressed from transcription units (see for example, Couture et al., 1996, TIG 12:510) inserted into DNA or RNA vectors. The recombinant vectors can be DNA plasmids or viral vectors. siRNA expressing viral vectors can be constructed based on, for example, but not limited to, adeno-associated virus, retrovirus, adenovirus, lentivirus or alphavirus. In another example, pol III based constructs are used to express nucleic acid molecules (see for example, Thompson, U.S. Pat. Nos. 5,902,880 and 6,146,886).

The recombinant vectors capable of expressing the siRNA molecules can be delivered as described above, and persist in target cells. Alternatively, viral vectors can be used that provide for transient expression of nucleic acid molecules. Such vectors can be repeatedly administered as necessary. Once expressed, the siRNA molecule interacts with the target mRNA and generates an RNAi response. Delivery of siRNA molecule expressing vectors can be systemic, such as by intravenous or intramuscular administration, by administration to target cells ex-planted from a subject followed by reintroduction into the subject, or by any other means that would allow for introduction into the desired target cell.

Generation of Antibodies

One of ordinary skill in the art can readily generate antibodies which specifically bind to the disclosed ovarian endothelial cell tumor-associated molecules. These antibodies can be monoclonal or polyclonal. They can be chimeric or humanized. Any functional fragment or derivative of an antibody can be used including Fab, Fab', Fab2, Fab'2, and single chain variable regions. So long as the fragment or derivative retains specificity of binding for the ovarian endothelial cell tumor-associated molecule it can be used in the methods provided herein. Antibodies can be tested for specificity of binding by comparing binding to appropriate antigen to binding to irrelevant antigen or antigen mixture under a given set of conditions. If the antibody binds to appropriate antigen at least 2, at least 5, at least 7 or 10 times more than to irrelevant antigen or antigen mixture, then it is considered to be specific.

In an example, monoclonal antibodies are generated to the ovarian endothelial cell tumor-associated molecules disclosed in Tables 1, 2, 4 or 5 that are upregulated in ovarian endothelial cell tumor cells. These monoclonal antibodies each include a variable heavy ($V_H$) and a variable light ($V_L$) chain and specifically bind to the specific ovarian endothelial cell tumor-associated molecules. For example, the antibody can bind the specific ovarian endothelial cell tumor-associated molecules with an affinity constant of at least $10^6$ $M^{-1}$, such as at least $10^7$ $M^{-1}$, at least $10^8$ $M^{-1}$, at least $5 \times 10^8$ $M^{-1}$, or at least $10^9$ $M^{-1}$.

The specific antibodies can include a $V_L$ polypeptide having amino acid sequences of the complementarity determining regions (CDRs) that are at least about 90% identical, such as at least about 95%, at least about 98%, or at least about 99% identical to the amino acid sequences of the specific ovarian endothelial cell tumor-associated molecules and a $V_H$ polypeptide having amino acid sequences of the CDRs that are at least about 90% identical, such as at least about 95%, at least about 98%, or at least about 99% identical to the amino acid sequences of the specific ovarian endothelial cell tumor-associated molecules.

In one example, the sequence of the specificity determining regions of each CDR is determined Residues that are outside the SDR (non-ligand contacting sites) are substituted. For example, in any of the CDR sequences, at most one, two or three amino acids can be substituted. The production of chimeric antibodies, which include a framework region from one antibody and the CDRs from a different antibody, is well known in the art. For example, humanized antibodies can be routinely produced. The antibody or antibody fragment can be a humanized immunoglobulin having CDRs from a donor monoclonal antibody that binds one of the disclosed ovarian endothelial cell tumor-associated molecules and immunoglobulin and heavy and light chain variable region frameworks from human acceptor immunoglobulin heavy and light chain frameworks. Generally, the humanized immunoglobulin specifically binds to one of the disclosed ovarian endothelial cell tumor-associated molecules with an affinity constant of at least $10^7$ $M^{-1}$, such as at least $10^8$ $M^{-1}$ at least $5 \times 10^8$ $M^{-1}$ or at least $10^9$ $M^{-1}$.

In another example, human monoclonal antibodies to the disclosed ovarian endothelial cell tumor-associated molecules in Tables 1, 2, 4 and 5 that are upregulated in ovarian endothelial tumor cells are produced. Human monoclonal antibodies can be produced by transferring donor complementarity determining regions (CDRs) from heavy and light variable chains of the donor mouse immunoglobulin into a human variable domain, and then substituting human residues in the framework regions when required to retain affinity. The use of antibody components derived from humanized monoclonal antibodies obviates potential problems associated with the immunogenicity of the constant regions of the donor antibody. For example, when mouse monoclonal antibodies are used therapeutically, the development of human anti-mouse antibodies (HAMA) leads to clearance of the murine monoclonal antibodies and other possible adverse events. Chimeric monoclonal antibodies, with human constant regions, humanized monoclonal antibodies, retaining only murine CDRs, and "fully human" monoclonal antibodies made from phage libraries or transgenic mice have all been used to reduce or eliminate the murine content of therapeutic monoclonal antibodies.

Techniques for producing humanized monoclonal antibodies are described, for example, by Jones et al., *Nature* 321: 522, 1986; Riechmann et al., *Nature* 332:323, 1988; Verhoeyen et al., *Science* 239:1534, 1988; Carter et al., *Proc. Natl. Acad. Sci. U.S.A.* 89:4285, 1992; Sandhu, *Crit. Rev. Biotech.* 12:437, 1992; and Singer et al., *J. Immunol.* 150:2844, 1993. The antibody may be of any isotype, but in several embodiments the antibody is an IgG, including but not limited to, $IgG_1$, $IgG_2$, $IgG_3$ and $IgG_4$.

In one example, the sequence of the humanized immunoglobulin heavy chain variable region framework can be at least about 65% identical to the sequence of the donor immunoglobulin heavy chain variable region framework. Thus, the sequence of the humanized immunoglobulin heavy chain variable region framework can be at least about 75%, at least about 85%, at least about 99% or at least about 95%, identical to the sequence of the donor immunoglobulin heavy chain variable region framework. Human framework regions, and mutations that can be made in a humanized antibody framework regions, are known in the art (see, for example, in U.S. Pat. No. 5,585,089).

Antibodies, such as murine monoclonal antibodies, chimeric antibodies, and humanized antibodies, include full length molecules as well as fragments thereof, such as Fab, $F(ab')_2$, and Fv, which include a heavy chain and light chain variable region and are capable of binding the epitopic determinant. These antibody fragments retain some ability to selectively bind with their epitope. These fragments include: (1) Fab, the fragment which contains a monovalent antigen-binding fragment of an antibody molecule, can be produced by digestion of whole antibody with the enzyme papain to yield an intact light chain and a portion of one heavy chain; (2) Fab', the fragment of an antibody molecule can be obtained by treating whole antibody with pepsin, followed by reduction, to yield an intact light chain and a portion of the heavy chain; two Fab' fragments are obtained per antibody molecule; (3) $(Fab')_2$, the fragment of the antibody that can be obtained by treating whole antibody with the enzyme pepsin without subsequent reduction; $F(ab')_2$ is a dimer of two Fab' fragments held together by two disulfide bonds; (4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule. Methods of making these fragments are known in the art (see for example, Harlow and Lane, *Antibodies: A Laboratory Manual*, Cold Spring Harbor Laboratory, New York, 1988. Fv antibodies are typically about 25 kDa and contain a complete antigen-binding site with three CDRs per each heavy chain and each light chain. To produce these antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments include $V_H$ and $V_L$ chains connected by a peptide linker. These single-chain antigen binding proteins (scFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242:423, 1988; U.S. Pat. No. 4,946,778; Pack et al., *Bio/Technology* 11:1271, 1993; and Sandhu, supra).

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted $F(ab')_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules Amino acid substitutions (such as at most one, at most two, at most three, at most four, or at most five amino acid substitutions) can be made in the $V_H$ and the $V_L$ regions to increase yield. Conservative amino acid substitution tables providing functionally similar amino acids are well known to one of ordinary skill in the art. The following six groups are examples of amino acids that are considered to be conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

In some examples, naked antibodies can be administered at least 5 mg per kg every two weeks, such as at least 10 mg per kg, at least 25 mg per kg, at least 30 mg per kg, at least 50 mg per kg (for example, 6, 7, 8, 9, 10, 15, 20, 25, 30, 35, 40, 45, 50 mg per kg), at least once a week, at least once every 2 weeks, at least once every 3 weeks, or at least once every month depending upon the ovarian cancer. In an example, the antibodies are administered continuously. In another example, antibodies or antibody fragments conjugated to cytotoxic agents (immunotoxins) are administered at least 10 µg per kg, such as at least 20, at least 30, at least 50, at least 70, at least 100 µg per kg, at least twice a week, at least once a week, at least once every two weeks, at least once every month depending upon the ovarian cancer. In one example, 50 µg per kg is administered twice a week for 2 to 3 weeks. In other examples, the subject is administered the therapeutic composition that a binding agent specific for one or more of the disclosed ovarian endothelial cell tumor-associated molecules daily for a period of at least 30 days, such as at least 2 months, at least 4 months, at least 6 months, at least 12 months, at least 24 months, or at least 36 months. Subjects can be monitored by methods known to those skilled in the art to determine ovarian tumor responsiveness to the antibody treatment. The subject can be monitored by non invasive techniques such as CT or MRI imaging to assess tumor response. It is contemplated that additional agents can be administered, such as antineoplastic agents in combination with or following treatment with the antibodies.

Methods of Evaluating the Effectiveness of an Ovarian Tumor Treatment

Methods are disclosed herein for determining the effectiveness of a binding agent specific for one of the disclosed ovarian endothelial cell tumor-associated molecules) for the treatment of an ovarian tumor in a subject with the ovarian tumor. In an example, the method includes detecting expression of an ovarian endothelial cell tumor-associated molecule in a sample from the subject following administration of the binding agent (such as an siRNA), for example at least 24 hours, at least 1 week, at least 2 weeks, or at least 4 weeks following administration of the agent. The expression of the ovarian endothelial cell tumor-associated molecule following administration can be compared to a control, such as a reference value. An alteration in the expression of the ovarian endothelial cell tumor-associated molecule relative to the control following administration indicates that the agent is effective for the treatment of the ovarian cancer in the subject.

In a specific example, the method includes detecting and comparing the protein expression levels of the ovarian endothelial cell tumor-associated molecules. In other examples, the method includes detecting and comparing the mRNA expression levels of the ovarian endothelial cell tumor-associated molecules. In certain examples, the treatment is considered effective if the expression levels are altered by at least 2-fold, such as by at least 3-fold, at least 4-fold, at least 6-fold or at least 10-fold relative to the control.

In one example, the specific ovarian endothelial cell tumor-associated molecule is detected in a biological sample. In a particular example, the biological sample is a tumor biopsy. In another example, the ovarian endothelial cell tumor-associated molecule is detected in a serum sample. For example, the ovarian endothelial cell tumor-associated molecule is detected in a serum sample if the specific molecule is known to be secreted or located on a cell surface susceptible to enzymatic cleavage.

Altering Ovarian Endothelial Cell Tumor-Associated Molecules' Activity Such as Expression In an example, an alteration in the expression of one or more of the disclosed ovarian endothelial cell tumor-associated molecules following administration includes an increase or decrease in production of a gene product/expression, such as RNA or protein. For example, an alteration can include processes that downregulate or decrease transcription of a gene or translation of mRNA whose expression or activity is increased in ovarian endothelial tumor cells. Gene downregulation includes any detectable decrease in the production of a gene product. In certain examples, production/expression of a gene product decreases by at least 2-fold, for example at least 3-fold, at least 4-fold, at least 6-fold, or at least 10-fold as compared to a control. Exemplary ovarian endothelial cell tumor-associated molecules that are up-regulated in ovarian tumor endothelial cells are presented in Tables 1, 2, 4 and 5. Thus, a decrease in the expression of one or more of the molecules listed in Tables 1, 2, 4 or 5 that is noted as being up-regulated in ovarian tumor endothelial cells following treatment indicates that the agent is of use for treating the ovarian cancer.

Exemplary ovarian endothelial cell tumor-associated molecules that are down-regulated in ovarian tumor endothelial cells are presented in Table 1 with specific examples provided in Table 3. Thus, an increase in the expression of one or more of the molecules listed in Table 3 following administration indicates that the agent is effective for the treatment of ovarian cancer.

In another example, an alteration can include processes that increase transcription of a gene or translation of mRNA. Gene up-regulation includes any detectable increase in the production of a gene product. In certain examples, production/expression of a gene product increases by at least 2-fold, for example at least 3-fold or at least 4-fold, at least 6-fold, at least 10-fold or at least 28-fold following treatment as compared to a control.

Detection of Ovarian Endothelial Cell Tumor-Associated Nucleic Acids

Nucleic acids can be detected by any method known in the art. In some examples, nucleic acids are isolated, amplified, or both, prior to detection. In an example, the biological sample can be incubated with primers that permit the amplification of one or more of the disclosed ovarian endothelial cell tumor-associated mRNAs, under conditions sufficient to permit amplification of such products. For example, the biological sample is incubated with probes that can bind to one or more of the disclosed ovarian endothelial cell tumor-associated nucleic acid sequences (such as cDNA, genomic DNA, or RNA (such as mRNA)) under high stringency conditions. The resulting hybridization can then be detected using methods known in the art. In one example, the effectiveness of an ovarian tumor treatment is identified by applying isolated nucleic acid molecules to an array in which the isolated nucleic acid molecules are obtained from a biological sample including ovarian endothelial cancer cells following treatment with the ovarian tumor treatment. In such example, the array includes oligonucleotides complementary to all ovarian endothelial cell tumor-associated genes listed in Table 1. In a particular example, the array is a commercially available array such as a U133 Plus 2.0 oligonucleotide array from AFFYMETRIX® (AFFYMETRIX®, Santa Clara, Calif.).

In an example, the isolated nucleic acid molecules are incubated with the array including oligonucleotides complementary to the ovarian endothelial cell tumor-associated molecules that are up-regulated in ovarian tumor endothelial cells, such as those listed in Table 2, Table 3, Table 4 and/or Table 5 for a time sufficient to allow hybridization between the isolated nucleic acid molecules and oligonucleotide probes, thereby forming isolated nucleic acid molecule:oligonucleotide complexes. The isolated nucleic acid molecule:oligonucleotide complexes are then analyzed to determine if expression of the isolated nucleic acid molecules is altered. In such example, an ovarian tumor treatment is effective if a decrease in the expression of ovarian endothelial tumor-associated molecules is observed as compared to a control (such as a normal endothelial cell) or reference value. In an additional example, the array includes oligonucleotides complementary to the ovarian endothelial cell tumor-associated molecules that down-regulated in ovarian tumor endothelial cells, such as those listed in Table 3. In this example, an ovarian tumor treatment is effective if an increase in the expression of one or more ovarian endothelial tumor-associated molecules is observed.

Gene Expression Profile

A gene expression profile is disclosed herein that can be used to identify the effectiveness of an ovarian tumor treatment. In an example, the gene expression profile includes at least two of the ovarian endothelial cell tumor-associated molecules listed in Table 1, such as at least 5, at least 7, at least 10, at least 20, at least 30, at least 40, at least 50, at least 60, at least 70, at least 80, at least 90, at least 100, at least 150, at least 200, at least 250, at least 300, at least 400, at least 500, at least 600, at least 700, at least 800, at least 900, at least 1000, or at least 1100 molecules (for example, 2, 6, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 120, 130, 140, 150, 175, 225, 275, 325, 350, 375, 450, 550, 650, 750, 850, 950, 1050 or 1149 of those listed).

In a particular example, the gene expression profile includes at least 2, at least 5, at least 7, at least 10, at least 20, at least 25, at least 27 molecules (for example, 2, 3, 4, 5, 6, 7, 8, 9, 10, 11, 12, 13, 14, 15, 16, 17, 18, 19, 20, 22, 24, 25, 26, 27, 28 or 29 molecules) listed in Table 2, Table 4 and/or Table 5 that are associated with an at least six-fold increase in expression in tumor endothelial cells. In a particular example, the at least two molecules include EGFL6 and TNFAIP6. In other particular examples, the at least two ovarian endothelial cell tumor-associated molecules include EGFL6, TNFAIP6, TWIST1, STC1, HOP, CSPG2, and PLXDC1.

In other particular examples, the gene expression profile includes at least 2, at least 5, at least 7, at least 10, at least 13, or at least 15 molecules (for example, 2, 3, 4, 5, 6, 7, 8, 9, 10, 11, 12, 13, 14, 15, 16 or 17 molecules) that are down-regulated in ovarian tumor endothelial cells as listed in Table 3. For example, the profile includes the seventeen ovarian endothelial cell tumor-associated molecules listed in Table 3.

Detecting Ovarian Endothelial Cell Tumor-Associated Proteins

As an alternative to analyzing the sample for the presence of nucleic acids, the presence of proteins can be determined. Proteins can be detected by any method known in the art. In some examples, proteins are purified prior to detection. For example, the effect of an ovarian tumor treatment can be determined by incubating the biological sample with one or more antibodies that specifically binds to one of the disclosed ovarian endothelial cell tumor-associated proteins encoded by the genes listed in Tables 1, Table 2, Table 3, Table 4 or Table 5 to detect expression. The primary antibody can include a detectable label. For example, the primary antibody can be directly labeled, or the sample can be subsequently incubated with a secondary antibody that is labeled (for example with a fluorescent label). The label can then be detected, for example by microscopy, ELISA, flow cytometry, or spectrophotometry. In another example, the biological sample is analyzed by Western blotting for the presence or absence of the specific ovarian endothelial cell tumor-associated molecule. In other examples, the biological sample is analyzed by mass spectrometry for the presence or absence of the specific ovarian endothelial cell tumor-associated molecule.

In one example, the antibody that specifically binds an ovarian endothelial cell tumor-associated molecule (such as those listed in Table 1) is directly labeled with a detectable label. In another example, each antibody that specifically binds an ovarian endothelial cell tumor-associated molecule (the first antibody) is unlabeled and a second antibody or other molecule that can bind the human antibody that specifically binds the respective ovarian endothelial cell tumor-associated molecule is labeled. As is well known to one of skill in the art, a second antibody is chosen that is able to specifically bind the specific species and class of the first antibody. For example, if the first antibody is a human IgG, then the secondary antibody can be an anti-human-IgG. Other molecules that can bind to antibodies include, without limitation, Protein A and Protein G, both of which are available commercially.

Suitable labels for the antibody or secondary antibody include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin A non-limiting exemplary luminescent material is luminol; a non-limiting exemplary magnetic agent is gadolinium, and non-limiting exemplary radioactive labels include $^{125}$I, $^{131}$I, $^{35}$S or $^{3}$H.

In an alternative example, ovarian endothelial cell tumor-associated molecules can be assayed in a biological sample by a competition immunoassay utilizing ovarian endothelial cell tumor-associated molecule standards labeled with a detectable substance and unlabeled antibody that specifically bind to the desired ovarian endothelial cell tumor-associated molecule. In this assay, the biological sample (such as serum, tissue biopsy, or cells isolated from a tissue biopsy), the labeled ovarian endothelial cell tumor-associated molecule standards and the antibody that specifically binds to ovarian endothelial cell tumor-associated molecule are combined and the amount of labeled ovarian endothelial cell tumor-associated molecule standard bound to the unlabeled antibody is determined. The amount of ovarian endothelial cell tumor-associated molecule in the biological sample is inversely proportional to the amount of labeled ovarian endothelial cell tumor-associated molecule standard bound to the antibody that specifically binds the ovarian endothelial cell tumor-associated molecule.

Identifying Agents to Treat Ovarian Cancer

Methods are provided herein for identifying agents to treat an ovarian cancer. For example, agents that decrease expression or activity of a gene that is upregulated in ovarian endothelial tumor cells (such as those listed in Tables 2 and 4), as well as agents that increase activity of a gene that is down-regulated in ovarian endothelial tumor cells (such as those listed in Table 3), can be identified using these methods. In an example, the method includes contacting an ovarian tumor endothelial cell with one or more test agents under conditions sufficient for the one or more test agents to alter the activity of at least one ovarian endothelial cell tumor-associated molecule listed in any of Tables 1-5. It is contemplated that several doses of the agent can be tested and then expression levels of nucleic acids or proteins can be determined. The method also includes detecting the activity or expression of the at least one ovarian endothelial cell tumor-associated molecule in the presence and absence of the one or more test agents. The activity or expression of the at least one ovarian endothelial cell tumor-associated molecule in the presence of the one or more test agents is then compared to the activity or expression of the at least one ovarian endothelial cell tumor-associated molecule in the absence of such agents to determine if there is differential expression of the at least one ovarian endothelial cell tumor associated molecule. In several examples, differential expression of the ovarian endothelial cell tumor-associated molecule in the presence of the agent (as compared to expression in the absence of the agent) indicates that the one or more test agents is of use to treat the ovarian tumor.

In an example, determining whether there is differential expression of one or more ovarian endothelial cell tumor-associated molecules includes generating a gene expression profile for the subject. For example, a gene expression profile for the subject can be generated by using an array of molecules including an ovarian endothelial cell tumor-associated expression profile.

Ovarian Endothelial Cell Tumor-Associated Molecules

Ovarian endothelial cell tumor-associated molecules can include nucleic acid sequences (such as DNA, cDNA, or mRNAs) and proteins. In a specific example, detecting differential expression of the ovarian endothelial cell tumor-associated molecules includes detecting differential mRNA expression of the disclosed ovarian endothelial cell tumor-associated molecules. For example, such differential expression can be measured by real time quantitative polymerase chain reaction or microarray analysis or other methods known in the art. In another example, detecting differential expression of the ovarian endothelial cell tumor-associated molecules includes detecting differential protein expression of the disclosed ovarian endothelial cell tumor-associated molecules. For example, protein differential expression is measured by Western blot analysis or a protein microarray.

Test Agents

The one or more test agents can be any substance, including, but not limited to, a protein (such as an antibody), a nucleic acid molecule (such as a siRNA), an organic compound, an inorganic compound, a small molecule or any other molecule of interest. In a particular example, the test agent is a siRNA that reduces or inhibits the activity (such as the expression) of one of the ovarian endothelial cell tumor-associated molecules listed in Tables 2, 4 or 5. For example, the siRNA is directed to an ovarian endothelial cell tumor-associated molecule listed in Table 2, 4 or 5 which is involved in angiogenesis, such as a molecule that is involved in at least one of cell proliferation, tube formation or cell motility.

In other examples, the test agent is an antibody. For example, the antibody is directed to specifically bind to an ovarian endothelial cell tumor-associated protein encoded by one of the genes listed in any of Tables 1, 2, 4 or 5 that are upregulated in ovarian endothelial tumor cells. In a particular example, the antibody is directed to an ovarian endothelial cell tumor-associated protein encoded by one of the genes listed in Tables 2, 4 or 5 that is upregulated in ovarian endothelial tumor cells and which is involved in angiogenesis, such as a gene that is involved in at least one of cell proliferation, tube formation or cell motility. In another example, the test agent is a nucleic acid encoding one or more of the proteins listed in Table 3. For example, the nucleic acid can be part of a vector suitable for gene therapy.

Altering Ovarian Endothelial Cell Tumor-Associated Molecules' Activity

In an example, an alteration in the activity of one or more of the disclosed ovarian endothelial cell tumor-associated molecules includes an increase or decrease in production of a gene product, such as RNA or protein. For example, an alteration can include processes that downregulate or decrease transcription of a gene or translation of mRNA. Gene downregulation includes any detectable decrease in the production of a gene product. In certain examples, production/expression of a gene product decreases by at least 2-fold, for example at least 3-fold, at least 4-fold, at least 6-fold, or at least 10-fold as compared to a control (such as a reference value or a normal endothelial cell). For example, a decrease in one or more of the disclosed ovarian endothelial cell tumor-associated molecules up-regulated in ovarian tumor endothelial cells (such as those listed in Tables 2, 4 and 5), is indicative of an agent that is effective at treating ovarian cancer.

In another example, an alteration can include processes that increase transcription of a gene or translation of mRNA. Gene up-regulation includes any detectable increase in the production of a gene product. In certain examples, production/expression of a gene product increases by at least 2-fold, for example at least 3-fold or at least 4-fold, at least 6-fold, at least 10-fold or at least 28-fold as compared to a control. For example, an increase in one or more of the disclosed ovarian endothelial cell tumor-associated molecules down-regulated in ovarian tumor endothelial cells (such as those listed in Table 3) is indicative of an agent that is effective at treating ovarian cancer.

Detection of Ovarian Endothelial Cell Tumor-Associated Nucleic Acids

Nucleic acids can be detected by any method known in the art, such as those described above. In one example, a therapeutic agent is identified by applying isolated nucleic acid molecules to an array in which the isolated nucleic acid molecules are obtained from a biological sample including ovarian endothelial cancer cells following treatment with the one or more test agents. In such example, the array includes oligonucleotides complementary to all ovarian endothelial cell tumor-associated genes listed in Table 1. In a particular example, the array is a commercially available array such as a U133 Plus 2.0 oligonucleotide array from AFFYMETRIX® (AFFYMETRIX®, Santa Clara, Calif.).

In an example, the isolated nucleic acid molecules are incubated with the array including oligonucleotides complementary to the ovarian endothelial cell tumor-associated molecules listed in Table 2, 4 and/or 5 for a time sufficient to allow hybridization between the isolated nucleic acid molecules and oligonucleotide probes, thereby forming isolated nucleic acid molecule:oligonucleotide complexes. The isolated nucleic acid molecule:oligonucleotide complexes are then analyzed to determine if expression of the isolated nucleic acid molecules is altered. In such example, an agent is considered is effective if the test agent decreases expression of ovarian endothelial tumor-associated molecules upregulated in ovarian endothelial cell tumors relative to the absence of the agent (such as a decrease of at least 2-, 3-, 4-, 5- or 10-fold). Similarly, an agent is considered is effective if the test agent increases expression of ovarian endothelial tumor-associated molecules downregulated in ovarian endothelial cell tumors relative to the absence of the agent (such as an increase of at least 2-, 3-, 4-, 5- or 10-fold).

Gene Expression Profile

The disclosed gene profile (as described above) can also be used to identify agents to treat an ovarian tumor, such as a cancer, in a subject. In an example, the gene expression profile includes at least two of the ovarian endothelial cell tumor-associated molecules listed in Table 1, such as at least 5, at least 7, at least 10, at least 20, at least 30, at least 40, at least 50, at least 60, at least 70, at least 80, at least 90, at least 100, at least 150, at least 200, at least 250, at least 300, at least 400, at least 500, at least 600, at least 700, at least 800, at least 900, at least 1000, or at least 1100 molecules (for example, 2, 6, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 120, 130, 140, 150, 175, 225, 275, 325, 350, 375, 450, 550, 650, 750, 850, 950, 1050 or 1149 of those listed).

In a particular example, the gene expression profile includes at least 2, at least 5, at least 7, at least 10, at least 20, at least 25, or at least 27 molecules (for example, 2, 3, 4, 5, 6, 7, 8, 9, 10, 11, 12, 13, 14, 15, 16, 17, 18, 19, 20, 22, 24, 25, 26, 27, 28 or 29 molecules) listed in Table 2, 4 and/or 5 that are associated with an at least six-fold increase in expression in tumor endothelial cells. In a particular example, the at least two molecules include EGFL6 and TNFAIP6. In other particular examples, the at least two ovarian endothelial cell tumor-associated molecules include EGFL6, TNFAIP6, TWIST1, STC1, HOP, CSPG2, and PLXDC1.

In other particular examples, the gene expression profile includes at least 2, at least 5, at least 7, at least 10, at least 13, or at least 15 molecules (for example, 2, 3, 4, 5, 6, 7, 8, 9, 10, 11, 12, 13, 14, 15, 16 or 17 molecules) that are down-regulated in ovarian tumor endothelial cells as listed in Table 3. For example, the profile includes the seventeen ovarian endothelial cell tumor-associated molecules listed in Table 3.

Detecting Ovarian Endothelial Cell Tumor-Associated Proteins

As an alternative to analyzing the sample for the presence of nucleic acids, the presence of proteins can be determined using any method known in the art. In some examples, proteins are purified before detection. For example, the effect of one or more test agents on an ovarian tumor can be determined by incubating the biological sample with an antibody that specifically binds to one of the disclosed ovarian endothelial cell tumor-associated proteins encoded by the genes listed in Tables 1-5. The primary antibody can include a detectable label. For example, the primary antibody can be directly labeled, or the sample can be subsequently incubated with a secondary antibody that is labeled (for example with a fluorescent label). The label can then be detected, for example by microscopy, ELISA, flow cytometry, or spectrophotometry. In another example, the biological sample is analyzed by Western blotting for the presence or absence of the specific ovarian endothelial cell tumor-associated molecule. In some examples, the biological sample is analyzed by mass spectrometry.

In one example, the antibody that specifically binds an ovarian endothelial cell tumor-associated molecule (such as those listed in Table 1) is directly labeled with a detectable label. In another example, each antibody that specifically binds an ovarian endothelial cell tumor-associated molecule (the first antibody) is unlabeled and a second antibody or other molecule that can bind the human antibody that specifically binds the respective ovarian endothelial cell tumor-associated molecule is labeled. As is well known to one of skill in the art, a second antibody is chosen that is able to specifically bind the specific species and class of the first antibody. For example, if the first antibody is a human IgG, then the secondary antibody can be an anti-human-IgG. Other molecules that can bind to antibodies include, without limitation, Protein A and Protein G, both of which are available commercially.

Suitable labels for the antibody or secondary antibody include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin A non-limiting exemplary luminescent material is luminol; a non-limiting exemplary magnetic agent is gadolinium, and non-limiting exemplary radioactive labels include $^{125}$I, $^{131}$I, $^{35}$S or $^{3}$H.

In an alternative example, ovarian endothelial cell tumor-associated molecules can be assayed in a biological sample by a competition immunoassay utilizing ovarian endothelial cell tumor-associated molecule standards labeled with a detectable substance and an unlabeled antibody that specifically binds the desired ovarian endothelial cell tumor-associated molecule. In this assay, the biological sample (such as serum, tissue biopsy, or cells isolated from a tissue biopsy), the labeled ovarian endothelial cell tumor-associated molecule standards and the antibody that specifically binds the desired ovarian endothelial cell tumor-associated molecule are combined and the amount of labeled ovarian endothelial cell tumor-associated molecule standard bound to the unlabeled antibody is determined. The amount of ovarian endothelial cell tumor-associated molecule in the biological sample is inversely proportional to the amount of labeled ovarian endothelial cell tumor-associated molecule standard bound to the antibody that specifically binds the ovarian endothelial cell tumor-associated molecule.

Methods of Diagnosing and Prognosing an Ovarian Tumor

Metastasis is a major complication in the pathogenesis of tumors, such as ovarian cancer, and is typically indicative of poor prognosis. It is also known that angiogenesis is a crucial factor in the progression of solid tumors and metastases, including ovarian cancer. The formation of the vascular stroma plays an important role in the pathophysiology of malignancy. For instance, in the absence of vascular support tumors may become necrotic, or even apoptotic. In contrast, the onset of angiogenesis marks a phase of rapid proliferation, local invasion, and ultimately metastasis.

Figure 5A:
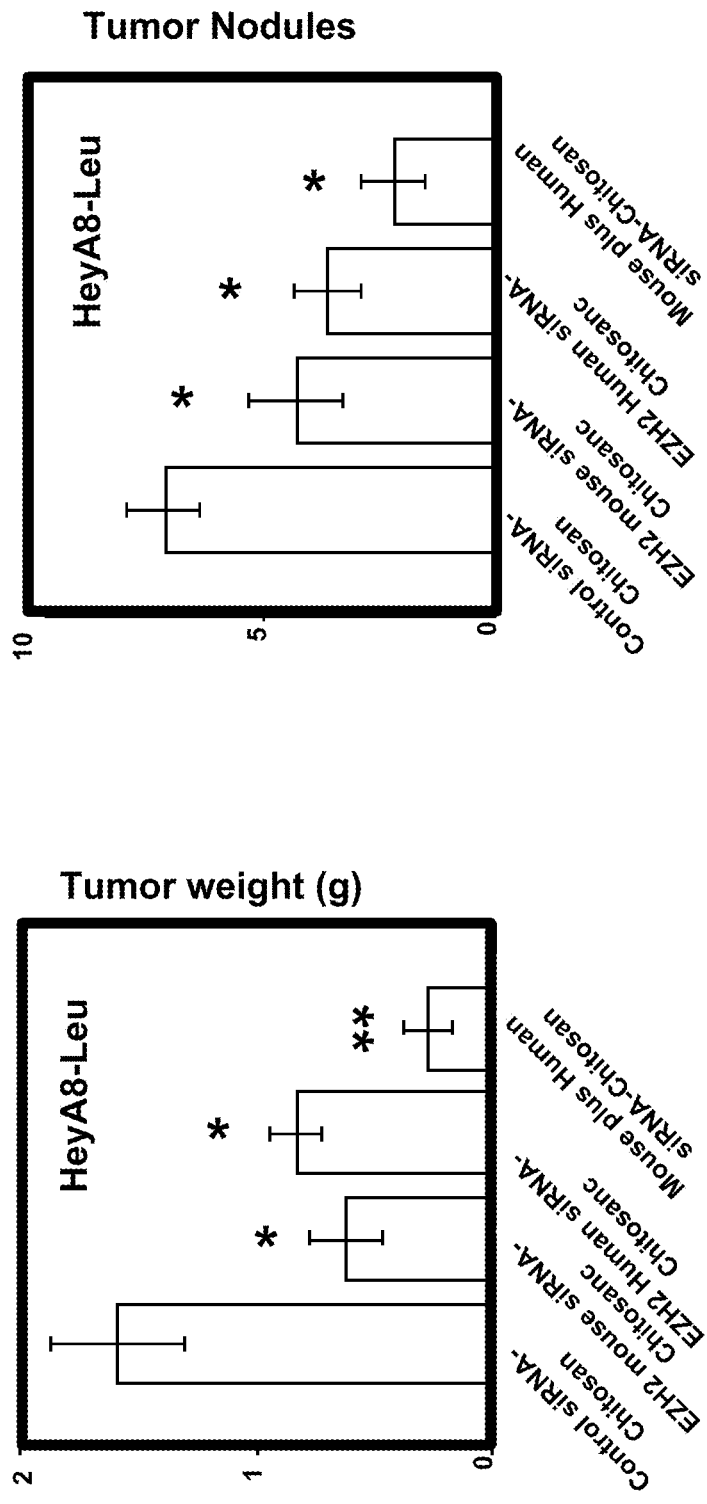
FIGS. 5A, 5B and 6 provide graphs illustrating the therapeutic effects of siRNA-mediated EZH2 down regulation on HeyA8 (FIG. 5A) and SKOV3ip1 (FIGS. 5B and 6) ovarian tumors.
Figure 5B:
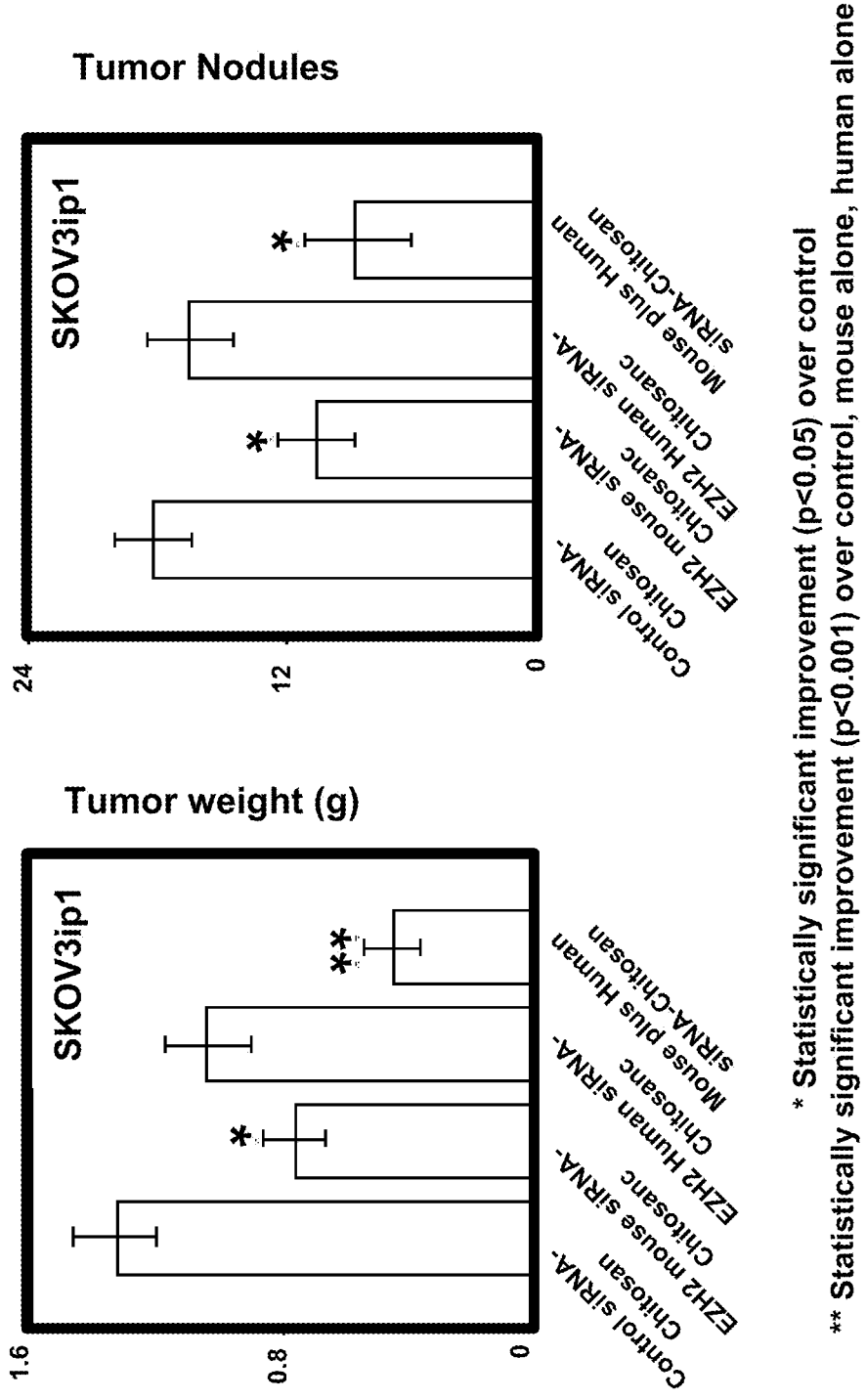

Without wishing to be bound to a particular theory, it is proposed that an alteration in the expression of the disclosed ovarian endothelial tumor-associated molecules associated with angiogenesis, such as molecules involved in cell proliferation, cell motility or tube formation, including those disclosed in FIG. 5 (such as EZH2), is related to enhanced ovarian tumor cell metastasis and a poor clinical outcome. Thus, methods of diagnosing or prognosing an ovarian tumor that overexpresses at least one pro-angiogenic ovarian endothelial cell tumor-associated molecule (such as those listed in Tables 1, 2, 4 and 5 that are upregulated in ovarian endothelial tumor cells; e.g., EZH2) or underexpresses at least one proangiogenic ovarian endothelial cell tumor associated molecule (such as those listed in Tables 1 and 3 that are downregulated in ovarian endothelial tumor cells), are disclosed. In some examples, such methods can be used to identify those subjects that will benefit from the disclosed treatment methods. For example, such diagnostic methods can be performed prior to the subject undergoing the treatments described above. In other examples, these methods are utilized to predict the metastatic potential of the ovarian cancer, a poor prognosis, or combinations thereof. In one particular example, these methods are utilized to predict a poor prognosis, such as to indicate a decreased survival time.

In an example, the method includes detecting expression of at least one angiogenic ovarian endothelial cell tumor-associated molecule listed in Tables 1-5, such as at least two, at least 5, at least 7, at least 10, at least 20, at least 30, at least 40, at least 50, at least 60, at least 70, at least 80, at least 90, at least 100, at least 150, at least 200 ovarian endothelial cell tumor-associated molecules related to angiogenesis (for example, 1, 2, 3, 4, 5, 6, 7, 8, 9, 10, 12, 15, 17, 20, 25, 30, 35, 40, 45, 50, 55, 60, 65, 70, 75, 80, 85, 90, 100, 125, 150, 175, 200, or 250 listed in Tables 1-5) in a sample from the subject exhibiting one or more symptoms associated with ovarian cancer.

In an example, the specific angiogenic ovarian endothelial cell tumor-associated molecule, such as EZH2, is detected in a biological sample. In a particular example, the biological sample is a sample taken from a subject with ovarian epithelial cancer. In a particular example, the biological sample is a tumor biopsy. In another example, the angiogenic ovarian endothelial cell tumor-associated molecule is detected in a serum sample. For example, the ovarian endothelial cell tumor-associated molecule is detected in a serum sample if the specific molecule is secreted or located on a cell surface susceptible to enzymatic cleavage.

In one example, detection of at least one angiogenic ovarian endothelial cell tumor-associated molecule listed in any of Tables 1, 2, 3, 4 or 5, such as detection of EZH2, in a biological sample from the subject is used to diagnose or prognose an ovarian tumor. Methods of detecting such molecules in a sample are known in the art and are routine. In some examples, the relative amount of pro-angiogenic ovarian endothelial cell tumor-associated molecules present is determined, for example by quantitating the expression level of such molecules. For example, the relative or absolute quantity of the at least one angiogenic ovarian endothelial cell tumor-associated molecule in a sample can be determined.

The activity such as the expression level of the disclosed pro-angiogenic ovarian endothelial cell tumor-associated molecules in a sample obtained from a subject is compared to a control. In one example, an increase in expression of one or more of the angiogenic ovarian endothelial cell tumor-associated molecules upregulated in ovarian tumor endothelial cells (such as those listed in Table 2) as compared to a non-tumor control or reference value indicates the presence of an ovarian tumor, the ovarian tumor is metastatic, the ovarian tumor is likely to become metastatic, a poor prognosis or a combination thereof. In some examples, a decrease in expression of one or more of the angiogenic ovarian endothelial cell tumor-associated molecules that is downregulated in ovarian tumor endothelial cells (such as those listed in Table 3 or VASH1) as compared to a non-tumor control or reference value indicates the presence of an ovarian tumor, the ovarian tumor is metastatic, the ovarian tumor is likely to become metastatic, a poor prognosis or a combination thereof.

For example, the level of the angiogenic ovarian endothelial cell tumor-associated molecules, such as the level of EZH2, detected can be compared to a non-tumor control or reference value, such as a value that represents a level of angiogenic ovarian endothelial cell tumor-associated molecules expected if an ovarian tumor is or is not metastatic or is a low grade tumor or early stage tumor. In one example, the angiogenic ovarian endothelial cell tumor-associated molecules detected in a tumor sample are compared to the level of such molecules detected in a sample obtained from a subject that does not have an ovarian tumor or has a non-metastatic ovarian tumor. In certain examples, detection of at least a 2-fold, such as by at least 3-fold, at least 4-fold, at least 6-fold or at least 10-fold alteration in the relative amount of the pro-angiogenic ovarian endothelial cell tumor-associated molecules in a tumor sample, as compared to the relative amount of such molecules in a control indicates that the subject has a tumor with metastatic potential, has a tumor that has metastasized, has a poor prognosis, or combinations thereof. In some examples, detection of statistically similar relative amounts of pro-angiogenic ovarian endothelial cell tumor-associated molecules observed in a tumor sample, as compared to the relative amount of such molecules in a control sample that is not metastatic, indicates that that subject does not have a tumor with metastatic potential, does not have a tumor that has metastasized, has a good prognosis, or combinations thereof.

In a specific example, the method includes detecting and comparing the nucleic acid expression levels of the pro-angiogenic ovarian endothelial cell tumor-associated molecules such as DNA, cDNA, or mRNAs. In a specific example, the method includes detecting and comparing the mRNA expression levels of the pro-angiogenic ovarian endothelial cell tumor-associated molecules. For example, such expression can be measured by real time quantitative polymerase chain reaction or microarray analysis. In a particular example, the disclosed gene expression profile is utilized to diagnosis and/or prognosis an ovarian tumor.

Detection of Ovarian Endothelial Cell Tumor-Associated Nucleic Acids

Nucleic acids can be detected by any method known in the art. In some examples, nucleic acids are isolated, amplified, or both, prior to detection. In an example, the biological sample can be incubated with primers that permit the amplification of one or more of the disclosed ovarian endothelial cell tumor-associated mRNAs, under conditions sufficient to permit amplification of such products. For example, the biological sample is incubated with probes that can bind to one or more of the disclosed ovarian endothelial cell tumor-associated nucleic acid sequences (such as cDNA, genomic DNA, or RNA (such as mRNA)) under high stringency conditions. The resulting hybridization can then be detected using methods known in the art. In one example, a therapeutic agent is identified by applying isolated nucleic acid molecules to an array in which the isolated nucleic acid molecules are obtained from a biological sample including ovarian endothelial cancer cells for example following treatment with the one or more test agents. In such example, the array includes oligonucleotides complementary to all ovarian endothelial cell tumor-associated genes listed in Table 1. In a particular example, the array is a commercially available array such as a U133 Plus 2.0 oligonucleotide array from AFFYMETRIX® (AFFYMETRIX®, Santa Clara, Calif.).

In an example, the isolated nucleic acid molecules are incubated with the array including oligonucleotides complementary to the ovarian endothelial cell tumor-associated molecules listed in Tables 2, 3, 4 and/or 5 for a time sufficient to allow hybridization between the isolated nucleic acid molecules and oligonucleotide probes, thereby forming isolated nucleic acid molecule:oligonucleotide complexes. In a particular example, the isolated nucleic acid molecules are incubated with the array including oligonucleotides complementary to at least EZH2. The isolated nucleic acid molecule:

oligonucleotide complexes are then analyzed to determine if expression of the isolated nucleic acid molecules is altered.

Gene Expression Profile

The disclosed gene profile (as described above) can also be used in the diagnosis and prognosis of an ovarian tumor in a subject. In an example, the gene expression profile includes at least two of the ovarian endothelial cell tumor-associated molecules listed in Table 1, such as at least 5, at least 7, at least 10, at least 20, at least 30, at least 40, at least 50, at least 60, at least 70, at least 80, at least 90, at least 100, at least 150, at least 200, at least 250, at least 300, at least 400, at least 500, at least 600, at least 700, at least 800, at least 900, at least 1000, or at least 1100 molecules (for example, 2, 6, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 120, 130, 140, 150, 175, 225, 275, 325, 350, 375, 450, 550, 650, 750, 850, 950, 1050 or 1149 of those listed).

In a particular example, the gene expression profile includes at least 1, at least 3, at least 5, at least 7, at least 10, at least 20, at least 25, or at least 27 molecules (for example, 2, 3, 4, 5, 6, 7, 8, 9, 10, 11, 12, 13, 14, 15, 16, 17, 18, 19, 20, 22, 24, 25, 26, 27, 28 or 29 molecules) listed in Table 2, 4 and/or 5 that are associated with angiogenesis, such as molecules involved in cell proliferation, cell motility and/or tube formation. In a particular example, the at least one molecule includes EZH2

In other particular examples, the gene expression profile includes at least 2, at least 5, at least 7, at least 10, at least 13, or at least 15 molecules (for example, 2, 3, 4, 5, 6, 7, 8, 9, 10, 11, 12, 13, 14, 15, 16 or 17 molecules) that are down-regulated in ovarian tumor endothelial cells as listed in Table 3. For example, the profile includes the seventeen ovarian endothelial cell tumor-associated molecules listed in Table 3.

Detecting Ovarian Endothelial Cell Tumor-Associated Proteins

As an alternative to analyzing the sample for the presence of nucleic acids, alterations in protein expression can be measured by methods known in the art such as Western blot analysis, mass spectrometry, immunoassay or a protein microarray (as described above). For example, the metastatic potential of an ovarian tumor can be determined by using a protein array that includes one or more capture agents, such as antibodies that are specific for the one or more disclosed ovarian endothelial tumor-associated molecules that are related to angiogenesis, such as molecules that play a role in cell proliferation, cell motility or tube formation, such as EZH2.

The disclosure is further illustrated by the following non-limiting Examples.

Example 1

Materials and Methods for Examples 2-7

Sample Preparation.

Fresh tissue samples (5 normal ovaries and 10 epithelial high-grade, stage III or IV invasive serous ovarian cancers) were obtained from patients undergoing primary surgical exploration at the M.D. Anderson Cancer Center. The minced tissue was digested with collagenase A, elastase and DNase 1 at 37° C. for 90 minutes to yield a single cell suspension. A number of negative selections followed including removal of platelets and red blood cells (RBCs) by Percoll separation, removal of epithelial cells using M450 beads, which are prebound to BerEP4 antibody, removal of leukocytes using anti-CD-14, CD-45, and CD-64 beads (Dynal Biotech, Brown Deer, Wis.). Positive selection was performed with P1H12 (CD 146) immunobeads (P1H12 antibody was from Chemicon, Temecula, Calif.), and the beads linked to secondary antibody were from Dynal Biotech. Immunostaining was then performed using von Willebrand factor and 4',6-diamidino-2-phenylindole nuclear staining to confirm the purification of endothelial cells.

Total RNA Amplification for AFFYMETRIX® GENE-CHIP® Hybridization and Image Acquisition.

To successfully generate sufficient labeled cRNA for microarray analysis from 25 ng of total RNA, two rounds of amplification were necessary. For the first round synthesis of double-stranded cDNA, 25 ng of total RNA was reverse transcribed using the Two-Cycle cDNA Synthesis Kit (AFFYMETRIX®, Santa Clara, Calif.) and oligo-dT24-T7

(SEQ ID NO: 1: 5'-GGCCAGTGAATTGTAATACGACTCACTATAGG GAGGCGG-3')

primer according to the manufacturer's instructions followed by amplification with the MEGA script T7 Kit (Ambion, Inc., Austin, Tex.). After cleanup of the cRNA with a GENE-CHIP® Sample Cleanup Module IVT column (AFFYMETRIX®), second round double stranded cDNA was amplified using the IVT Labeling Kit (AFFYMETRIX®). A 15.0 μg aliquot of labeled product was fragmented by heat and ion-mediated hydrolysis at 94° C. for 35 minutes in 24 μl $H_2O$ and 6 μl of 5× Fragmentation Buffer (AFFYMETRIX®). The fragmented cRNA was hybridized for 16 hr at 45° C. in a Hybridization Oven 640 to a U133 plus 2.0 oligonucleotide array (AFFYMETRIX®). Washing and staining of the arrays with phycoerythrin-conjugated streptavidin (Molecular Probes, Eugene, Oreg.) was completed in a Fluidics Station 450 (AFFYMETRIX®). The arrays were then scanned using a confocal laser GENECHIP® Scanner 3000 and GENE-CHIP® Operating Software (AFFYMETRIX®).

Data Normalization and Filtering.

Global normalization at a target value of 500 was applied to all 15 of the arrays under consideration using GENECHIP® Operating Software (AFFYMETRIX®). Normalized data were uploaded into the National Cancer Institute's Microarray Analysis Database (mAdb) for quality control screening and collation prior to downstream analyses. Biometric Research Branch (BRB) ArrayTools version 3.2.2 software developed by Drs. Richard Simon and Amy Peng Lam of the Biometrics Research Branch of the National Cancer Institute was used to filter and complete the statistical analysis of the array data. BRB-ArrayTools is a multifunctional Excel add-in that contains utilities for processing and analyzing microarray data using the R version 2.0.1 environment (R Development Core Team, 2004). Of the 47,000 transcripts represented on the array, hybridization control probe sets and probe sets scored as absent at $\alpha 1=0.05$ or marginal (M) at $\alpha\ 2=0.065$ were excluded. In addition, only those transcripts present in greater than 50% of the arrays and displaying a variance in the top 50th percentile were evaluated.

Class Comparison Analysis.

Differentially expressed genes were identified for tumor and normal endothelial cell specimens using a multivariate permutation test in BRB-ArrayTools (Simon et al., "Design and Analysis of DNA Microarray Investigations" Springer-Verlag, 2003). A total of 2000 permutations were completed to identify the list of probe sets with a false discovery rate less than 10% at a confidence of 95%. Differential expression was considered significant at a $p<0.001$. A random-variance t-test was selected to permit the sharing of information among probe sets within class variation without assuming that all of the probe sets possess the same variance (Wright et al., *Bioinformatics* 19: 2448-2455, 2003). A global assessment of whether expression profiles were different between classes was also performed. During each permutation the class labels were reassigned randomly and the p-value for each probe set recalculated. The proportion of permutations yielding at least as many significant genes as the actual data set at a p-value<0.001 was reported as the significance level of the global test.

Pathway Analysis.

Differentially regulated genes identified in a series of 48 late-stage (III and IV) high-grade (Hurwitz et al., *N. Engl. J. Med.* 350: 2335-2342, 2004) microdissected papillary serous ovarian carcinomas, as compared to 10 normal ovarian surface epithelial brushings (Bonome et al., *Cancer Res.* 65: 10602-10612, 2005), were categorized by cellular component according to the Gene Ontology (GO) ontological hierarchy. Epithelial genes associated with the cell membrane, extracellular matrix, and extracellular region were used as central nodes to identify signaling pathways modulated in tumor-associated endothelial cell isolates. This was accomplished using PathwayAssist version 3.0 software (Iobion Informatics LLC, La Jolla, Calif.). This software package contains over 500,000 documented protein interactions acquired from MedLine using the natural language processing algorithm MEDSCAN. The proprietary database can be used to develop a biological association network (BAN) to identify putative co-regulated signaling pathways using expression data.

qRT-PCR Validation.

Quantitative real-time PCR (qRT-PCR) was performed on 100 ng of double-amplified product from the 15 specimens using primer sets specific for 23 select genes, and the housekeeping genes GAPDH, GUSB, and cyclophilin. An iCycler iQ Real-Time PCR Detection System (BIORAD® Laboratories, Hercules, Calif.) was used in conjunction with the QuantiTect SYBR Green RT-PCR Kit (QIAGEN® Inc., Valencia, Calif.) according to previously described cycling conditions (Donninger et al., *Oncogene* 23: 8065-8077, 2004). To calculate the relative expression for each gene, the $2^{-\Delta\Delta C_T}$ method was used averaging the $C_T$ values for the three housekeeping genes for a single reference gene value (Livak and Schmittgen, *Methods* 25: 402-408, 2001).

Immunohistochemical Staining.

Paraffin sections were stained for the following antibodies: rabbit anti-Fyn at 1:400 (Santa Cruz Biotechnology, Inc., Santa Cruz, Calif.), or rabbit anti-Fak at 1:50, mouse anti-MMP-9 at 1:40 (Oncogene-Research Products, Boston, Mass.), anti-β2-Arrestin at 1:200 (Santa Cruz Biotechnology, Inc.), anti-PLXDC1 at 1:200 (Abcam, Inc., Cambridge, Mass.), or anti-Jagged1 at 1:200 (Santa Cruz Biotechnology, Inc.) diluted in PBS at 4° C. After three washes in PBS, sections were incubated with secondary antibody for 1 hr at room temperature. Positive reactions were rendered visible by incubating the slides with stable 3,3-diaminobenzidine for 5-10 min. The sections were rinsed with distilled water, counterstained with Gill's hematoxylin for 30 s, and mounted with Universal Mount (Research Genetics, Huntsville, Ala.). The intensity of protein expression in the endothelial cells was evaluated using OPTIMAS 6.5 software and the mean optical density (OD) was calculated from 5 normal ovarian and 5 ovarian cancer samples. Ten vessels were selected randomly from each sample for the measurements.

Small interfering RNA (siRNA).

The small interfering RNA (siRNA) constructs were purchased from QIAGEN® (Germantown, Md.): a control sequence with no homology to any human mRNA (as determined by BLAST search), and separate sequences designed to target EZH2, Jagged1, or PTK2 mRNA. The Jagged1 siRNA target sequence is SEQ ID NO: 2 (5'-CTGCATT-TAGGGAGTATTCTA-3'). The EZH2 siRNA was targeted to the region corresponding to residues 85-106 of human EZH2 (Gene accession No. NM004456; 5'-AACCATGTTTA-CAACTATCAA-3; SEQ ID NO: 3). The EZH2 siRNA sense sequence was 5'-CCAUGUUUACAACUAUCAAtt-3; SEQ ID NO: 4) and the antisense sequence was 3'-ttGGUA-CAAAUGUUGAUAGUU-5; SEQ ID NO: 5). For in vitro delivery, siRNA (5 μg) was incubated with 30 μL RNAiFect transfection reagent (QIAGEN®) for 10 min at room temperature and added to cells in culture at 80% confluence in 35 mm culture plates.

Cell Migration Assay.

Unstimulated motility was determined in membrane invasion culture system chambers containing polycarbonate filter (with 10 μm pores) that had been soaked in 0.1% gelatin, as described previously (Sood et al., *Am. J. Pathol.* 165: 1087-1095, 2004). HUVECs (1×105) were seeded in each upper well, allowed to incubate at 37° C. for 6 hr in Dulbecco's modified Eagle's medium (DMEM) containing 15% serum, and subsequently processed as described for the invasion assay.

Tube Formation Assay.

Matrigel (12.5 mg/ml) was thawed at 4° C. and 50 μl were quickly added to each well of a 96-well plate and allowed to solidify for 10 min at 37° C. The wells were then incubated for 6 h at 37° C. with HUVECs (20,000 cells/well), which had previously been treated for 18 h with the indicated siRNA. The formation of capillary-like structures was examined microscopically and photographs (50×) were taken using a RETIGA® 1300 camera and a ZEISS® Axiovert S100 microscope. The extent to which capillary-like structures formed in the gel was quantified by analysis of digitized images to determine the thread length of the capillary-like network, using a commercially available image analysis program (Northern Eclipse, North Tonawanda, N.Y.).

Example 2

Purity of Isolated Endothelial Cells

This example illustrates the purity of the endothelial cell samples utilized in the disclosed microarray analyses.

According to the methods described in Example 1, samples were immunostained with endothelial cell markers P1H12 and von Willebrand factor to determine endothelial cell purity. Immunostaining revealed that the employed purification technique yielded endothelial cell purity of >95% in all samples. Thus, the disclosed isolation technique resulted in a highly pure population of endothelial cells.

Example 3

Development of Gene Expression Profile for Ovarian Tumor-Endothelial Cells

This example provides a gene expression profile for ovarian tumor endothelial cells.

According to the methods described in Example 1, gene expression differences in purified endothelial cells from 10 invasive epithelial ovarian cancers and 5 normal (non-tumor) ovaries were determined by using the AFFYMETRIX® Human U133 Plus 2.0 Gene Chip platform. The nucleic acid sequence of each AFFYMETRIX® probe listed in the tables below is herein incorporated by reference, and is available from the AFFYMETRIX®website. As illustrated in Table 1, 1149 genes were identified as being differentially regulated ≧2-fold in endothelium derived from epithelial ovarian cancers compared to normal ovarian tissue. A positive fold change indicates the gene was upregulated in ovarian endothelial tumor sample and a negative fold change indicates the gene was downregulated in such sample. A multivariate permutation t-test (p<0.001) providing 95% confidence that the number of false discoveries did not exceed 10% of the complete gene list identified. In addition, global analysis of the gene list returned a p value<$5 \times 10^4$.

TABLE 1

Gene expression profile.

| Affymetrix Probe Set | Parametric P-Value | Fold Change (Tumor/Normal) | Gene Symbol | Description | Map |
|---|---|---|---|---|---|
| 117_at | 0.0005215 | 4.4 | HSPA6 | heat shock 70 kDa protein 6 (HSP70B') (HSPA6), mRNA. | 1q23 |
| 1552365_at | 0.0008711 | 6.6 | SCIN | scinderin (SCIN), mRNA. | 7p21.3 |
| 1552767_a_at | 0.0002277 | -6.5 | HS6ST2 | heparan sulfate 6-O-sulfotransferase 2 (HS6ST2), mRNA. | Xq26.2 |
| 1552790_a_at | 0.0009635 | -2.2 | TLOC1 | translocation protein 1 (TLOC1), mRNA. | 3q26.2 |
| 1552889_a_at | 0.0003238 | 2.5 | XTP7 | protein 7 transactivated by hepatitis B virus X antigen (HBxAg) (XTP7), mRNA. | 19q13.32 |
| 1553185_at | 0.000128 | 4.6 | RASEF | RAS and EF-hand domain containing | 9q21.32 |
| 1553186_x_at | 3.33E-05 | 5.3 | RASEF | RAS and EF-hand domain containing | 9q21.32 |
| 1553407_at | 0.0003912 | 2.5 | MACF1 | Glycine-rich protein (GRP3S) | 1p32-p31 |
| 1553538_s_at | 0.000594 | 2.2 | | Unknown | |
| 1553569_at | 0.0001391 | 2.6 | | Unknown | |
| 1553570_x_at | 0.0002337 | 2.5 | | Unknown | |
| 1553575_at | 2.80E-06 | 4.6 | | Unknown | |
| 1553909_x_at | 0.0005681 | 3.8 | C10orf6 | Chromosome 10 open reading frame 6 | 10q24.32 |
| 1553959_a_at | 0.0009778 | 2.3 | B3GALT6 | UDP-Gal:betaGal beta 1,3-galactosyltransferase polypeptide 6 (B3GALT6), mRNA. | 1p36.33 |
| 1553983_at | 0.000152 | 2.5 | DTYMK | deoxythymidylate kinase (thymidylate kinase) (DTYMK), mRNA. | 2q37.3 |
| 1554168_a_at | 0.0003894 | 2.1 | SH3KBP1 | SH3-domain kinase binding protein 1 (SH3KBP1), transcript variant 2, mRNA. | Xp22.1-p21.3 |
| 1554309_at | 0.0006114 | 2.3 | EIF4G3 | Eukaryotic translation initiation factor 4 gamma, 3 | 1p36.12 |
| 1554334_a_at | 7.15E-05 | 5.2 | DNAJA4 | DnaJ (Hsp40) homolog, subfamily A, member 4 (DNAJA4), mRNA. | 15q25.1 |
| 1554455_at | 0.0007696 | 2.4 | LINS1 | lines homolog 1 (*Drosophila*) (LINS1), transcript variant 2, mRNA. | 15q26.3 |
| 1554464_a_at | 0.000263 | -2.8 | CRTAP | cartilage associated protein (CRTAP), mRNA. | 3p22.3 |
| 1554595_at | 0.0005225 | 2.6 | SYMPK | Symplekin | 19q13.3 |
| 1554640_at | 0.0004537 | 2.6 | PALM2-AKAP2 | Paralemmin 2 | 9q31-q33 |
| 1554678_s_at | 0.0002435 | -2 | HNRPDL | Heterogeneous nuclear ribonucleoprotein D-like | 4q13-q21 |
| 1554703_at | 0.0008778 | 2.1 | ARHGEF10 | Rho guanine nucleotide exchange factor (GEF) 10 | 8p23 |
| 1555014_x_at | 0.0004322 | 3.5 | | OK/SW-cl.92 | |
| 1555241_at | 0.0001337 | 3.2 | | Hypothetical gene supported by BC055092 | 8q21.2 |
| 1555243_x_at | 0.0001753 | 2.8 | | Hypothetical gene supported by BC055092 | 8q21.2 |
| 1555374_at | 0.0003108 | 4 | TTL | Tubulin tyrosine ligase | 2q13 |
| 1555823_at | 0.0001833 | -2 | | BS 3076 | 14 |
| 1556126_s_at | 1.04E-05 | 3.5 | GPATC2 | G patch domain containing 2 | 1q41 |
| 1556138_a_at | 0.0001589 | 2.9 | COL5A1 | Collagen, type V, alpha 1 | 9q34.2-q34.3 |
| 1556185_a_at | 0.0002463 | 2.6 | | CDNA clone IMAGE: 5260162 | 7 |
| 1556242_a_at | 3.82E-05 | 2.1 | | *Homo sapiens*, clone IMAGE: 3885623, mRNA | 8 |
| 1556316_s_at | 0.0005561 | 3.3 | MIF | Macrophage migration inhibitory factor (glycosylation-inhibiting factor) | 22q11.23 |
| 1556499_s_at | 0.0005246 | 2.5 | COL1A1 | collagen, type I, alpha 1 (COL1A1), mRNA. | 17q21.3-q22.1 |
| 1556835_s_at | 0.0002018 | 2.2 | | Transcribed locus | 11 |
| 1557432_at | 0.0001321 | 3.6 | RASAL2 | RAS protein activator like 2 | 1q24 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 1557527_at | 0.0003572 | 2.5 | RUNX1 | Runt-related transcription factor 1 (acute myeloid leukemia 1; aml1 oncogene) | 21q22.3 |
| 1558019_at | 2.09E−05 | −2.9 | DST | Dystonin | 6p12-p11 |
| 1558048_x_at | 2.01E−05 | 4.1 | | Unknown | |
| 1558292_s_at | 0.0007105 | 2 | PIGW | phosphatidylinositol glycan, class W (PIGW), mRNA. | 17q12 |
| 1558426_x_at | 0.000189 | 2.9 | | Chromosome 7 open reading frame 19 | 7 |
| 1558487_a_at | 0.0002657 | −2.6 | TMED4 | Transmembrane emp24 protein transport domain containing 4 | 7p13 |
| 1558836_at | 5.35E−05 | 3.2 | | MRNA; cDNA DKFZp667A182 (from clone DKFZp667A182) | 2 |
| 1559060_a_at | 5.16E−05 | 3 | KIAA1961 | KIAA1961 gene | 5q23.3 |
| 1559078_at | 6.58E−05 | 4.6 | BCL11A | B-cell CLL/lymphoma 11A (zinc finger protein) | 2p16.1 |
| 1559101_at | 9.12E−05 | 2.6 | FYN | FYN oncogene related to SRC, FGR, YES | 6q21 |
| 1559410_at | 4.66E−05 | 3.6 | | Unknown | |
| 1559436_x_at | 4.54E−05 | 4.8 | ARRB2 | Arrestin, beta 2 | 17p13 |
| 1559585_at | 0.000489 | 3.2 | FLJ31033 | Hypothetical protein FLJ31033 | 4q32.3 |
| 1559593_a_at | 0.0005238 | 2.9 | CRSP7 | Cofactor required for Sp1 transcriptional activation, subunit 7, 70 kDa | 19p13.11 |
| 1560817_at | 0.0001564 | 2.5 | MOV10 | Mov10, Moloney leukemia virus 10, homolog (mouse) | 1p13.2 |
| 1562062_at | 0.000114 | 4 | | *Homo sapiens* transcribed sequence with weak similarity to protein ref: NP_055301.1 (*H. sapiens*) neuronal thread protein [*Homo sapiens*] | |
| 1562063_x_at | 0.0003481 | 3.4 | | *Homo sapiens* transcribed sequence with weak similarity to protein ref: NP_055301.1 (*H. sapiens*) neuronal thread protein [*Homo sapiens*] | |
| 1562270_at | 0.000382 | 4 | ARHGEF7 | Rho guanine nucleotide exchange factor (GEF) 7 | 13q34 |
| 1562271_x_at | 1.81E−05 | 3.9 | ARHGEF7 | Rho guanine nucleotide exchange factor (GEF) 7 | 13q34 |
| 1562456_at | 0.0008617 | 2.3 | | MRNA; cDNA DKFZp566C0924 (from clone DKFZp566C0924) | 11 |
| 1563357_at | 0.0002718 | 3.4 | SERPINB9 | serpin peptidase inhibitor, clade B (ovalbumin), member 9 (SERPINB9), mRNA. | 6p25 |
| 1565579_at | 0.0003108 | 3.7 | TATDN2 | TatD DNase domain containing 2 | 3p25.3 |
| 1565823_at | 1.91E−05 | 4.8 | 7-Sep | septin 7 (SEPT7), transcript variant 2, mRNA. | 7p14.3-p14.1 |
| 1565974_at | 0.0008723 | 2.8 | SUV420H1 | Suppressor of variegation 4-20 homolog 1 (*Drosophila*) | 11q13.2 |
| 1566887_x_at | 8.32E−05 | 4.3 | KIAA0284 | KIAA0284 | 14q32.33 |
| 1568619_s_at | 0.0002665 | 2.2 | LOC162073 | Hypothetical protein LOC162073 | 16p12.3 |
| 1568954_s_at | 0.0001751 | 2.2 | | Unknown | |
| 1569519_at | 0.0006199 | 2.5 | FLJ21272 | hypothetical protein FLJ21272 | 1q21.2 |
| 1569872_a_at | 0.0004892 | 2.4 | | *Homo sapiens*, clone IMAGE: 5242623 | 16 |
| 1570061_at | 8.83E−05 | 3.2 | | CDNA clone IMAGE: 4555030 | 3 |
| 1570143_at | 0.0005727 | 2.4 | | *Homo sapiens*, clone IMAGE: 3932570, mRNA | 8 |
| 1570185_at | 0.0003081 | 3 | | *Homo sapiens*, clone IMAGE: 5766850, mRNA | 10 |
| 200005_at | 0.0005509 | −2 | EIF3S7 | eukaryotic translation initiation factor 3, subunit 7 zeta, 66/67 kDa (EIF3S7), mRNA. | 22q13.1 |
| 200010_at | 0.0001997 | −2.2 | RPL11 | Ribosomal protein L11 | 1p36.1-p35 |
| 200013_at | 2.50E−05 | −2.6 | RPL24 | ribosomal protein L24 (RPL24), mRNA. | 3q12 |
| 200021_at | 0.0001035 | 2.5 | CFL1 | cofilin 1 (non-muscle) (CFL1), mRNA. | 11q13 |
| 200022_at | 0.0002003 | −2.1 | RPL18 | ribosomal protein L18 (RPL18), mRNA. | 19q13 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 200023_s_at | 1.61E−05 | −2.4 | EIF3S5 | eukaryotic translation initiation factor 3, subunit 5 epsilon, 47 kDa (EIF3S5), mRNA. | 11p15.4 |
| 200024_at | 0.0004964 | −2.5 | RPS5 | ribosomal protein S5 (RPS5), mRNA. | 19q13.4 |
| 200074_s_at | 0.0001721 | −2.2 | RPL14 | ribosomal protein L14 (RPL14), mRNA. | 3p22-p21.2 |
| 200081_s_at | 6.20E−06 | −3.3 | RPS6 | ribosomal protein S6 (RPS6), mRNA. | 9p21 |
| 200642_at | 0.0007047 | −2 | SOD1 | superoxide dismutase 1, soluble (amyotrophic lateral sclerosis 1 (adult)) (SOD1), mRNA. | 21q22.11 |
| 200651_at | 0.0001597 | −2.3 | GNB2L1 | guanine nucleotide binding protein (G protein), beta polypeptide 2-like 1 (GNB2L1), mRNA. | 5q35.3 |
| 200665_s_at | 0.00039 | 2.7 | SPARC | secreted protein, acidic, cysteine-rich (osteonectin) (SPARC), mRNA. | 5q31.3-q32 |
| 200676_s_at | 0.0007037 | −2.5 | UBE2L3 | ubiquitin-conjugating enzyme E2L 3 (UBE2L3), transcript variant 1, mRNA. | 22q11.21 |
| 200700_s_at | 4.15E−05 | 2.3 | KDELR2 | KDEL (Lys-Asp-Glu-Leu) endoplasmic reticulum protein retention receptor 2 (KDELR2), mRNA. | 7p22.1 |
| 200734_s_at | 6.61E−05 | 2.5 | ARF3 | ADP-ribosylation factor 3 (ARF3), mRNA. | 12q13 |
| 200735_x_at | 9.63E−05 | −2.1 | NACA | nascent-polypeptide-associated complex alpha polypeptide (NACA), mRNA. | 12q23-q24.1 |
| 200755_s_at | 0.0007055 | 2.1 | CALU | calumenin (CALU), mRNA. | 7q32 |
| 200760_s_at | 5.53E−05 | −2.6 | ARL6IP5 | ADP-ribosylation-like factor 6 interacting protein 5 (ARL6IP5), mRNA. | 3p14 |
| 200806_s_at | 0.0008155 | −2 | HSPD1 | heat shock 60 kDa protein 1 (chaperonin) (HSPD1), nuclear gene encoding mitochondrial protein, transcript variant 2, mRNA. | 2q33.1 |
| 200811_at | 1.25E−05 | −3.6 | CIRBP | cold inducible RNA binding protein (CIRBP), mRNA. | 19p13.3 |
| 200827_at | 0.0004906 | 2.3 | PLOD1 | procollagen-lysine 1,2-oxoglutarate 5-dioxygenase 1 (PLOD1), mRNA. | 1p36.3-p36.2 |
| 200866_s_at | 0.0004451 | −2.1 | PSAP | prosaposin (variant Gaucher disease and variant metachromatic leukodystrophy) (PSAP), mRNA. | 10q21-q22 |
| 200883_at | 7.19E−05 | −3.2 | UQCRC2 | ubiquinol-cytochrome c reductase core protein II (UQCRC2), mRNA. | 16p12 |
| 200906_s_at | 0.0002674 | −3.2 | KIAA0992 | palladin (KIAA0992), mRNA. | 4q32.3 |
| 200920_s_at | 0.0001341 | −2.3 | BTG1 | B-cell translocation gene 1, anti-proliferative (BTG1), mRNA. | 12q22 |
| 200937_s_at | 5.83E−05 | −2.4 | RPL5 | ribosomal protein L5 (RPL5), mRNA. | 1p22.1 |
| 200951_s_at | 0.000314 | 4.1 | CCND2 | cyclin D2 (CCND2), mRNA. | 12p13 |
| 200953_s_at | 0.0001997 | 2.6 | CCND2 | cyclin D2 (CCND2), mRNA. | 12p13 |
| 200965_s_at | 0.000112 | −5.9 | ABLIM1 | actin binding LIM protein 1 (ABLIM1), transcript variant 4, mRNA. | 10q25 |
| 200999_s_at | 0.0009198 | 2 | CKAP4 | cytoskeleton-associated protein 4 (CKAP4), mRNA. | 12q23.3 |
| 201008_s_at | 0.0009045 | −2.7 | TXNIP | thioredoxin interacting protein (TXNIP), mRNA. | 1q21.1 |
| 201009_s_at | 0.0004645 | −2.8 | TXNIP | thioredoxin interacting protein (TXNIP), mRNA. | 1q21.1 |
| 201018_at | 0.0007096 | −2.3 | EIF1AX | eukaryotic translation initiation factor 1A, X-linked (EIF1AX), mRNA. | Xp22.12 |
| 201023_at | 2.69E−05 | −2.4 | TAF7 | TAF7 RNA polymerase II, TATA box binding protein (TBP)-associated factor, 55 kDa (TAF7), mRNA. | 5q31 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 201030_x_at | 2.40E−05 | −2.2 | LDHB | lactate dehydrogenase B (LDHB), mRNA. | 12p12.2-p12.1 |
| 201036_s_at | 0.0005734 | −3.7 | HADHSC | L-3-hydroxyacyl-Coenzyme A dehydrogenase, short chain (HADHSC), mRNA. | 4q22-q26 |
| 201054_at | 1.41E−05 | −2.2 | HNRPA0 | heterogeneous nuclear ribonucleoprotein A0 (HNRPA0), mRNA. | 5q31 |
| 201076_at | 1.82E−05 | −2.4 | NHP2L1 | NHP2 non-histone chromosome protein 2-like 1 (*S. cerevisiae*) (NHP2L1), transcript variant 2, mRNA. | 22q13.2-q13.31 |
| 201085_s_at | 0.000222 | −2.3 | SON | SON DNA binding protein (SON), transcript variant a, mRNA. | 21q22.11 |
| 201088_at | 9.10E−06 | 2.7 | KPNA2 | karyopherin alpha 2 (RAG cohort 1, importin alpha 1) (KPNA2), mRNA. | 17q23.1-q23.3 |
| 201101_s_at | 3.64E−05 | −2.9 | BCLAF1 | BCL2-associated transcription factor 1 (BCLAF1), mRNA. | 6q22-q23 |
| 201129_at | 0.0002614 | −2.6 | SFRS7 | splicing factor, arginine/serine-rich 7, 35 kDa (SFRS7), transcript variant 1, mRNA. | 2p22.1 |
| 201133_s_at | 0.0001686 | −2.5 | PJA2 | praja 2, RING-H2 motif containing (PJA2), mRNA. | 2p22.1 |
| 201154_x_at | 0.0001159 | −2.2 | RPL4 | ribosomal protein L4 (RPL4), mRNA. | 15q22 |
| 201163_s_at | 0.0003882 | 2.2 | IGFBP7 | insulin-like growth factor binding protein 7 (IGFBP7), mRNA. | 4q12 |
| 201193_at | 0.0004945 | −2.9 | IDH1 | isocitrate dehydrogenase 1 (NADP+), soluble (IDH1), mRNA. | 2q33.3 |
| 201204_s_at | 1.43E−05 | 2.2 | RRBP1 | Ribosome binding protein 1 homolog 180 kDa (dog) | 20p12 |
| 201206_s_at | 0.0002058 | 2.5 | RRBP1 | ribosome binding protein 1 homolog 180 kDa (dog) (RRBP1), mRNA. | 20p12 |
| 201250_s_at | 0.0001573 | 3.1 | SLC2A1 | solute carrier family 2 (facilitated glucose transporter), member 1 (SLC2A1), mRNA. | 1p35-p31.3 |
| 201261_x_at | 0.0003831 | 4.3 | BGN | biglycan (BGN), mRNA. | Xq28 |
| 201302_at | 1.57E−05 | −3.1 | ANXA4 | annexin A4 (ANXA4), mRNA. | 2p13 |
| 201370_s_at | 0.0002857 | −2.3 | CUL3 | cullin 3 (CUL3), mRNA. | 2q36.3 |
| 201376_s_at | 0.0001535 | −2.4 | HNRPF | heterogeneous nuclear ribonucleoprotein F (HNRPF), mRNA. | 10q11.21-q11.22 |
| 201408_at | 3.95E−05 | −3.2 | PPP1CB | protein phosphatase 1, catalytic subunit, beta isoform (PPP1CB), transcript variant 2, mRNA. | 2p23 |
| 201425_at | 1.80E−06 | −2.9 | ALDH2 | aldehyde dehydrogenase 2 family (mitochondrial) (ALDH2), nuclear gene encoding mitochondrial protein, mRNA. | 12q24.2 |
| 201427_s_at | 0.0004665 | −2.5 | SEPP1 | selenoprotein P, plasma, 1 (SEPP1), mRNA. | 5q31 |
| 201431_s_at | 0.0003957 | −4.5 | DPYSL3 | dihydropyrimidinase-like 3 (DPYSL3), mRNA. | 5q32 |
| 201432_at | 2.09E−05 | −3.3 | CAT | catalase (CAT), mRNA. | 11p13 |
| 201455_s_at | 0.0004393 | −2.7 | NPEPPS | aminopeptidase puromycin sensitive (NPEPPS), mRNA. | 17q21 |
| 201482_at | 0.0004221 | −2.9 | QSCN6 | quiescin Q6 (QSCN6), transcript variant 2, mRNA. | 1q24 |
| 201484_at | 0.0001619 | −2.2 | SUPT4H1 | suppressor of Ty 4 homolog 1 (*S. cerevisiae*) (SUPT4H1), mRNA. | 17q21-q23 |
| 201487_at | 0.0002325 | 3.1 | CTSC | cathepsin C (CTSC), transcript variant 1, mRNA. | 11q14.1-q14.3 |
| 201496_x_at | 0.0005336 | −6.1 | MYH11 | myosin, heavy polypeptide 11, smooth muscle (MYH11), transcript variant SM2, mRNA. | 16p13.13-p13.12 |
| 201506_at | 0.0003278 | 3.3 | TGFBI | transforming growth factor, beta-induced, 68 kDa (TGFBI), mRNA. | 5q31 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 201529_s_at | 0.0001633 | −3 | RPA1 | replication protein A1, 70 kDa (RPA1), mRNA. | 17p13.3 |
| 201535_at | 6.72E−05 | −2.3 | UBL3 | ubiquitin-like 3 (UBL3), mRNA. | 13q12-q13 |
| 201554_x_at | 0.0003257 | −2.5 | GYG | glycogenin (GYG), mRNA. | 3q24-q25.1 |
| 201579_at | 0.0007798 | 2.6 | FAT | FAT tumor suppressor homolog 1 (Drosophila) (FAT), mRNA. | 4q34-q35 |
| 201581_at | 2.11E−05 | −2.4 | DJ971N18.2 | Hypothetical protein DJ971N18.2 | 20p12 |
| 201584_s_at | 0.0001736 | 2.3 | DDX39 | DEAD (Asp-Glu-Ala-Asp) box polypeptide 39 (DDX39), transcript variant 1, mRNA. | 19p13.12 |
| 201596_x_at | 1.62E−05 | 4.3 | KRT18 | keratin 18 (KRT18), transcript variant 2, mRNA. | 12q13 |
| 201600_at | 3.48E−05 | −2.3 | PHB2 | prohibitin 2 (PHB2), mRNA. | 12p13 |
| 201666_at | 0.0004812 | 3.4 | TIMP1 | TIMP metallopeptidase inhibitor 1 (TIMP1), mRNA. | Xp11.3-p11.23 |
| 201674_s_at | 0.0001795 | −3 | AKAP1 | A kinase (PRKA) anchor protein 1 (AKAP1), nuclear gene encoding mitochondrial protein, transcript variant 1, mRNA. | 17q21-q23 |
| 201696_at | 0.000121 | −2 | SFRS4 | splicing factor, arginine/serine-rich 4 (SFRS4), mRNA. | 1p35.3 |
| 201697_s_at | 0.0001256 | 2.4 | DNMT1 | DNA (cytosine-5-)-methyltransferase 1 (DNMT1), mRNA. | 19p13.2 |
| 201712_s_at | 0.0008422 | −2.2 | RANBP2 | RAN binding protein 2 (RANBP2), mRNA. | 2q12.3 |
| 201737_s_at | 5.10E−06 | −3.1 | 6-Mar | membrane-associated ring finger (C3HC4) 6 (MARCH6), mRNA. | 5p15.2 |
| 201756_at | 0.0003533 | −2 | RPA2 | replication protein A2, 32 kDa (RPA2), mRNA. | 1p35 |
| 201810_s_at | 0.0001904 | −3.2 | SH3BP5 | SH3-domain binding protein 5 (BTK-associated) (SH3BP5), transcript variant 2, mRNA. | 3p24.3 |
| 201816_s_at | 0.0004168 | −2.2 | GBAS | glioblastoma amplified sequence (GBAS), mRNA. | 7p12 |
| 201871_s_at | 0.0001348 | −2 | LOC51035 | ORF (LOC51035), mRNA. | 11q12.3 |
| 201891_s_at | 0.0007795 | 2 | B2M | beta-2-microglobulin (B2M), mRNA. | 15q21-q22.2 |
| 201893_x_at | 0.0006272 | −3.1 | DCN | decorin (DCN), transcript variant B, mRNA. | 12q21.33 |
| 201911_s_at | 0.0001467 | 3.4 | FARP1 | FERM, RhoGEF (ARHGEF) and pleckstrin domain protein 1 (chondrocyte-derived) (FARP1), transcript variant 1, mRNA. | 13q32.2 |
| 201922_at | 0.0001538 | −2 | TINP1 | TGF beta-inducible nuclear protein 1 (TINP1), mRNA. | 5q13.3 |
| 201960_s_at | 0.0002203 | −2 | MYCBP2 | MYC binding protein 2 (MYCBP2), mRNA. | 13q22 |
| 201973_s_at | 0.0004504 | 2 | C7orf28A | chromosome 7 open reading frame 28A (C7orf28A), mRNA. | 7p22.1 |
| 202016_at | 0.0001808 | 3.2 | MEST | mesoderm specific transcript homolog (mouse) (MEST), transcript variant 3, mRNA. | 7q32 |
| 202028_s_at | 0.0002331 | 3 | RPL38 | ribosomal protein L38 (RPL38), mRNA. | 17q23-q25 |
| 202029_x_at | 1.93E−05 | −2.1 | RPL38 | ribosomal protein L38 (RPL38), mRNA. | 17q23-q25 |
| 202037_s_at | 0.0002558 | −3.1 | SFRP1 | secreted frizzled-related protein 1 (SFRP1), mRNA. | 8p12-p11.1 |
| 202068_s_at | 0.0001171 | −4.1 | LDLR | low density lipoprotein receptor (familial hypercholesterolemia) (LDLR), mRNA. | 19p13.3 |
| 202073_at | 4.49E−05 | −2.6 | OPTN | optineurin (OPTN), transcript variant 2, mRNA. | 10p13 |
| 202105_at | 3.00E−07 | −3.2 | IGBP1 | immunoglobulin (CD79A) binding protein 1 (IGBP1), mRNA. | Xq13.1-q13.3 |
| 202119_s_at | 0.0002779 | −3.2 | CPNE3 | copine III (CPNE3), mRNA. | 8q21.3 |
| 202139_at | 0.0004872 | −2.1 | AKR7A2 | aldo-keto reductase family 7, member A2 (aflatoxin aldehyde reductase) (AKR7A2), mRNA. | 1p35.1-p36.23 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 202148_s_at | 0.0006205 | 2.2 | PYCR1 | pyrroline-5-carboxylate reductase 1 (PYCR1), transcript variant 2, mRNA. | 17q25.3 |
| 202156_s_at | 0.0004765 | −2.8 | CUGBP2 | CUG triplet repeat, RNA binding protein 2 (CUGBP2), transcript variant 2, mRNA. | 10p13 |
| 202157_s_at | 9.00E−07 | −6.1 | CUGBP2 | CUG triplet repeat, RNA binding protein 2 (CUGBP2), transcript variant 2, mRNA. | 10p13 |
| 202158_s_at | 2.99E−05 | −4.2 | CUGBP2 | CUG triplet repeat, RNA binding protein 2 (CUGBP2), transcript variant 2, mRNA. | 10p13 |
| 202172_at | 0.0006154 | −2.4 | ZNF161 | zinc finger protein 161 (ZNF161), mRNA. | 17q23.2 |
| 202202_s_at | 0.0002996 | 3.4 | LAMA4 | laminin, alpha 4 (LAMA4), mRNA. | 6q21 |
| 202214_s_at | 0.0005849 | −2 | CUL4B | Cullin 4B | Xq23 |
| 202232_s_at | 0.0002955 | −2.2 | hfl-B5 | dendritic cell protein (hfl-B5), mRNA. | 11p13 |
| 202259_s_at | 3.74E−05 | −3.2 | PFAAP5 | phosphonoformate immuno-associated protein 5 (PFAAP5), mRNA. | 13q12-q13 |
| 202260_s_at | 0.0005909 | −2.2 | STXBP1 | syntaxin binding protein 1 (STXBP1), transcript variant 2, mRNA. | 9q34.1 |
| 202286_s_at | 0.0003361 | 5.5 | TACSTD2 | tumor-associated calcium signal transducer 2 (TACSTD2), mRNA. | 1p32-p31 |
| 202292_x_at | 0.0001802 | 2.4 | LYPLA2 | lysophospholipase II (LYPLA2), mRNA. | 1p36.12-p35.1 |
| 202297_s_at | 6.25E−05 | 2.2 | RER1 | RER1 retention in endoplasmic reticulum 1 homolog (S. cerevisiae) (RER1), mRNA. | 1pter-q24 |
| 202314_at | 0.0001115 | −2.6 | CYP51A1 | cytochrome P450, family 51, subfamily A, polypeptide 1 (CYP51A1), mRNA. | 7q21.2-q21.3 |
| 202350_s_at | 0.0002121 | −3.7 | MATN2 | matrilin 2 (MATN2), transcript variant 2, mRNA. | 8q22 |
| 202364_at | 0.0002246 | −2.5 | MXI1 | MAX interactor 1 (MXI1), transcript variant 3, mRNA. | 10q24-q25 |
| 202378_s_at | 6.45E−05 | −2.2 | LEPROT | leptin receptor overlapping transcript (LEPROT), mRNA. | 1p31.2 |
| 202404_s_at | 0.000452 | 2.9 | COL1A2 | collagen, type I, alpha 2 (COL1A2), mRNA. | 7q22.1 |
| 202429_s_at | 0.0001255 | −2.4 | PPP3CA | protein phosphatase 3 (formerly 2B), catalytic subunit, alpha isoform (calcineurin A alpha) (PPP3CA), mRNA. | 4q21-q24 |
| 202464_s_at | 0.0009823 | 3.5 | PFKFB3 | 6-phosphofructo-2-kinase/fructose-2,6-biphosphatase 3 | 10p14-p15 |
| 202465_at | 9.80E−06 | 4.8 | PCOLCE | procollagen C-endopeptidase enhancer (PCOLCE), mRNA. | 7q22 |
| 202468_s_at | 7.84E−05 | −2.5 | CTNNAL1 | catenin (cadherin-associated protein), alpha-like 1 (CTNNAL1), mRNA. | 9q31.2 |
| 202502_at | 5.08E−05 | −2 | ACADM | acyl-Coenzyme A dehydrogenase, C-4 to C-12 straight chain (ACADM), nuclear gene encoding mitochondrial protein, mRNA. | 1p31 |
| 202510_s_at | 1.14E−05 | 3.7 | TNFAIP2 | tumor necrosis factor, alpha-induced protein 2 (TNFAIP2), mRNA. | 14q32 |
| 202512_s_at | 6.24E−05 | −2.2 | APG5L | APG5 autophagy 5-like (S. cerevisiae) (APG5L), mRNA. | 6q21 |
| 202536_at | 0.0002234 | −2 | CHMP2B | chromatin modifying protein 2B (CHMP2B), mRNA. | 3p12.1 |
| 202546_at | 0.0004572 | 5.6 | VAMP8 | vesicle-associated membrane protein 8 (endobrevin) (VAMP8), mRNA. | 2p12-p11.2 |
| 202547_s_at | 6.98E−05 | 3 | ARHGEF7 | Rho guanine nucleotide exchange factor (GEF) 7 (ARHGEF7), transcript variant 1, mRNA. | 13q34 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 202573_at | 0.0002474 | 2 | CSNK1G2 | casein kinase 1, gamma 2 (CSNK1G2), mRNA. | 19p13.3 |
| 202581_at | 0.0002675 | 2.8 | HSPA1B | heat shock 70 kDa protein 1B (HSPA1B), mRNA. | 6p21.3 |
| 202630_at | 6.64E−05 | −2.7 | APPBP2 | amyloid beta precursor protein (cytoplasmic tail) binding protein 2 (APPBP2), mRNA. | 17q21-q23 |
| 202665_s_at | 0.0003645 | 2.9 | WASPIP | Wiskott-Aldrich syndrome protein interacting protein (WASPIP), mRNA. | 2q31.1 |
| 202722_s_at | 0.0002949 | 2.1 | GFPT1 | glutamine-fructose-6-phosphate transaminase 1 (GEPT1), mRNA. | 2p13 |
| 202723_s_at | 2.20E−06 | −4 | FOXO1A | forkhead box O1A (rhabdomyosarcoma) (FOXO1A), mRNA. | 13q14.1 |
| 202724_s_at | 6.00E−07 | −3.3 | FOXO1A | forkhead box O1A (rhabdomyosarcoma) (FOXO1A), mRNA. | 13q14.1 |
| 202731_at | 0.0008149 | −2.6 | PDCD4 | programmed cell death 4 (neoplastic transformation inhibitor) (PDCD4), transcript variant 1, mRNA. | 10q24 |
| 202733_at | 0.0005751 | 3 | P4HA2 | procollagen-proline, 2-oxoglutarate 4-dioxygenase (proline 4-hydroxylase), alpha polypeptide II (P4HA2), transcript variant 3, mRNA. | 5q31 |
| 202746_at | 0.0005864 | −6.4 | ITM2A | integral membrane protein 2A (ITM2A), mRNA. | Xq13.3-Xq21.2 |
| 202749_at | 0.0009431 | −2.2 | WRB | Tryptophan rich basic protein | 21q22.3 |
| 202761_s_at | 0.0003908 | −2.3 | SYNE2 | spectrin repeat containing, nuclear envelope 2 (SYNE2), transcript variant 4, mRNA. | 14q23.2 |
| 202780_at | 0.0009309 | −2 | OXCT1 | 3-oxoacid CoA transferase 1 (OXCT1), nuclear gene encoding mitochondrial protein, mRNA. | 5p13.1 |
| 202820_at | 1.90E−05 | 3.3 | AHR | aryl hydrocarbon receptor (AHR), mRNA. | 7p15 |
| 202825_at | 0.0004002 | −2.1 | SLC25A4 | solute carrier family 25 (mitochondrial carrier; adenine nucleotide translocator), member 4 (SLC25A4), nuclear gene encoding mitochondrial protein, mRNA. | 4q35 |
| 202888_s_at | 0.0005702 | 4.7 | ANPEP | alanyl (membrane) aminopeptidase (aminopeptidase N, aminopeptidase M, microsomal aminopeptidase, CD13, p150) (ANPEP), mRNA. | 15q25-q26 |
| 202899_s_at | 5.55E−05 | −2.8 | SFRS3 | splicing factor, arginine/serine-rich 3 (SFRS3), mRNA. | 6p21 |
| 202908_at | 5.90E−06 | −3.4 | WFS1 | Wolfram syndrome 1 (wolframin) (WFS1), mRNA. | 4p16 |
| 202911_at | 0.0008837 | −2.1 | MSH6 | mutS homolog 6 (*E. coli*) (MSH6), mRNA. | 2p16 |
| 202920_at | 4.60E−06 | −4.2 | ANK2 | ankyrin 2, neuronal (ANK2), transcript variant 2, mRNA. | 4q25-q27 |
| 202952_s_at | 2.37E−05 | 7.6 | ADAM12 | ADAM metallopeptidase domain 12 (meltrin alpha) (ADAM12), transcript variant 1, mRNA. | 10q26.3 |
| 202954_at | 0.0006434 | 2.8 | UBE2C | ubiquitin-conjugating enzyme E2C (UBE2C), transcript variant 1, mRNA. | 20q13.12 |
| 202957_at | 0.000374 | 2.7 | HCLS1 | hematopoietic cell-specific Lyn substrate 1 (HCLS1), mRNA. | 3q13 |
| 202968_s_at | 0.0001551 | 2.3 | DYRK2 | dual-specificity tyrosine-(Y)-phosphorylation regulated kinase 2 (DYRK2), transcript variant 1, mRNA. | 12q15 |
| 202975_s_at | 2.87E−05 | −3.6 | RHOBTB3 | Rho-related BTB domain containing 3 (RHOBTB3), mRNA. | 5q15 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 202992_at | 0.000519 | −5.4 | C7 | complement component 7 (C7), mRNA. | 5p13 |
| 202998_s_at | 0.0006468 | 3 | LOXL2 | lysyl oxidase-like 2 (LOXL2), mRNA. | 8p21.3-p21.2 |
| 203088_at | 0.0008436 | −4.5 | FBLN5 | fibulin 5 (FBLN5), mRNA. | 14q32.1 |
| 203156_at | 3.37E−05 | −2.4 | AKAP11 | A kinase (PRKA) anchor protein 11 (AKAP11), transcript variant 1, mRNA. | 13q14.11 |
| 203166_at | 0.0001939 | −2.3 | CFDP1 | craniofacial development protein 1 (CFDP1), mRNA. | 16q22.2-q22.3 |
| 203178_at | 0.0002428 | −3.3 | GATM | glycine amidinotransferase (L-arginine:glycine amidinotransferase) (GATM), mRNA. | 15q21.1 |
| 203249_at | 0.0004075 | −2.5 | EZH1 | enhancer of zeste homolog 1 (Drosophila) (EZH1), mRNA. | 17q21.1-q21.3 |
| 203297_s_at | 4.33E−05 | 2.4 | JARID2 | Jumonji, AT rich interactive domain 2 (JARID2), mRNA. | 6p24-p23 |
| 203298_s_at | 0.0005468 | 2.1 | JARID2 | Jumonji, AT rich interactive domain 2 (JARID2), mRNA. | 6p24-p23 |
| 203349_s_at | 7.26E−05 | 2.8 | ETV5 | ets variant gene 5 (ets-related molecule) (ETV5), mRNA. | 3q28 |
| 203356_at | 7.77E−05 | −2.6 | CAPN7 | calpain 7 (CAPN7), mRNA. | 3p24 |
| 203358_s_at | 2.44E−05 | 2.9 | EZH2 | enhancer of zeste homolog 2 (Drosophila) (EZH2), transcript variant 2, mRNA. | 7q35-q36 |
| 203401_at | 0.0003991 | −3.8 | PRPS2 | phosphoribosyl pyrophosphate synthetase 2 (PRPS2), mRNA. | Xp22.3-p22.2 |
| 203423_at | 0.0008061 | −3.9 | RBP1 | retinol binding protein 1, cellular (RBP1), mRNA. | 3q23 |
| 203424_s_at | 0.0007037 | −3.8 | IGFBP5 | insulin-like growth factor binding protein 5 (IGFBP5), mRNA. | 2q33-q36 |
| 203427_at | 7.05E−05 | −2.6 | ASF1A | ASF1 anti-silencing function 1 homolog A (S. cerevisiae) (ASF1A), mRNA. | 6q22.31 |
| 203450_at | 0.0007322 | −2.1 | PGEA1 | PKD2 interactor, golgi and endoplasmic reticulum associated 1 (PGEA1), transcript variant 1, mRNA. | 22q12 |
| 203455_s_at | 0.0005583 | 2 | SAT | spermidine/spermine N1-acetyltransferase (SAT), mRNA. | Xp22.1 |
| 203459_s_at | 8.97E−05 | 2.1 | VPS16 | vacuolar protein sorting 16 (yeast) (VPS16), transcript variant 2, mRNA. | 20p13-p12 |
| 203468_at | 0.0009911 | 2.3 | CDK10 | cyclin-dependent kinase (CDC2-like) 10 (CDK10), transcript variant 2, mRNA. | 16q24 |
| 203476_at | 1.65E−05 | 2.6 | TPBG | trophoblast glycoprotein (TPBG), mRNA. | 6q14-q15 |
| 203493_s_at | 0.0009017 | −2.1 | PIG8 | translokin (PIG8), mRNA. | 11q21 |
| 203494_s_at | 0.0001224 | −2.2 | PIG8 | translokin (PIG8), mRNA. | 11q21 |
| 203505_at | 0.0001234 | 2.7 | ABCA1 | ATP-binding cassette, sub-family A (ABC1), member 1 | 9q31.1 |
| 203549_s_at | 0.0001406 | 3.9 | LPL | lipoprotein lipase (LPL), mRNA. | 8p22 |
| 203599_s_at | 0.0004137 | −2 | WBP4 | WW domain binding protein 4 (formin binding protein 21) (WBP4), mRNA. | 13q14.11 |
| 203640_at | 0.0002347 | −2 | MBNL2 | muscleblind-like 2 (Drosophila) (MBNL2), transcript variant 3, mRNA. | 13q32.1 |
| 203657_s_at | 0.0007798 | −2.3 | CTSF | cathepsin F (CTSF), mRNA. | 11q13 |
| 203680_at | 9.00E−07 | −6.1 | PRKAR2B | protein kinase, cAMP-dependent, regulatory, type II, beta (PRKAR2B), mRNA. | 7q22 |
| 203692_s_at | 0.0005974 | 2.2 | E2F3 | E2F transcription factor 3 (E2F3), mRNA. | 6p22 |
| 203695_s_at | 0.0009082 | −2.2 | DFNA5 | deafness, autosomal dominant 5 (DFNA5), mRNA. | 7p15 |
| 203758_at | 0.0002672 | −2 | CTSO | cathepsin O (CTSO), mRNA. | 4q31-q32 |
| 203762_s_at | 0.0003113 | −2.1 | D2LIC | dynein 2 light intermediate chain (D2LIC), transcript variant 1, mRNA. | 2p25.1-p24.1 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 203799_at | 1.06E−05 | −3.3 | CD302 | CD302 antigen (CD302), mRNA. | 2q24.2 |
| 203803_at | 3.79E−05 | −3.9 | PCYOX1 | prenylcysteine oxidase 1 (PCYOX1), mRNA. | 2p13.3 |
| 203845_at | 0.0001562 | −2.8 | PCAF | p300/CBP-associated factor (PCAF), mRNA. | 3p24 |
| 203878_s_at | 2.11E−05 | 3.7 | MMP11 | matrix metallopeptidase 11 (stromelysin 3) (MMP11), mRNA. | 22q11.23 |
| 203888_at | 0.0008536 | −4 | THBD | thrombomodulin (THBD), mRNA. | 20p12-cen |
| 203897_at | 7.35E−05 | −2.2 | LOC57149 | hypothetical protein A-211C6.1 (LOC57149), mRNA. | 16p11.2 |
| 203908_at | 0.0008304 | 2.7 | SLC4A4 | solute carrier family 4, sodium bicarbonate cotransporter, member 4 (SLC4A4), mRNA. | 4q21 |
| 203936_s_at | 0.0002019 | 9.4 | MMP9 | matrix metallopeptidase 9 (gelatinase B, 92 kDa gelatinase, 92 kDa type IV collagenase) (MMP9), mRNA. | 20q11.2-q13.1 |
| 204004_at | 1.50E−06 | −3.2 | PAWR | PRKC, apoptosis, WT1, regulator | 12q21 |
| 204029_at | 0.0005472 | 2.4 | CELSR2 | cadherin, EGF LAG seven-pass G-type receptor 2 (flamingo homolog, *Drosophila*) (CELSR2), mRNA. | 1p21 |
| 204041_at | 0.0003564 | −6.4 | MAOB | Monoamine oxidase B | Xp11.23 |
| 204045_at | 2.00E−07 | −4.5 | TCEAL1 | Transcription elongation factor A (SII)-like 1 | Xq22.1 |
| 204078_at | 0.0001645 | 2.6 | SC65 | synaptonemal complex protein SC65 (SC65), mRNA. | 17q21.2 |
| 204082_at | 0.0002318 | −2.8 | PBX3 | pre-B-cell leukemia transcription factor 3 (PBX3), mRNA. | 9q33-q34 |
| 204109_s_at | 0.0006487 | 2.5 | NFYA | nuclear transcription factor Y, alpha (NFYA), transcript variant 2, mRNA. | 6p21.3 |
| 204136_at | 7.18E−05 | 3.4 | COL7A1 | collagen, type VII, alpha 1 (epidermolysis bullosa, dystrophic, dominant and recessive) (COL7A1), mRNA. | 3p21.1 |
| 204184_s_at | 9.26E−05 | 3 | ADRBK2 | adrenergic, beta, receptor kinase 2 (ADRBK2), mRNA. | 22q12.1 |
| 204235_s_at | 2.45E−05 | −4.3 | GULP1 | GULP, engulfment adaptor PTB domain containing 1 (GULP1), mRNA. | 2q32.3-q33 |
| 204237_at | 1.32E−05 | −3.2 | GULP1 | GULP, engulfment adaptor PTB domain containing 1 (GULP1), mRNA. | 2q32.3-q33 |
| 204256_at | 0.0008289 | 2.1 | ELOVL6 | ELOVL family member 6, elongation of long chain fatty acids (FEN1/Elo2, SUR4/Elo3-like, yeast) (ELOVL6), mRNA. | 4q25 |
| 204285_s_at | 1.20E−06 | 7.7 | PMAIP1 | phorbol-12-myristate-13-acetate-induced protein 1 (PMAIP1), mRNA. | 18q21.32 |
| 204286_s_at | 3.50E−06 | 8.5 | PMAIP1 | phorbol-12-myristate-13-acetate-induced protein 1 (PMAIP1), mRNA. | 18q21.32 |
| 204387_x_at | 7.88E−05 | 2.6 | MRP63 | mitochondrial ribosomal protein 63 (MRP63), nuclear gene encoding mitochondrial protein, mRNA. | 13p11.1-q11 |
| 204454_at | 0.0002053 | −2.6 | LDOC1 | leucine zipper, down-regulated in cancer 1 (LDOC1), mRNA. | Xq27 |
| 204473_s_at | 0.0009569 | 2 | ZNF592 | zinc finger protein 592 (ZNF592), mRNA. | 15q25.3 |
| 204493_at | 0.0003505 | 2.7 | BID | BH3 interacting domain death agonist (BID), transcript variant 3, mRNA. | 22q11.1 |
| 204495_s_at | 0.0006319 | 2.8 | DKFZP434H132 | DKFZP434H132 protein | 15q23 |
| 204531_s_at | 0.0004972 | 2.5 | BRCA1 | breast cancer 1, early onset (BRCA1), transcript variant BRCA1-delta9-11, mRNA. | 17q21 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 204595_s_at | 1.40E−06 | 10.5 | STC1 | stanniocalcin 1 (STC1), mRNA. | 8p21-p11.2 |
| 204597_x_at | 0.0001207 | 7.5 | STC1 | stanniocalcin 1 (STC1), mRNA. | 8p21-p11.2 |
| 204619_s_at | 0.0005599 | 4.6 | CSPG2 | Chondroitin sulfate proteoglycan 2 (versican) | 5q14.3 |
| 204639_at | 1.47E−05 | 4.2 | ADA | adenosine deaminase (ADA), mRNA. | 20q12-q13.11 |
| 204641_at | 0.0006499 | 4.6 | NEK2 | NIMA (never in mitosis gene a)-related kinase 2 (NEK2), mRNA. | 1q32.2-q41 |
| 204669_s_at | 0.0008759 | 2 | RNF24 | ring finger protein 24 (RNF24), mRNA. | 20p13-p12.1 |
| 204731_at | 0.0002926 | −3.2 | TGFBR3 | transforming growth factor, beta receptor III (betaglycan, 300 kDa) (TGFBR3), mRNA. | 1p33-p32 |
| 204735_at | 3.38E−05 | 3.5 | PDE4A | phosphodiesterase 4A, cAMP-specific (phosphodiesterase E2 dunce homolog, *Drosophila*) (PDE4A), mRNA. | 19p13.2 |
| 204749_at | 0.0005462 | −3 | NAP1L3 | nucleosome assembly protein 1-like 3 (NAP1L3), mRNA. | Xq21.3-q22 |
| 204786_s_at | 1.59E−05 | 2.8 | IFNAR2 | interferon (alpha, beta and omega) receptor 2 (IFNAR2), transcript variant 1, mRNA. | 21q22.11 |
| 204793_at | 1.31E−05 | −4.2 | GPRASP1 | G protein-coupled receptor associated sorting protein 1 (GPRASP1), mRNA. | Xq22.1 |
| 204939_s_at | 0.0007407 | −5.7 | PLN | phospholamban (PLN), mRNA. | 6q22.1 |
| 204994_at | 4.91E−05 | 4.5 | MX2 | myxovirus (influenza virus) resistance 2 (mouse) (MX2), mRNA. | 21q22.3 |
| 205068_s_at | 2.40E−06 | 3.8 | ARHGAP26 | Rho GTPase activating protein 26 (ARHGAP26), mRNA. | 5q31 |
| 205079_s_at | 0.0003985 | −2 | MPDZ | multiple PDZ domain protein (MPDZ), mRNA. | 9p24-p22 |
| 205226_at | 0.0004657 | −3 | PDGFRL | platelet-derived growth factor receptor-like (PDGFRL), mRNA. | 8p22-p21.3 |
| 205231_s_at | 0.0008847 | −2 | EPM2A | epilepsy, progressive myoclonus type 2A, Lafora disease (laforin) (EPM2A), transcript variant 1, mRNA. | 6q24 |
| 205241_at | 4.20E−05 | 4.5 | SCO2 | SCO cytochrome oxidase deficient homolog 2 (yeast) (SCO2), nuclear gene encoding mitochondrial protein, mRNA. | 22q13.33 |
| 205259_at | 0.0002039 | −2.5 | NR3C2 | nuclear receptor subfamily 3, group C, member 2 (NR3C2), mRNA. | 4q31.1 |
| 205269_at | 4.00E−06 | 8.7 | LCP2 | lymphocyte cytosolic protein 2 (SH2 domain containing leukocyte protein of 76 kDa) (LCP2), mRNA. | 5q33.1-qter |
| 205270_s_at | 0.0006743 | 6.7 | LCP2 | lymphocyte cytosolic protein 2 (SH2 domain containing leukocyte protein of 76 kDa) (LCP2), mRNA. | 5q33.1-qter |
| 205304_s_at | 0.0007499 | 2.4 | KCNJ8 | potassium inwardly-rectifying channel, subfamily J, member 8 (KCNJ8), mRNA. | 12p11.23 |
| 205353_s_at | 3.92E−05 | −3.3 | PBP | prostatic binding protein (PBP), mRNA. | 12q24.23 |
| 205367_at | 0.0001487 | 2.7 | APS | adaptor protein with pleckstrin homology and src homology 2 domains (APS), mRNA. | 7q22 |
| 205370_x_at | 0.0004381 | 2.9 | DBT | dihydrolipoamide branched chain transacylase E2 (DBT), mRNA. | 1p31 |
| 205381_at | 0.0001503 | −5.4 | LRRC17 | leucine rich repeat containing 17 (LRRC17), transcript variant 1, mRNA. | 7q22.1 |
| 205406_s_at | 3.91E−05 | 2.5 | SPA17 | sperm autoantigenic protein 17 (SPA17), mRNA. | 11q24.2 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 205412_at | 6.30E−06 | −2.7 | ACAT1 | acetyl-Coenzyme A acetyltransferase 1 (acetoacetyl Coenzyme A thiolase) (ACAT1), nuclear gene encoding mitochondrial protein, mRNA. | 11q22.3-q23.1 |
| 205463_s_at | 0.000255 | 3.1 | PDGFA | Platelet-derived growth factor alpha polypeptide | 7p22 |
| 205466_s_at | 6.17E−05 | −4.7 | HS3ST1 | heparan sulfate (glucosamine) 3-O-sulfotransferase 1 (HS3ST1), mRNA. | 4p16 |
| 205479_s_at | 0.000306 | 3.8 | PLAU | plasminogen activator, urokinase (PLAU), mRNA. | 10q24 |
| 205483_s_at | 0.0001248 | 6.9 | G1P2 | interferon, alpha-inducible protein (clone IFI-15K) (G1P2), mRNA. | 1p36.33 |
| 205532_s_at | 0.0004946 | 2.8 | CDH6 | cadherin 6, type 2, K-cadherin (fetal kidney) (CDH6), mRNA. | 5p15.1-p14 |
| 205572_at | 0.0003915 | 5.4 | ANGPT2 | angiopoietin 2 (ANGPT2), mRNA. | 8p23.1 |
| 205687_at | 0.000463 | 2 | UBPH | similar to ubiquitin binding protein (UBPH), mRNA. | 16p12 |
| 205771_s_at | 0.0009058 | −2.3 | AKAP7 | A kinase (PRKA) anchor protein 7 (AKAP7), transcript variant alpha, mRNA. | 6q23 |
| 205812_s_at | 9.00E−06 | 2.4 | TMED9 | transmembrane emp24 protein transport domain containing 9 (TMED9), mRNA. | 5q35.3 |
| 205849_s_at | 0.0005492 | −2 | UQCRB | ubiquinol-cytochrome c reductase binding protein (UQCRB), mRNA. | 8q22 |
| 205862_at | 7.65E−05 | −8.6 | GREB1 | GREB1 protein (GREB1), transcript variant a, mRNA. | 2p25.1 |
| 205871_at | 0.0003369 | 3.1 | PLGLB1 | plasminogen-like B1 (PLGLB1), mRNA. | 2 |
| 205943_at | 0.0004032 | 4.4 | TDO2 | tryptophan 2,3-dioxygenase (TDO2), mRNA. | 4q31-q32 |
| 205961_s_at | 0.0002574 | −2.9 | PSIP1 | PC4 and SFRS1 interacting protein 1 (PSIP1), transcript variant 2, mRNA. | 9p22.3 |
| 206026_s_at | p < 1e−07 | 29.1 | TNFAIP6 | tumor necrosis factor, alpha-induced protein 6 (TNFAIP6), mRNA. | 2q23.3 |
| 206158_s_at | 0.0006831 | −2.2 | ZNF9 | zinc finger protein 9 (a cellular retroviral nucleic acid binding protein) (ZNF9), mRNA. | 3q21 |
| 206169_x_at | 0.0008428 | 3.9 | RoXaN | Zinc finger CCCH-type containing 7B | 22q13.2 |
| 206211_at | 0.0002057 | −8.9 | SELE | selectin E (endothelial adhesion molecule 1) (SELE), mRNA. | 1q22-q25 |
| 206247_at | 9.38E−05 | 3.3 | MICB | MHC class I polypeptide-related sequence B (MICB), mRNA. | 6p21.3 |
| 206359_at | 0.0004232 | −3.5 | SOCS3 | Suppressor of cytokine signaling 3 | 17q25.3 |
| 206377_at | 2.40E−06 | 6 | FOXF2 | forkhead box F2 (FOXF2), mRNA. | 6p25.3 |
| 206435_at | 0.0009321 | 3.2 | GALGT | UDP-N-acetyl-alpha-D-galactosamine:(N-acetylneuraminyl)-galactosylglucosylceramide N-acetylgalactosaminyltransferase (GalNAc-T) (GALGT), mRNA. | 12q13.3 |
| 206483_at | 0.0009412 | 2 | LRRC6 | leucine rich repeat containing 6 (LRRC6), mRNA. | 8q24.22 |
| 206551_x_at | 0.0001129 | 2.7 | DRE1 | DRE1 protein | 3q27.1 |
| 206571_s_at | 0.000131 | 2.7 | MAP4K4 | mitogen-activated protein kinase kinase kinase kinase 4 (MAP4K4), transcript variant 1, mRNA. | 2q11.2-q12 |
| 206621_s_at | 0.0002653 | −2.3 | WBSCR1 | Williams-Beuren syndrome chromosome region 1 (WBSCR1), transcript variant 2, mRNA. | 7q11.23 |
| 206637_at | 3.52E−05 | 4.8 | P2RY14 | purinergic receptor P2Y, G-protein coupled, 14 (P2RY14), mRNA. | 3q21-q25 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 206792_x_at | 6.82E−05 | 3.7 | PDE4C | phosphodiesterase 4C, cAMP-specific (phosphodiesterase E1 dunce homolog, Drosophila) (PDE4C), mRNA. | 19p13.11 |
| 206809_s_at | 0.0004239 | −2.8 | HNRPA3P1 | Heterogeneous nuclear ribonucleoprotein A3 pseudogene 1 | 10q11.21 |
| 206857_s_at | 0.0002413 | 2.5 | FKBP1B | FK506 binding protein 1B, 12.6 kDa (FKBP1B), transcript variant 1, mRNA. | 2p23.3 |
| 206874_s_at | 9.71E−05 | −2.9 | SLK | STE20-like kinase (yeast) | 10q25.1 |
| 206927_s_at | 0.0004319 | 3.3 | GUCY1A2 | guanylate cyclase 1, soluble, alpha 2 (GUCY1A2), mRNA. | 11q21-q22 |
| 207040_s_at | 1.56E−05 | −2.6 | ST13 | suppression of tumorigenicity 13 (colon carcinoma) (Hsp70 interacting protein) (ST13), mRNA. | 22q13.2 |
| 207132_x_at | 0.0002292 | −2.5 | PFDN5 | prefoldin 5 (PFDN5), transcript variant 1, mRNA. | 12q12 |
| 207147_at | 0.0007438 | 3.3 | DLX2 | distal-less homeo box 2 (DLX2), mRNA. | 2q32 |
| 207170_s_at | 1.76E−05 | −2.6 | LETMD1 | LETM1 domain containing 1 (LETMD1), transcript variant 3, mRNA. | 12q13.12 |
| 207239_s_at | 0.0002121 | 2.2 | PCTK1 | PCTAIRE protein kinase 1 (PCTK1), transcript variant 1, mRNA. | Xp11.3-p11.23 |
| 207365_x_at | 6.06E−05 | 3.7 | USP34 | Ubiquitin specific protease 34 | 2p15 |
| 207386_at | 0.0009685 | 2.7 | CYP7B1 | cytochrome P450, family 7, subfamily B, polypeptide 1 (CYP7B1), mRNA. | 8q21.3 |
| 207598_x_at | 0.0001463 | 3.5 | XRCC2 | X-ray repair complementing defective repair in Chinese hamster cells 2 (XRCC2), mRNA. | 7q36.1 |
| 207688_s_at | 0.0006478 | 2.4 | LOC387933 | PREDICTED: similar to heterogeneous nuclear ribonucleoprotein A3 (LOC387933), mRNA. | 13 |
| 207730_x_at | 0.0002746 | 3.1 | FLJ20700 | hypothetical protein FLJ20700 | 19p13.3 |
| 207761_s_at | 1.38E−05 | −4.2 | DKFZP586A0522 | DKFZP586A0522 protein (DKFZP586A0522), mRNA. | 12q13.12 |
| 207961_x_at | 0.0006679 | −3.8 | MYH11 | myosin, heavy polypeptide 11, smooth muscle (MYH11), transcript variant SM1, mRNA. | 16p13.13-p13.12 |
| 207974_s_at | 0.0001511 | −2.1 | SKP1A | S-phase kinase-associated protein 1A (p19A) (SKP1A), transcript variant 2, mRNA. | 5q31 |
| 207983_s_at | 0.0009431 | −2.3 | STAG2 | stromal antigen 2 (STAG2), mRNA. | Xq25 |
| 208092_s_at | 0.0004178 | 2.9 | FAM49A | family with sequence similarity 49, member A (FAM49A), mRNA. | 2p24.3-p24.2 |
| 208137_x_at | 0.0008157 | 2.6 | ZNF611 | Zinc finger protein 611 | 19q13.41 |
| 208238_x_at | 0.0007093 | 2.4 | LZLP | leucine zipper-like protein | 11q13.1 |
| 208246_x_at | 8.09E−05 | 3.6 | FLJ20006 | hypothetical protein FLJ20006 | 16q23.1 |
| 208248_x_at | 5.35E−05 | −3.5 | APLP2 | amyloid beta (A4) precursor-like protein 2 (APLP2), mRNA. | 11q24 |
| 208540_x_at | 0.0007507 | 2 | S100A14 | S100 calcium binding protein A14 (calgizzarin) | 7q22-q31.1 |
| 208626_s_at | 0.000509 | −2.1 | VAT1 | vesicle amine transport protein 1 homolog (T californica) (VAT1), mRNA. | 17q21 |
| 208631_s_at | 0.0003804 | −2.3 | HADHA | hydroxyacyl-Coenzyme A dehydrogenase/3-ketoacyl-Coenzyme A thiolase/enoyl-Coenzyme A hydratase (trifunctional protein), alpha subunit (HADHA), mRNA. | 2p23 |
| 208635_x_at | 8.57E−05 | −2 | NACA | nascent-polypeptide-associated complex alpha polypeptide (NACA), mRNA. | 12q23-q24.1 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 208643_s_at | 2.41E−05 | −2.9 | XRCC5 | X-ray repair complementing defective repair in Chinese hamster cells 5 (double-strand-break rejoining; Ku autoantigen, 80 kDa) (XRCC5), mRNA. | 2q35 |
| 208647_at | 0.0004172 | −2.1 | FDFT1 | farnesyl-diphosphate farnesyltransferase 1 (FDFT1), mRNA. | 8p23.1-p22 |
| 208653_s_at | 0.0002993 | 3 | CD164 | CD164 antigen, sialomucin (CD164), mRNA. | 6q21 |
| 208655_at | 0.0001893 | −2.8 | CCNI | Cyclin I | 4q21.1 |
| 208658_at | 0.0005959 | 2 | PDIA4 | protein disulfide isomerase family A, member 4 (PDIA4), mRNA. | 7q35 |
| 208662_s_at | 0.0009682 | −2.1 | TTC3 | tetratricopeptide repeat domain 3 (TTC3), transcript variant 2, mRNA. | 21q22.2 |
| 208666_s_at | 5.00E−07 | −4.5 | ST13 | suppression of tumorigenicity 13 (colon carcinoma) (Hsp70 interacting protein) (ST13), mRNA. | 22q13.2 |
| 208667_s_at | 4.53E−05 | −2.8 | ST13 | suppression of tumorigenicity 13 (colon carcinoma) (Hsp70 interacting protein) (ST13), mRNA. | 22q13.2 |
| 208671_at | 0.0005205 | −2 | TDE2 | tumor differentially expressed 2 (TDE2), mRNA. | 6q22.31 |
| 208673_s_at | 0.0005001 | −2.2 | SFRS3 | splicing factor, arginine/serine-rich 3 (SFRS3), mRNA. | 6p21 |
| 208697_s_at | 4.85E−05 | −2.4 | EIF3S6 | eukaryotic translation initiation factor 3, subunit 6 48 kDa (EIF3S6), mRNA. | 8q22-q23 |
| 208703_s_at | 0.0002231 | −3.7 | APLP2 | amyloid beta (A4) precursor-like protein 2 (APLP2), mRNA. | 11q24 |
| 208704_x_at | 4.90E−05 | −3.6 | APLP2 | amyloid beta (A4) precursor-like protein 2 (APLP2), mRNA. | 11q24 |
| 208740_at | 7.40E−05 | −2.2 | SAP18 | sin3-associated polypeptide, 18 kDa (SAP18), mRNA. | 13q12.11 |
| 208760_at | 7.17E−05 | −2.7 | UBE2I | Ubiquitin-conjugating enzyme E2I (UBC9 homolog, yeast) | 16p13.3 |
| 208770_s_at | 0.0005681 | −2 | EIF4EBP2 | eukaryotic translation initiation factor 4E binding protein 2 (EIF4EBP2), mRNA. | 10q21-q22 |
| 208771_s_at | 2.10E−05 | −2.6 | LTA4H | leukotriene A4 hydrolase (LTA4H), mRNA. | 12q22 |
| 208781_x_at | 0.0006007 | −2.2 | SNX3 | sorting nexin 3 (SNX3), transcript variant 1, mRNA. | 6q21 |
| 208791_at | 0.0001028 | −4.4 | CLU | clusterin (complement lysis inhibitor, SP-40,40, sulfated glycoprotein 2, testosterone-repressed prostate message 2, apolipoprotein J) (CLU), transcript variant 1, mRNA. | 8p21-p12 |
| 208792_s_at | 0.0001175 | −4.5 | CLU | clusterin (complement lysis inhibitor, SP-40,40, sulfated glycoprotein 2, testosterone-repressed prostate message 2, apolipoprotein J) (CLU), transcript variant 1, mRNA. | 8p21-p12 |
| 208794_s_at | 1.47E−05 | 2.4 | SMARCA4 | SWI/SNF related, matrix associated, actin dependent regulator of chromatin, subfamily a, member 4 (SMARCA4), mRNA. | 19p13.2 |
| 208796_s_at | 0.0001639 | −2.6 | CCNG1 | cyclin G1 (CCNG1), transcript variant 2, mRNA. | 5q32-q34 |
| 208848_at | 1.50E−06 | −3.7 | ADH5 | alcohol dehydrogenase 5 (class III), chi polypeptide (ADH5), mRNA. | 4q21-q25 |
| 208860_s_at | 0.0001719 | −2 | ATRX | alpha thalassemia/mental retardation syndrome X-linked (RAD54 homolog, S. cerevisiae) (ATRX), transcript variant 2, mRNA. | Xq13.1-q21.1 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 208873_s_at | 5.10E−05 | −2.1 | C5orf18 | chromosome 5 open reading frame 18 (C5orf18), mRNA. | 5q22-q23 |
| 208920_at | 0.0003111 | −2.3 | SRI | sorcin (SRI), transcript variant 2, mRNA. | 7q21.1 |
| 208925_at | 0.0005429 | −2.3 | C3orf4 | chromosome 3 open reading frame 4 (C3orf4), mRNA. | 3p11-q11 |
| 208950_s_at | 0.0004293 | −2.3 | ALDH7A1 | aldehyde dehydrogenase 7 family, member A1 (ALDH7A1), mRNA. | 5q31 |
| 208951_at | 4.20E−05 | −2.8 | ALDH7A1 | aldehyde dehydrogenase 7 family, member A1 (ALDH7A1), mRNA. | 5q31 |
| 208962_s_at | 0.0003548 | −2.4 | FADS1 | fatty acid desaturase 1 (FADS1), mRNA. | 11q12.2-q13.1 |
| 208990_s_at | 5.40E−05 | −2.2 | HNRPH3 | heterogeneous nuclear ribonucleoprotein H3 (2H9) (HNRPH3), transcript variant 2H9A, mRNA. | 10q22 |
| 209009_at | 1.50E−06 | −3 | ESD | esterase D/formylglutathione hydrolase (ESD), mRNA. | 13q14.1-q14.2 |
| 209030_s_at | 3.07E−05 | 2.6 | IGSF4 | immunoglobulin superfamily, member 4 (IGSF4), mRNA. | 11q23.2 |
| 209034_at | 3.20E−06 | −4.5 | PNRC1 | proline-rich nuclear receptor coactivator 1 (PNRC1), mRNA. | 6q15 |
| 209068_at | 1.00E−06 | −3.5 | HNRPDL | heterogeneous nuclear ribonucleoprotein D-like (HNRPDL), transcript variant 2, mRNA. | 4q13-q21 |
| 209081_s_at | 8.30E−06 | 5 | COL18A1 | collagen, type XVIII, alpha 1 (COL18A1), transcript variant 2, mRNA. | 21q22.3 |
| 209082_s_at | 4.04E−05 | 5.1 | COL18A1 | collagen, type XVIII, alpha 1 (COL18A1), transcript variant 2, mRNA. | 21q22.3 |
| 209137_s_at | 0.0007917 | −2.1 | USP10 | ubiquitin specific peptidase 10 (USP10), mRNA. | 16q24.1 |
| 209143_s_at | 0.0009179 | −2.1 | CLNS1A | chloride channel, nucleotide-sensitive, 1A (CLNS1A), mRNA. | 11q13.5-q14 |
| 209146_at | 0.0002317 | −3.2 | SC4MOL | sterol-C4-methyl oxidase-like (SC4MOL), transcript variant 2, mRNA. | 4q32-q34 |
| 209169_at | 0.0003677 | 4.2 | GPM6B | glycoprotein M6B (GPM6B), transcript variant 1, mRNA. | Xp22.2 |
| 209170_s_at | 0.00014 | 5.8 | GPM6B | glycoprotein M6B (GPM6B), transcript variant 4, mRNA. | Xp22.2 |
| 209243_s_at | 3.90E−06 | −7.7 | PEG3 | paternally expressed 3 (PEG3), mRNA. | 19q13.4 |
| 209305_s_at | 0.0001816 | −3.7 | GADD45B | growth arrest and DNA-damage-inducible, beta (GADD45B), mRNA. | 19p13.3 |
| 209337_at | 4.01E−05 | −3 | PSIP1 | PC4 and SFRS1 interacting protein 1 (PSIP1), transcript variant 2, mRNA. | 9p22.3 |
| 209357_at | 5.76E−05 | −3.3 | CITED2 | Cbp/p300-interacting transactivator, with Glu/Asp-rich carboxy-terminal domain, 2 (CITED2), mRNA. | 6q23.3 |
| 209360_s_at | 7.44E−05 | 4.8 | RUNX1 | runt-related transcription factor 1 (acute myeloid leukemia 1; aml1 oncogene) (RUNX1), transcript variant 1, mRNA. | 21q22.3 |
| 209384_at | 0.0002565 | −2 | PROSC | proline synthetase co-transcribed homolog (bacterial) (PROSC), mRNA. | 8p11.2 |
| 209385_s_at | 3.63E−05 | −2.6 | PROSC | proline synthetase co-transcribed homolog (bacterial) (PROSC), mRNA. | 8p11.2 |
| 209447_at | 3.84E−05 | −2.5 | SYNE1 | spectrin repeat containing, nuclear envelope 1 (SYNE1), transcript variant alpha, mRNA. | 6q25 |
| 209512_at | 3.90E−06 | −3.9 | HSDL2 | hydroxysteroid dehydrogenase like 2 (HSDL2), mRNA. | 9q32 |
| 209513_s_at | 1.94E−05 | −3.9 | HSDL2 | hydroxysteroid dehydrogenase like 2 (HSDL2), mRNA. | 9q32 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 209596_at | 4.80E−06 | 6.9 | MXRA5 | matrix-remodelling associated 5 (MXRA5), mRNA. | Xp22.33 |
| 209605_at | 0.0004157 | −2.4 | TST | thiosulfate sulfurtransferase (rhodanese) (TST), nuclear gene encoding mitochondrial protein, mRNA. | 22q13.1 |
| 209612_s_at | 0.0001328 | −4.5 | ADH1B | alcohol dehydrogenase IB (class I), beta polypeptide (ADH1B), mRNA. | 4q21-q23 |
| 209613_s_at | 0.0003092 | −5.8 | ADH1B | alcohol dehydrogenase IB (class I), beta polypeptide (ADH1B), mRNA. | 4q21-q23 |
| 209633_at | 0.0006246 | −2.2 | PPP2R3A | protein phosphatase 2 (formerly 2A), regulatory subunit B", alpha (PPP2R3A), transcript variant 2, mRNA. | 3q22.1 |
| 209657_s_at | 0.0003701 | −2.1 | HSF2 | heat shock transcription factor 2 (HSF2), mRNA. | 6q22.31 |
| 209685_s_at | 1.10E−05 | 3.7 | PRKCB1 | protein kinase C, beta 1 (PRKCB1), transcript variant 2, mRNA. | 16p11.2 |
| 209733_at | 1.64E−05 | −2.7 | LOC286440 | Hypothetical protein LOC286440 | Xq22.3 |
| 209737_at | 0.0003955 | −2.2 | MAGI2 | membrane associated guanylate kinase, WW and PDZ domain containing 2 (MAGI2), mRNA. | 7q21 |
| 209875_s_at | 9.40E−06 | 9.5 | SPP1 | secreted phosphoprotein 1 (osteopontin, bone sialoprotein I, early T-lymphocyte activation 1) (SPP1), mRNA. | 4q21-q25 |
| 209894_at | 0.0001625 | −4.2 | LEPR | leptin receptor (LEPR), transcript variant 2, mRNA. | 1p31 |
| 209897_s_at | 0.0001202 | 2.5 | SLIT2 | slit homolog 2 (*Drosophila*) (SLIT2), mRNA. | 4p15.2 |
| 209969_s_at | 1.51E−05 | 3.7 | STAT1 | signal transducer and activator of transcription 1, 91 kDa (STAT1), transcript variant beta, mRNA. | 2q32.2 |
| 210048_at | 0.0008484 | 2.2 | NAPG | N-ethylmaleimide-sensitive factor attachment protein, gamma (NAPG), mRNA. | 18p11.22 |
| 210069_at | 3.07E−05 | 2.8 | CPT1B | carnitine palmitoyltransferase 1B (muscle) (CPT1B), nuclear gene encoding mitochondrial protein, transcript variant 3, mRNA. | 22q13.33 |
| 210365_at | 0.0002181 | 2.6 | RUNX1 | Runt-related transcription factor 1 (acute myeloid leukemia 1; aml1 oncogene) | 21q22.3 |
| 210438_x_at | 0.0003684 | −2.7 | TROVE2 | TROVE domain family, member 2 (TROVE2), mRNA. | 1q31 |
| 210621_s_at | 0.0004078 | −2.1 | RASA1 | RAS p21 protein activator (GTPase activating protein) 1 (RASA1), transcript variant 2, mRNA. | 5q13.3 |
| 210664_s_at | 0.0006973 | 2.4 | TFPI | tissue factor pathway inhibitor (lipoprotein-associated coagulation inhibitor) (TFPI), transcript variant 1, mRNA. | 2q31-q32.1 |
| 210665_at | 0.0003981 | 3.1 | TFPI | tissue factor pathway inhibitor (lipoprotein-associated coagulation inhibitor) (TFPI), transcript variant 2, mRNA. | 2q31-q32.1 |
| 210679_x_at | 0.000265 | 3.4 | BCL7A | B-cell CLL/lymphoma 7A | 12q24.13 |
| 210788_s_at | 1.26E−05 | −3.1 | DHRS7 | dehydrogenase/reductase (SDR family) member 7 (DHRS7), mRNA. | 14q23.1 |
| 210800_at | 0.0009706 | 4.7 | MGC12262 | hypothetical protein MGC12262 | |
| 210809_s_at | 0.0002365 | 6.7 | POSTN | periostin, osteoblast specific factor (POSTN), mRNA. | 13q13.3 |
| 210944_s_at | 0.0009253 | 2.3 | CAPN3 | calpain 3, (p94) (CAPN3), transcript variant 7, mRNA. | 15q15.1-q21.1 |
| 210950_s_at | 1.38E−05 | −3.3 | FDFT1 | farnesyl-diphosphate farnesyltransferase 1 (FDFT1), mRNA. | 8p23.1-p22 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 211040_x_at | 0.0006364 | 2.4 | GTSE1 | G-2 and S-phase expressed 1 (GTSE1), mRNA. | 22q13.2-q13.3 |
| 211276_at | 8.52E−05 | −5.6 | TCEAL2 | transcription elongation factor A (SII)-like 2 (TCEAL2), mRNA. | Xq22.1-q22.3 |
| 211423_s_at | 0.000164 | −2.8 | SCSDL | sterol-C5-desaturase (ERG3 delta-5-desaturase homolog, fungal)-like (SC5DL), transcript variant 1, mRNA. | 11q23.3 |
| 211445_x_at | 0.0007153 | 3.6 | FKSG17 | FKSG17 | 8q22.3 |
| 211452_x_at | 5.23E−05 | 3.4 | LRRFIP1 | leucine rich repeat (in FLII) interacting protein 1 (LRRFIP1), mRNA. | 2q37.3 |
| 211454_x_at | 0.0006917 | 3.7 | | | |
| 211569_s_at | 2.66E−05 | −5.7 | HADHSC | L-3-hydroxyacyl-Coenzyme A dehydrogenase, short chain (HADHSC), mRNA. | 4q22-q26 |
| 211597_s_at | 1.00E−07 | 13.1 | HOP | homeodomain-only protein (HOP), transcript variant 2, mRNA. | 4q11-q12 |
| 211623_s_at | 0.0008386 | −2.2 | FBL | fibrillarin (FBL), mRNA. | 19q13.1 |
| 211666_x_at | 9.60E−06 | −2.6 | RPL3 | ribosomal protein L3 (RPL3), mRNA. | 22q13 |
| 211673_s_at | 5.65E−05 | 3.5 | MOCS1 | Molybdenum cofactor synthesis 1 | 6p21.3 |
| 211710_x_at | 0.0001136 | −2.2 | RPL4 | ribosomal protein L4 (RPL4), mRNA. | 15q22 |
| 211725_s_at | 0.0006346 | 2.4 | BID | BH3 interacting domain death agonist (BID), transcript variant 3, mRNA. | 22q11.1 |
| 211727_s_at | 0.0004584 | −2.5 | COX11 | COX11 homolog, cytochrome c oxidase assembly protein (yeast) (COX11), nuclear gene encoding mitochondrial protein, mRNA. | 17q22 |
| 211749_s_at | 7.41E−05 | −2.6 | VAMP3 | vesicle-associated membrane protein 3 (cellubrevin) (VAMP3), mRNA. | 1p36.23 |
| 211762_s_at | 0.0002377 | 2.3 | KPNA2 | karyopherin alpha 2 (RAG cohort 1, importin alpha 1) (KPNA2), mRNA. | 17q23.1-q23.3 |
| 211769_x_at | 4.67E−05 | −2.4 | TDE1 | tumor differentially expressed 1 (TDE1), transcript variant 1, mRNA. | 20q13.1-13.3 |
| 211813_x_at | 1.69E−05 | −4.8 | DCN | decorin (DCN), transcript variant D, mRNA. | 12q21.33 |
| 211896_s_at | 0.0006287 | −3.7 | DCN | decorin (DCN), transcript variant C, mRNA. | 12q21.33 |
| 211937_at | 0.0001012 | −3.2 | EIF4B | eukaryotic translation initiation factor 4B (EIF4B), mRNA. | 12q13.13 |
| 211938_at | 3.00E−07 | −3.2 | EIF4B | eukaryotic translation initiation factor 4B (EIF4B), mRNA. | 12q13.13 |
| 211941_s_at | 2.01E−05 | −2.3 | PBP | prostatic binding protein (PBP), mRNA. | 12q24.23 |
| 211942_x_at | 7.02E−05 | −2.8 | RPL13A | Ribosomal protein L13a | 19q13.3 |
| 211964_at | 0.0006935 | 3.4 | COL4A2 | Collagen, type IV, alpha 2 | 13q34 |
| 211980_at | 0.0005493 | 3.9 | COL4A1 | collagen, type IV, alpha 1 (COL4A1), mRNA. | 13q34 |
| 211986_at | 3.42E−05 | −3.3 | AHNAK | AHNAK nucleoprotein (desmoyokin) (AHNAK), transcript variant 1, mRNA. | 11q12.2 |
| 211988_at | 1.30E−05 | −2.2 | SMARCE1 | SWI/SNF related, matrix associated, actin dependent regulator of chromatin, subfamily e, member 1 (SMARCE1), mRNA. | 17q21.2 |
| 211994_at | 0.0001256 | −2 | | Transcribed locus, strongly similar to XP_508919.1 PREDICTED: similar to protein kinase, lysine deficient 1; kinase deficient protein [Pan troglodytes] | 12 |
| 211997_x_at | 5.21E−05 | −2.5 | H3F3B | H3 histone, family 3B (H3.3B) (H3F3B), mRNA. | 17q25 |
| 211998_at | 7.80E−05 | −3 | H3F3B | H3 histone, family 3B (H3.3B) (H3F3B), mRNA. | 17q25 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 212037_at | 0.0001271 | −2.7 | PNN | Pinin, desmosome associated protein | 14q21.1 |
| 212044_s_at | 9.00E−07 | 3.4 | RPL27A | ribosomal protein L27a (RPL27A), mRNA. | 11p15 |
| 212052_s_at | 0.0005363 | 2 | KIAA0676 | KIAA0676 protein (KIAA0676), transcript variant 2, mRNA. | 5q35.3 |
| 212094_at | 0.0001189 | −4.8 | PEG10 | PREDICTED: paternally expressed 10 (PEG10), mRNA. | 7 |
| 212096_s_at | 0.0002831 | −2.7 | MTUS1 | mitochondrial tumor suppressor 1 (MTUS1), nuclear gene encoding mitochondrial protein, transcript variant 5, mRNA. | 8p22 |
| 212131_at | 4.28E−05 | −2 | FAM61A | family with sequence similarity 61, member A (FAM61A), mRNA. | 19q13.11 |
| 212134_at | 0.0003033 | 2 | PHLDB1 | pleckstrin homology-like domain, family B, member 1 (PHLDB1), mRNA. | 11q23.3 |
| 212144_at | 0.0005431 | −2.1 | UNC84B | unc-84 homolog B (C. elegans) (UNC84B), mRNA. | 22q13.1 |
| 212148_at | 9.20E−06 | −2.9 | PBX1 | Pre-B-cell leukemia transcription factor 1 | 1q23 |
| 212151_at | 0.0001748 | −2.5 | PBX1 | Pre-B-cell leukemia transcription factor 1 | 1q23 |
| 212171_x_at | 0.0006474 | 3.3 | VEGF | vascular endothelial growth factor (VEGF), transcript variant 6, mRNA. | 6p12 |
| 212179_at | 0.0003184 | −2.5 | C6orf111 | Chromosome 6 open reading frame 111 | 6q16.3 |
| 212188_at | 0.000184 | −2.9 | KCTD12 | potassium channel tetramerisation domain containing 12 (KCTD12), mRNA. | 13q22.3 |
| 212195_at | 0.0002328 | −2.1 | IL6ST | Interleukin 6 signal transducer (gp130, oncostatin M receptor) | 5q11 |
| 212199_at | 0.0001637 | −2.5 | MRFAP1L1 | Morf4 family associated protein 1-like 1 (MRFAP1L1), transcript variant 2, mRNA. | 4p16.1 |
| 212215_at | 0.0001021 | −2.8 | PREPL | prolyl endopeptidase-like (PREPL), mRNA. | 2p22.1 |
| 212224_at | 1.18E−05 | −4.3 | ALDH1A1 | aldehyde dehydrogenase 1 family, member A1 (ALDH1A1), mRNA. | 9q21.13 |
| 212236_x_at | 0.0002768 | 5.3 | KRT17 | keratin 17 (KRT17), mRNA. | 17q12-q21 |
| 212254_s_at | 4.00E−06 | −2.7 | DST | dystonin (DST), transcript variant 1eA, mRNA. | 6p12-p11 |
| 212256_at | 0.0007645 | −2.9 | GALNT10 | UDP-N-acetyl-alpha-D-galactosamine:polypeptide N-acetylgalactosaminyltransferase 10 (GalNAc-T10) | 5q33.2 |
| 212323_s_at | 2.11E−05 | 2.5 | VPS13D | vacuolar protein sorting 13D (yeast) (VPS13D), transcript variant 2, mRNA. | 1p36.22-p36.21 |
| 212351_at | 8.00E−06 | 2.2 | EIF2B5 | eukaryotic translation initiation factor 2B, subunit 5 epsilon, 82 kDa (EIF2B5), mRNA. | 3q27.1 |
| 212353_at | 0.000225 | 3.6 | SULF1 | sulfatase 1 (SULF1), mRNA. | 8q13.2-q13.3 |
| 212354_at | 0.0002219 | 2.9 | SULF1 | sulfatase 1 (SULF1), mRNA. | 8q13.2-q13.3 |
| 212365_at | 0.0003347 | 4.1 | MYO1B | myosin IB (MYO1B), mRNA. | 2q12-q34 |
| 212368_at | 0.0002867 | −2.3 | ZNF292 | PREDICTED: zinc finger protein 292 (ZNF292), mRNA. | 6 |
| 212408_at | 1.41E−05 | −2.6 | TOR1AIP1 | torsin A interacting protein 1 (TOR1AIP1), mRNA. | 1q24.2 |
| 212413_at | 0.0005848 | 2 | 6-Sep | septin 6 (SEPT6), transcript variant II, mRNA. | Xq24 |
| 212414_s_at | 0.0001527 | 2.4 | 6-Sep | septin 6 (SEPT6), transcript variant II, mRNA. | Xq24 |
| 212435_at | 0.0003489 | −2.3 | TRIM33 | tripartite motif-containing 33 (TRIM33), transcript variant b, mRNA. | 1p13.1 |
| 212468_at | 0.0001247 | −2 | SPAG9 | Sperm associated antigen 9 | 17q21.33 |
| 212498_at | 1.50E−06 | −2.7 | MARCH-VI | Membrane-associated ring finger (C3HC4) 6 | 5p15.2 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 212510_at | 0.0004844 | −3.1 | GPD1L | glycerol-3-phosphate dehydrogenase 1-like (GPD1L), mRNA. | 3p24.1 |
| 212520_s_at | 3.25E−05 | 3.1 | SMARCA4 | SWI/SNF related, matrix associated, actin dependent regulator of chromatin, subfamily a, member 4 (SMARCA4), mRNA. | 19p13.2 |
| 212526_at | 6.11E−05 | −2.3 | SPG20 | spastic paraplegia 20, spartin (Troyer syndrome) (SPG20), mRNA. | 13q13.3 |
| 212549_at | 6.64E−05 | −2.4 | STAT5B | signal transducer and activator of transcription 5B (STAT5B), mRNA. | 17q11.2 |
| 212556_at | 0.0003565 | 2.8 | SCRIB | scribbled homolog (Drosophila) (SCRIB), transcript variant 2, mRNA. | 8q24.3 |
| 212586_at | 0.0004909 | −2.1 | CAST | calpastatin (CAST), transcript variant 2, mRNA. | 5q15-q21 |
| 212595_s_at | 0.0007053 | −2 | DAZAP2 | DAZ associated protein 2 (DAZAP2), mRNA. | 12q12 |
| 212609_s_at | 1.85E−05 | −2.4 | AKT3 | V-akt murine thymoma viral oncogene homolog 3 (protein kinase B, gamma) | 1q43-q44 |
| 212624_s_at | 5.40E−06 | 6.9 | CHN1 | chimerin (chimaerin) 1 (CHN1), transcript variant 2, mRNA. | 2q31-q32.1 |
| 212632_at | 0.0008287 | −2 | STX7 | Syntaxin 7 | 6q23.1 |
| 212638_s_at | 0.0007524 | −2.2 | WWP1 | WW domain containing E3 ubiquitin protein ligase 1 (WWP1), mRNA. | 8q21 |
| 212644_s_at | 0.0001184 | −2.3 | C14orf32 | chromosome 14 open reading frame 32 (C14orf32), mRNA. | 14q22.2-q22.3 |
| 212646_at | 0.0003295 | 2.6 | RAFTLIN | raft-linking protein (RAFTLIN), mRNA. | 3p25.1-p24.3 |
| 212653_s_at | 3.00E−07 | −3.8 | EHBP1 | EH domain binding protein 1 (EHBP1), mRNA. | 2p15 |
| 212675_s_at | 0.0003318 | −3.5 | KIAA0582 | KIAA0582 | 2p14 |
| 212730_at | 0.0006706 | −3.4 | DMN | desmuslin (DMN), transcript variant B, mRNA. | 15p26.3 |
| 212731_at | 0.000105 | −3.3 | ANKRD46 | ankyrin repeat domain 46 (ANKRD46), mRNA. | 8q22.3 |
| 212751_at | 0.0003336 | −2.7 | UBE2N | ubiquitin-conjugating enzyme E2N (UBC13 homolog, yeast) (UBE2N), mRNA. | 12q22 |
| 212769_at | 0.000184 | 2.7 | TLE3 | Transducin-like enhancer of split 3 (E(sp1) homolog, Drosophila) | 15q22 |
| 212776_s_at | 0.0004769 | −3 | KIAA0657 | PREDICTED: KIAA0657 protein (KIAA0657), mRNA. | 2 |
| 212779_at | 0.0005762 | −2 | KIAA1109 | PREDICTED: hypothetical protein KIAA1109 (KIAA1109), mRNA. | 4 |
| 212798_s_at | 3.32E−05 | −2 | ANKMY2 | ankyrin repeat and MYND domain containing 2 (ANKMY2), mRNA. | 7p21 |
| 212809_at | 7.32E−05 | 2.6 | NFATC2IP | nuclear factor of activated T-cells, cytoplasmic, calcineurin-dependent 2 interacting protein (NFATC2IP), mRNA. | 16p11.2 |
| 212841_s_at | 0.0004662 | 2.6 | PPFIBP2 | PTPRF interacting protein, binding protein 2 (liprin beta 2) (PPFIBP2), mRNA. | 11p15.4 |
| 212943_at | 0.0009511 | −2.2 | KIAA0528 | KIAA0528 gene product (KIAA0528), mRNA. | 12p12.1 |
| 212971_at | 0.0004892 | 2.2 | CARS | Cysteinyl-tRNA synthetase | 11p15.5 |
| 213002_at | 7.97E−05 | 3.8 | MARCKS | myristoylated alanine-rich protein kinase C substrate (MARCKS), mRNA. | 6q22.2 |
| 213005_s_at | 0.0003887 | −2.3 | ANKRD15 | ankyrin repeat domain 15 (ANKRD15), transcript variant 1, mRNA. | 9p24.3 |
| 213027_at | 0.0001503 | −2.1 | SSA2 | TROVE domain family, member 2 | 1q31 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 213029_at | 6.18E−05 | −2.4 | NFIB | Nuclear factor I/B | 9p24.1 |
| 213047_x_at | 0.0003826 | −2.6 | SET | SET translocation (myeloid leukemia-associated) (SET), mRNA. | 9q34 |
| 213074_at | 0.0002338 | −2.6 | PHIP | Pleckstrin homology domain interacting protein | 6q14 |
| 213085_s_at | 0.0005289 | 3.8 | KIBRA | KIBRA protein (KIBRA), mRNA. | 5q34 |
| 213093_at | 1.80E−05 | −2.8 | PRKCA | protein kinase C, alpha (PRKCA), mRNA. | 17q22-q23.2 |
| 213110_s_at | 5.00E−06 | −3.9 | COL4A5 | collagen, type IV, alpha 5 (Alport syndrome) (COL4A5), transcript variant 1, mRNA. | Xq22 |
| 213111_at | 0.0006152 | −2 | PIP5K3 | phosphatidylinositol-3-phosphate/phosphatidylinositol 5-kinase, type III (PIP5K3), transcript variant 1, mRNA. | 2q34 |
| 213117_at | 0.0008783 | −2 | KLHL9 | kelch-like 9 (Drosophila) (KLHL9), mRNA. | 9p22 |
| 213139_at | 0.0008306 | 2.6 | SNAI2 | snail homolog 2 (Drosophila) (SNAI2), mRNA. | 8q11 |
| 213146_at | 0.000125 | 2.9 | KIAA0346 | KIAA0346 protein | 17p13.1 |
| 213224_s_at | 0.0005954 | −2 | LOC92482 | PREDICTED: hypothetical protein LOC92482 (LOC92482), mRNA. | 10 |
| 213227_at | 0.0001677 | −2 | PGRMC2 | Progesterone receptor membrane component 2 | 4q26 |
| 213248_at | 0.0006637 | 2.4 | LOC221362 | Hypothetical protein LOC221362 | 6p12.3 |
| 213258_at | 3.10E−05 | 2.5 | TFPI | Tissue factor pathway inhibitor (lipoprotein-associated coagulation inhibitor) | 2q31-q32.1 |
| 213272_s_at | 6.80E−06 | −4 | LOC57146 | promethin (LOC57146), mRNA. | 16p12 |
| 213344_s_at | 3.91E−05 | 2.7 | H2AFX | H2A histone family, member X (H2AFX), mRNA. | 11q23.2-q23.3 |
| 213350_at | 1.20E−05 | 6.1 | RPS11 | ribosomal protein S11 (RPS11), mRNA. | 19q13.3 |
| 213364_s_at | 4.00E−07 | −3.7 | SNX1 | sorting nexin 1 (SNX1), transcript variant 2, mRNA. | 15q22.31 |
| 213370_s_at | 0.0001347 | 2.1 | SFMBT1 | Scm-like with four mbt domains 1 (SFMBT1), transcript variant 3, mRNA. | 3p21.1 |
| 213397_x_at | 4.30E−06 | −5.2 | RNASE4 | ribonuclease, RNase A family, 4 (RNASE4), transcript variant 3, mRNA. | 14q11.1 |
| 213405_at | 0.000663 | −2.4 | RAB22A | RAB22A, member RAS oncogene family (RAB22A), mRNA. | 20q13.32 |
| 213413_at | 0.000589 | −2.4 | SBLF | stoned B-like factor (SBLF), mRNA. | 2p16.3 |
| 213418_at | 3.79E−05 | 6.8 | HSPA6 | heat shock 70 kDa protein 6 (HSP70B') (HSPA6), mRNA. | 1q23 |
| 213464_at | 0.0005718 | 2.7 | SHC2 | SHC (Src homology 2 domain containing) transforming protein 2 | 19p13.3 |
| 213479_at | 2.75E−05 | 4.3 | NPTX2 | neuronal pentraxin II (NPTX2), mRNA. | 7q21.3-q22.1 |
| 213523_at | 5.86E−05 | 2.6 | CCNE1 | cyclin E1 (CCNE1), transcript variant 2, mRNA. | 19q12 |
| 213560_at | 0.0005733 | 2.4 | GADD45B | growth arrest and DNA-damage-inducible, beta (GADD45B), mRNA. | 19p13.3 |
| 213574_s_at | 1.00E−06 | −2.4 | KPNB1 | Karyopherin (importin) beta 1 | 17q21.32 |
| 213605_s_at | 0.0009961 | 2.5 | FLJ40092 | FLJ40092 protein | 5q13.2 |
| 213661_at | 8.00E−07 | 6.2 | DKFZP586H2123 | regeneration associated muscle protease (DKFZP586H2123), transcript variant 2, mRNA. | 11p13 |
| 213687_s_at | 0.0009746 | −2.1 | RPL35A | ribosomal protein L35a (RPL35A), mRNA. | 3q29-qter |
| 213693_s_at | 7.45E−05 | 6.2 | MUC1 | mucin 1, transmembrane (MUC1), transcript variant 4, mRNA. | 1q21 |
| 213778_x_at | 0.000467 | 2.2 | ZFP276 | zinc finger protein 276 homolog (mouse) (ZFP276), mRNA. | 16q24.3 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 213790_at | 7.51E−05 | 4.4 | ADAM12 | A disintegrin and metalloproteinase domain 12 (meltrin alpha) | 10q26.3 |
| 213803_at | p < 1e−07 | −3.6 | KPNB1 | Karyopherin (importin) beta 1 | 17q21.32 |
| 213836_s_at | 0.0001261 | 2.2 | WIPI49 | WD40 repeat protein Interacting with phosphoInositides of 49 kDa (WIPI49), mRNA. | 17q24.2 |
| 213848_at | 2.00E−07 | 3.1 | DUSP7 | Dual specificity phosphatase 7 | 3p21 |
| 213869_x_at | 0.0002103 | 4.6 | THY1 | Thy-1 cell surface antigen (THY1), mRNA. | 11q22.3-q23 |
| 213895_at | 0.0004485 | −2.5 | EMP1 | Epithelial membrane protein 1 | 12p12.3 |
| 213900_at | 3.89E−05 | −2.7 | C9orf61 | chromosome 9 open reading frame 61 (C9orf61), mRNA. | 9q13-q21 |
| 213905_x_at | 0.0001976 | 4.6 | BGN | Biglycan | Xq28 |
| 213943_at | 4.00E−07 | 19 | TWIST1 | twist homolog 1 (acrocephalosyndactyly 3; Saethre-Chotzen syndrome) (*Drosophila*) (TWIST1), mRNA. | 7p21.2 |
| 213979_s_at | 0.0002226 | 3.3 | CTBP1 | C-terminal binding protein 1 (CTBP1), transcript variant 1, mRNA. | 4p16 |
| 214023_x_at | 0.000646 | 2.8 | MGC8685 | Tubulin, beta polypeptide paralog | 6p25 |
| 214041_x_at | 0.000362 | 2.8 | RPL37A | Ribosomal protein L37a | 2q35 |
| 214052_x_at | 0.0005361 | 2.7 | BAT2D1 | BAT2 domain containing 1 (BAT2D1), mRNA. | 1q23.3 |
| 214057_at | 0.0005414 | 2.3 | MCL1 | myeloid cell leukemia sequence 1 (BCL2-related) (MCL1), transcript variant 2, mRNA. | 1q21 |
| 214081_at | 4.00E−07 | 10.2 | PLXDC1 | plexin domain containing 1 (PLXDC1), mRNA. | 17q21.1 |
| 214097_at | 2.29E−05 | −2.3 | RPS21 | Ribosomal protein S21 | 20q13.3 |
| 214110_s_at | 0.0001953 | 3 | | ESTs, Highly similar to A43542 lymphocyte-specific protein 1 [*H. sapiens*] | |
| 214140_at | 0.0004058 | 2 | SLC25A16 | solute carrier family 25 (mitochondrial carrier; Graves disease autoantigen), member 16 (SLC25A16), nuclear gene encoding mitochondrial protein, mRNA. | 10q21.3 |
| 214149_s_at | 0.0003428 | 3.4 | ATP6V0E | ATPase, H+ transporting, lysosomal 9 kDa, V0 subunit e | 5q35.1 |
| 214177_s_at | 0.0001027 | −2.2 | PBXIP1 | pre-B-cell leukemia transcription factor interacting protein 1 (PBXIP1), mRNA. | 1q22 |
| 214264_s_at | 0.0002244 | 2.1 | C14orf143 | chromosome 14 open reading frame 143 (C14orf143), mRNA. | 14q32.11 |
| 214316_x_at | 7.97E−05 | 2.4 | CALR | Calreticulin | 19p13.3-p13.2 |
| 214359_s_at | 0.0001495 | −3 | HSPCB | heat shock 90 kDa protein 1, beta (HSPCB), mRNA. | 6p12 |
| 214426_x_at | 0.0008417 | 2.1 | CHAF1A | chromatin assembly factor 1, subunit A (p150) (CHAF1A), mRNA. | 19p13.3 |
| 214435_x_at | 0.0005753 | 2.8 | RALA | v-ral simian leukemia viral oncogene homolog A (ras related) (RALA), mRNA. | 7p15-p13 |
| 214438_at | 0.0009565 | 3.4 | HLX1 | H2.0-like homeo box 1 (*Drosophila*) (HLX1), mRNA. | 1q41-q42.1 |
| 214527_s_at | 4.20E−06 | −2.3 | PQBP1 | polyglutamine binding protein 1 (PQBP1), transcript variant 5, mRNA. | Xp11.23 |
| 214594_x_at | 0.0002968 | 2.9 | ATP8B1 | ATPase, Class I, type 8B, member 1 | 18q21-q22 |
| 214707_x_at | 0.0003366 | 2.8 | ALMS1 | Alstrom syndrome 1 | 2p13 |
| 214715_x_at | 0.0002241 | 4.3 | ZNF160 | zinc finger protein 160 (ZNF160), transcript variant 1, mRNA. | 19q13.41 |
| 214724_at | 0.0006038 | −2.1 | DIXDC1 | DIX domain containing 1 (DIXDC1), mRNA. | 11q23.2 |
| 214737_x_at | 0.0004018 | −2.2 | HNRPC | heterogeneous nuclear ribonucleoprotein C (C1/C2) (HNRPC), transcript variant 2, mRNA. | 14q11.2 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 214855_s_at | 4.03E−05 | −2.6 | GARNL1 | GTPase activating Rap/RanGAP domain-like 1 (GARNL1), transcript variant 2, mRNA. | 14q13.2 |
| 214862_x_at | 0.0009591 | −2.8 | | MRNA; cDNA DKFZp564G1162 (from clone DKFZp564G1162) | 10 |
| 214924_s_at | 2.90E−06 | 3.8 | OIP106 | OGT(O-Glc-NAc transferase)-interacting protein 106 KDa (OIP106), mRNA. | 3p25.3-p24.1 |
| 215016_x_at | 1.50E−05 | −2.3 | DST | dystonin (DST), transcript variant 1, mRNA. | 6p12-p11 |
| 215046_at | 0.0006908 | −2.2 | FLJ23861 | hypothetical protein FLJ23861 (FLJ23861), mRNA. | 2q34 |
| 215073_s_at | 3.83E−05 | −2.1 | NR2F2 | nuclear receptor subfamily 2, group F, member 2 (NR2F2), mRNA. | 15q26 |
| 215076_s_at | 0.000876 | 3 | COL3A1 | collagen, type III, alpha 1 (Ehlers-Danlos syndrome type IV, autosomal dominant) (COL3A1), mRNA. | 2q31 |
| 215179_x_at | 6.80E−05 | 4.5 | PGF | Placental growth factor, vascular endothelial growth factor-related protein | 14q24-q31 |
| 215203_at | 0.0006265 | 2.2 | GOLGA4 | Golgi autoantigen, golgin subfamily a, 4 | 3p22-p21.3 |
| 215206_at | 0.0001618 | 3.1 | EXT1 | Exostoses (multiple) 1 | 8q24.11-q24.13 |
| 215208_x_at | 0.0006292 | 3.4 | RPL35A | Ribosomal protein L35a | 3q29-qter |
| 215294_s_at | 8.91E−05 | −2.9 | SMARCA1 | SWI/SNF related, matrix associated, actin dependent regulator of chromatin, subfamily a, member 1 (SMARCA1), transcript variant 2, mRNA. | Xq25 |
| 215306_at | 0.0008848 | −3.4 | LHCGR | Luteinizing hormone/choriogonadotropin receptor | 2p21 |
| 215336_at | 9.25E−05 | 2.7 | AKAP11 | A kinase (PRKA) anchor protein 11 (AKAP11), transcript variant 2, mRNA. | 13q14.11 |
| 215373_x_at | 0.0004506 | 2.8 | SET8 | PR/SET domain containing protein 8 | 12q24.31 |
| 215383_x_at | 0.0009763 | 2.6 | SPG21 | Spastic paraplegia 21 (autosomal recessive, Mast syndrome) | 15q21-q22 |
| 215404_x_at | 0.0005104 | 3.2 | FGFR1 | Fibroblast growth factor receptor 1 (fms-related tyrosine kinase 2, Pfeiffer syndrome) | 8p11.2-p11.1 |
| 215467_x_at | 0.0004682 | 3.9 | DHX9 | DEAH (Asp-Glu-Ala-His) box polypeptide 9 | 1q25 |
| 215504_x_at | 0.0006038 | 2.5 | ANKRD10 | Ankyrin repeat domain 10 | 13q34 |
| 215529_x_at | 0.0007444 | 2.6 | C21orf106 | Chromosome 21 open reading frame 106 | 21q22.3 |
| 215566_x_at | 0.0007954 | 2.2 | LYPLA2 | lysophospholipase II (LYPLA2), mRNA. | 1p36.12-p35.1 |
| 215577_at | 5.29E−05 | 2.4 | UBE2E1 | Ubiquitin-conjugating enzyme E2E 1 (UBC4/5 homolog, yeast) | 3p24.2 |
| 215588_x_at | 6.38E−05 | 3.7 | RIOK3 | RIO kinase 3 (yeast) | 18q11.2 |
| 215599_at | 4.10E−06 | 3.9 | SMA4 | SMA4 | 5q13 |
| 215600_x_at | 0.0005929 | 3.3 | FBXW12 | F-box and WD-40 domain protein 12 | 3p21.31 |
| 215604_x_at | 0.0003643 | 3.8 | UBE2D2 | Ubiquitin-conjugating enzyme E2D 2 (UBC4/5 homolog, yeast) | 5q31.2 |
| 215628_x_at | 0.0005005 | 2.7 | PPP2CA | Protein phosphatase 2 (formerly 2A), catalytic subunit, alpha isoform | 5q31.1 |
| 215978_x_at | 9.04E−05 | 5.6 | LOC152719 | ATP-binding cassette, sub-family A (ABC1), member 11 (pseudogene) | 4p16.3 |
| 216035_x_at | 0.000632 | −2 | TCF7L2 | Transcription factor 7-like 2 (T-cell specific, HMG-box) | 10q25.3 |
| 216051_x_at | 5.83E−05 | 5 | KIAA1217 | KIAA1217 | 10p12.31 |
| 216187_x_at | 0.0001456 | 3.7 | XRCC3 | X-ray repair complementing defective repair in Chinese hamster cells 3 | 14q32.3 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 216215_s_at | 7.67E−05 | −2.1 | RBM9 | RNA binding motif protein 9 | 22q13.1 |
| 216221_s_at | 0.0007062 | −2 | PUM2 | pumilio homolog 2 (*Drosophila*) (PUM2), mRNA. | 2p22-p21 |
| 216241_s_at | 0.0005875 | −2.1 | TCEA1 | transcription elongation factor A (SII), 1 (TCEA1), transcript variant 2, mRNA. | 8q11.2 |
| 216246_at | 0.0004251 | 2.7 | RPS20 | ribosomal protein S20 (RPS20), mRNA. | 8q12 |
| 216274_s_at | 0.0003437 | −2.3 | SEC11L1 | SEC11-like 1 (*S. cerevisiae*) (SEC11L1), mRNA. | 15q25.3 |
| 216733_s_at | 0.0005519 | −3.3 | GATM | glycine amidinotransferase (L-arginine:glycine amidinotransferase) (GATM), mRNA. | 15q21.1 |
| 216858_x_at | 0.0002005 | 4.1 | | | |
| 216859_x_at | 0.0004599 | 3.7 | | | |
| 216944_s_at | 0.0001923 | −2.7 | ITPR1 | inositol 1,4,5-triphosphate receptor, type 1 (ITPR1), mRNA. | 3p26-p25 |
| 217028_at | 0.000384 | 3.4 | CXCR4 | chemokine (C—X—C motif) receptor 4 (CXCR4), transcript variant 2, mRNA. | 2q21 |
| 217118_s_at | 2.15E−05 | 2.2 | C22orf9 | chromosome 22 open reading frame 9 (C22orf9), transcript variant 2, mRNA. | 22q13.31 |
| 217466_x_at | 0.0009002 | −2.2 | RPS2 | Ribosomal protein S2 | 16p13.3 |
| 217497_at | 0.0002299 | 3.3 | ECGF1 | Endothelial cell growth factor 1 (platelet-derived) | 22q13 |
| 217579_x_at | 0.0006875 | 2.5 | ARL6IP2 | ADP-ribosylation factor-like 6 interacting protein 2 | 2p22.2-p22.1 |
| 217586_x_at | 0.000568 | 2.9 | | ESTs | |
| 217679_x_at | 7.86E−05 | 4.8 | | ESTs, Weakly similar to hypothetical protein FLJ20489 [*Homo sapiens*] [*H. sapiens*] | |
| 217713_x_at | 0.0001301 | 3.4 | | ESTs, Weakly similar to ALU6_HUMAN ALU SUBFAMILY SP SEQUENCE CONTAMINATION WARNING ENTRY [*H. sapiens*] | |
| 217715_x_at | 0.0002336 | 3.9 | | ESTs | |
| 217773_s_at | 0.0002007 | −2.4 | NDUFA4 | NADH dehydrogenase (ubiquinone) 1 alpha subcomplex, 4, 9 kDa (NDUFA4), nuclear gene encoding mitochondrial protein, mRNA. | 7p21.3 |
| 217774_s_at | 0.0007057 | −2.1 | HSPC152 | hypothetical protein HSPC152 (HSPC152), mRNA. | 11q13.1 |
| 217781_s_at | 0.0003457 | −2.5 | ZFP106 | zinc finger protein 106 homolog (mouse) (ZFP106), mRNA. | 15q15.1 |
| 217787_s_at | 8.07E−05 | 2.7 | GALNT2 | UDP-N-acetyl-alpha-D-galactosamine:polypeptide N-acetylgalactosaminyltransferase 2 (GalNAc-T2) (GALNT2), mRNA. | 1q41-q42 |
| 217795_s_at | 0.0001341 | −2.1 | TMEM43 | transmembrane protein 43 (TMEM43), mRNA. | 3p25.1 |
| 217814_at | 0.0004705 | −2.2 | GK001 | GK001 protein (GK001), mRNA. | 17q23.3 |
| 217833_at | 0.000595 | −2.5 | SYNCRIP | Synaptotagmin binding, cytoplasmic RNA interacting protein | 6q14-q15 |
| 217862_at | 0.000351 | −2.6 | PIAS1 | Protein inhibitor of activated STAT, 1 | 15q |
| 217864_s_at | 0.0004053 | −2.2 | PIAS1 | protein inhibitor of activated STAT, 1 (PIAS1), mRNA. | 15q |
| 217888_s_at | 0.0003955 | 2.2 | ARFGAP1 | ADP-ribosylation factor GTPase activating protein 1 (ARFGAP1), transcript variant 1, mRNA. | 20q13.33 |
| 217915_s_at | 9.25E−05 | −2.2 | C15orf15 | chromosome 15 open reading frame 15 (C15orf15), mRNA. | 15q21 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 217989_at | 2.94E−05 | −2.7 | DHRS8 | dehydrogenase/reductase (SDR family) member 8 (DHRS8), mRNA. | 4q22.1 |
| 217992_s_at | 0.0003726 | 2.8 | EFHD2 | EF-hand domain family, member D2 (EFHD2), mRNA. | 1p36.21 |
| 218018_at | 3.65E−05 | 2.2 | PDXK | pyridoxal (pyridoxine, vitamin B6) kinase (PDXK), mRNA. | 21q22.3 |
| 218025_s_at | 2.20E−06 | −4.3 | PECI | peroxisomal D3,D2-enoyl-CoA isomerase (PECI), transcript variant 1, mRNA. | 6p24.3 |
| 218031_s_at | 4.00E−07 | −4.3 | CHES1 | checkpoint suppressor 1 (CHES1), mRNA. | 14q24.3-q32.11 |
| 218113_at | 0.000146 | 2 | TMEM2 | transmembrane protein 2 (TMEM2), mRNA. | 9q13-q21 |
| 218130_at | 0.0004049 | 2 | MGC4368 | hypothetical protein MGC4368 (MGC4368), mRNA. | 17q25.3 |
| 218131_s_at | 2.87E−05 | 2.9 | GATAD2A | GATA zinc finger domain containing 2A (GATAD2A), mRNA. | 19p13.11 |
| 218151_x_at | 0.0005594 | 2.2 | GPR172A | G protein-coupled receptor 172A (GPR172A), mRNA. | 8q24.3 |
| 218155_x_at | 0.000544 | 2.6 | FLJ10534 | hypothetical protein FLJ10534 (FLJ10534), mRNA. | 17p13.3 |
| 218158_s_at | 0.0001389 | −2.7 | APPL | adaptor protein containing pH domain, PTB domain and leucine zipper motif 1 (APPL), mRNA. | 3p21.1-p14.3 |
| 218167_at | 7.25E−05 | −2.4 | AMZ2 | archaemetzincins-2 (AMZ2), mRNA. | 17q24.2 |
| 218191_s_at | 6.81E−05 | −2.8 | LMBRD1 | LMBR1 domain containing 1 (LMBRD1), mRNA. | 6q13 |
| 218193_s_at | 0.0002316 | 2.8 | GOLT1B | golgi transport 1 homolog B (S. cerevisiae) (GOLT1B), mRNA. | 12p12.1 |
| 218204_s_at | 8.33E−05 | −2.3 | FYCO1 | FYVE and coiled-coil domain containing 1 (FYCO1), mRNA. | 3p21.31 |
| 218311_at | 0.0001916 | −2.3 | MAP4K3 | mitogen-activated protein kinase kinase kinase kinase 3 (MAP4K3), mRNA. | 2p22.1 |
| 218373_at | 0.0001922 | −2.3 | FTS | fused toes homolog (mouse) (FTS), transcript variant 2, mRNA. | 16q12.2 |
| 218383_at | 0.0003931 | −2.7 | C14orf94 | chromosome 14 open reading frame 94 (C14orf94), mRNA. | 14q11.2 |
| 218432_at | 0.0003175 | −2.1 | FBXO3 | F-box protein 3 (FBXO3), transcript variant 1, mRNA. | 11p13 |
| 218450_at | 0.0002984 | −2.5 | HEBP1 | heme binding protein 1 (HEBP1), mRNA. | 12p13.1 |
| 218504_at | 0.0005544 | −2 | FAHD2A | fumarylacetoacetate hydrolase domain containing 2A (FAHD2A), mRNA. | 2p24.3-p11.2 |
| 218528_s_at | 4.23E−05 | −2.3 | RNF38 | ring finger protein 38 (RNF38), transcript variant 4, mRNA. | 9p13-p12 |
| 218638_s_at | 0.0008018 | 4 | SPON2 | spondin 2, extracellular matrix protein (SPON2), mRNA. | 4p16.3 |
| 218730_s_at | 0.0002624 | −6.8 | OGN | osteoglycin (osteoinductive factor, mimecan) (OGN), transcript variant 3, mRNA. | 9q22 |
| 218739_at | 0.0002299 | 2.6 | ABHD5 | abhydrolase domain containing 5 (ABHD5), mRNA. | 3p21 |
| 218804_at | 1.58E−05 | 3.3 | TMEM16A | transmembrane protein 16A (TMEM16A), mRNA. | 11q13.3 |
| 218817_at | 0.0005521 | 2 | SPCS3 | signal peptidase complex subunit 3 homolog (S. cerevisiae) (SPCS3), mRNA. | 4q34.2 |
| 218820_at | 0.0007651 | −3 | C14orf132 | chromosome 14 open reading frame 132 (C14orf132), mRNA. | 14q32.2 |
| 218831_s_at | 7.99E−05 | −2.6 | FCGRT | Fc fragment of IgG, receptor, transporter, alpha (FCGRT), mRNA. | 19q13.3 |
| 218856_at | 2.20E−06 | 6.6 | TNFRSF21 | tumor necrosis factor receptor superfamily, member 21 (TNFRSF21), mRNA. | 6p21.1-12.2 |
| 218902_at | 4.33E−05 | 2.5 | NOTCH1 | Notch homolog 1, translocation-associated (Drosophila) (NOTCH1), mRNA. | 9q34.3 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 218919_at | 0.0001794 | −3.1 | ZFAND1 | zinc finger, AN1-type domain 1 (ZFAND1), mRNA. | 8q21.13 |
| 218929_at | 3.34E−05 | −2.1 | CARF | collaborates/cooperates with ARF (alternate reading frame) protein (CARF), mRNA. | 4q35.1 |
| 218961_s_at | 0.0007861 | 2 | PNKP | polynucleotide kinase 3′-phosphatase (PNKP), mRNA. | 19q13.3-q13.4 |
| 219023_at | 7.64E−05 | −3.1 | C4orf16 | chromosome 4 open reading frame 16 (C4orf16), mRNA. | 4q25 |
| 219025_at | 5.55E−05 | 4.3 | CD248 | CD248 antigen, endosialin (CD248), mRNA. | 11q13 |
| 219033_at | 0.0007081 | 2.3 | PARP8 | poly (ADP-ribose) polymerase family, member 8 (PARP8), mRNA. | 5q11.1 |
| 219054_at | 4.17E−05 | −2.6 | FLJ14054 | hypothetical protein FLJ14054 (FLJ14054), mRNA. | 5p13.3 |
| 219092_s_at | 2.14E−05 | 2.2 | C9orf12 | chromosome 9 open reading frame 12 (C9orf12), mRNA. | 9q21.33-q22.31 |
| 219099_at | 9.73E−05 | 2 | C12orf5 | chromosome 12 open reading frame 5 (C12orf5), mRNA. | 12p13.3 |
| 219102_at | 1.21E−05 | 3 | RCN3 | reticulocalbin 3, EF-hand calcium binding domain (RCN3), mRNA. | 19q13.33 |
| 219105_x_at | 9.00E−07 | 3.8 | ORC6L | origin recognition complex, subunit 6 homolog-like (yeast) (ORC6L), mRNA. | 16q12 |
| 219117_s_at | 0.0002973 | 2.4 | FKBP11 | FK506 binding protein 11, 19 kDa (FKBP11), mRNA. | 12q13.12 |
| 219263_at | 5.92E−05 | 4.2 | RNF128 | ring finger protein 128 (RNF128), transcript variant 2, mRNA. | Xq22.3 |
| 219279_at | 0.0002023 | 2.7 | DOCK10 | dedicator of cytokinesis 10 (DOCK10), mRNA. | 2q36.3 |
| 219289_at | 0.0001862 | 2.3 | FLJ20718 | hypothetical protein FLJ20718 (FLJ20718), transcript variant 1, mRNA. | 16q12.1 |
| 219290_x_at | 0.0009817 | 3.8 | DAPP1 | dual adaptor of phosphotyrosine and 3-phosphoinositides (DAPP1), mRNA. | 4q25-q27 |
| 219358_s_at | 1.60E−06 | 6.1 | CENTA2 | centaurin, alpha 2 (CENTA2), mRNA. | 17q11.2 |
| 219359_at | 4.00E−06 | 4.4 | FLJ22635 | hypothetical protein FLJ22635 (FLJ22635), mRNA. | 11p15.5 |
| 219368_at | 0.0009624 | −2.9 | NAP1L2 | nucleosome assembly protein 1-like 2 (NAP1L2), mRNA. | Xq13 |
| 219392_x_at | 3.14E−05 | 4.3 | FLJ11029 | hypothetical protein FLJ11029 (FLJ11029), mRNA. | 17q23.2 |
| 219407_s_at | 0.0009809 | 4.1 | LAMC3 | laminin, gamma 3 (LAMC3), mRNA. | 9q31-q34 |
| 219449_s_at | 0.0006528 | −2.5 | TMEM70 | transmembrane protein 70 (TMEM70), mRNA. | 8q21.11 |
| 219454_at | 4.00E−07 | 36.8 | EGFL6 | EGF-like-domain, multiple 6 (EGFL6), mRNA. | Xp22 |
| 219493_at | 0.0004597 | 2.6 | SHCBP1 | SHC SH2-domain binding protein 1 (SHCBP1), mRNA. | 16q11.2 |
| 219511_s_at | 7.70E−06 | −4.1 | SNCAIP | synuclein, alpha interacting protein (synphilin) (SNCAIP), mRNA. | 5q23.1-q23.3 |
| 219522_at | 1.00E−07 | 7.7 | FJX1 | four jointed box 1 (*Drosophila*) (FJX1), mRNA. | 11p13 |
| 219549_s_at | 0.0004199 | −2.2 | RTN3 | reticulon 3 (RTN3), transcript variant 4, mRNA. | 11q13 |
| 219582_at | 0.0004924 | 3 | OGFRL1 | opioid growth factor receptor-like 1 (OGFRL1), mRNA. | 6q13 |
| 219634_at | 8.10E−06 | 3.8 | CHST11 | carbohydrate (chondroitin 4) sulfotransferase 11 (CHST11), mRNA. | 12q |
| 219641_at | 0.0003308 | −2.1 | DET1 | de-etiolated homolog 1 (*Arabidopsis*) (DET1), mRNA. | 15q25.3 |
| 219700_at | 1.10E−06 | 7.7 | PLXDC1 | plexin domain containing 1 (PLXDC1), mRNA. | 17q21.1 |
| 219764_at | 9.00E−07 | 6.7 | FZD10 | frizzled homolog 10 (*Drosophila*) (FZD10), mRNA. | 12q24.33 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 219939_s_at | 2.10E−06 | −3.5 | CSDE1 | cold shock domain containing E1, RNA-binding (CSDE1), transcript variant 2, mRNA. | 1p22 |
| 219958_at | 0.000873 | 3.2 | C20orf46 | chromosome 20 open reading frame 46 (C20orf46), mRNA. | 20p13 |
| 219961_s_at | 0.0003792 | −2.5 | C20orf19 | chromosome 20 open reading frame 19 (C20orf19), mRNA. | 20pter-q11.23 |
| 220014_at | 1.38E−05 | 4.6 | LOC51334 | mesenchymal stem cell protein DSC54 (LOC51334), mRNA. | 5q23.1 |
| 220094_s_at | 0.0002242 | 2 | C6orf79 | chromosome 6 open reading frame 79 (C6orf79), transcript variant 1, mRNA. | 6p24.3-p23 |
| 220113_x_at | 0.0004047 | 3.1 | POLR1B | polymerase (RNA) I polypeptide B, 128 kDa (POLR1B), mRNA. | 2q13 |
| 220167_s_at | 0.0008187 | 2 | TP53TG3 | TP53TG3 protein (TP53TG3), transcript variant 2, mRNA. | 16p13 |
| 220232_at | 4.54E−05 | 4.8 | SCD5 | stearoyl-CoA desaturase 5 (SCD5), mRNA. | 4q21.3 |
| 220242_x_at | 0.0001347 | 2.2 | ZNF701 | zinc finger protein 701 (ZNF701), mRNA. | 19q13.41 |
| 220266_s_at | 1.44E−05 | −3.3 | KLF4 | Kruppel-like factor 4 (gut) (KLF4), mRNA. | 9q31 |
| 220301_at | 1.76E−05 | 5.8 | C18orf14 | chromosome 18 open reading frame 14 (C18orf14), mRNA. | 18q22.1 |
| 220327_at | 8.86E−05 | −2.7 | VGL-3 | vestigial-like 3 (VGL-3), mRNA. | 3p12.1 |
| 220334_at | 0.0003043 | 3.1 | RGS17 | regulator of G-protein signalling 17 (RGS17), mRNA. | 6q25.3 |
| 220432_s_at | 0.000473 | −3.2 | CYP39A1 | cytochrome P450, family 39, subfamily A, polypeptide 1 (CYP39A1), mRNA. | 6p21.1-p11.2 |
| 220575_at | 4.48E−05 | 3.4 | FLJ11800 | hypothetical protein FLJ11800 (FLJ11800), mRNA. | 17p11.2 |
| 220603_s_at | 0.0001617 | 3.9 | MCTP2 | Multiple C2-domains with two transmembrane regions 2 | 15q26.2 |
| 220720_x_at | 0.0005432 | 3.3 | FLJ14346 | Hypothetical protein FLJ14346 | 2q21.1 |
| 220796_x_at | 0.0002356 | 4.1 | SLC35E1 | Solute carrier family 35, member E1 | 19p13.11 |
| 220817_at | 4.50E−06 | 4.1 | TRPC4 | transient receptor potential cation channel, subfamily C, member 4 (TRPC4), mRNA. | 13q13.1-q13.2 |
| 220952_s_at | 0.000293 | −2.1 | PLEKHA5 | pleckstrin homology domain containing, family A member 5 (PLEKHA5), mRNA. | 12p12 |
| 220992_s_at | 0.0003763 | −2.1 | C1orf25 | Chromosome 1 open reading frame 25 | 1q25.2 |
| 221012_s_at | 0.0004784 | 2 | TRIM8 | tripartite motif-containing 8 (TRIM8), mRNA. | 10q24.3 |
| 221059_s_at | 2.20E−06 | 4.1 | COTL1 | coactosin-like 1 (Dictyostelium) (COTL1), mRNA. | 16q24.1 |
| 221127_s_at | 0.000454 | 3.7 | DKK3 | dickkopf homolog 3 (Xenopus laevis) (DKK3), transcript variant 3, mRNA. | 11p15.2 |
| 221222_s_at | 0.0005338 | 2.2 | C1orf56 | chromosome 1 open reading frame 56 (C1orf56), mRNA. | 1q21.2 |
| 221476_s_at | 4.74E−05 | −2.4 | RPL15 | ribosomal protein L15 (RPL15), mRNA. | 3p24.2 |
| 221486_at | 0.0004058 | −2 | ENSA | endosulfine alpha (ENSA), transcript variant 7, mRNA. | 1q21.2 |
| 221538_s_at | 0.0004626 | 2.4 | PLXNA1 | plexin A1 (PLXNA1), mRNA. | 3q21.3 |
| 221558_s_at | 1.86E−05 | 4.6 | LEF1 | lymphoid enhancer-binding factor 1 (LEF1), mRNA. | 4q23-q25 |
| 221577_x_at | 0.0006888 | 4.5 | GDF15 | growth differentiation factor 15 (GDF15), mRNA. | 19p13.1-13.2 |
| 221588_x_at | 0.0001441 | −2.4 | ALDH6A1 | aldehyde dehydrogenase 6 family, member A1 (ALDH6A1), nuclear gene encoding mitochondrial protein, mRNA. | 14q24.3 |
| 221589_s_at | 1.20E−06 | −4.3 | ALDH6A1 | Aldehyde dehydrogenase 6 family, member A1 | 14q24.3 |
| 221590_s_at | 0.0008671 | −2.3 | ALDH6A1 | Aldehyde dehydrogenase 6 family, member A1 | 14q24.3 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 221689_s_at | 0.000155 | −2 | DSCR5 | Down syndrome critical region gene 5 (DSCR5), transcript variant 2, mRNA. | 21q22.2 |
| 221691_x_at | 1.46E−05 | −3.2 | NPM1 | nucleophosmin (nucleolar phosphoprotein B23, numatrin) (NPM1), mRNA. | 5q35 |
| 221725_at | 3.60E−05 | −2.1 | WASF2 | WAS protein family, member 2 | 1p36.11-p34.3 |
| 221726_at | 1.93E−05 | −2.9 | RPL22 | ribosomal protein L22 (RPL22), mRNA. | 1p36.3-p36.2 |
| 221727_at | 0.0001534 | −2.3 | PC4 | Activated RNA polymerase II transcription cofactor 4 | 5p13.3 |
| 221729_at | 0.0004594 | 3.1 | COL5A2 | collagen, type V, alpha 2 (COL5A2), mRNA. | 2q14-q32 |
| 221730_at | 0.0007972 | 3.4 | COL5A2 | collagen, type V, alpha 2 (COL5A2), mRNA. | 2q14-q32 |
| 221731_x_at | 2.57E−05 | 10.4 | CSPG2 | chondroitin sulfate proteoglycan 2 (versican) (CSPG2), mRNA. | 5q14.3 |
| 221747_at | 0.0003412 | −2.2 | TNS | Tensin 1 | 2q35-q36 |
| 221771_s_at | 0.000498 | −2.1 | HSMPP8 | M-phase phosphoprotein, mpp8 | 13q12.11 |
| 221840_at | 0.0002221 | 3.2 | PTPRE | protein tyrosine phosphatase, receptor type, E (PTPRE), transcript variant 2, mRNA. | 10q26 |
| 221882_s_at | 0.0003013 | 2.2 | TMEM8 | transmembrane protein 8 (five membrane-spanning domains) (TMEM8), mRNA. | 16p13.3 |
| 221943_x_at | 0.0002266 | 2.4 | RPL38 | ribosomal protein L38 (RPL38), mRNA. | 17q23-q25 |
| 221988_at | 1.59E−05 | −2.3 | MGC2747 | Hypothetical protein MGC2747 | 19p13.11 |
| 222108_at | 5.57E−05 | −4.4 | AMIGO2 | adhesion molecule with Ig-like domain 2 (AMIGO2), mRNA. | 12q13.11 |
| 222207_x_at | 0.0003362 | 3.2 | | CDNA: FLJ20949 fis, clone ADSE01902 | 7 |
| 222212_s_at | 0.0001439 | −2.3 | LASS2 | LAG1 longevity assurance homolog 2 (S. cerevisiae) (LASS2), transcript variant 3, mRNA. | 1q21.2 |
| 222252_x_at | 5.29E−05 | 4 | LRRC51 | leucine rich repeat containing 51 (LRRC51), mRNA. | 11q13.4 |
| 222253_s_at | 0.000969 | 4.6 | DKFZP434P211 | POM121-like protein | 22q11.22 |
| 222358_x_at | 7.05E−05 | 3.1 | | ESTs, Weakly similar to hypothetical protein FLJ20378 [Homo sapiens] [H. sapiens] | |
| 222372_at | 0.0006654 | 2.5 | BAIAP1 | Membrane associated guanylate kinase, WW and PDZ domain containing 1 | 3p14.1 |
| 222379_at | 1.13E−05 | 3.5 | KCNE4 | Potassium voltage-gated channel, Isk-related family, member 4 | 2q36.3 |
| 222394_at | 1.44E−05 | −2.8 | PDCD6IP | programmed cell death 6 interacting protein (PDCD6IP), mRNA. | 3p23 |
| 222423_at | 9.81E−05 | −2.8 | NDFIP1 | Nedd4 family interacting protein 1 | 5q31.3 |
| 222431_at | 0.0002108 | −2.2 | SPIN | Spindlin | 9q22.1-q22.3 |
| 222437_s_at | 0.0006141 | −2 | VPS24 | vacuolar protein sorting 24 (yeast) (VPS24), transcript variant 2, mRNA. | 2p24.3-p24.1 |
| 222449_at | 7.80E−06 | 4.1 | TMEPAI | transmembrane, prostate androgen induced RNA (TMEPAI), transcript variant 3, mRNA. | 20q13.31-q13.33 |
| 222453_at | 4.19E−05 | −2.7 | CYBRD1 | cytochrome b reductase 1 (CYBRD1), mRNA. | 2q31.1 |
| 222482_at | 1.85E−05 | −2.4 | SSBP3 | Single stranded DNA binding protein 3 | 1p32.3 |
| 222486_s_at | 5.80E−06 | −4.9 | ADAMTS1 | ADAM metallopeptidase with thrombospondin type 1 motif, 1 (ADAMTS1), mRNA. | 21q21.2 |
| 222488_s_at | 9.10E−05 | −2.4 | DCTN4 | dynactin 4 (p62) (DCTN4), mRNA. | 5q31-q32 |
| 222494_at | 4.00E−06 | −2.8 | CHES1 | checkpoint suppressor 1 (CHES1), mRNA. | 14q24.3-q32.11 |
| 222503_s_at | 0.0003949 | 2.5 | WDR41 | WD repeat domain 41 (WDR41), mRNA. | 5q13.3 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 222533_at | 0.0001299 | −2.1 | CRBN | cereblon (CRBN), mRNA. | 3p26.2 |
| 222538_s_at | 0.0007304 | −3.2 | APPL | adaptor protein containing pH domain, PTB domain and leucine zipper motif 1 (APPL), mRNA. | 3p21.1-p14.3 |
| 222605_at | 1.64E−05 | −3.1 | RCOR3 | REST corepressor 3 (RCOR3), mRNA. | 1q32.3 |
| 222722_at | 1.25E−05 | −8.7 | OGN | osteoglycin (osteoinductive factor, mimecan) (OGN), transcript variant 3, mRNA. | 9q22 |
| 222753_s_at | 0.0001335 | 2.1 | SPCS3 | signal peptidase complex subunit 3 homolog (S. cerevisiae) (SPCS3), mRNA. | 4q34.2 |
| 222791_at | 1.20E−06 | −3.4 | RSBN1 | round spermatid basic protein 1 (RSBN1), mRNA. | 1p13.2 |
| 222834_s_at | 0.0006523 | −2.1 | GNG12 | guanine nucleotide binding protein (G protein), gamma 12 (GNG12), mRNA. | 1p31.2 |
| 222968_at | 5.98E−05 | 2.9 | C6orf48 | chromosome 6 open reading frame 48 (C6orf48), mRNA. | 6p21.3 |
| 222975_s_at | 9.41E−05 | −2.9 | CSDE1 | cold shock domain containing E1, RNA-binding (CSDE1), transcript variant 2, mRNA. | 1p22 |
| 223007_s_at | 0.0007305 | −2.7 | C9orf5 | chromosome 9 open reading frame 5 (C9orf5), mRNA. | 9q31 |
| 223010_s_at | 0.0005426 | −2.2 | OCIAD1 | OCIA domain containing 1 (OCIAD1), mRNA. | 4p11 |
| 223011_s_at | 0.0008498 | −2 | OCIAD1 | OCIA domain containing 1 (OCIAD1), mRNA. | 4p11 |
| 223050_s_at | 0.0003276 | 2 | FBXW5 | F-box and WD-40 domain protein 5 (FBXW5), transcript variant 1, mRNA. | 9q34.3 |
| 223082_at | 0.0003668 | 2.1 | SH3KBP1 | SH3-domain kinase binding protein 1 (SH3KBP1), transcript variant 1, mRNA. | Xp22.1-p21.3 |
| 223170_at | 0.0001428 | −2.6 | DKFZP564K1964 | DKFZP564K1964 protein (DKFZP564K1964), mRNA. | 17q11.2 |
| 223189_x_at | 9.46E−05 | −2.4 | MLL5 | myeloid/lymphoid or mixed-lineage leukemia 5 (trithorax homolog, Drosophila) (MLL5), mRNA. | 7q22.1 |
| 223208_at | 0.0009547 | 2 | KCTD10 | potassium channel tetramerisation domain containing 10 (KCTD10), mRNA. | 12q24.11 |
| 223227_at | 0.0006403 | −2.2 | BBS2 | Bardet-Biedl syndrome 2 (BBS2), mRNA. | 16q21 |
| 223263_s_at | 0.0003743 | −2.1 | FGFR1OP2 | FGFR1 oncogene partner 2 (FGFR1OP2), mRNA. | 12p11.23 |
| 223276_at | 5.10E−05 | 2.9 | NID67 | putative small membrane protein NID67 (NID67), mRNA. | 5q33.1 |
| 223283_s_at | 0.0009337 | −2.5 | SDCCAG33 | serologically defined colon cancer antigen 33 (SDCCAG33), mRNA. | 18q22.3 |
| 223306_at | 6.02E−05 | −2.4 | EBPL | emopamil binding protein-like (EBPL), mRNA. | 13q12-q13 |
| 223366_at | 0.0008475 | −2.9 | | CDNA FLJ16218 fis, clone CTONG3001501, highly similar to Mus musculus glucocorticoid-induced gene 1 mRNA | 8 |
| 223384_s_at | 0.0009265 | −2.1 | TRIM4 | tripartite motif-containing 4 (TRIM4), transcript variant beta, mRNA. | 7q22-q31.1 |
| 223395_at | 9.35E−05 | −6.6 | ABI3BP | ABI gene family, member 3 (NESH) binding protein (ABI3BP), mRNA. | 3q12 |
| 223437_at | 0.0004419 | −2.2 | PPARA | peroxisome proliferative activated receptor, alpha (PPARA), transcript variant 3, mRNA. | 22q13.31 |
| 223464_at | 0.0004952 | 2.3 | OSBPL5 | oxysterol binding protein-like 5 (OSBPL5), transcript variant 2, mRNA. | 11p15.4 |
| 223501_at | 0.0004401 | 4.3 | TNFSF13B | Tumor necrosis factor (ligand) superfamily, member 13b | 13q32-34 |

TABLE 1-continued

Gene expression profile.

| Affymetrix Probe Set | Parametric P-Value | Fold Change (Tumor/Normal) | Gene Symbol | Description | Map |
| --- | --- | --- | --- | --- | --- |
| 223538_at | 0.0008098 | 2 | SERF1A | Small EDRK-rich factor 1A (telomeric) | 5q12.2-q13.3 |
| 223566_s_at | 0.0007174 | −2.7 | BCOR | BCL6 co-repressor (BCOR), transcript variant 1, mRNA. | Xp21.2-p11.4 |
| 223617_x_at | 3.01E−05 | 2.6 | ATAD3B | ATPase family, AAA domain containing 3B (ATAD3B), mRNA. | 1p36.33 |
| 223629_at | 0.0008805 | −2.4 | PCDHB5 | protocadherin beta 5 (PCDHB5), mRNA. | 5q31 |
| 223672_at | 0.0001002 | 4.8 | SGIP1 | SH3-domain GRB2-like (endophilin) interacting protein 1 (SGIP1), mRNA. | 1p31.2 |
| 223697_x_at | 0.0001465 | 4.6 | C9orf64 | chromosome 9 open reading frame 64 (C9orf64), mRNA. | 9q21.32 |
| 223991_s_at | 2.42E−05 | 2.6 | GALNT2 | UDP-N-acetyl-alpha-D-galactosamine:polypeptide N-acetylgalactosaminyltransferase 2 (GalNAc-T2) (GALNT2), mRNA. | 1q41-q42 |
| 224254_x_at | 2.71E−05 | 5.5 | TF | Transferrin | 3q22.1 |
| 224445_s_at | 1.11E−05 | −3 | ZFYVE21 | zinc finger, FYVE domain containing 21 (ZFYVE21), mRNA. | 14q32.33 |
| 224549_x_at | 6.50E−06 | 8 | | | |
| 224598_at | 3.68E−05 | 2.4 | MGAT4B | mannosyl (alpha-1,3-)-glycoprotein beta-1,4-N-acetylglucosaminyltransferase, isoenzyme B (MGAT4B), transcript variant 1, mRNA. | 5q35 |
| 224605_at | 0.0002548 | −2.2 | LOC401152 | HCV F-transactivated protein 1 (LOC401152), mRNA. | 4q26 |
| 224612_s_at | 6.79E−05 | 2.2 | DNAJC5 | DnaJ (Hsp40) homolog, subfamily C, member 5 | 20q13.33 |
| 224618_at | 0.0001475 | 2 | ROD1 | ROD1 regulator of differentiation 1 (S. pombe) | 9q32 |
| 224660_at | 0.0008567 | −2.1 | MGC14156 | hypothetical protein MGC14156 (MGC14156), mRNA. | 4q22.1 |
| 224664_at | 0.0003695 | −2.3 | C10orf104 | chromosome 10 open reading frame 104 (C10orf104), mRNA. | 10q22.1 |
| 224665_at | 0.0004075 | −2.2 | C10orf104 | chromosome 10 open reading frame 104 (C10orf104), mRNA. | 10q22.1 |
| 224667_x_at | 0.0002844 | 3.1 | | Transcribed locus | |
| 224689_at | 0.0001149 | −2 | MANBAL | mannosidase, beta A, lysosomal-like (MANBAL), transcript variant 2, mRNA. | 20q11.23-q12 |
| 224734_at | 0.0001511 | −2.9 | HMGB1 | High-mobility group box 1 | 13q12 |
| 224741_x_at | 0.0001144 | −2.5 | GAS5 | Growth arrest-specific 5 | 1q23.3 |
| 224754_at | 0.000206 | −2.2 | SP1 | Sp1 transcription factor (SP1), mRNA. | 12q13.1 |
| 224755_at | 0.0001441 | −2.2 | SMBP | SM-11044 binding protein | 10q24.1 |
| 224763_at | 5.30E−06 | −3.9 | RPL37 | ribosomal protein L37 (RPL37), mRNA. | 5p13 |
| 224780_at | 0.0008827 | −2 | RBM17 | RNA binding motif protein 17 (RBM17), mRNA. | 10p15.1 |
| 224812_at | 0.0001992 | −2.3 | HIBADH | 3-hydroxyisobutyrate dehydrogenase (HIBADH), mRNA. | 7p15.2 |
| 224841_x_at | 0.0001078 | −2.6 | RNU47 | PREDICTED: RNA, U47 small nuclear (RNU47), misc RNA. | 1 |
| 224856_at | 0.0004439 | −2.6 | FKBP5 | FK506 binding protein 5 (FKBP5), mRNA. | 6p21.3-21.2 |
| 224893_at | 0.0003585 | −2.8 | DKFZP564J0863 | DKFZP564J0863 protein | 11q13.1 |
| 224895_at | 0.000307 | −2.6 | YAP1 | Yes-associated protein 1, 65 kDa (YAP1), mRNA. | 11q13 |
| 224901_at | 1.70E−05 | −3.5 | SCD4 | Stearoyl-CoA desaturase 5 | 4q21.3 |
| 224950_at | 0.0009862 | 2.2 | PTGFRN | prostaglandin F2 receptor negative regulator (PTGFRN), mRNA. | 1p13.1 |
| 224967_at | 5.98E−05 | 2.7 | UGCG | UDP-glucose ceramide glucosyltransferase | 9q31 |
| 224970_at | 5.88E−05 | −2.5 | NFIA | Nuclear factor I/A | 1p31.3-p31.2 |
| 225050_at | 4.85E−05 | −2.5 | ZNF512 | zinc finger protein 512 (ZNF512), mRNA. | 2p23 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 225060_at | 0.0001496 | −2.4 | LRP11 | low density lipoprotein receptor-related protein 11 (LRP11), mRNA. | 6q25.1 |
| 225078_at | 0.0002343 | −3.4 | EMP2 | Epithelial membrane protein 2 | 16p13.2 |
| 225098_at | 0.0001021 | −2 | ABI2 | Abl interactor 2 | 2q33 |
| 225106_s_at | 0.0005784 | 2.9 | FLJ10826 | hypothetical protein FLJ10826 (FLJ10826), transcript variant 2, mRNA. | 16q12.2 |
| 225123_at | 4.00E−07 | −3.1 | SESN3 | Sestrin 3 | 11q21 |
| 225125_at | 3.50E−05 | −3.1 | TMEM32 | transmembrane protein 32 (TMEM32), mRNA. | Xq26.3 |
| 225132_at | 0.0001306 | −2 | FBXL3 | F-box and leucine-rich repeat protein 3 (FBXL3), mRNA. | 13q22 |
| 225133_at | 4.79E−05 | −2.6 | KLF3 | Kruppel-like factor 3 (basic) | 4p14 |
| 225147_at | 1.50E−06 | 3.7 | PSCD3 | pleckstrin homology, Sec7 and coiled-coil domains 3 (PSCD3), mRNA. | 7p22.1 |
| 225162_at | 1.40E−05 | −3.8 | SH3D19 | SH3 domain protein D19 (SH3D19), mRNA. | 4q31.3 |
| 225179_at | 0.0001313 | −2.1 | HIP2 | Huntingtin interacting protein 2 | 4p14 |
| 225198_at | 2.56E−05 | −2.7 | VAPA | VAMP (vesicle-associated membrane protein)-associated protein A, 33 kDa (VAPA), transcript variant 2, mRNA. | 18p11.22 |
| 225207_at | 0.0001018 | −3.4 | PDK4 | pyruvate dehydrogenase kinase, isoenzyme 4 (PDK4), mRNA. | 7q21.3-q22.1 |
| 225219_at | 2.70E−05 | −3.5 | SMAD5 | SMAD, mothers against DPP homolog 5 (*Drosophila*) (SMAD5), transcript variant 3, mRNA. | 5q31 |
| 225220_at | 0.00074 | −2.2 | | *Homo sapiens*, clone IMAGE: 4249217, mRNA | 4 |
| 225223_at | 2.89E−05 | −2 | SMAD5 | SMAD, mothers against DPP homolog 5 (*Drosophila*) (SMAD5), transcript variant 3, mRNA. | 5q31 |
| 225239_at | 0.0004432 | 4.3 | | Immunoglobulin light chain variable region | 11 |
| 225243_s_at | 0.0001227 | −2.6 | SLMAP | sarcolemma associated protein (SLMAP), mRNA. | 3p21.2-p14.3 |
| 225274_at | 2.80E−06 | −3 | SNRPG | Small nuclear ribonucleoprotein polypeptide G | 2p13.3 |
| 225310_at | 0.000177 | −2.2 | RBMX | RNA binding motif protein, X-linked | Xq26.3 |
| 225326_at | 8.88E−05 | −2 | RBM27 | PREDICTED: RNA binding motif protein 27 (RBM27), mRNA. | 5 |
| 225330_at | 0.0002697 | −2.1 | IGF1R | Insulin-like growth factor 1 receptor | 15q26.3 |
| 225332_at | 5.78E−05 | −2.1 | KRTAP4-7 | Keratin associated protein 4-7 | 17q12-q21 |
| 225344_at | 0.0004132 | 2.8 | NCOA7 | nuclear receptor coactivator 7 (NCOA7), mRNA. | 6q22.32 |
| 225352_at | 0.0001828 | −2.3 | TLOC1 | translocation protein 1 (TLOC1), mRNA. | 3q26.2 |
| 225381_at | 0.0006635 | −4.3 | LOC399959 | PREDICTED: hypothetical LOC399959 (LOC399959), mRNA. | 11 |
| 225387_at | 3.43E−05 | −3.2 | TM4SF9 | Tetraspanin 5 | 4q23 |
| 225416_at | 0.0003496 | −2.2 | RNF12 | Ring finger protein 12 | Xq13-q21 |
| 225421_at | 0.0009226 | −3.1 | ACY1L2 | aminoacylase 1-like 2 (ACY1L2), mRNA. | 6q15 |
| 225426_at | 6.78E−05 | −2.5 | PPP6C | Protein phosphatase 6, catalytic subunit | 9q33.3 |
| 225480_at | 0.0002718 | 2.2 | C1orf122 | chromosome 1 open reading frame 122 (C1orf122), mRNA. | 1p34.3 |
| 225489_at | 3.71E−05 | −2 | TMEM18 | transmembrane protein 18 (TMEM18), mRNA. | 2p25.3 |
| 225498_at | 7.45E−05 | −2.2 | CHMP4B | chromatin modifying protein 4B (CHMP4B), mRNA. | 20q11.22 |
| 225505_s_at | 1.90E−06 | 4.1 | C20orf81 | chromosome 20 open reading frame 81 (C20orf81), mRNA. | 20p13 |
| 225509_at | 1.01E−05 | −2.9 | SAP30L | Hypothetical protein LOC56757 | 5q33.2 |
| 225524_at | 5.00E−05 | −3.1 | ANTXR2 | anthrax toxin receptor 2 (ANTXR2), mRNA. | 4q21.21 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 225526_at | 0.0004149 | −2 | MKLN1 | muskelin 1, intracellular mediator containing kelch motifs (MKLN1), mRNA. | 7q32 |
| 225546_at | 4.45E−05 | −2.7 | EEF2K | Eukaryotic elongation factor-2 kinase | 16p12.1 |
| 225571_at | 0.000188 | −4.7 | LIFR | leukemia inhibitory factor receptor (LIFR), mRNA. | 5p13-p12 |
| 225574_at | 8.57E−05 | −2.4 | MGC10198 | hypothetical protein MGC10198 (MGC10198), mRNA. | 4q35.1 |
| 225575_at | 0.0003237 | −4.5 | LIFR | leukemia inhibitory factor receptor (LIFR), mRNA. | 5p13-p12 |
| 225611_at | 0.0004119 | −2.6 | MAST4 | Microtubule associated serine/threonine kinase family member 4 | 5q12.3 |
| 225626_at | 0.0003153 | 4.8 | PAG1 | phosphoprotein associated with glycosphingolipid microdomains 1 (PAG1), mRNA. | 8q21.13 |
| 225636_at | 0.000278 | 2.5 | STAT2 | signal transducer and activator of transcription 2, 113 kDa (STAT2), mRNA. | 12q13.3 |
| 225646_at | 1.50E−05 | 4.4 | CTSC | cathepsin C (CTSC), transcript variant 2, mRNA. | 11q14.1-q14.3 |
| 225647_s_at | 0.0009077 | 2.5 | CTSC | cathepsin C (CTSC), transcript variant 1, mRNA. | 11q14.1-q14.3 |
| 225686_at | 0.0003333 | 2.2 | FAM33A | family with sequence similarity 33, member A (FAM33A), mRNA. | 17q23.2 |
| 225698_at | 3.41E−05 | −3.2 | TIGA1 | TIGA1 (TIGA1), mRNA. | 5q21-q22 |
| 225728_at | 0.0006083 | −2.8 | ARGBP2 | Arg/Abl-interacting protein ArgBP2 | 4q35.1 |
| 225793_at | 0.000103 | −2.1 | MGC46719 | Lix1 homolog (mouse) like | 1q21.1 |
| 225799_at | 2.29E−05 | 5.2 | MGC4677 | hypothetical protein MGC4677 (MGC4677), mRNA. | 2p11.2 |
| 225811_at | 5.44E−05 | −2.1 |  | Transcribed locus, weakly similar to XP_510104.1 PREDICTED: similar to hypothetical protein FLJ25224 [Pan troglodytes] | 11 |
| 225845_at | 0.0003774 | −3.4 | BTBD15 | BTB (POZ) domain containing 15 (BTBD15), mRNA. | 11q24.3 |
| 225855_at | 7.78E−05 | −2.4 | EPB41L5 | erythrocyte membrane protein band 4.1 like 5 (EPB41L5), mRNA. | 2q14.2 |
| 225886_at | 0.0005086 | −2.2 | DDX5 | RNA-binding protein 45 (RBP45), putative | 17q21 |
| 225915_at | 3.50E−05 | −3.4 | CAB39L | Calcium binding protein 39-like | 13q14.2 |
| 225939_at | 0.0001338 | −2.8 | EIF4E3 | Eukaryotic translation initiation factor 4E member 3 | 3p14 |
| 225941_at | 0.0002862 | −2.2 | EIF4E3 | Eukaryotic translation initiation factor 4E member 3 | 3p14 |
| 225946_at | 0.0003511 | −2.3 | C12orf2 | Chromosome 12 open reading frame 2 | 12p12.3 |
| 225947_at | 5.75E−05 | 2.3 | MYOHD1 | myosin head domain containing 1 (MYOHD1), mRNA. | 17q12 |
| 225967_s_at | 0.0001375 | 2.5 | LOC284184 | PREDICTED: hypothetical LOC284184 (LOC284184), mRNA. | 17 |
| 225976_at | 0.0003271 | −2 | BTF3L4 | basic transcription factor 3-like 4 (BTF3L4), mRNA. | 1p32.3 |
| 225987_at | 0.0003503 | 3.3 | TNFAIP9 | STEAP family member 4 | 7q21.12 |
| 225996_at | 0.0006306 | −9.3 |  | MRNA; cDNA DKFZp686N1345 (from clone DKFZp686N1345) | 2 |
| 226017_at | 0.000301 | 2.3 | CKLFSF7 | chemokine-like factor superfamily 7 (CKLFSF7), transcript variant 2, mRNA. | 3p23 |
| 226020_s_at | 7.89E−05 | −2.2 | OMA1 | OMA1 homolog, zinc metallopeptidase (S. cerevisiae) (OMA1), mRNA. | 1p32.2-p32.1 |
| 226038_at | 0.0002389 | −3.2 | LONRF1 | LON peptidase N-terminal domain and ring finger 1 (LONRF1), mRNA. | 8p23.1 |
| 226063_at | 4.00E−06 | 3.3 | VAV2 | vav 2 oncogene (VAV2), mRNA. | 9q34.1 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 226066_at | 0.0005179 | −3 | MITF | microphthalmia-associated transcription factor (MITF), transcript variant 5, mRNA. | 3p14.2-p14.1 |
| 226117_at | 8.72E−05 | −2.7 | TIFA | TRAF-interacting protein with a forkhead-associated domain (TIFA), mRNA. | 4q25 |
| 226120_at | 0.0001436 | −2.7 | TTC8 | tetratricopeptide repeat domain 8 (TTC8), transcript variant 3, mRNA. | 14q31.3 |
| 226180_at | 0.0009691 | −2 | WDR36 | WD repeat domain 36 (WDR36), mRNA. | 5q22.1 |
| 226184_at | 3.75E−05 | −3.6 | FMNL2 | formin-like 2 (FMNL2), transcript variant 2, mRNA. | 2q23.3 |
| 226203_at | 0.0003968 | −2 | | CDNA clone IMAGE: 5299888 | 15 |
| 226223_at | 0.0002488 | −2.6 | PAWR | PRKC, apoptosis, WT1, regulator | 12q21 |
| 226225_at | 0.0003786 | −3.2 | MCC | Mutated in colorectal cancers | 5q21-q22 |
| 226230_at | 0.0002589 | −2.4 | KIAA1387 | KIAA1387 protein | 2p16.1 |
| 226280_at | 3.34E−05 | −2.8 | BNIP2 | BCL2/adenovirus E1B 19 kDa interacting protein 2 | 15q22.2 |
| 226297_at | 8.43E−05 | −2.1 | | ESTs | |
| 226303_at | 0.0003656 | −2.9 | PGM5 | phosphoglucomutase 5 (PGM5), mRNA. | 9q13 |
| 226336_at | 0.0001456 | −2 | PPIA | Peptidylprolyl isomerase A (cyclophilin A) | 7p13-p11.2 |
| 226344_at | 0.0009627 | −2.9 | ZMAT1 | zinc finger, matrin type 1 (ZMAT1), transcript variant 1, mRNA. | Xq21 |
| 226403_at | 9.20E−06 | 3.8 | TMC4 | transmembrane channel-like 4 (TMC4), mRNA. | 19q13.42 |
| 226472_at | 0.0007652 | −2 | PPIL4 | peptidylprolyl isomerase (cyclophilin)-like 4 (PPIL4), mRNA. | 6q24-q25 |
| 226484_at | 0.0009077 | 2 | ZNF651 | zinc finger protein 651 (ZNF651), mRNA. | 3p22.1 |
| 226499_at | 0.0009453 | 2.8 | MGC61598 | Similar to ankyrin-repeat protein Nrarp | 9q34.3 |
| 226521_s_at | 0.0006084 | −2.1 | FLJ13614 | hypothetical protein FLJ13614 (FLJ13614), mRNA. | 4q21.21-q21.23 |
| 226529_at | 4.85E−05 | −2.3 | FLJ11273 | hypothetical protein FLJ11273 (FLJ11273), mRNA. | 7p21.3 |
| 226541_at | 0.0001172 | −2.3 | FBXO30 | F-box protein 30 (FBXO30), mRNA. | 6q24 |
| 226561_at | 0.0006025 | −2.1 | LOC285086 | Hypothetical protein LOC285086 | 2q36.3 |
| 226599_at | 0.0002151 | 2.3 | KIAA1727 | KIAA1727 protein (KIAA1727), mRNA. | 4q31.3 |
| 226625_at | 7.30E−06 | −3.8 | TGFBR3 | Transforming growth factor, beta receptor III (betaglycan, 300 kDa) | 1p33-p32 |
| 226663_at | 8.60E−06 | 2.8 | ANKRD10 | Ankyrin repeat domain 10 | 13q34 |
| 226668_at | 0.0003707 | −2.6 | WDSUB1 | WD repeat, SAM and U-box domain containing 1 (WDSUB1), mRNA. | 2q24.2 |
| 226688_at | 0.0002101 | −3.3 | C3orf23 | chromosome 3 open reading frame 23 (C3orf23), transcript variant 1, mRNA. | 3p21.33-p21.32 |
| 226695_at | 0.0001301 | 2.5 | PRRX1 | paired related homeobox 1 (PRRX1), transcript variant pmx-1b, mRNA. | 1q24 |
| 226705_at | 0.0002111 | −2 | FGFR1 | Fibroblast growth factor receptor 1 (fms-related tyrosine kinase 2, Pfeiffer syndrome) | 8p11.2-p11.1 |
| 226713_at | 1.81E−05 | −2.9 | C3orf6 | Chromosome 3 open reading frame 6 | 3 |
| 226747_at | 0.0006894 | −3.7 | KIAA1344 | KIAA1344 (KIAA1344), mRNA. | 14q22.1 |
| 226751_at | 8.30E−06 | −2.4 | C2orf32 | chromosome 2 open reading frame 32 (C2orf32), mRNA. | 2p14 |
| 226765_at | 0.0002842 | 2.2 | SPTBN1 | Spectrin, beta, non-erythrocytic 1 | 2p21 |
| 226777_at | 5.39E−05 | 4.9 | ADAM12 | A disintegrin and metalloproteinase domain 12 (meltrin alpha) | 10q26.3 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 226806_s_at | 1.95E−05 | −2.8 | | MRNA; cDNA DKFZp686J23256 (from clone DKFZp686J23256) | 1 |
| 226829_at | 0.0006675 | 2.9 | KIAA1914 | KIAA1914 (KIAA1914), transcript variant 2, mRNA. | 10q25.3 |
| 226867_at | 0.0008554 | −2 | C9orf55 | Chromosome 9 open reading frame 55 | 9p22.1 |
| 226873_at | 0.0002067 | −2.8 | | Transcribed locus | 16 |
| 226899_at | 3.10E−06 | 3.1 | UNC5B | unc-5 homolog B (*C. elegans*) (UNC5B), mRNA. | 10q22.1 |
| 226909_at | 0.0004528 | −2 | KIAA1729 | KIAA1729 protein (KIAA1729), mRNA. | 4p16.1 |
| 226911_at | 1.20E−05 | 3.7 | FLJ39155 | hypothetical protein FLJ39155 (FLJ39155), transcript variant 4, mRNA. | 5p13.2-p13.1 |
| 226933_s_at | 5.79E−05 | 3.8 | ID4 | inhibitor of DNA binding 4, dominant negative helix-loop-helix protein (ID4), mRNA. | 6p22-p21 |
| 226943_at | 0.0004664 | 2 | | MRNA; cDNA DKFZp547P055 (from clone DKFZp547P055) | 12 |
| 226994_at | 0.0002644 | −2.3 | DNAJA2 | DnaJ (Hsp40) homolog, subfamily A, member 2 | 16q11.1-q11.2 |
| 226997_at | 0.0002372 | 3.7 | | CDNA FLJ10196 fis, clone HEMBA1004776 | 5 |
| 227031_at | 0.0001825 | −2.4 | SNX13 | Sorting nexin 13 | 7p21.1 |
| 227070_at | 0.0003008 | −2.7 | GLT8D2 | glycosyltransferase 8 domain containing 2 (GLT8D2), mRNA. | 12q |
| 227082_at | 0.0007234 | −2 | | MRNA; cDNA DKFZp586K1922 (from clone DKFZp586K1922) | 3 |
| 227121_at | 0.0006088 | −2.1 | | MRNA; cDNA DKFZp586K1922 (from clone DKFZp586K1922) | 3 |
| 227132_at | 0.0002728 | −2.4 | LOC51123 | HSPC038 protein (LOC51123), mRNA. | 8q22.3 |
| 227138_at | 0.0008198 | −2.1 | CRTAP | cartilage associated protein (CRTAP), mRNA. | 3p22.3 |
| 227148_at | 0.0001511 | −3.4 | PLEKHH2 | pleckstrin homology domain containing, family H (with MyTH4 domain) member 2 (PLEKHH2), mRNA. | 2p21 |
| 227178_at | 0.0005124 | −3.9 | CUGBP2 | CUG triplet repeat, RNA binding protein 2 (CUGBP2), transcript variant 2, mRNA. | 10p13 |
| 227197_at | 0.000108 | −2.9 | SGEF | Src homology 3 domain-containing guanine nucleotide exchange factor | 3q25.2 |
| 227214_at | 0.0002058 | 2.1 | GOPC | Golgi associated PDZ and coiled-coil motif containing | 6q21 |
| 227221_at | 0.0004345 | 2.1 | | CDNA FLJ31683 fis, clone NT2RI2005353 | 3 |
| 227260_at | 0.0001678 | 3 | | Transcribed locus | 1 |
| 227273_at | 4.47E−05 | −2.6 | | Transcribed locus | 10 |
| 227278_at | 0.0005386 | 2.3 | | Transcribed locus, weakly similar to XP_510104.1 PREDICTED: similar to hypothetical protein FLJ25224 [*Pan troglodytes*] | 1 |
| 227293_at | 8.47E−05 | −2.2 | LNX | Ligand of numb-protein X | 4q12 |
| 227295_at | 2.70E−06 | 3.4 | IKIP | IKK interacting protein (IKIP), transcript variant 3.1, mRNA. | 12q23.1 |
| 227317_at | 0.0003721 | 2.3 | LMCD1 | LIM and cysteine-rich domains 1 (LMCD1), mRNA. | 3p26-p24 |
| 227347_x_at | 2.86E−05 | 4 | HES4 | hairy and enhancer of split 4 (*Drosophila*) (HES4), mRNA. | 1p36.33 |
| 227372_s_at | 0.0004102 | 3.4 | BAIAP2L1 | BAI1-associated protein 2-like 1 (BAIAP2L1), mRNA. | 7q21.3-q22.1 |
| 227383_at | 0.0005636 | 2.4 | | Similar to KIAA0454 protein | 1q21.1 |
| 227384_s_at | 0.000128 | 2.6 | | Similar to KIAA0454 protein | 1q21.1 |
| 227396_at | 0.0001476 | 2.6 | | *Homo sapiens*, clone IMAGE: 4454331, mRNA | 11 |
| 227407_at | 9.42E−05 | −2.3 | FLJ90013 | hypothetical protein FLJ90013 (FLJ90013), mRNA. | 4p15.32 |
| 227529_s_at | 0.0001731 | −2.9 | AKAP12 | A kinase (PRKA) anchor protein (gravin) 12 | 6q24-q25 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 227530_at | 8.47E−05 | −3 | AKAP12 | A kinase (PRKA) anchor protein (gravin) 12 | 6q24-q25 |
| 227636_at | 0.0003391 | −2.3 | THAP5 | THAP domain containing 5 | 7q31.1 |
| 227703_s_at | 1.29E−05 | −5.9 | SYTL4 | synaptotagmin-like 4 (granuphilin-a) (SYTL4), mRNA. | Xq21.33 |
| 227708_at | 0.0006098 | −2.1 | EEF1A1 | Eukaryotic translation elongation factor 1 alpha 1 | 6q14.1 |
| 227719_at | 4.00E−06 | −3.6 | | CDNA FLJ37828 fis, clone BRSSN2006575 | 13 |
| 227728_at | 6.11E−05 | −2.9 | PPM1A | Protein phosphatase 1A (formerly 2C), magnesium-dependent, alpha isoform | 14q23.1 |
| 227827_at | 0.0008248 | −4.5 | ARGBP2 | Arg/Abl-interacting protein ArgBP2 | 4q35.1 |
| 227850_x_at | 0.0001134 | 2.9 | CDC42EP5 | CDC42 effector protein (Rho GTPase binding) 5 (CDC42EP5), mRNA. | 19q13.42 |
| 227866_at | 0.0007379 | −2 | RBM16 | RNA binding motif protein 16 | 6q25.1-q25.3 |
| 227945_at | 0.0003107 | −2.3 | TBC1D1 | TBC1 (tre-2/USP6, BUB2, cdc16) domain family, member 1 (TBC1D1), mRNA. | 4p14 |
| 227952_at | 0.0001513 | 4.1 | | Full length insert cDNA clone YI46G04 | 4 |
| 227971_at | 3.26E−05 | −4.1 | NRK | Nik related kinase (NRK), mRNA. | Xq22.3 |
| 228012_at | 0.0006848 | −2 | MATR3 | Matrin 3 | 5q31.2 |
| 228027_at | 3.77E−05 | −4 | GPRASP2 | G protein-coupled receptor associated sorting protein 2 (GPRASP2), transcript variant 2, mRNA. | Xq22.1 |
| 228030_at | 0.0005637 | 3 | RBM6 | RNA binding motif protein 6 | 3p21.3 |
| 228098_s_at | 0.0009902 | 2.2 | MYLIP | myosin regulatory light chain interacting protein (MYLIP), mRNA. | 6p23-p22.3 |
| 228202_at | 0.0001345 | −9.3 | PLN | Phospholamban | 6q22.1 |
| 228204_at | 1.00E−07 | 2.9 | PSMB4 | proteasome (prosome, macropain) subunit, beta type, 4 (PSMB4), mRNA. | 1q21 |
| 228253_at | 1.10E−05 | 3.8 | LOXL3 | lysyl oxidase-like 3 (LOXL3), mRNA. | 2p13 |
| 228297_at | 0.0004293 | 3.3 | CNN3 | calponin 3, acidic (CNN3), mRNA. | 1p22-p21 |
| 228310_at | 8.10E−06 | −3.3 | ENAH | enabled homolog (Drosophila) (ENAH), transcript variant 2, mRNA. | 1q42.12 |
| 228331_at | 0.0002123 | 3.4 | C11orf31 | Chromosome 11 open reading frame 31 | 11q12.1 |
| 228333_at | 0.0005407 | −2.2 | | Full length insert cDNA clone YT94E02 | 2 |
| 228335_at | 0.0008785 | −3.8 | CLDN11 | claudin 11 (oligodendrocyte transmembrane protein) (CLDN11), mRNA. | 3q26.2-q26.3 |
| 228497_at | 0.0001644 | 3.2 | SLC22A15 | solute carrier family 22 (organic cation transporter), member 15 (SLC22A15), mRNA. | 1p13.1 |
| 228523_at | 0.0004047 | 2 | NANOS1 | nanos homolog 1 (Drosophila) (NANOS1), transcript variant 2, mRNA. | 10q26.11 |
| 228551_at | 3.95E−05 | −3.1 | MGC24039 | Hypothetical protein MGC24039 | 12p11.21 |
| 228554_at | 1.35E−05 | −4.7 | | MRNA; cDNA DKFZp586G0321 (from clone DKFZp586G0321) | 11 |
| 228569_at | 0.0006815 | −2.2 | PAPOLA | Poly(A) polymerase alpha | 14q32.31 |
| 228573_at | 0.0001917 | −2.5 | ANTXR2 | Anthrax toxin receptor 2 | 4q21.21 |
| 228577_x_at | 0.0003076 | 2.8 | ODF2L | outer dense fiber of sperm tails 2-like (ODF2L), transcript variant 2, mRNA. | 1p22.3 |
| 228579_at | 7.00E−07 | 5.2 | KCNQ3 | Potassium voltage-gated channel, KQT-like subfamily, member 3 | 8q24 |
| 228785_at | 0.0006036 | 2.2 | ZNF281 | Zinc finger protein 281 | 1q32.1 |
| 228805_at | 0.0003526 | −3 | FLJ44216 | FLJ44216 protein (FLJ44216), mRNA. | 5q35.2 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 228841_at | 0.0004789 | −2 | | CDNA FLJ32429 fis, clone SKMUS2001014 | 5 |
| 228850_s_at | 0.0005294 | 2.8 | SLIT2 | Slit homolog 2 (*Drosophila*) | 4p15.2 |
| 228885_at | 1.82E−05 | −4 | MAMDC2 | MAM domain containing 2 (MAMDC2), mRNA. | 9q21.11 |
| 228905_at | 0.0001087 | −2.4 | | Transcribed locus, moderately similar to XP_517655.1 PREDICTED: similar to KIAA0825 protein [*Pan troglodytes*] | 8 |
| 228961_at | 0.0004391 | −2.1 | FLJ35954 | Hypothetical protein FLJ35954 | 5q11.2 |
| 229085_at | 0.0003123 | 2.5 | LRRC3B | leucine rich repeat containing 3B (LRRC3B), mRNA | 3p24 |
| 229114_at | 0.0002683 | −2 | GAB1 | GRB2-associated binding protein 1 | 4q31.21 |
| 229119_s_at | 0.0001491 | −2.2 | TTC19 | Hypothetical protein LOC125150 | 17p12 |
| 229129_at | 0.0006968 | −2.2 | HNRPD | Heterogeneous nuclear ribonucleoprotein D (AU-rich element RNA binding protein 1, 37 kDa) | 4q21.1-q21.2 |
| 229130_at | 0.0002067 | −3 | LOC285535 | Hypothetical protein LOC285535 | 4p16.1 |
| 229145_at | 4.45E−05 | −4.2 | C10orf104 | chromosome 10 open reading frame 104 (C10orf104), mRNA. | 10q22.1 |
| 229160_at | 0.0003552 | −6.5 | MUM1L1 | melanoma associated antigen (mutated) 1-like 1 (MUM1L1), mRNA. | Xq22.3 |
| 229200_at | 0.000156 | 2.3 | | Hypothetical LOC400813 | 1q44 |
| 229204_at | 0.0003007 | 2.2 | HP1-BP74 | Heterochromatin protein 1, binding protein 3 | 1p36.12 |
| 229218_at | 0.0003816 | 3.3 | COL1A2 | Collagen, type I, alpha 2 | 7q22.1 |
| 229221_at | 0.0006672 | 4.1 | CD44 | CD44 antigen (homing function and Indian blood group system) | 11p13 |
| 229287_at | 0.0007653 | −2.8 | | Full-length cDNA clone CS0DK010YA20 of HeLa cells Cot 25-normalized of *Homo sapiens* (human) | 14 |
| 229299_at | 0.0001103 | −2.2 | FLJ30596 | hypothetical protein FLJ30596 (FLJ30596), mRNA. | 5p13.2 |
| 229308_at | 2.94E−05 | −5.4 | | Transcribed locus | 18 |
| 229319_at | 0.0001521 | −2.4 | | *Homo sapiens*, clone IMAGE: 4105966, mRNA | 6 |
| 229331_at | 0.0007515 | 2.3 | SPATA18 | spermatogenesis associated 18 homolog (rat) (SPATA18), mRNA. | 4q11 |
| 229339_at | 0.0002425 | −5 | MYOCD | Myocardin | 17p11.2 |
| 229354_at | 0.000578 | 3.3 | PDCD6 | Aryl-hydrocarbon receptor repressor | 5pter-p15.2 |
| 229431_at | 0.000216 | −2.1 | RFXAP | regulatory factor X-associated protein (RFXAP), mRNA. | 13q14 |
| 229483_at | 0.0002012 | 2.5 | UBE2H | Ubiquitin-conjugating enzyme E2H (UBC8 homolog, yeast) | 7q32 |
| 229515_at | 0.0002226 | −2.2 | PAWR | PRKC, apoptosis, WT1 regulator | 12q21 |
| 229520_s_at | 0.0001174 | 2.3 | C14orf118 | Chromosome 14 open reading frame 118 | 14q22.1-q24.3 |
| 229531_at | 0.0007976 | −2.2 | | Mitochondrial carrier triple repeat 6 | Xq22.2 |
| 229553_at | 0.0008476 | 2 | PGM2L1 | phosphoglucomutase 2-like 1 (PGM2L1), mRNA. | 11q13.4 |
| 229580_at | 0.0008828 | −6.5 | | Transcribed locus | 3 |
| 229638_at | 0.0008539 | 2.9 | IRX3 | iroquois homeobox protein 3 (IRX3), mRNA. | 16q12.2 |
| 229642_at | 0.0002914 | 4.2 | ARHGEF7 | Rho guanine nucleotide exchange factor (GEF) 7 (ARHGEF7), transcript variant 2, mRNA. | 13q34 |
| 229665_at | 0.0001871 | 2.2 | CSTF3 | Hypothetical protein LOC283267 | 11p13 |
| 229711_s_at | 0.0003052 | 2.1 | | CDNA FLJ37519 fis, clone BRCAN2004699 | 12 |
| 229748_x_at | 0.0001962 | 2.7 | LOC285458 | Hypothetical protein LOC285458 | 4 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 229795_at | 0.0002666 | 3.4 | | Transcribed locus | 12 |
| 229801_at | 0.0001036 | 3.4 | C10orf47 | chromosome 10 open reading frame 47 (C10orf47), mRNA. | 10p14 |
| 229830_at | 0.0004695 | 3.9 | PDGFA | Platelet-derived growth factor alpha polypeptide | 7p22 |
| 229844_at | 0.0001747 | −2.2 | | Transcribed locus | 3 |
| 229891_x_at | 1.34E−05 | −2.9 | KIAA1704 | KIAA1704 | 13q13-q14 |
| 229969_at | 0.0003327 | −2.5 | | Transcribed locus, moderately similar to XP_508230.1 PREDICTED: zinc finger protein 195 [*Pan troglodytes*] | 6 |
| 229994_at | 0.0002738 | −3 | | MRNA; cDNA DKFZp686J23256 (from clone DKFZp686J23256) | 1 |
| 230000_at | 0.0004792 | 2.7 | C17orf27 | Chromosome 17 open reading frame 27 | 17q25.3 |
| 230030_at | 0.0003377 | −5.2 | HS6ST2 | heparan sulfate 6-O-sulfotransferase 2 (HS6ST2), mRNA. | Xq26.2 |
| 230068_s_at | 8.34E−05 | −3.2 | PEG3 | paternally expressed 3 (PEG3), mRNA. | 19q13.4 |
| 230077_at | 0.0001004 | 3.9 | TFRC | Transferrin receptor (p90, CD71) | 3q29 |
| 230081_at | 5.00E−07 | −6.1 | PLCXD3 | phosphatidylinositol-specific phospholipase C, X domain containing 3 (PLCXD3), mRNA. | 5p13.1 |
| 230130_at | 9.27E−05 | 3 | SLIT2 | Slit homolog 2 (*Drosophila*) | 4p15.2 |
| 230141_at | 0.0002042 | −2 | ARID4A | AT rich interactive domain 4A (RBP1-like) | 14q23.1 |
| 230174_at | 0.0008233 | −2.1 | LYPLAL1 | Lysophospholipase-like 1 | 1q41 |
| 230178_s_at | 9.98E−05 | −2.4 | STATIP1 | Signal transducer and activator of transcription 3 interacting protein 1 | 18q12.2 |
| 230270_at | 7.57E−05 | 2.9 | | ESTs | |
| 230333_at | 0.0008148 | 2.5 | SAT | Spermidine/spermine N1-acetyltransferase | Xp22.1 |
| 230336_at | 0.0008645 | 2.7 | | Transcribed locus | 4 |
| 230369_at | 0.0005567 | −2.1 | GPR161 | G protein-coupled receptor 161 | 1q24.2 |
| 230387_at | 0.0001569 | 3.1 | ATP2C1 | ATPase, Ca++ transporting, type 2C, member 1 | 3q22.1 |
| 230440_at | 2.81E−05 | 3.3 | ZNF469 | PREDICTED: zinc finger protein 469 (ZNF469), mRNA. | 16 |
| 230561_s_at | 0.0001454 | −2.9 | FLJ23861 | hypothetical protein FLJ23861 (FLJ23861), mRNA. | 2q34 |
| 230574_at | 0.0008056 | 2.9 | | Hypothetical LOC388480 | 18q21.33 |
| 230746_s_at | 1.50E−06 | 13.3 | STC1 | stanniocalcin 1 (STC1), mRNA. | 8p21-p11.2 |
| 230758_at | 0.00064 | −2.6 | | Transcribed locus | X |
| 230793_at | 7.34E−05 | −3.1 | LRRC16 | leucine rich repeat containing 16 (LRRC16), mRNA. | 6p22.2 |
| 230850_at | 0.0001807 | 3 | FMNL3 | Formin-like 3 | 12q13.12 |
| 230885_at | 0.0001271 | 2.2 | SPG7 | Spastic paraplegia 7, paraplegin (pure and complicated autosomal recessive) | 16q24.3 |
| 230958_s_at | 4.15E−05 | −2.1 | | MRNA; cDNA DKFZp686J23256 (from clone DKFZp686J23256) | 1 |
| 231130_at | 0.0009273 | −2 | FKBP7 | FK506 binding protein 7 | 2q31.2 |
| 231183_s_at | 0.000129 | 4.3 | JAG1 | jagged 1 (Alagille syndrome) (JAG1), mRNA. | 20p12.1-p11.23 |
| 231202_at | 0.0002962 | 3.1 | FLJ38508 | Aldehyde dehydrogenase 1 family, member L2 | 12q23.3 |
| 231411_at | 0.0001224 | 3.2 | LHFP | lipoma HMGIC fusion partner (LHFP), mRNA. | 13q12 |
| 231597_x_at | 0.0001876 | 15.9 | | ESTs, Weakly similar to T47135 hypothetical protein DKFZp761L0812.1 [*H. sapiens*] | |
| 231806_s_at | 0.0009603 | 2.1 | STK36 | serine/threonine kinase 36 (fused homolog, *Drosophila*) (STK36), mRNA. | 2q35 |
| 231825_x_at | 8.13E−05 | 3.6 | ATF7IP | Activating transcription factor 7 interacting protein | 12p13.1 |
| 231882_at | 0.0002463 | 2.7 | | CDNA FLJ10674 fis, clone NT2RP2006436 | 22 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 231886_at | 0.0003613 | 3 | | Similar to hypothetical protein LOC284701 | 3q29 |
| 232034_at | 0.0008165 | 3.9 | LOC203274 | Hypothetical protein LOC203274 | 9q21.11 |
| 232145_at | 0.0002539 | 2.1 | LOC388969 | hypothetical LOC388969 (LOC388969), mRNA. | 2p11.2 |
| 232150_at | 2.29E−05 | 3.1 | C20orf18 | Chromosome 20 open reading frame 18 | 20p13 |
| 232169_x_at | 0.0002893 | 3.1 | NDUFS8 | NADH dehydrogenase (ubiquinone) Fe—S protein 8, 23 kDa (NADH-coenzyme Q reductase) | 11q13 |
| 232174_at | 7.00E−06 | 4.1 | EXT1 | Exostoses (multiple) 1 | 8q24.11-q24.13 |
| 232180_at | 8.56E−05 | 3.2 | UGP2 | UDP-glucose pyrophosphorylase 2 | 2p14-p13 |
| 232215_x_at | 0.0001855 | 3.4 | FLJ11029 | Hypothetical protein FLJ11029 | 17q23.2 |
| 232254_at | 8.75E−05 | 2.5 | FBXO25 | F-box protein 25 | 8p23.3 |
| 232266_x_at | 0.0001426 | 3.9 | CDC2L5 | Cell division cycle 2-like 5 (cholinesterase-related cell division controller) | 7p13 |
| 232304_at | 2.60E−06 | 4 | PELI1 | Pellino homolog 1 (*Drosophila*) | 2p13.3 |
| 232347_x_at | 0.0001636 | 2.6 | CBR4 | Carbonic reductase 4 | 4q32.3 |
| 232406_at | 0.0001583 | 2.9 | JAG1 | Jagged 1 (Alagille syndrome) | 20p12.1-p11.23 |
| 232458_at | 1.67E−05 | 4.1 | COL3A1 | Collagen, type III, alpha 1 (Ehlers-Danlos syndrome type IV, autosomal dominant) | 2q31 |
| 232516_x_at | 7.53E−05 | 3.3 | YAP | YY1 associated protein 1 | 1q22 |
| 232530_at | 0.0006114 | 2.8 | PLD1 | Phospholipase D1, phophatidylcholine-specific | 3q26 |
| 232538_at | 0.0008933 | 2.4 | | CDNA: FLJ23573 fis, clone LNG12520 | 16 |
| 232541_at | 0.0007593 | 3.5 | EGFR | Epidermal growth factor receptor (erythroblastic leukemia viral (v-erb-b) oncogene homolog, avian) | 7p12 |
| 232617_at | 8.18E−05 | 3.2 | CTSS | cathepsin S (CTSS), mRNA. | 1q21 |
| 232653_at | 0.000473 | 3.5 | | *Homo sapiens* cDNA FLJ14044 fis, clone HEMBA1006124 | |
| 232702_at | 0.0006941 | 3 | RABGAP1L | RAB GTPase activating protein 1-like | 1q24 |
| 232797_at | 0.0008213 | 2.3 | ITGAV | Integrin, alpha V (vitronectin receptor, alpha polypeptide, antigen CD51) | 2q31-q32 |
| 232814_x_at | 0.0005021 | 2.8 | C14orf153 | Chromosome 14 open reading frame 153 | 14q32.32-q32.33 |
| 232889_at | 0.0003899 | 2.6 | | CDNA clone IMAGE: 5576908 | 5 |
| 232952_at | 0.0001405 | 2.7 | DDEF1 | HSPC054 protein | 8q24.1-q24.2 |
| 233041_x_at | 0.0004112 | 3 | BTBD9 | BTB (POZ) domain containing 9 | 6p21 |
| 233180_at | 1.17E−05 | 2.8 | RNF152 | Ring finger protein 152 | 18q21.33 |
| 233274_at | 3.00E−07 | 3.6 | NCK1 | NCK adaptor protein 1 | 3q21 |
| 233319_x_at | 0.0001543 | 3.1 | PHACTR4 | Phosphatase and actin regulator 4 | 1p35.3 |
| 233330_s_at | 4.59E−05 | 5.6 | | Similar to Ribosome biogenesis protein BMS1 homolog | 9q13 |
| 233406_at | 0.0002846 | 2.9 | KIAA0256 | KIAA0256 gene product | 15q21.1 |
| 233496_s_at | 0.0003586 | −2 | CFL2 | Cofilin 2 (muscle) | 14q12 |
| 233702_x_at | 0.0007629 | 3.1 | | CDNA: FLJ20946 fis, clone ADSE01819 | 7 |
| 233849_s_at | 0.0005935 | −2.3 | ARHGAP5 | Rho GTPase activating protein 5 (ARHGAP5), transcript variant 2, mRNA. | 14q12 |
| 233912_x_at | 1.73E−05 | 4.4 | ELMOD2 | ELMO domain containing 2 | 4q31.21 |
| 234192_s_at | 0.0001567 | −3.1 | GKAP1 | G kinase anchoring protein 1 (GKAP1), mRNA. | 9q21.32 |
| 234339_s_at | 6.34E−05 | −2.4 | GLTSCR2 | glioma tumor suppressor candidate region gene 2 (GLTSCR2), mRNA. | 19q13.3 |
| 234464_s_at | 4.21E−05 | 3 | EME1 | essential meiotic endonuclease 1 homolog 1 (*S. pombe*) (EME1), mRNA. | 17q21.33 |
| 234512_x_at | 2.40E−06 | −3.1 | LOC442159 | PREDICTED: similar to Rpl7a protein (LOC442159), mRNA. | 6 |
| 234562_x_at | 1.80E−06 | 8.6 | CKLFSF8 | Chemokine-like factor super family 8 | 3p23 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 234578_at | 7.26E−05 | 4.9 | | MRNA; cDNA DKFZp434E1812 (from clone DKFZp434E1812) | 1 |
| 234675_x_at | 6.52E−05 | 4.3 | | CDNA: FLJ23566 fis, clone LNG10880 | 14 |
| 234723_x_at | 1.50E−06 | 9.4 | | CDNA: FLJ21228 fis, clone COL00739 | 7 |
| 234753_x_at | 0.0002577 | 5.7 | | | |
| 234762_x_at | 8.75E−05 | 4.1 | NLN | Neurolysin (metallopeptidase M3 family) | 5q12.3 |
| 234788_x_at | 0.0001541 | 3.3 | FLJ13611 | Hypothetical protein FLJ13611 | 5q12.3 |
| 234873_x_at | 0.000607 | −2 | | | |
| 234981_x_at | 9.85E−05 | 4.4 | LOC134147 | Similar to mouse 2310016A09Rik gene | 5p15.2 |
| 234985_at | 9.30E−06 | 2.9 | LOC143458 | Hypothetical protein LOC143458 | 11p13 |
| 234998_at | 0.0009467 | −2.7 | | CDNA clone IMAGE: 5313062 | 15 |
| 235005_at | 0.0003344 | −2.3 | MGC4562 | Hypothetical protein MGC4562 | 15q22.31 |
| 235061_at | 0.0002578 | −2.9 | PPM1K | protein phosphatase 1K (PP2C domain containing) (PPM1K), mRNA. | 4q22.1 |
| 235072_s_at | 6.66E−05 | −3 | | Transcribed locus | 6 |
| 235122_at | 5.42E−05 | 3.1 | | CDNA clone IMAGE: 6254031 | 1 |
| 235151_at | 0.0004926 | −2.1 | LOC283357 | Hypothetical protein LOC283357 | 12p13.33 |
| 235204_at | 1.87E−05 | 3.1 | ENTPD7 | Ectonucleoside triphosphate diphosphohydrolase 7 | 10 |
| 235205_at | 0.0001252 | 3.5 | LOC346887 | PREDICTED: similar to solute carrier family 16 (monocarboxylic acid transporters), member 14 (LOC346887), mRNA. | 8 |
| 235278_at | 0.0002619 | −3.6 | C20orf133 | chromosome 20 open reading frame 133 (C20orf133), transcript variant 2, mRNA. | 20p12.1 |
| 235309_at | p < 1e−07 | −4.9 | | CDNA clone IMAGE: 4140029 | 16 |
| 235327_x_at | 0.0002751 | 2.9 | UBXD4 | UBX domain containing 4 (UBXD4), mRNA. | 2p23.3 |
| 235343_at | 3.96E−05 | 4.2 | FLJ12505 | Hypothetical protein FLJ12505 | 1q32.3 |
| 235374_at | 3.04E−05 | 2.7 | MDH1 | Malate dehydrogenase 1, NAD (soluble) | 2p13.3 |
| 235412_at | 0.0002124 | 3.2 | ARHGEF7 | Rho guanine nucleotide exchange factor (GEF) 7 | 13q34 |
| 235433_at | 0.0003304 | −2.2 | SATL1 | Spermidine/spermine N1-acetyl transferase-like 1 | Xq21.1 |
| 235556_at | 0.0001833 | −2 | | Transcribed locus, weakly similar to NP_703324.1 glutamic acid-rich protein (garp) [*Plasmodium falciparum* 3D7] | 5 |
| 235601_at | 0.0003888 | 2.7 | | ESTs | |
| 235612_at | 2.90E−05 | −3.1 | | Transcribed locus, moderately similar to NP_858931.1 NES1 nitrogen fixation 1 isoform b precursor; cysteine desulfurase; nitrogen-fixing bacteria S-like protein; nitrogen fixation 1 (*S. cerevisiae*, homolog) [*Homo sapiens*] | 1 |
| 235628_x_at | 0.0004866 | 2.4 | | Hypothetical protein LOC133926 | 5q23.2 |
| 235693_at | 0.0003764 | 2.9 | | Transcribed locus | 5 |
| 235725_at | 0.0004132 | −2.2 | | Transcribed locus | 14 |
| 235927_at | 6.41E−05 | 2.4 | XPO1 | Exportin 1 (CRM1 homolog, yeast) | 2p16 |
| 235944_at | 0.0004031 | 3.3 | HMCN1 | hemicentin 1 (HMCN1), mRNA. | 1q25.3-q31.1 |
| 236249_at | 1.54E−05 | 2.7 | IKIP | IKK interacting protein (IKIP), transcript variant 1, mRNA. | 12q23.1 |
| 236251_at | 8.16E−05 | 2.7 | ITGAV | Integrin, alpha V (vitronectin receptor, alpha polypeptide, antigen CD51) | 2q31-q32 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 236678_at | 0.0005987 | 2.8 | JAG1 | Jagged 1 (Alagille syndrome) | 20p12.1-p11.23 |
| 236715_x_at | 0.0002206 | 2.5 | UACA | uveal autoantigen with coiled-coil domains and ankyrin repeats (UACA), transcript variant 1, mRNA. | 15q22-q24 |
| 236829_at | 6.57E−05 | 2.9 | TMF1 | TATA element modulatory factor 1 | 3p21-p12 |
| 236883_at | 0.0003076 | 2.6 | | ESTs | |
| 236936_at | 0.0007927 | −2.4 | | Transcribed locus | 8 |
| 236966_at | 0.0004757 | 2.6 | TXNDC6 | thioredoxin domain containing 6 (TXNDC6), mRNA. | 3q22.3 |
| 236974_at | 0.0003599 | 2.5 | CCNI | Cyclin I | 4q21.1 |
| 237206_at | 0.0003483 | −5.9 | MYOCD | Myocardin | 17p11.2 |
| 237333_at | 0.0008796 | −2 | SYNCOILIN | Syncoilin, intermediate filament 1 | 1p34.3-p33 |
| 237475_x_at | 0.0001562 | 4.3 | SEPP1 | Selenoprotein P, plasma, 1 | 5q31 |
| 237494_at | 2.03E−05 | 3.2 | | Transcribed locus | 15 |
| 237868_x_at | 0.000358 | 3 | | ESTs, Weakly similar to ALUF_HUMAN !!!! ALU CLASS F WARNING ENTRY !!! [*H. sapiens*] | |
| 238026_at | 0.0007905 | −2 | RPL35A | Ribosomal protein L35a | 3q29-qter |
| 238142_at | 0.000678 | 2.4 | LOC253982 | Hypothetical protein LOC253982 | 16q11.2 |
| 238183_at | 0.0001644 | 3.7 | | ESTs | |
| 238273_at | 0.0007281 | 2 | | Full-length cDNA clone CS0DB005YG10 of Neuroblastoma Cot 10-normalized of *Homo sapiens* (human) | 7 |
| 238327_at | 6.09E−05 | 2.6 | | Similar to MGC52679 protein | 22q13.33 |
| 238478_at | 0.000183 | −3.7 | BNC2 | Basonuclin 2 | 9p22.3-p22.2 |
| 238584_at | 0.0002196 | 3.3 | IQCA | IQ motif containing with AAA domain | 2q37.2-q37.3 |
| 238613_at | 8.97E−05 | −2.7 | ZAK | sterile alpha motif and leucine zipper containing kinase AZK (ZAK), transcript variant 2, mRNA. | 2q24.2 |
| 238642_at | 0.0003128 | 3 | LOC338692 | Ankyrin repeat domain 13 family, member D | 11q13.2 |
| 238673_at | 6.02E−05 | 4.7 | | Transcribed locus | 8 |
| 238714_at | 0.0001825 | 2.5 | | RAB12, member RAS oncogene family | 18p11.22 |
| 238719_at | 0.0004981 | −2.5 | PPP2CA | Protein phosphatase 2 (formerly 2A), catalytic subunit, alpha isoform | 5q31.1 |
| 238852_at | 0.0003011 | 2.3 | | ESTs | |
| 238878_at | 0.0006945 | −6.2 | ARX | Aristaless related homeobox | Xp22.1-p21.3 |
| 239227_at | 9.04E−05 | 3 | EXT1 | Exostoses (multiple) 1 | 8q24.11-q24.13 |
| 239246_at | 0.0002103 | 3 | FARP1 | FERM, RhoGEF (ARHGEF) and pleckstrin domain protein 1 (chondrocyte-derived) | 13q32.2 |
| 239258_at | 0.0009901 | 3.1 | RHOQ | Ras homolog gene family, member Q | 2p21 |
| 239262_at | 3.72E−05 | −3.8 | | CDNA FLJ26242 fis, clone DMC00770 | 11 |
| 239264_at | 0.0003642 | 2.2 | SEC8L1 | SEC8-like 1 (*S. cerevisiae*) | 7q31 |
| 239367_at | 0.0001649 | 3.1 | BDNF | brain-derived neurotrophic factor (BDNF), transcript variant 6, mRNA. | 11p13 |
| 239516_at | 0.0001834 | 2.7 | LYPLAL1 | Lysophospholipase-like 1 | 1q41 |
| 239540_at | 0.0009106 | 2.6 | GTF3C1 | General transcription factor IIIC, polypeptide 1, alpha 220 kDa | 16p12 |
| 239748_x_at | 0.0003286 | 3.7 | OCIA | ovarian carcinoma immunoreactive antigen | 4p11 |
| 239806_at | 0.000252 | 4.4 | | Transcribed locus | 2 |
| 239848_at | 0.0005816 | −2.7 | GA17 | Dendritic cell protein | 11p13 |
| 240216_at | 0.0001639 | 2.6 | ZBTB20 | Zinc finger and BTB domain containing 20 | 3q13.2 |
| 240421_x_at | 0.0001971 | 3.7 | | CDNA clone IMAGE: 5268630 | 4 |
| 240655_at | 3.01E−05 | 4.3 | ALCAM | Activated leukocyte cell adhesion molecule | 3q13.1 |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 240795_at | 0.0001514 | 2.3 | | CDNA clone IMAGE: 5288566 | 5 |
| 241223_x_at | 0.0002281 | 3.2 | | ESTs, Weakly similar to ALU1_HUMAN ALU SUBFAMILY J SEQUENCE CONTAMINATION WARNING ENTRY [H. sapiens] | |
| 241268_x_at | 0.0008446 | 3.5 | SAMHD1 | SAM domain and HD domain 1 | 20pter-q12 |
| 241303_x_at | 0.0007123 | 2.9 | | ESTs | |
| 241387_at | 0.0008125 | 2.7 | PTK2 | PTK2 protein tyrosine kinase 2 | 8q24-qter |
| 241421_at | 0.0005012 | 2.6 | | Transcribed locus | 1 |
| 241435_at | 1.52E−05 | 4.4 | ETS1 | V-ets erythroblastosis virus E26 oncogene homolog 1 (avian) | 11q23.3 |
| 241617_x_at | 0.000334 | 2.6 | | ESTs, Weakly similar to 810024C cytochrome oxidase I [H. sapiens] | |
| 241627_x_at | 0.0005548 | 2.9 | FLJ10357 | Hypothetical protein FLJ10357 | 14q11.2 |
| 241632_x_at | 3.70E−06 | 3.3 | | ESTs | |
| 241686_x_at | 3.28E−05 | 4.4 | | ESTs, Weakly similar to hypothetical protein FLJ20378 [Homo sapiens] [H. sapiens] | |
| 241718_x_at | 7.37E−05 | 3.4 | | ESTs | |
| 241727_x_at | 0.0003166 | 2.3 | DHFRL1 | dihydrofolate reductase-like 1 (DHFRL1), mRNA. | 3q11.2 |
| 241769_at | 0.0004802 | 2.5 | ITGAV | Integrin, alpha V (vitronectin receptor, alpha polypeptide, antigen CD51) | 2q31-q32 |
| 241809_at | 0.0001618 | 2.5 | LOC284465 | Hypothetical protein LOC284465 | 1p13.2 |
| 242029_at | 9.60E−06 | 3.7 | FNDC3B | Fibronectin type III domain containing 3B | 3q26.31 |
| 242051_at | 6.20E−06 | −3.7 | | Transcribed locus | X |
| 242100_at | 2.40E−06 | 4.8 | CSS3 | chondroitin sulfate synthase 3 (CSS3), mRNA. | 5q23.3 |
| 242171_at | 0.0007535 | 3.1 | | ESTs, Weakly similar to ALU1_HUMAN ALU SUBFAMILY J SEQUENCE CONTAMINATION WARNING ENTRY [H. sapiens] | |
| 242233_at | 7.63E−05 | 2.4 | KIAA1219 | KIAA1219 protein | 20q11.23 |
| 242240_at | 0.0001413 | 3 | PTK2 | PTK2 protein tyrosine kinase 2 | 8q24-qter |
| 242329_at | 8.94E−05 | 3.1 | LOC401317 | PREDICTED: hypothetical LOC401317 (LOC401317), mRNA. | 7 |
| 242363_at | 9.05E−05 | −2.7 | DNCI2 | Dynein, cytoplasmic, intermediate polypeptide 2 | 2q31.1 |
| 242364_x_at | 0.0001237 | 3.1 | EVER1 | Epidermodysplasia verruciformis 1 | 17q25.3 |
| 242369_x_at | 7.20E−06 | 4.1 | NCOA2 | Nuclear receptor coactivator 2 | 8q13.3 |
| 242398_x_at | 3.00E−06 | 6.1 | MEP50 | WD repeat domain 77 | 1p13.2 |
| 242405_at | 4.08E−05 | 2 | MAML2 | Mastermind-like 2 (Drosophila) | 11q21 |
| 242488_at | 2.11E−05 | −4.7 | | CDNA FLJ38396 fis, clone FEBRA2007957 | 1 |
| 242500_at | 0.0007278 | 2.6 | | Transcribed locus | 6 |
| 242546_at | 2.70E−06 | 5.4 | | LOC440156 | 14q11.1 |
| 242578_x_at | 0.0002453 | 4 | SLC22A3 | Solute carrier family 22 (extraneuronal monoamine transporter), member 3 | 6q26-q27 |
| 242862_x_at | 6.29E−05 | 5.2 | | ESTs | |
| 242999_at | 0.0007732 | 2.3 | ARHGEF7 | Rho guanine nucleotide exchange factor (GEF) 7 (ARHGEF7), transcript variant 2, mRNA. | 13q34 |
| 243_g_at | 9.74E−05 | 2.1 | MAP4 | microtubule-associated protein 4 (MAP4), transcript variant 2, mRNA. | 3p21 |
| 243006_at | 1.10E−06 | 4.7 | FYN | FYN oncogene related to SRC, FGR, YES | 6q21 |
| 243147_x_at | 7.12E−05 | 5.7 | | ESTs, Weakly similar to RMS1_HUMAN REGULATOR OF MITOTIC SPINDLE ASSEMBLY 1 [H. sapiens] | |

TABLE 1-continued

Gene expression profile.

| Affymetrix Probe Set | Parametric P-Value | Fold Change (Tumor/Normal) | Gene Symbol | Description | Map |
|---|---|---|---|---|---|
| 243249_at | 7.21E−05 | 2.4 | | ESTs, Weakly similar to hypothetical protein FLJ20378 [*Homo sapiens*] [*H. sapiens*] | |
| 243305_at | 0.0003329 | 2.9 | KIAA1340 | Kelch domain containing 5 | 12p11.22 |
| 243442_x_at | 0.0001001 | 3.7 | | ESTs, Weakly similar to ALU1_HUMAN ALU SUBFAMILY J SEQUENCE CONTAMINATION WARNING ENTRY [*H. sapiens*] | |
| 243846_x_at | 0.0007887 | 3 | FLJ32810 | Hypothetical protein FLJ32810 | 11q22.1 |
| 243915_at | 0.0001482 | 2.9 | | ESTs, Weakly similar to 2109260A B cell growth factor [*H. sapiens*] | |
| 244007_at | 0.000373 | −2 | | Transcribed locus | 9 |
| 244022_at | 0.0007683 | 2 | FNDC3B | Fibronectin type III domain containing 3B | 3q26.31 |
| 244050_at | 0.0001908 | −2.6 | LOC401494 | similar to RIKEN 4933428I03 (LOC401494), mRNA. | 9p21.3 |
| 244188_at | 0.0004372 | 3.1 | FLJ21924 | Hypothetical protein FLJ21924 | 11p13 |
| 244193_at | 0.0003257 | 2.1 | FLJ13236 | Hypothetical protein FLJ13236 | 12q13.12 |
| 244197_x_at | 2.30E−05 | 3.3 | CNOT2 | CCR4-NOT transcription complex, subunit 2 | 12q15 |
| 244457_at | 8.66E−05 | 3.1 | ITPR2 | Inositol 1,4,5-triphosphate receptor, type 2 | 12p11 |
| 244503_at | 0.0004105 | 2.5 | | ESTs | |
| 244633_at | 0.000111 | 2.5 | PIAS2 | Protein inhibitor of activated STAT, 2 | 18q21.1 |
| 244648_at | 0.0003403 | 3.5 | FLJ10996 | Hypothetical protein FLJ10996 | 2q14.1 |
| 244745_at | 0.0006739 | −2.7 | RERG | RAS-like, estrogen-regulated, growth inhibitor (RERG), mRNA. | 12p12.3 |
| 31874_at | 8.21E−05 | 2.9 | GAS2L1 | Growth arrest-specific 2 like 1 | 22q12.2 |
| 33323_r_at | 0.0001426 | 5.1 | SFN | Stratifin | 1p36.11 |
| 38069_at | 0.0003197 | 2 | CLCN7 | chloride channel 7 (CLCN7), mRNA. | 16p13 |
| 38671_at | 0.0003864 | 2.4 | PLXND1 | plexin D1 (PLXND1), mRNA. | 3q21.3 |
| 39549_at | 0.0008832 | 2.5 | NPAS2 | neuronal PAS domain protein 2 (NPAS2), mRNA. | 2q11.2 |
| 39891_at | 0.0005541 | 2.2 | DKFZp547K1113 | Hypothetical protein DKFZp547K1113 | 15q26.1 |
| 40524_at | 3.70E−05 | 2.8 | PTPN21 | protein tyrosine phosphatase, non-receptor type 21 (PTPN21), mRNA. | 14q31.3 |
| 41856_at | 0.0008627 | 2.3 | UNC5B | Unc-5 homolog B (*C. elegans*) | 10q22.1 |
| 44783_s_at | 6.85E−05 | 3 | HEY1 | hairy/enhancer-of-split related with YRPW motif 1 (HEY1), mRNA. | 8q21 |
| 46665_at | 5.11E−05 | 2.4 | SEMA4C | sema domain, immunoglobulin domain (Ig), transmembrane domain (TM) and short cytoplasmic domain, (semaphorin) 4C (SEMA4C), mRNA. | 2q11.2 |
| 47550_at | 3.40E−05 | 4.4 | LZTS1 | leucine zipper, putative tumor suppressor 1 (LZTS1), mRNA. | 8p22 |
| 50376_at | 0.000154 | 2.1 | ZNF444 | zinc finger protein 444 (ZNF444), mRNA. | 19q13.43 |
| 52255_s_at | 1.15E−05 | 6.1 | COL5A3 | collagen, type V, alpha 3 (COL5A3), mRNA. | 19p13.2 |
| 55583_at | 0.0001374 | 3.2 | DOCK6 | dedicator of cytokinesis 6 (DOCK6), mRNA. | 19p13.2 |
| 57539_at | 0.0006736 | 2.1 | ZGPAT | zinc finger, CCCH-type with G patch domain (ZGPAT), transcript variant 3, mRNA. | 20q13.3 |
| 57703_at | 0.0001957 | 2.4 | SENP5 | SUMO1/sentrin specific peptidase 5 (SENP5), mRNA. | 3q29 |
| 57739_at | 0.0004289 | 2.2 | DND1 | Dead end homolog 1 (zebrafish) | 5q31.3 |
| 59433_at | 5.44E−05 | 2.2 | | Transcribed locus | X |
| 61734_at | 3.36E−05 | 2.7 | RCN3 | Reticulocalbin 3, EF-hand calcium binding domain | 19q13.33 |

As indicated in Table 1, 652 genes were up-regulated ≧2-fold in ovarian cancer endothelium samples. Of the 652 genes that were up-regulated ≧2-fold, 35 genes were elevated at least 6-fold in tumor endothelium (Table 2), with 7 being elevated more than 10-fold and 2 being elevated more than 28-fold.

TABLE 2

Genes up-regulated by ≧6-fold in the tumor associated endothelium.

| Entrez Gene ID | Gene | Description | Fold difference | chromosomal location | Function |
|---|---|---|---|---|---|
| 25975 | EGFL6 | EGF-like-domain, Multiple 6 | 36.8 | Xp22 | May regulate cell cycle and oncogenesis |
| 7130 | TNFAIP6 | Tumor necrosis factor, Alpha-induced protein 6 | 29.1 | 2q23.3 | Anti-inflammatory and chondroprotective effect |
| 7291 | TWIST1 | Basic helix-loop-helix (bHLH) transcription factor | 19.0 | 7p21.2 | Inhibits chondrogenesis |
| 6781 | STC1 | Stanniocalcin 1 | 13.3 | 8p21-p11.2 | Regulates calcium/ phosphate homeostasis, and cell metabolism |
| 84525 | HOP | Homeodomain-only Protein, transcript variant 2 | 13.1 | 4q11-q12 | Transcriptional repressor. Modulates serum response factor-dependent cardiac-specific gene expression and cardiac development |
| 1462 | CSPG2 | Chondroitin sulfate proteoglycan 2 (versican) | 10.4 | 5q14.3 | Extracellular matrix component of the vitreous gel. Anti-cell adhesive. |
| 57125 | PLXDC1 | Plexin domain containing 1 | 10.2 | 17q21.1 | Unknown |
| 6696 | SPP1 | Secreted phosphoprotein 1 (osteopontin, bone sialoproteinI, Early T-lymphocyte activation1) | 9.5 | 4q21-q25 | Expressed during embryogenesis, wound healing, and tumorigenesis. Regulates the assembly of heterotypic fibers composed of both type 1 and type V collagen. |
| 4318 | MMP9 | Matrix metallopeptidase 9 (gelatinase B, 92 kDa type IV collagenase) | 9.4 | 20q11.2-q13.1 | Breakdown of extracellular matrix. Plays a role in angiogenesis and tumor invasion |
| 3937 | LCP2/SLP76 | Lymphocyte cytosolic protein 2 (SH2 domain containing Leukocyte protein of 76 kDa) | 8.7 | 5q33.1-qter | Promotes T-cell development and activation |
| 152189 | CKLFSF8 | Chemokine-like factor Superfamily 8 | 8.6 | 3p23 | Regulates EGF-induced signaling. Regulates cell proliferation |
| 5366 | PMAIP1 | Phorbol-12-myristate-13-acetate-induced protein 1 | 8.5 | 18q21.32 | Unknown |
| 24147 | FJX1 | Four jointed box 1 (*drosophila*) | 7.7 | 11p13 | In *drosophila*, a downstream target of the Notch signaling pathway, regulates cell growth and differentiation. Not known in human |
| 8038 | ADAM12 | ADAM metallo-peptidase domain 12 (meltrin alpha) | 7.6 | 10q26.3 | Critical for tumor development. Involved in cell-cell and cell-matrix interactions. |
| 9636 | GIP2 | Interferon, alpha-inducible protein (clone IFI-15K) | 6.9 | 1p36.33 | Unclear, may be related to regulation of cell proliferation and differentiation |
| 25878 | MXRA5 | Matrix-remodeling associated 5 | 6.9 | Xp22.33 | Matrix remodeling |
| 1123 | CNH1 | Chimerin (chimaerin) 1 | 6.9 | 2q31-q32.1 | Rho GTPase activating protein |
| 3310 | HSPA6 | Heat shock 70 KDa protein 6 (HSP70B) | 6.8 | 1q23 | Involved in protein conformational interactions |
| 11211 | FZD10 | Frizzled homolog 10 (*Drosophila*) | 6.7 | 12q24.33 | Receptor for the wingless Type MMTV integration site family. |
| 10631 | POSTN | Periostin, osteoblast specific factor | 6.7 | 13q13.3 | Promotes integrin-dependent cell adhesion and motility, involved in extracellular matrix deposition |
| 85477 | SCIN | Scinderin | 6.6 | 7p21.3 | $Ca^{2+}$ dependent actin filament severing protein, regulates cortical actin network dynamics |

TABLE 2-continued

Genes up-regulated by ≥6-fold in the tumor associated endothelium.

| Entrez Gene ID | Gene | Description | Fold difference | chromosomal location | Function |
|---|---|---|---|---|---|
| 27242 | TNFRSF21 | Tumor necrosis factor Receptor superfamily, Member 21 | 6.6 | 6p21.1-12.2 | Unclear; maybe related to activation of NF-kappaB and MAPK8/JNK, induces cell apoptosis, involved in inflammation and immune regulation. |
| 25891 | DKFZP586-H2123 | Regeneration associated muscle protease, transcript variant 2 | 6.2 | 11p13 | Unknown |
| 4582 | MUC1 | Mucin 1, transmembrane, transcript variant 4 | 6.2 | 1q21 | Regulates cell aggregation, adhesion |
| 79084 | MEP50 | WD repeat domain 77, WDR77 | 6.1 | 1p13.2 | Involved in the methylation and assembly of spliceosomal snRNAs Sm proteins |
| 50509 | COL5A3 | Collagen, type V, alpha 3 | 6.1 | 19p13.2 | Extracellular protein, associated with formation of fibrils, and some connective tissue pathology such as inflammation, cancer and atherosclerosis |
| 6205 | RPS11 | Ribosomal protein S11 | 6.1 | 19q13.3 | Involved in the recognition of termination codons. |
| 55803 | CENTA2 | Centaurin, alpha 2 | 6.1 | 17q11.2 | A phosphatidylinositide-binding protein present in the dense membrane fractions of cell extracts |
| 2295 | FOXF2 | Forkhead box F2 | 6.0 | 6p25.3 | Regulates cell proliferation and survival, associated with BMP and Wnt signaling |

TABLE 3

Genes down-regulated in tumor associated endothelium.

| Entrez Gene ID | Gene | Description | Fold difference | Chromosomal location | Function |
|---|---|---|---|---|---|
| 5350 | PLN | Phospholamban | 0.108 | 6q22.1 | Inhibits sarcoplasmic reticulum Ca(2+)-ATPase activity |
| 6401 | SELE | Selectin E, endothelial Adhesion molecule 1 | 0.112 | 1q22-q25 | Cell surface lycoprotein. Inhibits cell adhesion. Early marker of inflammation |
| 9687 | GREB1 | GREB1 protein, transcript variant a | 0.116 | 2p25.1 | Transcription factor, inhibits cell proliferation |
| 4969 | OGN | Osteoglycin osteoinductive Factor, mimecan), transcript variant 3 | 0.147 | 9q22 | Regulates collagen fibrillogenesis |
| 25890 | AB13BP | ABI gene family, member 3 (NESH) binding protein | 0.152 | 3q12 | May play a role in cell motility by regulating NESH function |
| 90161 | HS6ST2 | Heparn sulfate 6-O-sulfotransferase 2 | 0.153 | Xq26.2 | Plays a role in growth factor signaling, cell adhesion, and enzymatic catalysis. Maybe involved in vascularization by mediating FGF signaling |
| 139221 | MUM1L1 | Melanoma associated antigen (mutated) 1-like 1 | 0.155 | Xq22.3 | Encodes tumor specific antigens |
| 4129 | MAOB | Monoamine oxidase B | 0.156 | Xp11.23 | Regulates neurotransmitters in central nervous system |
| 9452 | ITM2A | Integral membrane protein 2A | 0.156 | Xq13.3-Xq21.2 | Transmembrane protein. Marker of early stage of endochondral ossification |

TABLE 3-continued

Genes down-regulated in tumor associated endothelium.

| Entrez Gene ID | Gene | Description | Fold difference | Chromosomal location | Function |
| --- | --- | --- | --- | --- | --- |
| 170302 | ARX | Aristaless related homeobox | 0.162 | Xp22.1-p21.3 | Organ development. Bifunctional transcription factor |
| 10659 | CUGBP2 | CUG triplet repeat, RNA binding Protein 2, transcript variant 2 | 0.163 | 10p13 | Binds and stabilizes COX2 mRNA, inhibits its translation |
| 5577 | PRKAR2B | Protein kinase, cAMP-dependent regulatory, type II, beta | 0.163 | 7q22 | Encodes a regulatory subunit RII beta of human cAMP-dependent protein kinase A |
| 345557 | LCXD3 | Phosphatidylinositol-specific phospholipase C, X domain containing 3 | 0.165 | 5p13.1 | Quantitatively solubilizes AChE from purified synaptic plasma membranes and intact synaptosomes of Torpedo ocellata electric organ |

Multiple genes encoding proteins involved in extracellular matrix function, such as collagens, TNFAIP6, ADAMTS4, MMP9, MMP11, had increased expression in tumor vasculature compared with normal ovarian vasculature. The $\alpha_v$ integrin (vitronectin receptor) was elevated 2.5-fold in tumor endothelium. Several transcription factors were upregulated in the ovarian cancer vasculature. For example, HEYL was increased 3-fold. In addition, several transcription factors were identified including E2F transcription factor 3 (E2F3; plays a role in cell proliferation) (Black, Proc Natl Acad Sci U.S.A. 102: 15948-15953, 2005); runt-related transcription factor 1 (RUNX1; plays a role in angiogenesis) (Iwatsuki et al., Oncogene 24: 1129-1137, 2005), signal transducer and activator of transcription 2 (STAT2; role in cellular proliferation) (Gomez and Reich, J. Immunol. 170: 5373-5381, 2003), the SNAIL-related zinc-finger transcription factor, SLUG (SNAI2) (Perez-Mancera et al., Oncogene 24: 3073-3082, 2005), and Twist1 (Mironchik et al. Cancer Res. 65: 10801-10809, 2005). These genes were elevated 2-18 fold in the ovarian cancer vasculature relative to normal ovarian endothelial cells.

Additional genes were identified as being overexpressed in ovarian tumor endothelial cells that had previously been reported to be overexpressed in tumor cells. For example, epidermal growth factor receptor (EGFR) expression was increased by 3.5-fold in the tumor endothelium. EGFR is known to be overexpressed in ovarian carcinomas and is predictive of poor outcome (Berchuck et al., Am. J. Obstet. Gynecol. 164: 669-674, 1991). Similarly, non-receptor kinases such as focal adhesion kinase (FAK or PTK2; 3.1-fold increase) and Fyn (4.7 fold increase), which are play functional roles for tumor cells were detected. Genes that are overexpressed on both tumor cells and tumor-associated endothelial cells are targets for anti-vascular therapy due to the ability to target both the epithelial and stromal compartments.

In addition to the 652 genes that were identified as being up-regulated in ovarian tumor endothelial cells, 497 genes were down-regulated $\geq$2-fold in ovarian cancer endothelium samples (Table 1). FIG. 1 illustrates the fold changes observed in the relative expression levels between microarray data and real-time quantitative RT-PCR data from the pro-angiogenic gene signature provided in Table 1. Of the 497 genes that were down-regulated $\geq$2-fold, 17 genes were decreased at least 6-fold (as provide in Table 3). For example, monoamine oxidase B (MAOB), a gene responsible for detoxification and degradation of monoamines was decreased by 6.4-fold in the tumor endothelial cells (Grimsby et al., Nat. Genet. 17: 206-210, 1997). Decorin, a small multi-functional proteoglycan with anti-angiogenic properties, was decreased by 4.8-fold (Sulochana et al., J. Biol. Chem. 280: 27935-27948, 2005). Several other genes with potential anti-angiogenic or anti-proliferative roles such as Fibulin-5 (FBLN-5) and checkpoint suppressor 1 (CHES1) were down-regulated by 4.5-fold and 4.3-fold, respectively (Albig and Schiemann, DNA Cell Biol. 23: 367-379, 2004; and Scott and Plon, Gene 359: 119-126, 2005). These findings indicate that tumor endothelial cell and non-tumor endothelial cell isolates possess distinct expression profiles.

Example 4

Identification of Tumor Endothelial Markers

This example provides specific tumor endothelial cell markers.

Differentially regulated genes expressed in tumor-associated endothelium were identified by comparing tumor-associated endothelium versus normal endothelium with tumor-associated epithelial cells versus ovarian surface epithelium (OSE). The expression profile of microdissected papillary serous ovarian cancers using the same microarray methods has previously been reported (Bonome et al. Cancer Res. 65: 10602-10612, 2005). The current disclosed list of differentially expressed genes in tumor-associated endothelial cells was compared with the gene list identified for laser microdissected tumor-epithelial cells. A total of 534 differentially regulated genes were uniquely altered (up- or down-regulated) in the endothelial cells. The 28 genes with the greatest level of increase in ovarian tumor endothelial cells are listed in Table 4, of which 23 genes had a $\geq$6-fold increase in expression. A complete listing of the 534 differentially regulated genes is provided in Table 5. Further, FIG. 2 illustrates protein expression levels detected in ovarian endothelial cells following staining of samples with immunofluorescently-labeled PTK2, Fyn, MMP-9, β2-arrestin, Jagged1 and PLXDC1, respectively.

These findings identify tumor endothelial cell specific genes that can be used as biomarkers and potential targets for treatment of ovarian cancer.

TABLE 4

| Entrez Gene ID | Gene | Description | Fold difference | Chromosomal location | Function |
|---|---|---|---|---|---|
| 25975 | EGFL6 | EGF-like-domain, multiple 6 (EGFL6) | 36.848 | Xp22 | May regulate cell cycle and oncogenesis |
| 7130 | TNFAIP6 | Tumor necrosis factor, alpha-induced protein 6 (TNFAIP6) | 29.062 | 2q23.3 | Anti-inflammatory and chondroprotective effect |
| 7291 | TWIST1 | Twist homolog 1 (acrocephalosyndactyly 3; Saethre-Chotzen syndrome) (Drosophila) (TWIST1) | 18.969 | 7p21.2 | Inhibits chondrogenesis |
| 6781 | STC1 | Stanniocalcin 1 (STC1) | 13.326 | 8p21-p11.2 | Regulates calcium/phosphate homeostasis, and cell metabolism |
| 84525 | HOP | Homeodomain-only protein (HOP), transcript variant 2 | 13.144 | 4q11-q12 | Transcriptional repressor. Modulates serum response factor-dependent cardiac-specific gene expression and cardiac development |
| 1462 | CSPG2 | Chondroitin sulfate proteoglycan 2 (versican) (CSPG2) | 10.355 | 5q14.3 | Extracellular matrix component of the vitreous gel. Anti-cell adhesive. |
| 57125 | PLXDC1 | Plexin domain containing 1 (PLXDC1) | 10.215 | 17q21.1 | Unknown |
| 4318 | MMP9 | Matrix metallopeptidase 9 (gelatinase B, 92 kDa gelatinase, 92 kDa type IV collagenase) (MMP9) | 9.389 | 20q11.2-q13.1 | Breakdown of extracellular matrix. Plays a role in angiogenesis and tumor invasion |
| 3937 | LCP2 | Lymphocyte cytosolic protein 2 (SH2 domain containing leukocyte protein of 76 kDa) (LCP2) | 8.744 | 5q33.1-qter | Promotes T-cell development and activation |
| 5366 | PMAIP1 | Phorbol-12-myristate-13-acetate-induced protein 1 (PMAIP1) | 8.543 | 18q21.32 | Unknown |
| 8038 | ADAM12 | ADAM metallopeptidase domain 12 (meltrin alpha) (ADAM12), transcript variant 1 | 7.605 | 10q26.3 | Involved in cell-cell and cell-matrix interactions |
| 25878 | MXRA5 | Matrix-remodeling associated 5 (MXRA5) | 6.865 | Xp22.33 | Matrix remodeling |
| 1123 | CHN1 | Chimerin (chimaerin) 1 (CHN1) | 6.857 | 2q31-q32.1 | Rho GTPase activating protein |
| 3310 | HSPA6 | Heat shock 70 kDa protein 6 | 6.76 | 1q23 | Involved in protein conformational interactions |
| 10631 | POSTN | Periostin, osteoblast specific factor (POSTN) | 6.732 | 13q13.3 | Promotes integrin-dependent cell adhesion and motility, involved in extracellular matrix deposition |
| 11211 | FZD10 | Frizzled homolog 10 (Drosophila) (FZD10) | 6.701 | 12q24.33 | Receptor for the wingless type MMTV integration site family |
| 27242 | TNFRSF21 | Tumor necrosis factor receptor superfamily, member 21 (TNFRSF21) | 6.649 | 6p21.1-12.2 | Activates NF-kappaB and MAPK8/JNK, induces cell apoptosis, involved in inflammation and immune regulation. |
| 25891 | DKFZP586H2123 | Regeneration associated muscle protease, transcript variant 2 | 6.199 | 11p13 | Unknown |
| 79084 | MEP50 | WD repeat domain 77 | 6.144 | 1p13.2 | Involved in the methylation and assembly of spliceosomal snRNAs Sm proteins |
| 50509 | COL5A3 | Collagen, type V, alpha 3 (COL5A3) | 6.118 | 19p13.2 | Extracellular protein, associated with formation of fibrils, and some connective tissue pathology such as inflammation, cancer and atherosclerosis |

TABLE 4-continued

Genes specifically regulated in tumor-endothelium

| Entrez Gene ID | Gene | Description | Fold difference | Chromosomal location | Function |
|---|---|---|---|---|---|
| 6205 | RPS11 | Ribosomal protein S11 (RPS11) | 6.095 | 19q13.3 | Involved in the recognition of termination codons |
| 55803 | CENTA2 | Centaurin, alpha 2 (CENTA2) | 6.09 | 17q11.2 | A phosphatidylinositide-binding protein present in the dense membrane fractions of cell extracts |
| 90161 | HS6ST2 | Heparan sulfate 6-O-sulfotransferase 2 (HS6ST2) | 0.153 | Xq26.2 | Plays a role in growth factor signaling, cell adhesion, and enzymatic catalysis. Maybe involved in vascularization by mediating FGF signaling |
| 4969 | OGN | Osteoglycin (osteoinductive factor, mimecan) (OGN), transcript variant 3 | 0.147 | 9q22 | Regulates collagen fibrillogenesis |
| 9687 | GREB1 | GREB1 protein, transcript variant a | 0.116 | 2p25.1 | Transcription factor; inhibits cell proliferation |
| 6401 | SELE | Selectin E (endothelial adhesion molecule 1) (SELE) | 0.112 | 1q22-q25 | Cell surface lycoprotein. Inhibits cell adhesion. Early marker of inflammation |
| 5350 | PLN | Phospholamban | 0.108 | 6q22.1 | Inhibits sarcoplasmic reticulum Ca(2+)-ATPase activity |

TABLE 5

Genes specifically regulated in tumor endothelium.

| Parametric p-value | Fold difference of geom means (Tumor/Normal) | Probe set | Description | UG cluster | Gene symbol | Map |
|---|---|---|---|---|---|---|
| $p < 1e-07$ | 29.062 | 206026_s_at | tumor necrosis factor, alpha-induced protein 6 (TNFAIP6), mRNA. | Hs.437322 | TNFAIP6 | 2q23.3 |
| $p < 1e-07$ | 0.274 | 213803_at | Karyopherin (importin) beta 1 | Hs.532793 | KPNB1 | 17q21.32 |
| $p < 1e-07$ | 0.205 | 235309_at | CDNA clone IMAGE: 4140029 | | Hs.526499 | 16 |
| 1e-007 | 2.85 | 228204_at | proteasome (prosome, macropain) subunit, beta type, 4 (PSMB4), mRNA. | Hs.89545 | PSMB4 | 1q21 |
| 1e-007 | 13.144 | 211597_s_at | homeodomain-only protein (HOP), transcript variant 2, mRNA. | Hs.121443 | HOP | 4q11-q12 |
| 2e-007 | 3.116 | 213848_at | Dual specificity phosphatase 7 | Hs.3843 | DUSP7 | 3p21 |
| 3e-007 | 3.599 | 233274_at | NCK adaptor protein 1 | Hs.477693 | NCK1 | 3q21 |
| 3e-007 | 0.266 | 212653_s_at | EH domain binding protein 1 (EHBP1), mRNA. | Hs.271667 | EHBP1 | 2p15 |
| 4e-007 | 10.215 | 214081_at | plexin domain containing 1 (PLXDC1), mRNA. | Hs.125036 | PLXDC1 | 17q21.1 |
| 4e-007 | 0.27 | 213364_s_at | sorting nexin 1 (SNX1), transcript variant 2, mRNA. | Hs.188634 | SNX1 | 15q22.31 |
| 4e-007 | 36.848 | 219454_at | EGF-like-domain, multiple 6 (EGFL6), mRNA. | Hs.12844 | EGFL6 | Xp22 |
| 4e-007 | 18.969 | 213943_at | twist homolog 1 (acrocephalosyndactyly 3; Saethre-Chotzen syndrome) (*Drosophila*) (TWIST), mRNA. | Hs.66744 | TWIST1 | 7p21.2 |

TABLE 5-continued

Genes specifically regulated in tumor endothelium.

| Parametric p-value | Fold difference of geom means (Tumor/Normal) | Probe set | Description | UG cluster | Gene symbol | Map |
|---|---|---|---|---|---|---|
| 4e−007 | 0.327 | 225123_at | Sestrin 3 | Hs.120633 | SESN3 | 11q21 |
| 5e−007 | 0.165 | 230081_at | phosphatidylinositol-specific phospholipase C, X domain containing 3 (PLCXD3), mRNA. | Hs.145404 | PLCXD3 | 5p13.1 |
| 7e−007 | 5.249 | 228579_at | Potassium voltage-gated channel, KQT-like subfamily, member 3 | Hs.374023 | KCNQ3 | 8q24 |
| 8e−007 | 6.199 | 213661_at | regeneration associated muscle protease (DKFZP586H2123), transcript variant 2, mRNA. | Hs.55044 | DKFZP586H2123 | 11p13 |
| 9e−007 | 6.701 | 219764_at | frizzled homolog 10 (*Drosophila*) (FZD10), mRNA. | Hs.31664 | FZD10 | 12q24.33 |
| 9e−007 | 3.38 | 212044_s_at | ribosomal protein L27a (RPL27A), mRNA. | Hs.523463 | RPL27A | 11p15 |
| 1e−006 | 0.42 | 213574_s_at | Karyopherin (importin) beta 1 | Hs.532793 | KPNB1 | 17q21.32 |
| 1.1e−006 | 7.684 | 219700_at | plexin domain containing 1 (PLXDC1), mRNA. | Hs.125036 | PLXDC1 | 17q21.1 |
| 1.2e−006 | 0.294 | 222791_at | round spermatid basic protein 1 (RSBN1), mRNA. | Hs.486285 | RSBN1 | 1p13.2 |
| 1.2e−006 | 0.232 | 221589_s_at | Aldehyde dehydrogenase 6 family, member A1 | Hs.293970 | ALDH6A1 | 14q24.3 |
| 1.2e−006 | 7.724 | 204285_s_at | phorbol-12-myristate-13-acetate-induced protein 1 (PMAIP1), mRNA. | Hs.96 | PMAIP1 | 18q21.32 |
| 1.4e−006 | 10.546 | 204595_s_at | stanniocalcin 1 (STC1), mRNA. | Hs.25590 | STC1 | 8p21-p11.2 |
| 1.5e−006 | 3.695 | 225147_at | pleckstrin homology, Sec7 and coiled-coil domains 3 (PSCD3), mRNA. | Hs.487479 | PSCD3 | 7p22.1 |
| 1.5e−006 | 9.368 | 234723_x_at | CDNA: FLJ21228 fis, clone COL00739 | Hs.306716 | | 7 |
| 1.5e−006 | 0.374 | 212498_at | Membrane-associated ring finger (C3HC4) 6 | Hs.432862 | MARCH-VI | 5p15.2 |
| 1.5e−006 | 13.326 | 230746_s_at | stanniocalcin 1 (STC1), mRNA. | Hs.25590 | STC1 | 8p21-p11.2 |
| 1.6e−006 | 6.09 | 219358_s_at | centaurin, alpha 2 (CENTA2), mRNA. | Hs.514063 | CENTA2 | 17q11.2 |
| 1.8e−006 | 0.346 | 201425_at | aldehyde dehydrogenase 2 family (mitochondrial) (ALDH2), nuclear gene encoding mitochondrial protein, mRNA. | Hs.436437 | ALDH2 | 12q24.2 |
| 1.9e−006 | 4.094 | 225505_s_at | chromosome 20 open reading frame 81 (C20orf81), mRNA. | Hs.29341 | C20orf81 | 20p13 |
| 2.1e−006 | 0.284 | 219939_s_at | cold shock domain containing E1, RNA-binding (CSDE1), transcript variant 2, mRNA. | Hs.69855 | CSDE1 | 1p22 |
| 2.2e−006 | 4.136 | 221059_s_at | coactosin-like 1 (Dictyostelium) (COTL1), mRNA. | Hs.289092 | COTL1 | 16q24.1 |
| 2.2e−006 | 6.649 | 218856_at | tumor necrosis factor receptor superfamily, member 21 (TNFRSF21), mRNA. | Hs.443577 | TNFRSF21 | 6p21.1-12.2 |
| 2.4e−006 | 3.826 | 205068_s_at | Rho GTPase activating protein 26 (ARHGAP26), | Hs.293593 | ARHGAP26 | 5q31 |
| 2.4e−006 | 4.807 | 242100_at | chondroitin sulfate synthase 3 (CSS3), mRNA. | Hs.213137 | CSS3 | 5q23.3 |
| 2.4e−006 | 5.981 | 206377_at | forkhead box F2 (FOXF2), mRNA. | Hs.484423 | FOXF2 | 6p25.3 |

TABLE 5-continued

Genes specifically regulated in tumor endothelium.

| Parametric p-value | Fold difference of geom means (Tumor/Normal) | Probe set | Description | UG cluster | Gene symbol | Map |
|---|---|---|---|---|---|---|
| 2.4e−006 | 0.327 | 234512_x_at | PREDICTED: similar to Rpl7a protein (LOC442159), mRNA. | Hs.535174 | LOC442159 | 6 |
| 2.6e−006 | 4.037 | 232304_at | Pellino homolog 1 (Drosophila) | Hs.7886 | PELI1 | 2p13.3 |
| 2.7e−006 | 5.391 | 242546_at | LOC440156 | Hs.529095 | | 14q11.1 |
| 2.7e−006 | 3.362 | 227295_at | IKK interacting protein (IKIP), transcript variant 3.1, mRNA. | Hs.252543 | IKIP | 12q23.1 |
| 2.8e−006 | 4.563 | 1553575_at | Unknown | | | |
| 2.9e−006 | 3.761 | 214924_s_at | OGT(O-Glc-NAc transferase)-interacting protein 106 KDa (OIP106), mRNA. | Hs.535711 | OIP106 | 3p25.3-p24.1 |
| 3e−006 | 6.144 | 242398_x_at | WD repeat domain 77 | Hs.204773 | MEP50 | 1p13.2 |
| 3.5e−006 | 8.543 | 204286_s_at | phorbol-12-myristate-13-acetate-induced protein 1 (PMAIP1), mRNA. | Hs.96 | PMAIP1 | 18q21.32 |
| 3.7e−006 | 3.271 | 241632_x_at | ESTs | | | |
| 3.9e−006 | 0.258 | 209512_at | hydroxysteroid dehydrogenase like 2 (HSDL2), mRNA. | Hs.59486 | HSDL2 | 9q32 |
| 4e−006 | 4.384 | 219359_at | hypothetical protein FLJ22635 (FLJ22635), mRNA. | Hs.353181 | FLJ22635 | 11p15.5 |
| 4e−006 | 0.279 | 227719_at | CDNA FLJ37828 fis, clone BRSSN2006575 | Hs.123119 | | 13 |
| 4e−006 | 3.268 | 226063_at | vav 2 oncogene (VAV2), mRNA. | Hs.369921 | VAV2 | 9q34.1 |
| 4e−006 | 8.744 | 205269_at | lymphocyte cytosolic protein 2 (SH2 domain containing leukocyte protein of 76 kDa) (LCP2), mRNA. | Hs.304475 | LCP2 | 5q33.1-qter |
| 4.1e−006 | 3.906 | 215599_at | SMA4 | Hs.482411 | SMA4 | 5q13 |
| 4.2e−006 | 0.434 | 214527_s_at | polyglutamine binding protein 1 (PQBP1), transcript variant 5, mRNA. | | PQBP1 | Xp11.23 |
| 4.5e−006 | 4.068 | 220817_at | transient receptor potential cation channel, subfamily C, member 4 (TRPC4), mRNA. | Hs.262960 | TRPC4 | 13q13.1-q13.2 |
| 4.6e−006 | 0.237 | 202920_at | ankyrin 2, neuronal (ANK2), transcript variant 2, mRNA. | Hs.137367 | ANK2 | 4q25-q27 |
| 4.8e−006 | 6.865 | 209596_at | matrix-remodelling associated 5 (MXRA5), mRNA. | Hs.369422 | MXRA5 | Xp22.33 |
| 5.1e−006 | 0.324 | 201737_s_at | membrane-associated ring finger (C3HC4) 6 (MARCH6), mRNA. | Hs.432862 | 38417 | 5p15.2 |
| 5.3e−006 | 0.256 | 224763_at | ribosomal protein L37 (RPL37), mRNA. | Hs.80545 | RPL37 | 5p13 |
| 5.4e−006 | 6.857 | 212624_s_at | chimerin (chimaerin) 1 (CHN1), transcript variant 2, mRNA. | Hs.380138 | CHN1 | 2q31-q32.1 |
| 5.8e−006 | 0.203 | 222486_s_at | ADAM metallopeptidase with thrombospondin type 1 motif, 1 (ADAMTS1), mRNA. | Hs.534115 | ADAMTS1 | 21q21.2 |
| 5.9e−006 | 0.294 | 202908_at | Wolfram syndrome 1 (wolframin) (WFS1), mRNA. | Hs.518602 | WFS1 | 4p16 |
| 6.2e−006 | 0.267 | 242051_at | Transcribed locus | Hs.130260 | | X |
| 6.3e−006 | 0.376 | 205412_at | acetyl-Coenzyme A acetyltransferase 1 (acetoacetyl Coenzyme A thiolase) (ACAT1), nuclear gene encoding mitochondrial protein, mRNA. | Hs.232375 | ACAT1 | 11q22.3-q23.1 |
| 6.5e−006 | 7.988 | 224549_x_at | | | | |
| 6.8e−006 | 0.253 | 213272_s_at | promethin (LOC57146), mRNA. | Hs.258212 | LOC57146 | 16p12 |

TABLE 5-continued

Genes specifically regulated in tumor endothelium.

| Parametric p-value | Fold difference of geom means (Tumor/Normal) | Probe set | Description | UG cluster | Gene symbol | Map |
|---|---|---|---|---|---|---|
| 7.2e−006 | 4.12 | 242369_x_at | Nuclear receptor coactivator 2 | Hs.446678 | NCOA2 | 8q13.3 |
| 7.3e−006 | 0.26 | 226625_at | Transforming growth factor, beta receptor III (betaglycan, 300 kDa) | Hs.482390 | TGFBR3 | 1p33-p32 |
| 7.7e−006 | 0.245 | 219511_s_at | synuclein, alpha interacting protein (synphilin) (SNCAIP), mRNA. | Hs.426463 | SNCAIP | 5q23.1-q23.3 |
| 7.8e−006 | 4.059 | 222449_at | transmembrane, prostate androgen induced RNA (TMEPAI), transcript variant 3, mRNA. | Hs.517155 | TMEPAI | 20q13.31-q13.33 |
| 8e−006 | 2.237 | 212351_at | eukaryotic translation initiation factor 2B, subunit 5 epsilon, 82 kDa (EIF2B5), mRNA. | Hs.283551 | EIF2B5 | 3q27.1 |
| 8.1e−006 | 3.836 | 219634_at | carbohydrate (chondroitin 4) sulfotransferase 11 (CHST11), mRNA. | Hs.17569 | CHST11 | 12q |
| 8.3e−006 | 0.418 | 226751_at | chromosome 2 open reading frame 32 (C2orf32), mRNA. | Hs.212885 | C2orf32 | 2p14 |
| 8.3e−006 | 5.037 | 209081_s_at | collagen, type XVIII, alpha 1 (COL18A1), transcript variant 2, mRNA. | Hs.517356 | COL18A1 | 21q22.3 |
| 9e−006 | 2.362 | 205812_s_at | transmembrane emp24 protein transport domain containing 9 (TMED9), mRNA. | Hs.279929 | TMED9 | 5q35.3 |
| 9.3e−006 | 2.862 | 234985_at | Hypothetical protein LOC143458 | Hs.205865 | LOC143458 | 11p13 |
| 9.6e−006 | 3.652 | 242029_at | Fibronectin type III domain containing 3B | Hs.159430 | FNDC3B | 3q26.31 |
| 9.6e−006 | 0.386 | 211666_x_at | ribosomal protein L3 (RPL3), mRNA. | Hs.119598 | RPL3 | 22q13 |
| 9.8e−006 | 4.815 | 202465_at | procollagen C-endopeptidase enhancer (PCOLCE), mRNA. | Hs.202097 | PCOLCE | 7q22 |
| 1.06e−005 | 0.303 | 203799_at | CD302 antigen (CD302), mRNA. | Hs.130014 | CD302 | 2q24.2 |
| 1.1e−005 | 3.787 | 228253_at | lysyl oxidase-like 3 (LOXL3), mRNA. | Hs.469045 | LOXL3 | 2p13 |
| 1.1e−005 | 3.674 | 209685_s_at | protein kinase C, beta 1 (PRKCB1), transcript variant 2, mRNA. | Hs.460355 | PRKCB1 | 16p11.2 |
| 1.11e−005 | 0.33 | 224445_s_at | zinc finger, FYVE domain containing 21 (ZFYVE21), mRNA. | Hs.549192 | ZFYVE21 | 14q32.33 |
| 1.13e−005 | 3.466 | 222379_at | Potassium voltage-gated channel, Isk-related family, member 4 | Hs.348522 | KCNE4 | 2q36.3 |
| 1.15e−005 | 6.118 | 52255_s_at | collagen, type V, alpha 3 (COL5A3), mRNA. | Hs.235368 | COL5A3 | 19p13.2 |
| 1.17e−005 | 2.821 | 233180_at | Ring finger protein 152 | Hs.465316 | RNF152 | 18q21.33 |
| 1.18e−005 | 0.232 | 212224_at | aldehyde dehydrogenase 1 family, member A1 (ALDH1A1), mRNA. | Hs.76392 | ALDH1A1 | 9q21.13 |
| 1.2e−005 | 6.095 | 213350_at | ribosomal protein S11 (RPS11), mRNA. | Hs.433529 | RPS11 | 19q13.3 |
| 1.2e−005 | 3.729 | 226911_at | hypothetical protein FLJ39155 (FLJ39155), transcript variant 4, mRNA. | Hs.20103 | FLJ39155 | 5p13.2-p13.1 |
| 1.21e−005 | 2.975 | 219102_at | reticulocalbin 3, EF-hand calcium binding domain (RCN3), mRNA. | Hs.439184 | RCN3 | 19q13.33 |
| 1.25e−005 | 0.115 | 222722_at | osteoglycin (osteoinductive factor, mimecan) (OGN), transcript variant 3, mRNA. | Hs.109439 | OGN | 9q22 |

TABLE 5-continued

Genes specifically regulated in tumor endothelium.

| Parametric p-value | Fold difference of geom means (Tumor/Normal) | Probe set | Description | UG cluster | Gene symbol | Map |
|---|---|---|---|---|---|---|
| 1.29e-005 | 0.17 | 227703_s_at | synaptotagmin-like 4 (granuphilin-a) (SYTL4), mRNA. | Hs.522054 | SYTL4 | Xq21.33 |
| 1.3e-005 | 0.46 | 211988_at | SWI/SNF related, matrix associated, actin dependent regulator of chromatin, subfamily e, member 1 (SMARCE1), mRNA. | Hs.463010 | SMARCE1 | 17q21.2 |
| 1.31e-005 | 0.238 | 204793_at | G protein-coupled receptor associated sorting protein 1 (GPRASP1), mRNA. | Hs.522730 | GPRASP1 | Xq22.1 |
| 1.34e-005 | 0.339 | 229891_x_at | KIAA1704 | Hs.507922 | KIAA1704 | 13q13-q14 |
| 1.35e-005 | 0.215 | 228554_at | MRNA; cDNA DKFZp586G0321 (from clone DKFZp586G0321) | Hs.32405 | | 11 |
| 1.38e-005 | 0.299 | 210950_s_at | farnesyl-diphosphate farnesyltransferase 1 (FDFT1), mRNA. | Hs.546253 | FDFT1 | 8p23.1-p22 |
| 1.38e-005 | 4.593 | 220014_at | mesenchymal stem cell protein DSC54 (LOC51334), mRNA. | Hs.157461 | LOC51334 | 5q23.1 |
| 1.4e-005 | 0.262 | 225162_at | SH3 domain protein D19 (SH3D19), mRNA. | Hs.519018 | SH3D19 | 4q31.3 |
| 1.41e-005 | 0.387 | 212408_at | torsin A interacting protein 1 (TOR1AIP1), mRNA. | Hs.496459 | TOR1AIP1 | 1q24.2 |
| 1.41e-005 | 0.446 | 201054_at | heterogeneous nuclear ribonucleoprotein A0 (HNRPA0), mRNA. | Hs.96996 | HNRPA0 | 5q31 |
| 1.47e-005 | 4.235 | 204639_at | adenosine deaminase (ADA), mRNA. | Hs.407135 | ADA | 20q12-q13.11 |
| 1.5e-005 | 4.351 | 225646_at | cathepsin C (CTSC), transcript variant 2, mRNA. | | CTSC | 11q14.1-q14.3 |
| 1.51e-005 | 3.657 | 209969_s_at | signal transducer and activator of transcription 1, 91 kDa (STAT1), transcript variant beta, mRNA. | Hs.470943 | STAT1 | 2q32.2 |
| 1.54e-005 | 2.663 | 236249_at | IKK interacting protein (IKIP), transcript variant 1, mRNA. | Hs.252543 | IKIP | 12q23.1 |
| 1.58e-005 | 3.274 | 218804_at | transmembrane protein 16A (TMEM16A), mRNA. | Hs.503074 | TMEM16A | 11q13.3 |
| 1.59e-005 | 0.427 | 221988_at | Hypothetical protein MGC2747 | Hs.356467 | MGC2747 | 19p13.11 |
| 1.59e-005 | 2.779 | 204786_s_at | interferon (alpha, beta and omega) receptor 2 (IFNAR2), transcript variant 1, mRNA. | Hs.549042 | IFNAR2 | 21q22.11 |
| 1.61e-005 | 0.413 | 200023_s_at | eukaryotic translation initiation factor 3, subunit 5 epsilon, 47 kDa (EIF3S5), mRNA. | Hs.516023 | EIF3S5 | 11p15.4 |
| 1.62e-005 | 4.278 | 201596_x_at | keratin 18 (KRT18), transcript variant 2, mRNA. | Hs.406013 | KRT18 | 12q13 |
| 1.64e-005 | 0.32 | 222605_at | REST corepressor 3 (RCOR3), mRNA. | Hs.356399 | RCOR3 | 1q32.3 |
| 1.64e-005 | 0.371 | 209733_at | Hypothetical protein LOC286440 | Hs.348844 | LOC286440 | Xq22.3 |
| 1.67e-005 | 4.144 | 232458_at | Collagen, type III, alpha 1 (Ehlers-Danlos syndrome type IV, autosomal dominant) | Hs.443625 | COL3A1 | 2q31 |
| 1.7e-005 | 0.282 | 224901_at | Stearoyl-CoA desaturase 5 | Hs.379191 | SCD4 | 4q21.3 |
| 1.73e-005 | 4.385 | 233912_x_at | ELMO domain containing 2 | Hs.450105 | ELMOD2 | 4q31.21 |
| 1.76e-005 | 5.792 | 220301_at | chromosome 18 open reading frame 14 (C18orf14), mRNA. | Hs.280781 | C18orf14 | 18q22.1 |

TABLE 5-continued

Genes specifically regulated in tumor endothelium.

| Parametric p-value | Fold difference of geom means (Tumor/Normal) | Probe set | Description | UG cluster | Gene symbol | Map |
|---|---|---|---|---|---|---|
| 1.76e−005 | 0.388 | 207170_s_at | LETM1 domain containing 1 (LETMD1), transcript variant 3, mRNA. | Hs.370457 | LETMD1 | 12q13.12 |
| 1.82e−005 | 0.418 | 201076_at | NHP2 non-histone chromosome protein 2-like 1 (S. cerevisiae) (NHP2L1), transcript variant 2, mRNA. | Hs.182255 | NHP2L1 | 22q13.2-q13.31 |
| 1.82e−005 | 0.252 | 228885_at | MAM domain containing 2 (MAMDC2), mRNA. | Hs.127386 | MAMDC2 | 9q21.11 |
| 1.85e−005 | 0.411 | 212609_s_at | V-akt murine thymoma viral oncogene homolog 3 (protein kinase B, gamma) | Hs.498292 | AKT3 | 1q43-q44 |
| 1.86e−005 | 4.564 | 221558_s_at | lymphoid enhancer-binding factor 1 (LEF1), mRNA. | Hs.555947 | LEF1 | 4q23-q25 |
| 1.87e−005 | 3.054 | 235204_at | Ectonucleoside triphosphate diphosphohydrolase 7 | Hs.369424 | ENTPD7 | 10 |
| 1.9e−005 | 3.283 | 202820_at | aryl hydrocarbon receptor (AHR), mRNA. | Hs.171189 | AHR | 7p15 |
| 1.91e−005 | 4.787 | 1565823_at | septin 7 (SEPT7), transcript variant 2 mRNA. | Hs.191346 | 38602 | 7p14.3-p14.1 |
| 1.93e−005 | 0.342 | 221726_at | ribosomal protein L22 (RPL22), mRNA. | Hs.515329 | RPL22 | 1p36.3-p36.2 |
| 1.93e−005 | 0.485 | 202029_x_at | ribosomal protein L38 (RPL38), mRNA. | Hs.380953 | RPL38 | 17q23-q25 |
| 1.94e−005 | 0.258 | 209513_s_at | hydroxysteroid dehydrogenase like 2 (HSDL2), mRNA. | Hs.59486 | HSDL2 | 9q32 |
| 1.95e−005 | 0.356 | 226806_s_at | MRNA; cDNA DKFZp686J23256 (from clone DKFZp686J23256) | | Hs.379253 | 1 |
| 2.01e−005 | 4.146 | 1558048_x_at | Unknown | | | |
| 2.03e−005 | 3.183 | 237494_at | Transcribed locus | | Hs.174934 | 15 |
| 2.09e−005 | 0.306 | 201432_at | catalase (CAT), mRNA. | Hs.502302 | CAT | 11p13 |
| 2.11e−005 | 3.698 | 203878_s_at | matrix metallopeptidase 11 (stromelysin 3) (MMP11), mRNA. | Hs.143751 | MMP11 | 22q11.23 |
| 2.11e−005 | 2.481 | 212323_s_at | vacuolar protein sorting 13D (yeast) (VPS13D), transcript variant 2, mRNA. | Hs.439381 | VPS13D | 1p36.22-p36.21 |
| 2.11e−005 | 0.215 | 242488_at | CDNA FLJ38396 fis, clone FEBRA2007957 | | Hs.155736 | 1 |
| 214e−005 | 2.201 | 219092_s_at | chromosome 9 open reading frame 12 (C9orf12), mRNA. | Hs.16603 | C9orf12 | 9q21.33-q22.31 |
| 215e−005 | 2.239 | 217118_s_at | chromosome 22 open reading frame 9 (C22orf9), transcript variant 2, mRNA. | Hs.369682 | C22orf9 | 22q13.31 |
| 2.29e−005 | 0.44 | 214097_at | Ribosomal protein S21 | Hs.190968 | RPS21 | 20q13.3 |
| 2.29e−005 | 5.232 | 225799_at | hypothetical protein MGC4677 (MGC4677), mRNA. | Hs.446688 | MGC4677 | 2p11.2 |
| 2.3e−005 | 3.258 | 244197_x_at | CCR4-NOT transcription complex, subunit 2 | Hs.133350 | CNOT2 | 12q15 |
| 2.37e−005 | 7.605 | 202952_s_at | ADAM metallopeptidase domain 12 (meltrin alpha) (ADAM12), transcript variant 1, mRNA. | Hs.386283 | ADAM12 | 10q26.3 |
| 2.4e−005 | 0.462 | 201030_x_at | lactate dehydrogenase B (LDHB), mRNA. | Hs.446149 | LDHB | 12p12.2-p12.1 |

TABLE 5-continued

Genes specifically regulated in tumor endothelium.

| Parametric p-value | Fold difference of geom means (Tumor/Normal) | Probe set | Description | UG cluster | Gene symbol | Map |
|---|---|---|---|---|---|---|
| 2.41e−005 | 0.349 | 208643_s_at | X-ray repair complementing defective repair in Chinese hamster cells 5 (double-strand-break rejoining; Ku autoantigen, 80 kDa) (XRCC5), mRNA. | Hs.388739 | XRCC5 | 2q35 |
| 2.5e−005 | 0.381 | 200013_at | ribosomal protein L24 (RPL24), mRNA. | Hs.477028 | RPL24 | 3q12 |
| 2.57e−005 | 10.355 | 221731_x_at | chondroitin sulfate proteoglycan 2 (versican) (CSPG2), mRNA. | Hs.443681 | CSPG2 | 5q14.3 |
| 2.66e−005 | 0.175 | 211569_s_at | L-3-hydroxyacyl-Coenzyme A dehydrogenase, short chain (HADHSC), mRNA. | Hs.438289 | HADHSC | 4q22-q26 |
| 2.69e−005 | 0.412 | 201023_at | TAF7 RNA polymerase II, TATA box binding protein (TBP)-associated factor, 55 kDa (TAF7), mRNA. | Hs.438838 | TAF7 | 5q31 |
| 2.71e−005 | 5.473 | 224254_x_at | Transferrin | Hs.518267 | TF | 3q22.1 |
| 2.75e−005 | 4.279 | 213479_at | neuronal pentraxin II (NPTX2), mRNA. | Hs.3281 | NPTX2 | 7q21.3-q22.1 |
| 2.81e−005 | 3.34 | 230440_at | PREDICTED: zinc finger protein 469 (ZNF469), mRNA. | Hs.54925 | ZNF469 | 16 |
| 2.86e−005 | 3.995 | 227347_x_at | hairy and enhancer of split 4 (Drosophila) (HES4), mRNA. | Hs.154029 | HES4 | 1p36.33 |
| 2.87e−005 | 2.894 | 218131_s_at | GATA zinc finger domain containing 2A (GATAD2A), mRNA. | Hs.118964 | GATAD2A | 19p13.11 |
| 2.9e−005 | 0.327 | 235612_at | Transcribed locus, moderately similar to NP_858931.1 NFS1 nitrogen fixation 1 isoform b precursor; cysteine desulfurase; nitrogen-fixing bacteria S-like protein; nitrogen fixation 1 (S. cerevisiae, homolog) [Homo sapiens] | | Hs.396796 | 1 |
| 2.94e−005 | 0.186 | 229308_at | Transcribed locus | | Hs.355689 | 18 |
| 3.01e−005 | 2.617 | 223617_x_at | ATPase family, AAA domain containing 3B (ATAD3B), mRNA. | Hs.23413 | ATAD3B | 1p36.33 |
| 3.01e−005 | 4.273 | 240655_at | Activated leukocyte cell adhesion molecule | Hs.150693 | ALCAM | 3q13.1 |
| 3.07e−005 | 2.553 | 209030_s_at | immunoglobulin superfamily, member 4 (IGSF4), mRNA. | Hs.370510 | IGSF4 | 11q23.2 |
| 3.07e−005 | 2.812 | 210069_at | carnitine palmitoyltransferase 1B (muscle) (CPT1B), nuclear gene encoding mitochondrial protein, transcript variant 3, mRNA. | Hs.439777 | CPT1B | 22q13.33 |
| 3.1e−005 | 2.462 | 213258_at | Tissue factor pathway inhibitor (lipoprotein-associated coagulation inhibitor) | Hs.516578 | TFPI | 2q31-q32.1 |
| 3.28e−005 | 4.4 | 241686_x_at | ESTs, Weakly similar to hypothetical protein FLJ20378 [Homo sapiens] [H. sapiens] | | | |
| 3.33e−005 | 5.315 | 1553186_x_at | RAS and EF-hand domain containing | Hs.129136 | RASEF | 9q21.32 |
| 3.34e−005 | 0.361 | 226280_at | BCL2/adenovirus E1B 19 kDa interacting protein 2 | Hs.283454 | BNIP2 | 15q22.2 |

TABLE 5-continued

Genes specifically regulated in tumor endothelium.

| Parametric p-value | Fold difference of geom means (Tumor/Normal) | Probe set | Description | UG cluster | Gene symbol | Map |
|---|---|---|---|---|---|---|
| 3.34e−005 | 0.481 | 218929_at | collaborates/cooperates with ARF (alternate reading frame) protein (CARF), mRNA. | Hs.32922 | CARF | 4q35.1 |
| 3.36e−005 | 2.651 | 61734_at | Reticulocalbin 3, EF-hand calcium binding domain | Hs.439184 | RCN3 | 19q13.33 |
| 3.38e−005 | 3.492 | 204735_at | phosphodiesterase 4A, cAMP-specific (phosphodiesterase E2 dunce homolog, Drosophila) (PDE4A), mRNA. | Hs.89901 | PDE4A | 19p13.2 |
| 3.4e−005 | 4.417 | 47550_at | leucine zipper, putative tumor suppressor 1 (LZTS1), mRNA. | Hs.521432 | LZTS1 | 8p22 |
| 3.41e−005 | 0.309 | 225698_at | TIGA1 (TIGA1), mRNA. | Hs.12082 | TIGA1 | 5q21-q22 |
| 3.42e−005 | 0.304 | 211986_at | AHNAK nucleoprotein (desmoyokin) (AHNAK), transcript variant 1, mRNA. | Hs.502756 | AHNAK | 11q12.2 |
| 3.43e−005 | 0.31 | 225387_at | Tetraspanin 5 | Hs.118118 | TM4SF9 | 4q23 |
| 3.48e−005 | 0.442 | 201600_at | prohibitin 2 (PHB2), mRNA. | Hs.504620 | PHB2 | 12p13 |
| 3.5e−005 | 0.323 | 225125_at | transmembrane protein 32 (TMEM32), mRNA. | Hs.110702 | TMEM32 | Xq26.3 |
| 3.52e−005 | 4.82 | 206637_at | purinergic receptor P2Y, G-protein coupled, 14 (P2RY14), mRNA. | Hs.2465 | P2RY14 | 3q21-q25 |
| 3.6e−005 | 0.475 | 221725_at | WAS protein family, member 2 | Hs.469244 | WASF2 | 1p36.11-p34.3 |
| 3.63e−005 | 0.387 | 209385_s_at | proline synthetase co-transcribed homolog (bacterial) (PROSC), mRNA. | Hs.304792 | PROSC | 8p11.2 |
| 3.65e−005 | 2.247 | 218018_at | pyridoxal (pyridoxine, vitamin B6) kinase (PDXK), mRNA. | Hs.284491 | PDXK | 21q22.3 |
| 3.68e−005 | 2.36 | 224598_at | mannosyl (alpha-1,3-)-glycoprotein beta-1,4-N-acetylglucosaminyltransferase, isoenzyme B (MGAT4B), transcript variant 1, mRNA. | Hs.437277 | MGAT4B | 5q35 |
| 3.71e−005 | 0.502 | 225489_at | transmembrane protein 18 (TMEM18), mRNA. | Hs.43899 | TMEM18 | 2p25.3 |
| 3.72e−005 | 0.264 | 239262_at | CDNA FLJ26242 fis, clone DMC00770 | Hs.377660 | | 11 |
| 3.75e−005 | 0.277 | 226184_at | formin-like 2 (FMNL2), transcript variant 2, mRNA. | Hs.149566 | FMNL2 | 2q23.3 |
| 3.77e−005 | 0.251 | 228027_at | G protein-coupled receptor associated sorting protein 2 (GPRASP2), transcript variant 2, mRNA. | Hs.348493 | GPRASP2 | Xq22.1 |
| 3.79e−005 | 0.257 | 203803_at | prenylcysteine oxidase 1 (PCYOX1), mRNA. | Hs.551542 | PCYOX1 | 2p13.3 |
| 3.79e−005 | 6.76 | 213418_at | heat shock 70 kDa protein 6 (HSP70B') (HSPA6), mRNA. | Hs.3268 | HSPA6 | 1q23 |
| 3.82e−005 | 2.139 | 1556242_a_at | *Homo sapiens*, clone IMAGE: 3885623, mRNA | Hs.547780 | | 8 |
| 3.84e−005 | 0.407 | 209447_at | spectrin repeat containing, nuclear envelope 1 (SYNE1), transcript variant alpha, mRNA. | Hs.12967 | SYNE1 | 6q25 |
| 3.89e−005 | 0.367 | 213900_at | chromosome 9 open reading frame 61 (C9orf61), mRNA. | Hs.118003 | C9orf61 | 9q13-q21 |
| 3.91e−005 | 2.496 | 205406_s_at | sperm autoantigenic protein 17 (SPA17), mRNA. | Hs.286233 | SPA17 | 11q24.2 |

TABLE 5-continued

Genes specifically regulated in tumor endothelium.

| Parametric p-value | Fold difference of geom means (Tumor/Normal) | Probe set | Description | UG cluster | Gene symbol | Map |
|---|---|---|---|---|---|---|
| 3.91e-005 | 2.719 | 213344_s_at | H2A histone family, member X (H2AFX), mRNA. | Hs.477879 | H2AFX | 11q23.2-q23.3 |
| 3.95e-005 | 0.318 | 228551_at | Hypothetical protein MGC24039 | Hs.118166 | MGC24039 | 12p11.21 |
| 3.96e-005 | 4.16 | 235343_at | Hypothetical protein FLJ12505 | Hs.96885 | FLJ12505 | 1q32.3 |
| 4.04e-005 | 5.126 | 209082_s_at | collagen, type XVIII, alpha 1 (COL18A1), transcript variant 2, mRNA. | Hs.517356 | COL18A1 | 21q22.3 |
| 4.15e-005 | 0.476 | 230958_s_at | MRNA; cDNA DKFZp686J23256 (from clone DKFZp686J23256) | Hs.379253 | | 1 |
| 4.17e-005 | 0.38 | 219054_at | hypothetical protein FLJ14054 (FLJ14054), mRNA. | Hs.13528 | FLJ14054 | 5p13.3 |
| 4.2e-005 | 0.358 | 208951_at | aldehyde dehydrogenase 7 family, member A1 (ALDH7A1), mRNA. | Hs.483239 | ALDH7A1 | 5q31 |
| 4.2e-005 | 4.533 | 205241_at | SCO cytochrome oxidase deficient homolog 2 (yeast) (SCO2), nuclear gene encoding mitochondrial protein, mRNA. | Hs.549099 | SCO2 | 22q13.33 |
| 4.23e-005 | 0.434 | 218528_s_at | ring finger protein 38 (RNF38), transcript variant 4, mRNA. | Hs.333503 | RNF38 | 9p13-p12 |
| 4.28e-005 | 0.489 | 212131_at | family with sequence similarity 61, member A (FAM61A), mRNA. | Hs.407368 | FAM61A | 19q13.11 |
| 4.45e-005 | 0.365 | 225546_at | Eukaryotic elongation factor-2 kinase | Hs.549151 | EEF2K | 16p12.1 |
| 4.45e-005 | 0.237 | 229145_at | chromosome 10 open reading frame 104 (C10orf104), mRNA. | Hs.426296 | C10orf104 | 10q22.1 |
| 4.47e-005 | 0.387 | 227273_at | Transcribed locus | Hs.483955 | | 10 |
| 4.48e-005 | 3.428 | 220575_at | hypothetical protein FLJ11800 (FLJ11800), mRNA. | Hs.287456 | FLJ11800 | 17p11.2 |
| 4.49e-005 | 0.379 | 202073_at | optineurin (OPTN), transcript variant 2, mRNA. | Hs.332706 | OPTN | 10p13 |
| 4.54e-005 | 4.845 | 1559436_x_at | Arrestin, beta 2 | Hs.435811 | ARRB2 | 17p13 |
| 4.54e-005 | 4.79 | 220232_at | stearoyl-CoA desaturase 5 (SCD5), mRNA. | Hs.379191 | SCD5 | 4q21.3 |
| 4.59e-005 | 5.647 | 233330_s_at | Similar to Ribosome biogenesis protein BMS1 homolog | Hs.455494 | | 9q13 |
| 4.66e-005 | 3.575 | 1559410_at | Unknown | | | |
| 4.67e-005 | 0.425 | 211769_x_at | tumor differentially expressed 1 (TDE1), transcript variant 1, mRNA. | Hs.272168 | TDE1 | 20q13.1-13.3 |
| 4.85e-005 | 0.443 | 226529_at | hypothetical protein FLJ11273 (FLJ11273), mRNA. | Hs.396358 | FLJ11273 | 7p21.3 |
| 4.85e-005 | 0.413 | 208697_s_at | eukaryotic translation initiation factor 3, subunit 6 48 kDa (EIF3S6), mRNA. | Hs.405590 | EIF3S6 | 8q22-q23 |
| 4.85e-005 | 0.404 | 225050_at | zinc finger protein 512 (ZNF512), mRNA. | Hs.529178 | ZNF512 | 2p23 |
| 4.9e-005 | 0.277 | 208704_x_at | amyloid beta (A4) precursor-like protein 2 (APLP2), mRNA. | Hs.370247 | APLP2 | 11q24 |
| 5.08e-005 | 0.501 | 202502_at | acyl-Coenzyme A dehydrogenase, C-4 to C-12 straight chain (ACADM), nuclear gene encoding mitochondrial protein, mRNA. | Hs.445040 | ACADM | 1p31 |

TABLE 5-continued

Genes specifically regulated in tumor endothelium.

| Parametric p-value | Fold difference of geom means (Tumor/Normal) | Probe set | Description | UG cluster | Gene symbol | Map |
|---|---|---|---|---|---|---|
| 5.1e−005 | 2.907 | 223276_at | putative small membrane protein NID67 (NID67), mRNA. | Hs.29444 | NID67 | 5q33.1 |
| 5.1e−005 | 0.484 | 208873_s_at | chromosome 5 open reading frame 18 (C5orf18), mRNA. | Hs.429608 | C5orf18 | 5q22-q23 |
| 5.11e−005 | 2.383 | 46665_at | sema domain, immunoglobulin domain (Ig), transmembrane domain (TM) and short cytoplasmic domain, (semaphorin) 4C (SEMA4C), mRNA. | Hs.516220 | SEMA4C | 2q11.2 |
| 5.16e−005 | 3 | 1559060_a_at | KIAA1961 gene | Hs.483329 | KIAA1961 | 5q23.3 |
| 5.29e−005 | 2.423 | 215577_at | Ubiquitin-conjugating enzyme E2E 1 (UBC4/5 homolog, yeast) | Hs.164853 | UBE2E1 | 3p24.2 |
| 5.29e−005 | 4.015 | 222252_x_at | leucine rich repeat containing 51 (LRRC51), mRNA. | Hs.317243 | LRRC51 | 11q13.4 |
| 5.35e−005 | 0.284 | 208248_x_at | amyloid beta (A4) precursor-like protein 2 (APLP2), mRNA. | Hs.370247 | APLP2 | 11q24 |
| 5.35e−005 | 3.191 | 1558836_at | MRNA; cDNA DKFZp667A182 (from clone DKFZp667A182) | Hs.157344 | | 2 |
| 5.35e−005 | 0.538 | 209066_x_at | ubiquinol-cytochrome c reductase binding protein (UQCRB), mRNA. | Hs.131255 | UQCRB | 8q22 |
| 5.39e−005 | 4.851 | 226777_at | A disintegrin and metalloproteinase domain 12 (meltrin alpha) | Hs.386283 | ADAM12 | 10q26.3 |
| 5.4e−005 | 0.459 | 208990_s_at | heterogeneous nuclear ribonucleoprotein H3 (2H9) (HNRPH3), transcript variant 2H9A, mRNA. | Hs.499891 | HNRPH3 | 10q22 |
| 5.42e−005 | 3.146 | 235122_at | CDNA clone IMAGE: 6254031 | Hs.403972 | | 1 |
| 5.44e−005 | 2.185 | 59433_at | Transcribed locus | Hs.416792 | | X |
| 5.44e−005 | 0.473 | 225811_at | Transcribed locus, weakly similar to XP_510104.1 PREDICTED: similar to hypothetical protein FLJ25224 [Pan troglodytes] | Hs.78050 | | 11 |
| 5.53e−005 | 0.39 | 200760_s_at | ADP-ribosylation-like factor 6 interacting protein 5 (ARL6IP5), mRNA. | Hs.518060 | ARL6IP5 | 3p14 |
| 5.55e−005 | 4.287 | 219025_at | CD248 antigen, endosialin (CD248), mRNA. | Hs.195727 | CD248 | 11q13 |
| 5.65e−005 | 3.458 | 211673_s_at | Molybdenum cofactor synthesis 1 | Hs.357128 | MOCS1 | 6p21.3 |
| 5.75e−005 | 2.33 | 225947_at | myosin head domain containing 1 (MYOHD1), mRNA. | Hs.302051 | MYOHD1 | 17q12 |
| 5.78e−005 | 0.468 | 225332_at | Keratin associated protein 4-7 | Hs.549512 | KRTAP4-7 | 17q12-q21 |
| 5.79e−005 | 3.761 | 226933_s_at | inhibitor of DNA binding 4, dominant negative helix-loop-helix protein (ID4), mRNA. | Hs.519601 | ID4 | 6p22.p21 |
| 5.83e−005 | 0.421 | 200937_s_at | ribosomal protein L5 (RPL5), mRNA. | Hs.532359 | RPL5 | 1p22.1 |
| 5.92e−005 | 4.185 | 219263_at | ring finger protein 128 (RNF128), transcript variant 2, mRNA. | Hs.496542 | RNF128 | Xq22.3 |
| 5.98e−005 | 2.652 | 224967_at | UDP-glucose ceramide glucosyltransferase | Hs.304249 | UGCG | 9q31 |

TABLE 5-continued

Genes specifically regulated in tumor endothelium.

| Parametric p-value | Fold difference of geom means (Tumor/Normal) | Probe set | Description | UG cluster | Gene symbol | Map |
|---|---|---|---|---|---|---|
| 5.98e−005 | 2.885 | 222968_at | chromosome 6 open reading frame 48 (C6orf48), mRNA. | Hs.109798 | C6orf48 | 6p21.3 |
| 6.02e−005 | 4.748 | 238673_at | Transcribed locus | Hs.359393 | | 8 |
| 6.02e−005 | 0.418 | 223306_at | emopamil binding protein-like (EBPL), mRNA. | Hs.433278 | EBPL | 13q12-q13 |
| 6.09e−005 | 2.563 | 238327_at | Similar to MGC52679 protein | Hs.531314 | | 22q13.33 |
| 6.11e−005 | 0.341 | 227728_at | Protein phosphatase 1A (formerly 2C), magnesium-dependent, alpha isoform | Hs.130036 | PPM1A | 14q23.1 |
| 6.17e−005 | 0.212 | 205466_s_at | heparan sulfate (glucosamine) 3-O-sulfotransferase 1 (HS3ST1), mRNA. | Hs.507348 | HS3ST1 | 4p16 |
| 6.24e−005 | 0.452 | 202512_s_at | APG5 autophagy 5-like (S. cerevisiae) (APG5L), mRNA. | Hs.486063 | APG5L | 6q21 |
| 6.25e−005 | 2.159 | 202297_s_at | RER1 retention in endoplasmic reticulum 1 homolog (S. cerevisiae) (RER1), mRNA. | Hs.525527 | RER1 | 1pter-q24 |
| 6.29e−005 | 5.165 | 242862_x_at | ESTs | | | |
| 6.34e−005 | 0.41 | 234339_s_at | glioma tumor suppressor candidate region gene 2 (GLTSCR2), mRNA. | Hs.421907 | GLTSCR2 | 19q13.3 |
| 6.38e−005 | 3.706 | 215588_x_at | RIO kinase 3 (yeast) | Hs.445511 | RIOK3 | 18q11.2 |
| 6.45e−005 | 0.446 | 202378_s_at | leptin receptor overlapping transcript (LEPROT), mRNA. | Hs.23581 | LEPROT | 1p31.2 |
| 6.52e−005 | 4.272 | 234675_x_at | CDNA: FLJ23566 fis, clone LNG10880 | Hs.532596 | | 14 |
| 6.61e−005 | 2.48 | 200734_s_at | ADP-ribosylation factor 3 (ARF3), mRNA. | Hs.119177 | ARF3 | 12q13 |
| 6.64e−005 | 0.373 | 202630_at | amyloid beta precursor protein (cytoplasmic tail) binding protein 2 (APPBP2), mRNA. | Hs.84084 | APPBP2 | 17q21-q23 |
| 6.64e−005 | 0.417 | 212549_at | signal transducer and activator of transcription 5B (STAT5B), mRNA. | Hs.132864 | STAT5B | 17q11.2 |
| 6.66e−005 | 0.332 | 235072_s_at | Transcribed locus | Hs.94499 | | 6 |
| 6.72e−005 | 0.441 | 201535_at | ubiquitin-like 3 (UBL3), mRNA. | Hs.145575 | UBL3 | 13q12-q13 |
| 6.79e−005 | 2.242 | 224612_s_at | DnaJ (Hsp40) homolog, subfamily C, member 5 | Hs.164419 | DNAJC5 | 20q13.33 |
| 6.8e−005 | 4.528 | 215179_x_at | Placental growth factor, vascular endothelial growth factor-related protein | Hs.252820 | PGF | 14q24-q31 |
| 6.81e−005 | 0.361 | 218191_s_at | LMBR1 domain containing 1 (LMBRD1), mRNA. | Hs.271643 | LMBRD1 | 6q13 |
| 6.82e−005 | 3.714 | 206792_x_at | phosphodiesterase 4C, cAMP-specific (phosphodiesterase E1 dunce homolog, Drosophila) (PDE4C), mRNA. | Hs.437211 | PDE4C | 19p13.11 |
| 6.85e−005 | 2.964 | 44783_s_at | hairy/enhancer-of-split related with YRPW motif 1 (HEY1), mRNA. | Hs.234434 | HEY1 | 8q21 |
| 7.02e−005 | 0.354 | 211942_x_at | Ribosomal protein L13a | Hs.546356 | RPL13A | 19q13.3 |
| 7.05e−005 | 3.112 | 222358_x_at | ESTs, Weakly similar to hypothetical protein FLJ20378 [Homo sapiens] [H. sapiens] | | | |
| 7.05e−005 | 0.387 | 203427_at | ASF1 anti-silencing function 1 homolog A (S. cerevisiae) (ASF1A), mRNA. | Hs.292316 | ASF1A | 6q22.31 |

TABLE 5-continued

Genes specifically regulated in tumor endothelium.

| Parametric p-value | Fold difference of geom means (Tumor/Normal) | Probe set | Description | UG cluster | Gene symbol | Map |
|---|---|---|---|---|---|---|
| 7.12e−005 | 5.701 | 243147_x_at | ESTs, Weakly similar to RMS1_HUMAN REGULATOR OF MITOTIC SPINDLE ASSEMBLY 1 [H. sapiens] | | | |
| 7.15e−005 | 5.24 | 1554334_a_at | DnaJ (Hsp40) homolog, subfamily A, member 4 (DNAJA4), mRNA. | Hs.513053 | DNAJA4 | 15q25.1 |
| 7.18e−005 | 3.411 | 204136_at | collagen, type VII, alpha 1 (epidermolysis bullosa, dystrophic, dominant and recessive) (COL7A1), mRNA. | Hs.476218 | COL7A1 | 3p21.1 |
| 7.19e−005 | 0.308 | 200883_at | ubiquinol-cytochrome c reductase core protein II (UQCRC2), mRNA. | Hs.528803 | UQCRC2 | 16p12 |
| 7.21e−005 | 2.399 | 243249_at | ESTs, Weakly similar to hypothetical protein FLJ20378 [Homo sapiens] [H. sapiens] | | | |
| 7.25e−005 | 0.412 | 218167_at | archaemetzincins-2 (AMZ2), mRNA. | Hs.268122 | AMZ2 | 17q24.2 |
| 7.26e−005 | 4.893 | 234578_at | MRNA; cDNA DKFZp434E1812 (from clone DKFZp434E1812) | | Hs.537604 | 1 |
| 7.26e−005 | 2.797 | 203349_s_at | ets variant gene 5 (ets-related molecule) (ETV5), mRNA. | Hs.43697 | ETV5 | 3q28 |
| 7.32e−005 | 2.605 | 212809_at | nuclear factor of activated T-cells, cytoplasmic, calcineurin-dependent 2 interacting protein (NFATC2IP), mRNA. | Hs.513470 | NFATC2IP | 16p11.2 |
| 7.34e−005 | 0.32 | 230793_at | leucine rich repeat containing 16 (LRRC16), mRNA. | Hs.116470 | LRRC16 | 6p22.2 |
| 7.35e−005 | 0.448 | 203897_at | hypothetical protein A-211C6.1 (LOC57149), mRNA. | Hs.185489 | LOC57149 | 16p11.2 |
| 7.37e−005 | 3.381 | 241718_x_at | ESTs | | | |
| 7.4e−005 | 0.451 | 208740_at | sin3-associated polypeptide, 18 kDa (SAP18), mRNA. | Hs.524899 | SAP18 | 13q12.11 |
| 7.41e−005 | 0.392 | 211749_s_at | vesicle-associated membrane protein 3 (cellubrevin) (VAMP3), mRNA. | Hs.66708 | VAMP3 | 1p36.23 |
| 7.44e−005 | 4.754 | 209360_s_at | runt-related transcription factor 1 (acute myeloid leukemia 1; aml1 oncogene) (RUNX1), transcript variant 1, mRNA. | Hs.149261 | RUNX1 | 21q22.3 |
| 7.45e−005 | 0.461 | 225498_at | chromatin modifying protein 4B (CHMP4B), mRNA. | Hs.472471 | CHMP4B | 20q11.22 |
| 7.51e−005 | 4.374 | 213790_at | A disintegrin and metalloproteinase domain 12 (meltrin alpha) | Hs.386283 | ADAM12 | 10q26.3 |
| 7.57e−005 | 2.898 | 230270_at | ESTs | | | |
| 7.64e−005 | 0.321 | 219023_at | chromosome 4 open reading frame 16 (C4orf16), mRNA. | Hs.435991 | C4orf16 | 4q25 |
| 7.65e−005 | 0.116 | 205862_at | GREB1 protein (GREB1), transcript variant a, mRNA. | Hs.467733 | GREB1 | 2p25.1 |
| 7.86e−005 | 4.771 | 217679_x_at | ESTs, Weakly similar to hypothetical protein FLJ20489 [Homo sapiens] [H. sapiens] | | | |
| 7.88e−005 | 2.558 | 204387_x_at | mitochondrial ribosomal protein 63 (MRP63), nuclear gene encoding mitochondrial protein, mRNA. | Hs.458367 | MRP63 | 13p11.1-q11 |
| 7.89e−005 | 0.454 | 226020_s_at | OMA1 homolog, zinc metallopeptidase (S. cerevisiae) (OMA1), mRNA. | Hs.425769 | OMA1 | 1p32.2-p32.1 |

TABLE 5-continued

Genes specifically regulated in tumor endothelium.

| Parametric p-value | Fold difference of geom means (Tumor/Normal) | Probe set | Description | UG cluster | Gene symbol | Map |
|---|---|---|---|---|---|---|
| 7.97e−005 | 2.379 | 214316_x_at | Calreticulin | Hs.515162 | CALR | 19p13.3-p13.2 |
| 7.99e−005 | 0.39 | 218831_s_at | Fc fragment of IgG, receptor, transporter, alpha (FCGRT), mRNA. | Hs.111903 | FCGRT | 19q13.3 |
| 8.09e−005 | 3.577 | 208246_x_at | hypothetical protein FLJ20006 | | FLJ20006 | 16q23.1 |
| 8.13e−005 | 3.611 | 231825_x_at | Activating transcription factor 7 interacting protein | Hs.546406 | ATF7IP | 12p13.1 |
| 8.16e−005 | 2.701 | 236251_at | Integrin, alpha V (vitronectin receptor, alpha polypeptide, antigen CD51) | Hs.436873 | ITGAV | 2q31-q32 |
| 8.18e−005 | 3.162 | 232617_at | cathepsin S (CTSS), mRNA. | Hs.181301 | CTSS | 1q21 |
| 8.21e−005 | 2.949 | 31874_at | Growth arrest-specific 2 like 1 | Hs.322852 | GAS2L1 | 22q12.2 |
| 8.32e−005 | 4.254 | 1566887_x_at | KIAA0284 | Hs.533721 | KIAA0284 | 14q32.33 |
| 8.43e−005 | 0.475 | 226297_at | ESTs | | | |
| 8.47e−005 | 0.458 | 227293_at | Ligand of numb-protein X | Hs.407755 | LNX | 4q12 |
| 8.47e−005 | 0.337 | 227530_at | A kinase (PRKA) anchor protein (gravin) 12 | Hs.371240 | AKAP12 | 6q24-q25 |
| 8.52e−005 | 0.178 | 211276_at | transcription elongation factor A (SII)-like 2 (TCEAL2), mRNA. | Hs.401835 | TCEAL2 | Xq22.1-q22.3 |
| 8.57e−005 | 0.489 | 208635_x_at | nascent-polypeptide-associated complex alpha polypeptide (NACA), mRNA. | Hs.505735 | NACA | 12q23-q24.1 |
| 8.57e−005 | 0.416 | 225574_at | hypothetical protein MGC10198 (MGC10198), mRNA. | Hs.133337 | MGC10198 | 4q35.1 |
| 8.66e−005 | 3.115 | 244457_at | Inositol 1,4,5-triphosphate receptor, type 2 | Hs.512235 | ITPR2 | 12p11 |
| 8.72e−005 | 0.373 | 226117_at | TRAF-interacting protein with a forkhead-associated domain (TIFA), mRNA. | Hs.310640 | TIFA | 4q25 |
| 8.75e−005 | 4.112 | 234762_x_at | Neurolysin (metallopeptidase M3 family) | Hs.247460 | NLN | 5q12.3 |
| 8.75e−005 | 2.496 | 232254_at | F-box protein 25 | Hs.438454 | FBXO25 | 8p23.3 |
| 8.83e−005 | 3.223 | 1570061_at | CDNA clone IMAGE: 4555030 | | Hs.372904 | 3 |
| 8.86e−005 | 0.372 | 220327_at | vestigial-like (VGL-3), mRNA. | Hs.435013 | VGL-3 | 3p12.1 |
| 8.88e−005 | 0.501 | 225326_at | PREDICTED: RNA binding motif protein 27 (RBM27), mRNA. | Hs.61441 | RBM27 | 5 |
| 8.91e−005 | 0.347 | 215294_s_at | SWI/SNF related, matrix associated, actin dependent regulator of chromatin, subfamily a, member 1 (SMARCA1), transcript variant 2, mRNA. | Hs.152292 | SMARCA1 | Xq25 |
| 8.94e−005 | 3.111 | 242329_at | PREDICTED: hypothetical LOC401317 (LOC401317), mRNA. | Hs.437075 | LOC401317 | 7 |
| 8.97e−005 | 0.37 | 238613_at | sterile alpha motif and leucine zipper containing kinase AZK (ZAK), transcript variant 2, mRNA. | Hs.444451 | ZAK | 2q24.2 |
| 8.97e−005 | 2.137 | 203459_s_at | vacuolar protein sorting 16 (yeast) (VPS16), transcript variant 2, mRNA. | Hs.269577 | VPS16 | 20p13-p12 |
| 9.04e−005 | 5.612 | 215978_x_at | ATP-binding cassette, sub-family A (ABC1), member 11 (pseudogene) | Hs.478916 | LOC152719 | 4p16.3 |
| 9.1e−005 | 0.419 | 222488_s_at | dynactin 4 (p62) (DCTN4), mRNA. | Hs.328865 | DCTN4 | 5q31-q32 |

TABLE 5-continued

Genes specifically regulated in tumor endothelium.

| Parametric p-value | Fold difference of geom means (Tumor/Normal) | Probe set | Description | UG cluster | Gene symbol | Map |
|---|---|---|---|---|---|---|
| 9.25e−005 | 0.449 | 217915_s_at | chromosome 15 open reading frame 15 (C15orf15), mRNA. | Hs.274772 | C15orf15 | 15q21 |
| 9.26e−005 | 3.027 | 204184_s_at | adrenergic, beta, receptor kinase 2 (ADRBK2), mRNA. | Hs.517493 | ADRBK2 | 22q12.1 |
| 9.35e−005 | 0.152 | 223395_at | ABI gene family, member 3 (NESH) binding protein (ABI3BP), mRNA. | Hs.477015 | ABI3BP | 3q12 |
| 9.38e−005 | 3.287 | 206247_at | MHC class I polypeptide-related sequence B (MICB), mRNA. | Hs.211580 | MICB | 6p21.3 |
| 9.41e−005 | 0.341 | 222975_s_at | cold shock domain containing E1, RNA-binding (CSDE1), transcript variant 2, mRNA. | Hs.69855 | CSDE1 | 1p22 |
| 9.42e−005 | 0.43 | 227407_at | hypothetical protein FLJ90013 (FLJ90013), mRNA. | Hs.479223 | FLJ90013 | 4p15.32 |
| 9.46e−005 | 0.424 | 223189_x_at | myeloid/lymphoid or mixed-lineage leukemia 5 (trithorax homolog, Drosophila) (MLL5), mRNA. | Hs.369356 | MLL5 | 7q22.1 |
| 9.63e−005 | 0.474 | 200735_x_at | nascent-polypeptide-associated complex alpha polypeptide (NACA), mRNA. | Hs.505735 | NACA | 12q23-q24.1 |
| 9.73e−005 | 2.027 | 219099_at | chromosome 12 open reading frame 5 (C12orf5), mRNA. | Hs.504545 | C12orf5 | 12p13.3 |
| 9.74e−005 | 2.083 | 243_g_at | microtubule-associated protein 4 (MAP4), transcript variant 2, mRNA. | Hs.517949 | MAP4 | 3p21 |
| 9.85e−005 | 4.389 | 234981_x_at | Similar to mouse 2310016A09Rik gene | Hs.192586 | LOC134147 | 5p15.2 |
| 9.87e−005 | 0.544 | 208756_at | eukaryotic translation initiation factor 3, subunit 2 beta, 36 kDa (EIF3S2), mRNA. | Hs.530096 | EIF3S2 | 1p34.1 |
| 0.0001001 | 3.738 | 243442_x_at | ESTs, Weakly similar to ALU1_HUMAN ALU SUBFAMILY J SEQUENCE CONTAMINATION WARNING ENTRY [*H. sapiens*] | | | |
| 0.0001002 | 4.754 | 223672_at | SH3-domain GRB2-like (endophilin) interacting protein 1 (SGIP1), mRNA. | Hs.132121 | SGIP1 | 1p31.2 |
| 0.0001004 | 3.899 | 230077_at | Transferrin receptor (p90, CD71) | Hs.529618 | TFRC | 3q29 |
| 0.0001021 | 0.362 | 212215_at | prolyl endopeptidase-like (PREPL), mRNA. | Hs.112916 | PREPL | 2p22.1 |
| 0.0001021 | 0.507 | 225098_at | Abl interactor 2 | Hs.471156 | ABI2 | 2q33 |
| 0.0001023 | 0.556 | 218142_s_at | cereblon (CRBN), mRNA. | Hs.18925 | CRBN | 3p26.2 |
| 0.0001027 | 0.445 | 214177_s_at | pre-B-cell leukemia transcription factor interacting protein 1 (PBXIP1), mRNA. | Hs.505806 | PBXIP1 | 1q22 |
| 0.0001028 | 0.227 | 208791_at | clusterin (complement lysis inhibitor, SP-40,40, sulfated glycoprotein 2, testosterone-repressed prostate message 2, apolipoprotein J) (CLU), transcript variant 1, mRNA. | Hs.436657 | CLU | 8p21-p12 |
| 0.0001035 | 2.522 | 200021_at | cofilin 1 (non-muscle) (CFL1), mRNA. | Hs.170622 | CFL1 | 11q13 |
| 0.0001036 | 3.432 | 229801_at | chromosome 10 open reading frame 47 (C10orf47), mRNA. | Hs.435775 | C10orf47 | 10p14 |

TABLE 5-continued

Genes specifically regulated in tumor endothelium.

| Parametric p-value | Fold difference of geom means (Tumor/Normal) | Probe set | Description | UG cluster | Gene symbol | Map |
|---|---|---|---|---|---|---|
| 0.000105 | 0.303 | 212731_at | ankyrin repeat domain 46 (ANKRD46), mRNA. | Hs.530199 | ANKRD46 | 8q22.3 |
| 0.0001078 | 0.389 | 224841_x_at | PREDICTED: RNA, U47 small nuclear (RNU47), misc RNA. | | RNU47 | 1 |
| 0.0001087 | 0.419 | 228905_at | Transcribed locus, moderately similar to XP_517655.1 PREDICTED: similar to KIAA0825 protein [Pan troglodytes] | Hs.554337 | | 8 |
| 0.0001115 | 0.379 | 202314_at | cytochrome P450, family 51, subfamily A, polypeptide 1 (CYP51A1), mRNA. | Hs.417077 | CYP51A1 | 7q21.2-q21.3 |
| 0.000112 | 0.169 | 200965_s_at | actin binding LIM protein 1 (ABLIM1), transcript variant 4, mRNA. | Hs.438236 | ABLIM1 | 10q25 |
| 0.0001134 | 2.869 | 227850_x_at | CDC42 effector protein (Rho GTPase binding) 5 (CDC42EP5), mRNA. | Hs.415791 | CDC42EP5 | 19q13.42 |
| 0.0001136 | 0.451 | 211710_x_at | ribosomal protein L4 (RPL4), mRNA. | Hs.432898 | RPL4 | 15q22 |
| 0.000114 | 4.037 | 1562062_at | *Homo sapiens* transcribed sequence with weak similarity to protein ref: NP_055301.1 (*H. sapiens*) neuronal thread protein [*Homo sapiens*] | | | |
| 0.0001144 | 0.403 | 224741_x_at | Growth arrest-specific 5 | Hs.531856 | GAS5 | 1q23.3 |
| 0.0001149 | 0.503 | 224689_at | mannosidase, beta A, lysosomal-like (MANBAL), transcript variant 2, mRNA. | Hs.6126 | MANBAL | 20q11.23-q12 |
| 0.0001159 | 0.449 | 201154_x_at | ribosomal protein L4 (RPL4), mRNA. | Hs.432898 | RPL4 | 15q22 |
| 0.0001171 | 0.243 | 202068_s_at | low density lipoprotein receptor (familial hypercholesterolemia) (LDLR), mRNA. | Hs.213289 | LDLR | 19p13.3 |
| 0.0001172 | 0.438 | 226541_at | F-box protein 30 (FBXO30), mRNA. | Hs.421095 | FBXO30 | 6q24 |
| 0.0001174 | 2.25 | 229520_s_at | Chromosome 14 open reading frame 118 | Hs.410231 | C14orf118 | 14q22.1-q24.3 |
| 0.0001175 | 0.224 | 208792_s_at | clusterin (complement lysis inhibitor, SP-40,40, sulfated glycoprotein 2, testosterone-repressed prostate message 2, apolipoprotein J) (CLU), transcript variant 1, mRNA. | Hs.436657 | CLU | 8p21-p12 |
| 0.0001184 | 0.438 | 212644_s_at | chromosome 14 open reading frame 32 (C14orf32), mRNA. | Hs.437831 | C14orf32 | 14q22.2-q22.3 |
| 0.0001189 | 0.207 | 212094_at | PREDICTED: paternally expressed 10 (PEG10), mRNA. | Hs.147492 | PEG10 | 7 |
| 0.0001207 | 7.544 | 204597_x_at | stanniocalcin 1 (STC1), mRNA. | Hs.25590 | STC1 | 8p21-p11.2 |
| 0.000121 | 0.518 | 201696_at | splicing factor, arginine/serine-rich 4 (SFRS4), mRNA. | Hs.469970 | SFRS4 | 1p35.3 |
| 0.0001224 | 3.248 | 231411_at | lipoma HMGIC fusion partner (LHFP), mRNA. | Hs.507798 | LHFP | 13q12 |
| 0.0001224 | 0.45 | 203494_s_at | translokin (PIG8), mRNA. | Hs.101014 | PIG8 | 11q21 |
| 0.0001227 | 0.391 | 225243_s_at | sarcolemma associated protein (SLMAP), mRNA. | Hs.476432 | SLMAP | 3p21.2-p14.3 |
| 0.0001234 | 2.695 | 203505_at | ATP-binding cassette, sub-family A (ABC1), member 1 | Hs.429294 | ABCA1 | 9q31.1 |
| 0.000125 | 2.866 | 213146_at | KIAA0346 protein | | KIAA0346 | 17p13.1 |
| 0.0001252 | 3.538 | 235205_at | PREDICTED: similar to solute carrier family 16 (monocarboxylic acid transporters), member 14 (LOC346887), mRNA. | Hs.127286 | LOC346887 | 8 |

TABLE 5-continued

Genes specifically regulated in tumor endothelium.

| Parametric p-value | Fold difference of geom means (Tumor/Normal) | Probe set | Description | UG cluster | Gene symbol | Map |
|---|---|---|---|---|---|---|
| 0.0001256 | 0.494 | 211994_at | Transcribed locus, strongly similar to XP_508919.1 PREDICTED: similar to protein kinase, lysine deficient 1; kinase deficient protein [Pan troglodytes] | Hs.524171 | | 12 |
| 0.0001261 | 2.214 | 213836_s_at | WD40 repeat protein Interacting with phosphoInositides of 49 kDa (WIPI49), mRNA. | Hs.463964 | WIPI49 | 17q24.2 |
| 0.0001271 | 0.372 | 212037_at | Pinin, desmosome associated protein | Hs.409965 | PNN | 14q21.1 |
| 0.000128 | 2.586 | 227384_s_at | Similar to KIAA0454 protein | Hs.429365 | | 1q21.1 |
| 0.000128 | 4.614 | 1553185_at | RAS and EF-hand domain containing | Hs.129136 | RASEF | 9q21.32 |
| 0.000129 | 4.274 | 231183_s_at | jagged 1 (Alagille syndrome) (JAG1), mRNA. | Hs.224012 | JAG1 | 20p12.1-p11.23 |
| 0.0001299 | 0.482 | 222533_at | cereblon (CRBN), mRNA. | Hs.18925 | CRBN | 3p26.2 |
| 0.0001301 | 2.543 | 226695_at | paired related homeobox 1 (PRRX1), transcript variant pmx-1b, mRNA. | Hs.283416 | PRRX1 | 1q24 |
| 0.0001301 | 3.433 | 217713_x_at | ESTs, Weakly similar to ALU6_HUMAN ALU SUBFAMILY SP SEQUENCE CONTAMINATION WARNING ENTRY [H. sapiens] | | | |
| 0.0001306 | 0.497 | 225132_at | F-box and leucine-rich repeat protein 3 (FBXL3), mRNA. | Hs.508284 | FBXL3 | 13q22 |
| 0.0001313 | 0.484 | 225179_at | Huntingtin interacting protein 2 | Hs.50308 | HIP2 | 4p14 |
| 0.0001321 | 3.609 | 1557432_at | RAS protein activator like 2 | Hs.555904 | RASAL2 | 1q24 |
| 0.0001328 | 0.224 | 209612_s_at | alcohol dehydrogenase IB (class I), beta polypeptide (ADH1B), mRNA. | Hs.4 | ADH1B | 4q21-q23 |
| 0.0001335 | 2.071 | 222753_s_at | signal peptidase complex subunit 3 homolog (S. cerevisiae) (SPCS3), mRNA. | Hs.42194 | SPCS3 | 4q34.2 |
| 0.0001337 | 3.162 | 1555241_at | Hypothetical gene supported by BC055092 | Hs.443072 | | 8q21.2 |
| 0.0001338 | 0.357 | 225939_at | Eukaryotic translation initiation factor 4E member 3 | Hs.476782 | EIF4E3 | 3p14 |
| 0.0001341 | 0.475 | 217795_s_at | transmembrane protein 43 (TMEM43), mRNA. | Hs.517817 | TMEM43 | 3p25.1 |
| 0.0001341 | 0.442 | 200920_s_at | B-cell translocation gene 1, anti-proliferative (BTG1), mRNA. | Hs.255935 | BTG1 | 12q22 |
| 0.0001345 | 0.108 | 228202_at | Phospholamban | Hs.170839 | PLN | 6q22.1 |
| 0.0001347 | 2.158 | 220242_x_at | zinc finger protein 701 (ZNF701), mRNA. | Hs.412951 | ZNF701 | 19q13.41 |
| 0.0001348 | 0.507 | 201871_s_at | ORF (LOC51035), mRNA. | Hs.351296 | LOC51035 | 11q12.3 |
| 0.0001374 | 3.17 | 55583_at | dedicator of cytokinesis 6 (DOCK6), mRNA. | Hs.465918 | DOCK6 | 19p13.2 |
| 0.0001375 | 2.507 | 225967_s_at | PREDICTED: hypothetical LOC284184 (LOC284184), mRNA. | Hs.356545 | LOC284184 | 17 |
| 0.0001389 | 0.374 | 218158_s_at | adaptor protein containing pH domain, PTB domain and leucine zipper motif 1 (APPL), mRNA. | Hs.555928 | APPL | 3p21.1-p14.3 |
| 0.0001391 | 2.647 | 1553569_at | Unknown | | | |
| 0.0001405 | 2.672 | 232952_at | HSPC054 protein | Hs.106015 | DDEF1 | 8q24.1-q24.2 |
| 0.0001406 | 3.884 | 203549_s_at | lipoprotein lipase (LPL), mRNA. | Hs.180878 | LPL | 8p22 |

TABLE 5-continued

Genes specifically regulated in tumor endothelium.

| Parametric p-value | Fold difference of geom means (Tumor/Normal) | Probe set | Description | UG cluster | Gene symbol | Map |
|---|---|---|---|---|---|---|
| 0.0001436 | 0.369 | 226120_at | tetratricopeptide repeat domain 8 (TTC8), transcript variant 3, mRNA. | Hs.303055 | TTC8 | 14q31.3 |
| 0.0001439 | 0.436 | 222212_s_at | LAG1 longevity assurance homolog 2 (*S. cerevisiae*) (LASS2), transcript variant 3, mRNA. | Hs.285976 | LASS2 | 1q21.2 |
| 0.0001441 | 0.45 | 224755_at | SM-11044 binding protein | Hs.500674 | SMBP | 10q24.1 |
| 0.0001441 | 0.409 | 221588_x_at | aldehyde dehydrogenase 6 family, member A1 (ALDH6A1), nuclear gene encoding mitochondrial protein, mRNA. | Hs.293970 | ALDH6A1 | 14q24.3 |
| 0.0001443 | 0.533 | 207769_s_at | polyglutamine binding protein 1 (PQBP1), transcript variant 5, mRNA. | | PQBP1 | Xp11.23 |
| 0.0001456 | 0.496 | 226336_at | Peptidylprolyl isomerase A (cyclophilin A) | Hs.356331 | PPIA | 7p13-p11.2 |
| 0.0001456 | 3.669 | 216187_x_at | X-ray repair complementing defective repair in Chinese hamster cells 3 | Hs.549075 | XRCC3 | 14q32.3 |
| 0.000146 | 2.047 | 218113_at | transmembrane protein 2 (TMEM2), mRNA. | Hs.494146 | TMEM2 | 9q13-q21 |
| 0.0001463 | 3.512 | 207598_x_at | X-ray repair complementing defective repair in Chinese hamster cells 2 (XRCC2), mRNA. | Hs.129727 | XRCC2 | 7q36.1 |
| 0.0001465 | 4.648 | 223697_x_at | chromosome 9 open reading frame 64 (C9orf64), mRNA. | Hs.208914 | C9orf64 | 9q21.32 |
| 0.0001476 | 2.584 | 227396_at | Homo sapiens, clone IMAGE: 4454331, mRNA | Hs.374451 | | 11 |
| 0.0001482 | 2.94 | 243915_at | ESTs, Weakly similar to 2109260A B cell growth factor [*H. sapiens*] | | | |
| 0.0001487 | 2.694 | 205367_at | adaptor protein with pleckstrin homology and src homology 2 domains (APS), mRNA. | Hs.489448 | APS | 7q22 |
| 0.0001491 | 0.447 | 229119_s_at | Hypothetical protein LOC125150 | Hs.462316 | TTC19 | 17p12 |
| 0.0001495 | 0.332 | 214359_s_at | heat shock 90 kDa protein 1, beta (HSPCB), mRNA. | Hs.509736 | HSPCB | 6p12 |
| 0.0001503 | 0.185 | 205381_at | leucine rich repeat containing 17 (LRRC17), transcript variant 1, mRNA. | | LRRC17 | 7q22.1 |
| 0.0001503 | 0.482 | 213027_at | TROVE domain family, member 2 | Hs.288178 | SSA2 | 1q31 |
| 0.0001511 | 0.348 | 224734_at | High-mobility group box 1 | Hs.434102 | HMGB1 | 13q12 |
| 0.0001511 | 0.474 | 207974_s_at | S-phase kinase-associated protein 1A (p19A) (SKP1A), transcript variant 2, mRNA. | Hs.171626 | SKP1A | 5q31 |
| 0.0001513 | 4.07 | 227952_at | Full length insert cDNA clone YI46G04 | Hs.355711 | | 4 |
| 0.0001514 | 2.32 | 240795_at | CDNA clone IMAGE: 5288566 | Hs.19452 | | 5 |
| 0.0001521 | 0.411 | 229319_at | Homo sapiens, clone IMAGE: 4105966, mRNA | Hs.33519 | | 6 |
| 0.0001527 | 2.413 | 212414_s_at | septin 6 (SEPT6), transcript variant II, mRNA. | Hs.496666 | 38601 | Xq24 |
| 0.0001535 | 0.424 | 201376_s_at | heterogeneous nuclear ribonucleoprotein F (HNRPF), mRNA. | Hs.808 | HNRPF | 10q11.21-q11.22 |
| 0.000154 | 2.059 | 50376_at | zinc finger protein 444 (ZNF444), mRNA. | Hs.24545 | ZNF444 | 19q13.43 |
| 0.0001543 | 3.085 | 233319_x_at | Phosphatase and actin regulator 4 | Hs.225641 | PHACTR4 | 1p35.3 |
| 0.000155 | 0.507 | 221689_s_at | Down syndrome critical region gene 5 (DSCR5), transcript variant 2, mRNA. | Hs.408790 | DSCR5 | 21q22.2 |

TABLE 5-continued

Genes specifically regulated in tumor endothelium.

| Parametric p-value | Fold difference of geom means (Tumor/Normal) | Probe set | Description | UG cluster | Gene symbol | Map |
|---|---|---|---|---|---|---|
| 0.000156 | 2.319 | 229200_at | Hypothetical LOC400813 | Hs.13742 | | 1q44 |
| 0.0001562 | 4.302 | 237475_x_at | Selenoprotein P, plasma, 1 | Hs.275775 | SEPP1 | 5q31 |
| 0.0001564 | 2.541 | 1560817_at | Mov10, Moloney leukemia virus 10, homolog (mouse) | Hs.514941 | MOV10 | 1p13.2 |
| 0.0001583 | 2.899 | 232406_at | Jagged 1 (Alagille syndrome) | Hs.224012 | JAG1 | 20p12.1-p11.23 |
| 0.0001589 | 2.919 | 1556138_a_at | Collagen, type V, alpha 1 | Hs.210283 | COL5A1 | 9q34.2-q34.3 |
| 0.0001597 | 0.435 | 200651_at | guanine nucleotide binding protein (G protein), beta polypeptide 2-like 1 (GNB2L1), mRNA. | Hs.5662 | GNB2L1 | 5q35.3 |
| 0.0001618 | 2.498 | 241809_at | Hypothetical protein LOC284465 | Hs.193406 | LOC284465 | 1p13.2 |
| 0.0001619 | 0.456 | 201484_at | suppressor of Ty 4 homolog 1 (*S. cerevisiae*) (SUPT4H1), mRNA. | Hs.439481 | SUPT4H1 | 17q21-q23 |
| 0.0001621 | 0.526 | 225475_at | mesoderm induction early response 1 homolog (*Xenopus laevis*) (MIER1), mRNA. | Hs.21757 | MIER1 | 1p31.2 |
| 0.0001633 | 0.329 | 201529_s_at | replication protein A1, 70 kDa (RPA1), mRNA. | Hs.461925 | RPA1 | 17p13.3 |
| 0.0001637 | 0.403 | 212199_at | Morf4 family associated protein 1-like 1 (MRFAP1L1), transcript variant 2, mRNA. | Hs.518608 | MRFAP1L1 | 4p16.1 |
| 0.0001639 | 0.387 | 208796_s_at | cyclin G1 (CCNG1), transcript variant 2, mRNA. | Hs.79101 | CCNG1 | 5q32-q34 |
| 0.0001644 | 3.72 | 238183_at | ESTs | | | |
| 0.0001644 | 3.205 | 228497_at | solute carrier family 22 (organic cation transporter), member 15 (SLC22A15), mRNA. | Hs.125482 | SLC22A15 | 1p13.1 |
| 0.0001645 | 2.614 | 204078_at | synaptonemal complex protein SC65 (SC65), mRNA. | Hs.446459 | SC65 | 17q21.2 |
| 0.0001649 | 3.055 | 239367_at | brain-derived neurotrophic factor (BDNF), transcript variant 6, mRNA. | Hs.502182 | BDNF | 11p13 |
| 0.0001678 | 2.961 | 227260_at | Transcribed locus | Hs.537755 | | 1 |
| 0.0001721 | 0.452 | 200074_s_at | ribosomal protein L14 (RPL14), mRNA. | Hs.446522 | RPL14 | 3p22-p21.2 |
| 0.0001731 | 0.346 | 227529_s_at | A kinase (PRKA) anchor protein (gravin) 12 | Hs.371240 | AKAP12 | 6q24-q25 |
| 0.0001747 | 0.451 | 229844_at | Transcribed locus | Hs.59368 | | 3 |
| 0.0001751 | 2.202 | 1568954_s_at | Unknown | | | |
| 0.0001753 | 2.848 | 1555243_x_at | Hypothetical gene supported by BC055092 | Hs.443072 | | 8q21.2 |
| 0.0001794 | 0.326 | 218919_at | zinc finger, AN1-type domain 1 (ZFAND1), mRNA. | Hs.390395 | ZFAND1 | 8q21.13 |
| 0.0001795 | 0.337 | 201674_s_at | A kinase (PRKA) anchor protein 1 (AKAP1), nuclear gene encoding mitochondrial protein, transcript variant 1, mRNA. | Hs.463506 | AKAP1 | 17q21-q23 |
| 0.0001802 | 2.365 | 202292_x_at | lysophospholipase II (LYPLA2), mRNA. | Hs.533479 | LYPLA2 | 1p36.12-p35.1 |
| 0.0001807 | 3.042 | 230850_at | Formin-like 3 | Hs.179838 | FMNL3 | 12q13.12 |
| 0.0001808 | 3.249 | 202016_at | mesoderm specific transcript homolog (mouse) (MEST), transcript variant 3, mRNA. | Hs.270978 | MEST | 7q32 |
| 0.0001816 | 0.269 | 209305_s_at | growth arrest and DNA-damage-inducible, beta (GADD45B), mRNA. | Hs.110571 | GADD45B | 19p13.3 |
| 0.0001825 | 2.505 | 238714_at | RAB12, member RAS oncogene family | Hs.270074 | | 18p11.22 |

TABLE 5-continued

Genes specifically regulated in tumor endothelium.

| Parametric p-value | Fold difference of geom means (Tumor/Normal) | Probe set | Description | UG cluster | Gene symbol | Map |
|---|---|---|---|---|---|---|
| 0.0001828 | 0.441 | 225352_at | translocation protein 1 (TLOC1), mRNA. | Hs.529591 | TLOC1 | 3q26.2 |
| 0.0001833 | 0.509 | 235556_at | Transcribed locus, weakly similar to NP_703324.1 glutamic acid-rich protein (garp) [*Plasmodium falciparum* 3D7] | Hs.445247 | | 5 |
| 0.0001833 | 0.505 | 1555823_at | BS 3076 | Hs.170421 | | 14 |
| 0.000184 | 0.349 | 212188_at | potassium channel tetramerisation domain containing 12 (KCTD12), mRNA. | Hs.109438 | KCTD12 | 13q22.3 |
| 0.000184 | 2.716 | 212769_at | Transducin-like enhancer of split 3 (E(sp1) homolog, *Drosophila*) | Hs.287362 | TLE3 | 15q22 |
| 0.0001862 | 2.329 | 219289_at | hypothetical protein FLJ20718 (FLJ20718) transcript variant 1, mRNA. | Hs.313917 | FLJ20718 | 16q12.1 |
| 0.0001871 | 2.234 | 229665_at | Hypothetical protein LOC283267 | Hs.44402 | CSTF3 | 11p13 |
| 0.0001876 | 15.895 | 231597_x_at | ESTs, Weakly similar to T47135 hypothetical protein DKFZp761L0812.1 [*H. sapiens*] | | | |
| 0.000189 | 2.944 | 1558426_x_at | Chromosome 7 open reading frame 19 | Hs.534807 | | 7 |
| 0.0001908 | 0.386 | 244050_at | similar to RIKEN 4933428I03 (LOC401494), mRNA. | Hs.136247 | LOC401494 | 9p21.3 |
| 0.0001916 | 0.44 | 218311_at | mitogen-activated protein kinase kinase kinase kinase 3 (MAP4K3), mRNA. | Hs.468239 | MAP4K3 | 2p22.1 |
| 0.0001922 | 0.441 | 218373_at | fused toes homolog (mouse) (FTS), transcript variant 2, mRNA. | Hs.380897 | FTS | 16q12.2 |
| 0.0001939 | 0.429 | 203166_at | craniofacial development protein 1 (CFDP1), mRNA. | Hs.461361 | CFDP1 | 16q22.2-q22.3 |
| 0.0001953 | 3.032 | 214110_s_at | ESTs, Highly similar to A43542 lymphocyte-specific protein 1 [*H. sapiens*] | | | |
| 0.0001962 | 2.652 | 229748_x_at | Hypothetical protein LOC285458 | Hs.487562 | LOC285458 | 4 |
| 0.0001971 | 3.714 | 240421_x_at | CDNA clone IMAGE: 5268630 | Hs.547654 | | 4 |
| 0.0001976 | 4.61 | 213905_x_at | Biglycan | Hs.821 | BGN | Xq28 |
| 0.0001992 | 0.426 | 224812_at | 3-hydroxyisobutyrate dehydrogenase (HIBADH), mRNA. | Hs.406758 | HIBADH | 7p15.2 |
| 0.0001997 | 0.46 | 200010_at | Ribosomal protein L11 | Hs.388664 | RPL11 | 1p36.1-p35 |
| 0.0002003 | 0.474 | 200022_at | ribosomal protein L18 (RPL18), mRNA. | Hs.515517 | RPL18 | 19q13 |
| 0.0002005 | 4.122 | 216858_x_at | | | | |
| 0.0002007 | 0.421 | 217773_s_at | NADH dehydrogenase (ubiquinone) 1 alpha subcomplex, 4, 9 kDa (NDUFA4), nuclear gene encoding mitochondrial protein, mRNA. | Hs.50098 | NDUFA4 | 7p21.3 |
| 0.0002018 | 2.22 | 1556835_s_at | Transcribed locus | Hs.548301 | | 11 |
| 0.0002019 | 9.389 | 203936_s_at | matrix metallopeptidase 9 (gelatinase B, 92 kDa gelatinase, 92 kDa type IV collagenase) (MMP9), mRNA. | Hs.297413 | MMP9 | 20q11.2-q13.1 |
| 0.0002023 | 2.731 | 219279_at | dedicator of cytokinesis 10 (DOCK10), mRNA. | Hs.46578 | DOCK10 | 2q36.3 |
| 0.0002042 | 0.49 | 230141_at | AT rich interactive domain 4A (RBP1-like) | Hs.161000 | ARID4A | 14q23.1 |
| 0.0002053 | 0.39 | 204454_at | leucine zipper, down-regulated in cancer 1 (LDOC1), mRNA. | Hs.45231 | LDOC1 | Xq27 |

TABLE 5-continued

Genes specifically regulated in tumor endothelium.

| Parametric p-value | Fold difference of geom means (Tumor/Normal) | Probe set | Description | UG cluster | Gene symbol | Map |
|---|---|---|---|---|---|---|
| 0.0002057 | 0.112 | 206211_at | selectin E (endothelial adhesion molecule 1) (SELE), mRNA. | Hs.89546 | SELE | 1q22-q25 |
| 0.0002058 | 2.146 | 227214_at | Golgi associated PDZ and coiled-coil motif containing | Hs.191539 | GOPC | 6q21 |
| 0.000206 | 0.448 | 224754_at | Sp1 transcription factor (SP1), mRNA. | Hs.524461 | SP1 | 12q13.1 |
| 0.0002067 | 0.353 | 226873_at | Transcribed locus | Hs.548339 | | 16 |
| 0.0002101 | 0.306 | 226688_at | chromosome 3 open reading frame 23 (C3orf23), transcript variant 1, mRNA. | Hs.55131 | C3orf23 | 3p21.33-p21.32 |
| 0.0002108 | 0.459 | 222431_at | Spindlin | Hs.146804 | SPIN | 9q22.1-q22.3 |
| 0.0002111 | 0.507 | 226705_at | Fibroblast growth factor receptor 1 (fms-related tyrosine kinase 2, Pfeiffer syndrome) | Hs.264887 | FGFR1 | 8p11.2-p11.1 |
| 0.0002121 | 0.267 | 202350_s_at | matrilin 2 (MATN2), transcript variant 2, mRNA. | Hs.189445 | MATN2 | 8q22 |
| 0.0002123 | 3.369 | 228331_at | Chromosome 11 open reading frame 31 | Hs.502630 | C11orf31 | 11q12.1 |
| 0.0002151 | 2.308 | 226599_at | KIAA1727 protein (KIAA1727), mRNA. | Hs.132629 | KIAA1727 | 4q31.3 |
| 0.000216 | 0.472 | 229431_at | regulatory factor X-associated protein (RFXAP), mRNA. | Hs.24422 | RFXAP | 13q14 |
| 0.0002181 | 2.628 | 210365_at | Runt-related transcription factor 1 (acute myeloid leukemia 1; aml1 oncogene) | Hs.149261 | RUNX1 | 21q22.3 |
| 0.0002196 | 3.303 | 238584_at | IQ motif containing with AAA domain | Hs.129174 | IQCA | 2q37.2-q37.3 |
| 0.0002203 | 0.512 | 201960_s_at | MYC binding protein 2 (MYCBP2), mRNA. | Hs.151411 | MYCBP2 | 13q22 |
| 0.0002206 | 2.459 | 236715_x_at | uveal autoantigen with coiled-coil domains and ankyrin repeats (UACA), transcript variant 1, mRNA. | Hs.108049 | UACA | 15q22-q24 |
| 0.0002226 | 3.297 | 213979_s_at | C-terminal binding protein 1 (CTBP1), transcript variant 1, mRNA. | Hs.208597 | CTBP1 | 4p16 |
| 0.0002231 | 0.271 | 208703_s_at | amyloid beta (A4) precursor-like protein 2 (APLP2), mRNA. | Hs.370247 | APLP2 | 11q24 |
| 0.0002234 | 0.507 | 202536_at | chromatin modifying protein 2B (CHMP2B), mRNA. | Hs.476930 | CHMP2B | 3p12.1 |
| 0.0002241 | 4.333 | 214715_x_at | zinc finger protein 160 (ZNF160), transcript variant 1, mRNA. | Hs.467236 | ZNF160 | 19q13.41 |
| 0.0002246 | 0.401 | 202364_at | MAX interactor 1 (MXI1), transcript variant 3, mRNA. | Hs.501023 | MXI1 | 10q24-q25 |
| 0.0002266 | 2.374 | 221943_x_at | ribosomal protein L38 (RPL38), mRNA. | Hs.380953 | RPL38 | 17q23-q25 |
| 0.0002277 | 0.153 | 1552767_a_at | heparan sulfate 6-O-sulfotransferase 2 (HS6ST2), mRNA. | Hs.385956 | HS6ST2 | Xq26.2 |
| 0.0002281 | 3.22 | 241223_x_at | ESTs, Weakly similar to ALU1_HUMAN ALU SUBFAMILY J SEQUENCE CONTAMINATION WARNING ENTRY [*H. sapiens*] | | | |
| 0.0002292 | 0.399 | 207132_x_at | prefoldin 5 (PFDN5), transcript variant 1, mRNA. | Hs.288856 | PFDN5 | 12q12 |
| 0.0002299 | 2.574 | 218739_at | abhydrolase domain containing 5 (ABHD5), mRNA. | Hs.19385 | ABHD5 | 3p21 |
| 0.0002299 | 3.3 | 217497_at | Endothelial cell growth factor 1 (platelet-derived) | Hs.546251 | ECGF1 | 22q13 |

TABLE 5-continued

Genes specifically regulated in tumor endothelium.

| Parametric p-value | Fold difference of geom means (Tumor/Normal) | Probe set | Description | UG cluster | Gene symbol | Map |
|---|---|---|---|---|---|---|
| 0.0002316 | 2.781 | 218193_s_at | golgi transport 1 homolog B (*S. cerevisiae*) (GOLT1B), mRNA. | Hs.62275 | GOLT1B | 12p12.1 |
| 0.0002317 | 0.315 | 209146_at | sterol-C4-methyl oxidase-like (SC4MOL), transcript variant 2, mRNA. | Hs.105269 | SC4MOL | 4q32-q34 |
| 0.0002325 | 3.134 | 201487_at | cathepsin C (CTSC), transcript variant 1, mRNA. | Hs.128065 | CTSC | 11q14.1-q14.3 |
| 0.0002331 | 3.007 | 202028_s_at | ribosomal protein L38 (RPL38), mRNA. | Hs.380953 | RPL38 | 17q23-q25 |
| 0.0002336 | 3.872 | 217715_x_at | ESTs | | | |
| 0.0002337 | 2.486 | 1553570_x_at | Unknown | | | |
| 0.0002364 | 0.558 | 201178_at | F-box protein 7 (FBXO7), transcript variant 2, mRNA. | | FBXO7 | 22q12-q13 |
| 0.0002365 | 6.732 | 210809_s_at | periostin, osteoblast specific factor (POSTN), mRNA. | Hs.136348 | POSTN | 13q13.3 |
| 0.0002372 | 3.675 | 226997_at | CDNA FLJ10196 fis, clone HEMBA1004776 | Hs.12680 | | 5 |
| 0.0002389 | 0.316 | 226038_at | LON peptidase N-terminal domain and ring finger 1 (LONRF1), mRNA. | Hs.180178 | LONRF1 | 8p23.1 |
| 0.0002408 | 2.579 | AFFX-BioDn-5_at | Unknown | | | |
| 0.0002413 | 2.498 | 206857_s_at | FK506 binding protein 1B, 12.6 kDa (FKBP1B), transcript variant 1, mRNA. | Hs.306834 | FKBP1B | 2p23.3 |
| 0.0002425 | 0.201 | 229339_at | Myocardin | Hs.462257 | MYOCD | 17p11.2 |
| 0.0002453 | 3.977 | 242578_x_at | Solute carrier family 22 (extraneuronal monoamine transporter), member 3 | Hs.242721 | SLC22A3 | 6q26-q27 |
| 0.0002463 | 2.667 | 231882_at | CDNA FLJ10674 fis, clone NT2RP2006436 | Hs.536634 | | 22 |
| 0.0002463 | 2.619 | 1556185_a_at | CDNA clone IMAGE: 5260162 | Hs.287168 | | 7 |
| 0.0002474 | 1.938 | 202573_at | casein kinase 1, gamma 2 (CSNK1G2), mRNA. | Hs.181390 | CSNK1G2 | 19p13.3 |
| 0.0002491 | 0.533 | 57715_at | Family with sequence similarity 26, member B | Hs.241545 | FAM26B | 10pter-q26.12 |
| 0.000252 | 4.351 | 239806_at | Transcribed locus | Hs.136017 | | 2 |
| 0.0002539 | 2.067 | 232145_at | hypothetical LOC388969 (LOC388969), mRNA. | Hs.516159 | LOC388969 | 2p11.2 |
| 0.0002541 | 0.522 | 235570_at | CDNA FLJ36544 fis, clone TRACH2006378 | Hs.101689 | | 3 |
| 0.0002548 | 0.455 | 224605_at | HCV F-transactivated protein 1 (LOC401152), mRNA. | Hs.173705 | LOC401152 | 4q26 |
| 0.000255 | 3.099 | 205463_s_at | Platelet-derived growth factor alpha polypeptide | Hs.376032 | PDGFA | 7p22 |
| 0.0002565 | 0.51 | 209384_at | proline synthetase co-transcribed homolog (bacterial) (PROSC), mRNA. | Hs.304792 | PROSC | 8p11.2 |
| 0.0002577 | 5.738 | 234753_x_at | | | | |
| 0.0002578 | 0.348 | 235061_at | protein phosphatase 1K (PP2C domain containing) (PPM1K), mRNA. | Hs.291000 | PPM1K | 4q22.1 |
| 0.0002619 | 0.279 | 235278_at | chromosome 20 open reading frame 133 (C20orf133), transcript variant 2, mRNA. | | C20orf133 | 20p12.1 |
| 0.0002624 | 0.147 | 218730_s_at | osteoglycin (osteoinductive factor, mimecan) (OGN), transcript variant 3, mRNA. | Hs.109439 | OGN | 9q22 |
| 0.000263 | 0.362 | 1554464_a_at | cartilage associated protein (CRTAP), mRNA. | Hs.517888 | CRTAP | 3p22.3 |

TABLE 5-continued

Genes specifically regulated in tumor endothelium.

| Parametric p-value | Fold difference of geom means (Tumor/Normal) | Probe set | Description | UG cluster | Gene symbol | Map |
|---|---|---|---|---|---|---|
| 0.0002644 | 0.438 | 226994_at | DnaJ (Hsp40) homolog, subfamily A, member 2 | Hs.368078 | DNAJA2 | 16q11.1-q11.2 |
| 0.000265 | 3.356 | 210679_x_at | B-cell CLL/lymphoma 7A | | BCL7A | 12q24.13 |
| 0.0002653 | 0.437 | 206621_s_at | Williams-Beuren syndrome chromosome region 1 (WBSCR1), transcript variant 2, mRNA. | Hs.520943 | WBSCR1 | 7q11.23 |
| 0.0002657 | 0.392 | 1558487_a_at | Transmembrane emp24 protein transport domain containing 4 | Hs.510745 | TMED4 | 7p13 |
| 0.0002665 | 2.208 | 1568619_s_at | Hypothetical protein LOC162073 | Hs.530899 | LOC162073 | 16p12.3 |
| 0.0002666 | 3.366 | 229795_at | Transcribed locus | Hs.48945 | | 12 |
| 0.0002674 | 0.312 | 200906_s_at | palladin (KIAA0992), mRNA. | Hs.151220 | KIAA0992 | 4q32.3 |
| 0.0002675 | 2.764 | 202581_at | heat shock 70 kDa protein 1B (HSPA1B), mRNA. | Hs.274402 | HSPA1B | 6p21.3 |
| 0.0002697 | 0.479 | 225330_at | Insulin-like growth factor 1 receptor | Hs.20573 | IGF1R | 15q26.3 |
| 0.0002718 | 2.171 | 225480_at | chromosome 1 open reading frame 122 (C1orf122), mRNA. | Hs.532749 | C1orf122 | 1p34.3 |
| 0.0002728 | 0.412 | 227132_at | HSPC038 protein (LOC51123), mRNA. | Hs.374485 | LOC51123 | 8q22.3 |
| 0.0002731 | 0.533 | 200031_s_at | ribosomal protein S11 (RPS11), mRNA. | Hs.433529 | RPS11 | 19q13.3 |
| 0.0002738 | 0.328 | 229994_at | MRNA; cDNA DKFZp686J23256 (from clone DKFZp686J23256) | Hs.379253 | | 1 |
| 0.0002746 | 3.124 | 207730_x_at | hypothetical protein FLJ20700 | | FLJ20700 | 19p13.3 |
| 0.0002751 | 2.866 | 235327_x_at | UBX domain containing 4 (UBXD4), mRNA. | Hs.516018 | UBXD4 | 2p23.3 |
| 0.0002768 | 5.302 | 212236_x at | keratin 17 (KRT17), mRNA. | Hs.2785 | KRT17 | 17q12-q21 |
| 0.0002777 | 1.816 | 218159_at | chromosome 20 open reading frame 116 (C20orf116), mRNA. | Hs.471975 | C20orf116 | 20p13 |
| 0.0002779 | 0.309 | 202119_s_at | copine III (CPNE3), mRNA. | Hs.191219 | CPNE3 | 8q21.3 |
| 0.000278 | 2.474 | 225636_at | signal transducer and activator of transcription 2, 113 kDa (STAT2), mRNA. | Hs.530595 | STAT2 | 12q13.3 |
| 0.0002844 | 3.057 | 224667_x_at | Transcribed locus | Hs.558150 | | |
| 0.0002846 | 2.854 | 233406_at | KIAA0256 gene product | Hs.9997 | KIAA0256 | 15q21.1 |
| 0.0002862 | 0.464 | 225941_at | Eukaryotic translation initiation factor 4E member 3 | Hs.476782 | EIF4E3 | 3p14 |
| 0.0002867 | 0.43 | 212368_at | PREDICTED: zinc finger protein 292 (ZNF292), mRNA. | Hs.485892 | ZNF292 | 6 |

Example 5

Array Validation

This example provides further support for the use of the endothelial cell tumor-associated molecules provided in Examples 3 and 4 to identify ovarian tumor endothelial cells.

To substantiate the findings provided by the microarray analysis described in Examples 3 and 4, a series of 17 genes were selected at random spanning a range of fold-changes (3.6 to 155.3; FIG. 2). Of 17 primer sets, 15 yielded specific qRT-PCR products when analyzed using Universal Human Reference RNA (Stratagene, La Jolla, Calif.), with 13 reaching statistical significance in tumor (n=10) and normal (n=5) isolates (p<0.05) including PLXDC1, ARBB2, HES4, PGF, EGFL6, ADAM12, COL5A3, COL18A1, PCOLCE, PMAIP1, CENTA2, TMEPAI, and NPTX2. In order to substantiate the pathway analysis (presented below), a second set of genes implicated in endothelial tumor cell signaling was assessed. From a series of 12 genes, suitable primer sets were obtained for 10 genes. All 10 pathway members were successfully validated (p<0.05) including FYN, VAV2, ECGF1, PTK2, TNFAIP6, EZH2, STC1, MMP9, JAG1, and CSPG2 (FIG. 1).

To further examine whether the gene expression alterations identified by the microarray analysis also occur at the protein level, immunohistochemical staining was performed for selected proteins on 5 normal ovaries and 5 invasive epithelial ovarian cancers. The microarray analysis identified FAK (PTK2; 3.1-fold), Fyn (4.7-fold), MMP-9 (9.4-fold), β2-arrestin (4.8-fold), Jagged1 (4.3-fold), and PLXDC1 (10.2-fold) as being significantly increased in tumor-associated endothelial cells, and these changes were validated by real-time RT-PCR.

Immunohistochemical-peroxidase staining confirmed that both FAK and Fyn were indeed overexpressed in the tumor-associated endothelial cells in all samples. There were no obvious differences in protein expression between arterioles and venules. Similarly, increased expression of MMP-9, β2-arrestin, Jagged1, and PLXDC1 was also confirmed at the protein level (FIG. 2). These results provide further support for the use of the specific endothelial cell tumor-associated molecules provided in Examples 3 and 4 to identify ovarian tumor endothelial cells.

Example 6

Modulation of Endothelial Cell Tumor-Associated Molecules

This example illustrates signaling pathways that are modulated in tumor endothelium and their functional significance.

Ovarian epithelial carcinomas arise from molecular events occurring in the epithelial layer, which affect changes in gene expression within surrounding non-epithelial cell populations. For endothelial cells, this altered signaling environment stimulates proliferation, migration, and tumor vascularization. To identify epithelial genes that may be responsible for these changes and the endothelial signaling pathways that are impacted, a series of laser microdissected papillary serous epithelial cell isolates and ovarian surface epithelial brushings were compared, as previously described (Bonome et al., Cancer Res. 65: 10602-10612, 2005). Pathway diagrams were generated using Pathway Assist version 3.0 software. The genes comprising the pathway indicate involvement in endothelial cell proliferation, tube-formation, and cell motility.

Figure 3D:
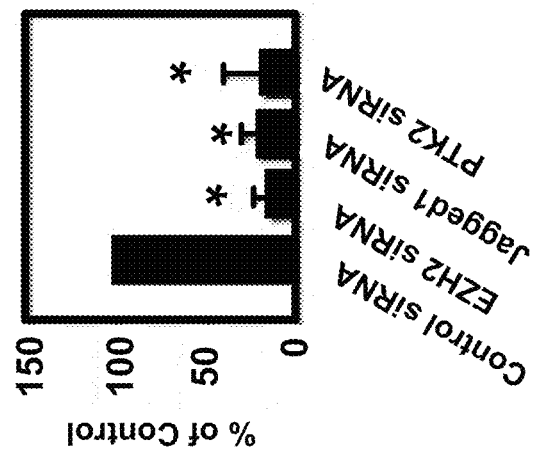
FIG. 3D is a graph illustrating the effect of EZH2, Jagged1 or PTK2 silencing on human umbilical vein endothelial cell (HUVEC) tube formation.
Figure 3A:
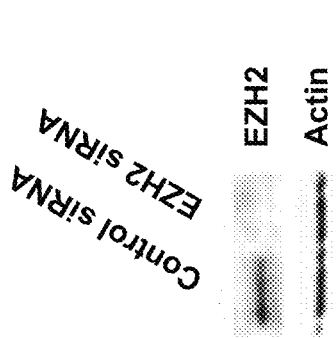
FIGS. 3A, 3B and 3C are digital images of siRNA-mediated silencing of (FIG. 3A) EZH2, (FIG. 3B) Jagged1 and (FIG. 3C) protein tyrosine kinase 2 (PTK2), as assessed using Western blot analyses.
Figure 3B:
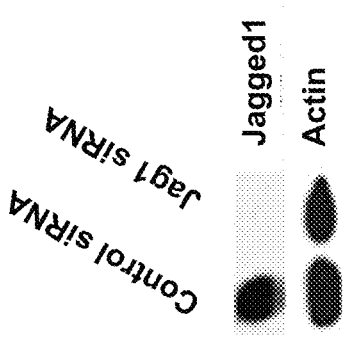
Figure 3C:
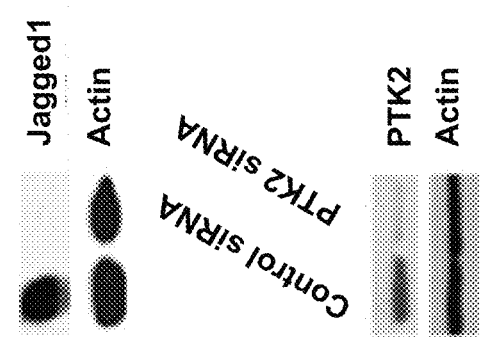
Figure 3E:
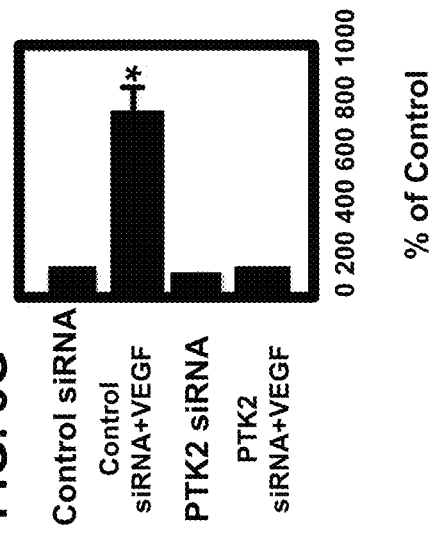
FIG. 3E is a graph illustrating the effect of EZH2 silencing on HUVEC migration.
Figure 3F:
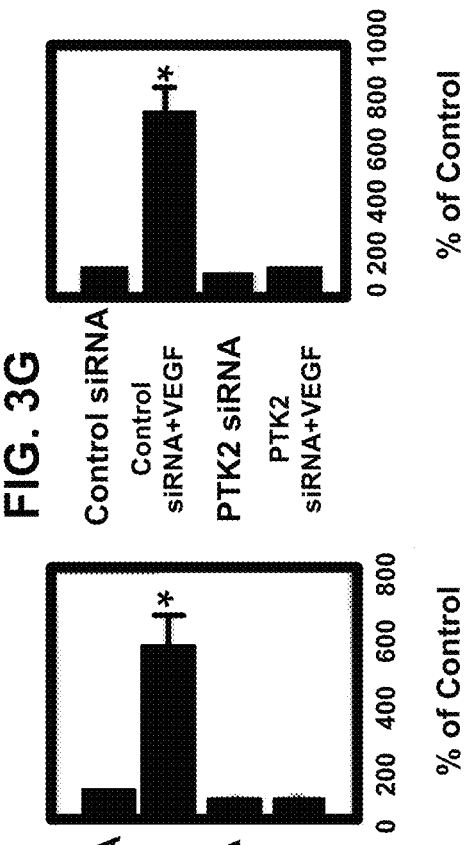
FIG. 3F is a graph illustrating the effect of Jagged1 silencing on HUVEC migration.
Figure 3G:
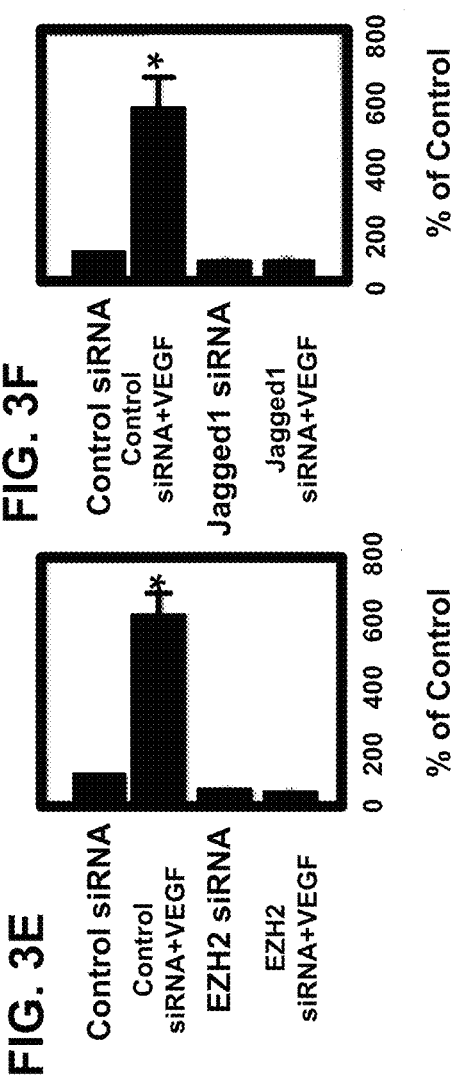
FIG. 3G is a graph illustrating the effect of PTK2 silencing on HUVEC migration.

To test the biological significance of some of these genes, three genes were selected—EZH2, Jagged1, and PTK2 EZH2 plays an important role in many biological processes and is downstream of Akt activation, making it a potential anti-angiogenic target. siRNA was used to inhibit EZH2 expression (FIG. 3A) in HUVEC cells and its effects on tube formation (FIG. 3D) and migration (FIG. 3E) were examined. In comparison to control non-silencing siRNA, EZH2 silencing resulted in an 85% decrease in endothelial tube-formation on Matrigel (FIG. 3D) EZH2-targeted siRNA completely blocked VEGF-stimulated migration of HUVEC cells (FIG. 3E). Similarly, to determine the functional relevance of Jagged1 for endothelial cell function, the effects of inhibiting Jagged1 expression with siRNA were evaluated (FIG. 3B) on tube-formation (FIG. 3D) and migration (FIG. 3F). Jagged1-targeted siRNA reduced tube-formation by 80% (FIG. 3D) and blocked VEGF-stimulated HUVEC migration (FIG. 3F). Similar results were noted with PTK2 expression inhibition with PTK2-targeted siRNA (FIGS. 3D and 3G). These data indicate that the novel differentially expressed genes in the tumor-associated endothelial cells play functionally significant roles in angiogenesis.

The ability of siRNA to be delivered directly into ovarian tumor cells was investigated by staining tumor tissues with (A) primary rat anti-mouse CD31 antibody to detect endothelial cells and (B) anti-f4/80 to detect scavenging macrophages and then Alexa 488-tagged secondary antibody. Fluorescent siRNA was not only trapped onto blood vessels, but was also effectively delivered deep into tumor parenchyma. Macrophages were observed to surround nests of tumor cells that contained perinuclear siRNA, and had less amount of siRNA compared to tumor cells suggesting that siRNAs were delivered directly into the tumor cells.

Figure 4:
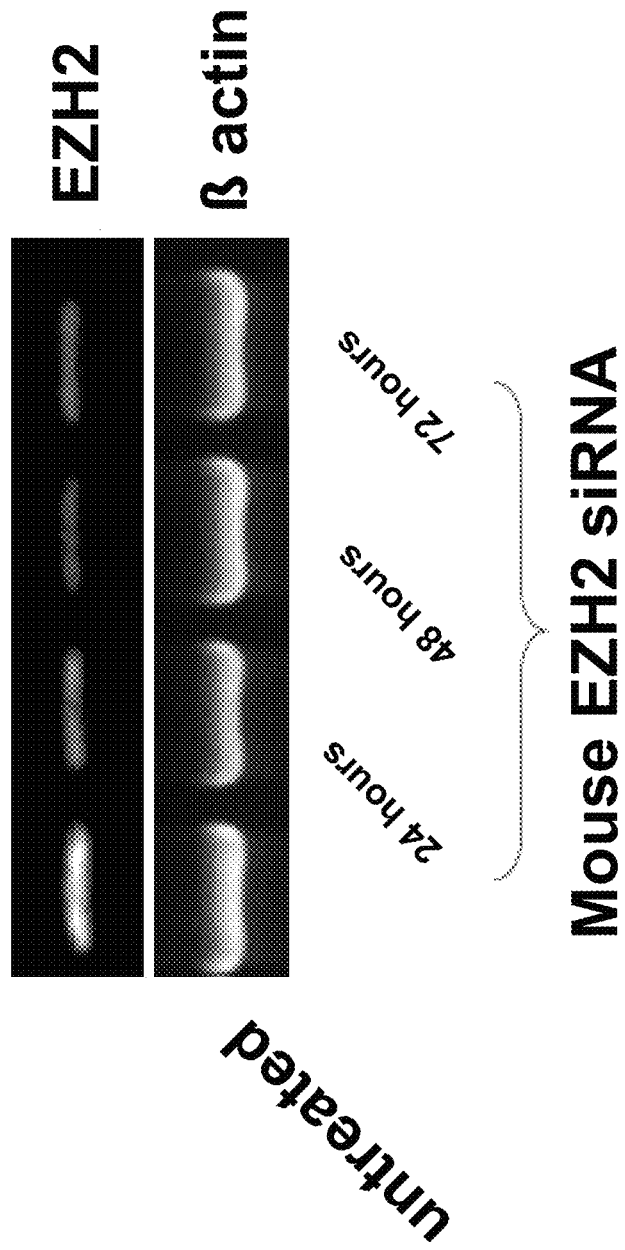
FIG. 4 is a digital image illustrating down regulation of EZH2 by mouse EZH2 siRNA in mouse ovarian endothelial cells.

The effect of mouse EZH2 siRNA on EZH2-expression in mouse ovarian endothelial cells was also determined. Cells were trypsinized at different time intervals (24 h, 48 h and 72 h) after transfection with mouse EZH2 siRNA and checked for EZH2 mRNA down regulation using RT-PCR analysis. As illustrated in FIG. 4, EZH2 gene expression was significantly decreased after 24 hours of treatment, indicating that the administered siRNA was capable of down-regulating EZH2 mRNA in vitro.

Example 7

Inhibition of Tumor Growth and Vascularization in a Mouse Model

This example describes methods for significantly reducing ovarian tumor growth and vascularization in a mouse model. One of skill in the art will appreciate that similar methods can be used in other mammals and other siRNAs can be used in place of those described herein. Further, a conversion formula known to those of skill in the art can be employed to determine the appropriate doses in other mammals, including humans.

Figure 6:
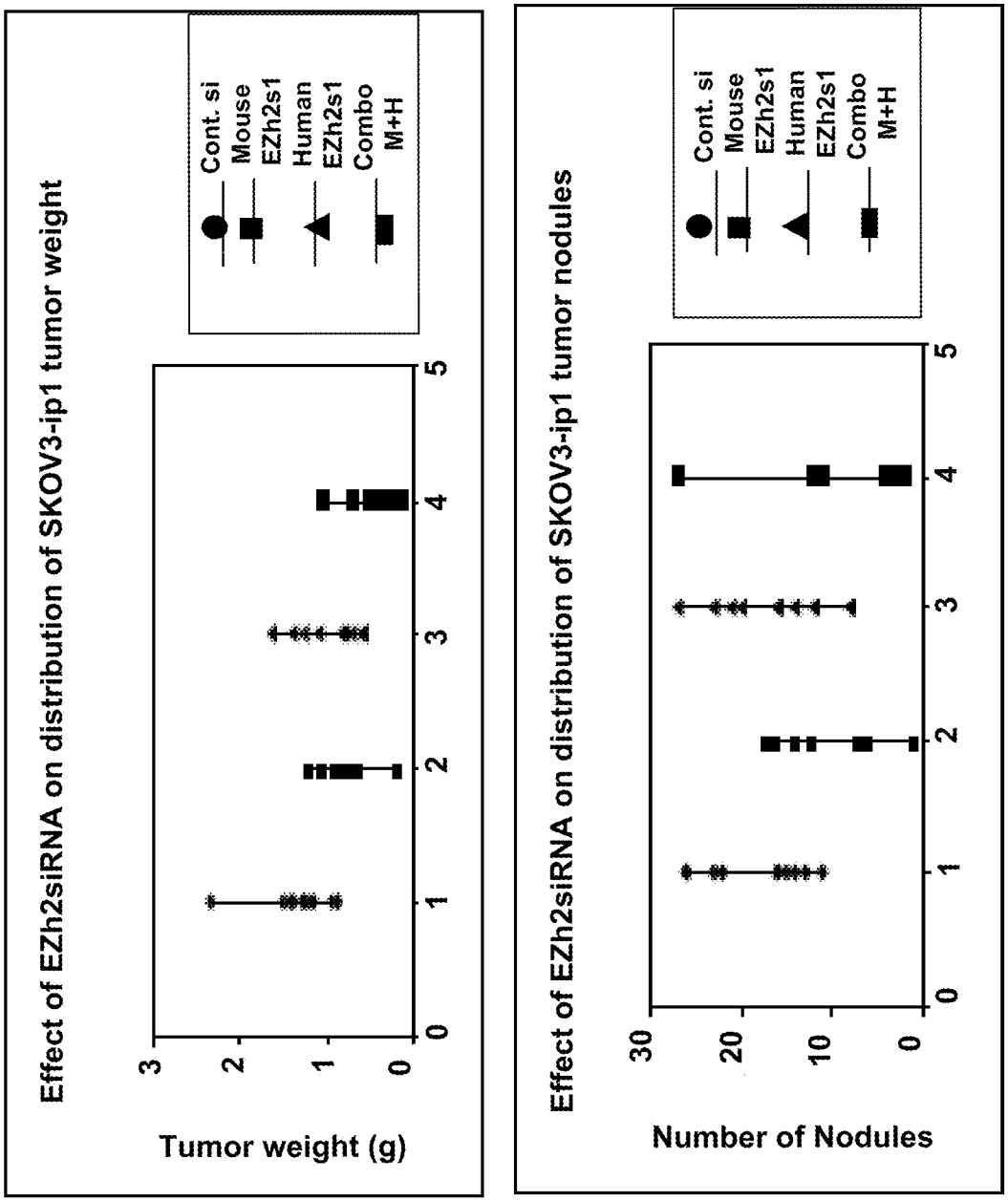

Nude mice were injected (via i.p.) with either $2.5 \times 10^5$ HeyA8 or $1.0 \times 10^6$ SKOV3ip1 cells. Mice were randomly divided into 4 groups: 1) control siRNA-chitosan, 2) mouse EZH2 siRNA-chitosan, 3) Human EZH2 siRNA-chitosan, and 4) combination of mouse plus human EZH2 siRNA-chitosan. Therapy was started on the seventh day by injecting chitosan siRNA twice weekly (150 µg/kg). Therapy was started on the seventh day by injecting chitosan siRNA twice weekly (150 µg/kg). Animals were sacrificed when mice became moribund (3-5 weeks after cell injection). Mouse weight, tumor weight, number of tumor nodules and tumor location were recorded. As illustrated in FIGS. 5 and 6, mice treated with mouse-EZH2 siRNA exhibited significant decrease in tumor burden compared to control siRNA (70% and 42% reduction in tumor weight of HeyA8 and SKOV3ip1 respectively, p=0.05). Human EZH2 siRNA also reduced the tumor burden (50% in HeyA8 and 24% reduction in SKOV3ip1, p=0.05 of only HeyA8 tumors) compared to mouse targeted EZH2 siRNA. However, the greatest reduction was observed when treating the mouse with a combination of mouse plus human EZH2 siRNA (84% and 65% reduction in HeyA8 and SKOV3ip1 tumors, respectively, (p=0.001). In the case of tumor nodules, again combination of mouse plus human EZH2-siRNA group consistently produced fewer tumor nodules with 75% and 53% reduction compared to control group (p=0.05). The effect of EZH2 siRNA on microvessel density was determined by harvesting tumors from the four different groups stated above and staining such tumors for CD31. The mouse targeted EZH2 siRNA group showed decreased number of blood vessels compared to human EZH2 siRNA and control siRNA treated tumors. Microvessel density of the combination treated group using both mouse and human EZH2 siRNA was significantly reduced when compared to that of the control group. These studies demonstrate the ability of EZH2-targeted siRNA to inhibit tumor growth and vascularization in vivo.

Example 8

This example illustrates that increased EZH2 expression in either tumor cells or in tumor vasculature is predictive of poor clinical outcome and that the anti-angiogenesis effect of EZH2 silencing is mediated via silencing VASH1.

Material and Methods.

Human Ovarian Cancer Specimens.

One-hundred and thirty paraffin-embedded epithelial ovarian cancer specimens with available clinical outcome data and confirmed diagnosis by a board-certified gynecologic pathologist were obtained from the Karmanos Cancer Institute tumor bank. All patients were diagnosed from 1985 to 2004 following primary cytoreductive surgery. Slides of tumor samples were obtained for EZH2, CD34, and VEGF expression analysis. Clinical variables obtained for correlative analyses included age at diagnosis, tumor stage and grade, and vital status of patients relative to disease-specific survival at the time of chart review.

Cell Lines and Culture.

The HeyA8 and SKOV3ip1 human epithelial ovarian cancer cells were maintained as described previously. The derivation and characterization of the murine ovarian endothelial cells (MOEC) has been described previously. The EAhy926 endothelial hybridoma cell line was provided by Dr. Robert Danner, CCMD, NIH, and was maintained as described previously, with sodium hypoxanthine and thymidine (HT) supplement (Invitrogen, Carlsbad, Calif.) instead of sodium hypoxanthine aminopterin and thymidine (HAT) supplement (Invitrogen). HUVEC were purchased from Cambrex (Walkersville, Md.) and maintained with heparin and gentamicin/amphotericin-B, as previously described.

EZH2 Promoter Construct.

The EZH2 promoter was amplified by PCR from the Roswell Park Cancer Institute (RPCI) human BAC library 11, Clone-ID RP11-992C19 purchased from the Children's Hospital Oakland Research Institute (Oakland, Calif.), and then cloned into the pGL3-Basic Vector (Promega Corp., Madison, Wis.). The EZH2 promoter construct was amplified using primers (Table 6) with XhoI and HindIII restriction endonuclease sites added to the ends. Purified PCR product was then cloned upstream of the luc+ gene in the pGL3-Basic Vector (Promega Corp.) using XhoI and HindIII.

TABLE 6

Primers and siRNA sequences used.

EZH2 promoter (Human):

5'-GATACTCGAGGTCGGGAGTTCGAGACCA-3' (forward; SEQ ID NO: 6)
5'-GTTTAAGCTTACTCGCGTTGTTCCCGCG-3' (reverse; SEQ ID NO: 7)

VASH1 promoter (Human):

5'-CATGGGAGGGCTTGATGAAGG-3' (forward; SEQ ID NO: 8)
5'-GCCTAGTCCATGCTGACCTTG-3' (reverse; SEQ ID NO: 9)

Real time quantitative RT-PCR and ChIP assay:
Murine EZH2:

5'-GCTGAGCGTATAAAGACACC-3' (forward; SEQ ID NO: 10)
5'-TCTACATCCTCAGTGGGAAC-3' (reverse; SEQ ID NO: 11)

Human EZH2:

5'-TCATGCAACACCCAACAC-3' (forward; SEQ ID NO: 12)
5'-CACAACCGGTGTTTCCTC-3' (reverse; SEQ ID NO: 13)

Murine VASH1:

5'-CATCAGGGAGCTGCAGTACA-3' (forward; SEQ ID NO: 14)
5'-CCCAGCTTCACCTTCTTCAG-3' (reverse; SEQ ID NO: 15)

Human VASH1:

5-CATGGGAGGGCTTGATGAAGG-3' (forward; SEQ ID NO: 16)
5'-CAAGGTCAGCATGGACTAGGC-3' (reverse; SEQ ID NO: 17)

Murine E2F1:

5'-TGGATCTGGAGACTGACCAT-3' (forward; SEQ ID NO: 18)
5'-AGTTGCAGCTGTGTGGTACA-3' (reverse; SEQ ID NO: 19)

Murine E2F2:

5'-GCTCCTGACCAAGAAGTTCA-3' (forward; SEQ ID NO: 20)
5'-GCAATCACTGTCTGCTCCTT-3' (reverse; SEQ ID NO: 21)

Murine E2F3:

5'-TGCAGTCTGTCTGAGGATGG-3' (forward; SEQ ID NO: 22)
5'-GAGGCCAGAGGAGAGAGGTT-3' (reverse; SEQ ID NO: 23)

Murine E2F4:

5'-AAGAACTGGACCAGCACAAG-3' (forward; SEQ ID NO: 24)
5'-ACTATCCAGCAGTGCAGAGG-3' (reverse; SEQ ID NO: 25)

TABLE 6-continued

Primers and siRNA sequences used.

Murine E2F5:

5'-AGTTGTGGCTACAGCAAAGC-3' (forward; SEQ ID NO: 26)
5'-GGAGAAAGCCGTAAAAGAGG-3' (reverse; SEQ ID NO: 27)

SiRNA target sequences:
Nonsilencing control siRNA:

5'-TTCTCCGAACGTGTCACGT[dT] [dT]-3' (Sense; SEQ ID NO: 28)
5'-ACGTGACACGTTCGGAGAA [dT] [dT]-3' (Antisense; SEQ ID NO: 29)

Human EZH2 siRNA: Validated sequence
Murine EZH2 siRNA1:

5'-GCTCTTACTGCTGAGCGTA[dT] [dT]-3' (Sense; SEQ ID NO: 30)
5'-TACGCTCAGCAGTAAGAGC [dT] [dT]-3' (Antisense; SEQ ID NO: 31)

Murine EZH2 siRNA2:

5'-GAGCAAAGCTTGCATTCAT[dT] [dT]-3' (Sense; SEQ ID NO: 32)
5'-ATGAATGCAAGCTTTGCTC [dT] [dT]-3' (Antisense; SEQ ID NO: 33)

Murine EZH2 siRNA3:

5'-CATTGGTACTTACTACGAT[dT] [dT]-3' (Sense; SEQ ID NO: 34)
5'-ATCGTAGTAAGTACCAATG [dT] [dT]-3' (Antisense; SEQ ID NO: 35)

Human VASH1 siRNA:

5'-GCGATGACTTCCGCAAGGA[dT] [dT]-3' (Sense; SEQ ID NO: 36)
5'-TCCTTGCGGAAGTCATCGC [dT] [dT]-3' (Antisense; SEQ ID NO: 37)

Murine VASH1 siRNA:

5'-GTGAGCTCGTGCTGGACTA[dT] [dT]-3' (Sense; SEQ ID NO: 38)
5'-TAGTCCAGCACGAGCTCAC [dT] [dT]-3' (Antisense; SEQ ID NO: 39)

Murine E2F3 siRNA:

5'-GTTTCTACAGCAAACCTCT[dT] [dT]-3' (Sense; SEQ ID NO: 40)
5'-AGAGGTTTGCTGTAGAAAC [dT] [dT]-3' (Antisense; SEQ ID NO: 41)

Murine E2F5 siRNA:

5'-CAATTGCTTTCATGGTGAT[dT] [dT]-3' (Sense; SEQ ID NO: 42)
5'-ATCACCATGAAAGCAATTG [dT] [dT]-3' (Antisense; SEQ ID NO: 43)

Luciferase Reporter Assay.

Relative activity of the EZH2 promoter in the EAhy926 cell line was determined by luciferase reporter assay. Cells were transfected in low-serum medium (0.5% serum) with the firefly luciferase plasmid, either empty vector (pGL3-Basic) or the EZH2 promoter construct vector (EZH2prom-pGL3-Basic), in 12-well plates using Effectene® Transfection Reagent from Qiagen (Valencia, Calif.). The primer sequence of EZH2 promoter are given in Table 6. Cells were then maintained in low-serum medium for 18 hours, washed in warm 1× phosphate-buffered saline (PBS), and treated in triplicate at 37° C. for 6 hours. Treatments included recombinant human (rh) EGF (EGF; 25 ng/mL; Invitrogen) and rhVEGF$_{165}$ (VEGF; 50 ng/mL; Peprotech, Rocky Hill, N.J.), each in fresh medium plus 0.5% serum, fresh complete medium plus 10% serum, and conditioned media from immortalized ovarian surface epithelium (IOSE120) and from papillary serous ovarian cancer cell lines (OVCA420 and SKOV3). Medium in control wells (pGL3-Basic transfectants) was not changed on the day of treatment. Following treatment, cells were washed briefly in cold 1×PBS and lysates were collected and processed using the Dual-Luciferase® Reporter Assay System (Promega Corp.). Firefly luciferase readings were averaged and normalized to pGL3-Basic control readings for percent fold changes.

Chromatin Immunoprecipitation (ChIP) Assay.

HUVEC were cultured in low serum medium (0.5% serum) for 18 h and then treated with or without VEGF (50 ng/mL) for 6 hours. After treatment, ChIP assays were performed using EZ ChIP™ kit (Milllipore, Temecula, Calif.) as described by the manufacturer. Briefly, cross-linked cells were collected, lysed, sonicated and subsequently subjected to immunoprecipitation with EZH2 (Cell signaling) antibody or mouse IgG (mIgG) control. Immunocomplexes were collected with protein G agarose beads and eluted. Cross-links were reversed by incubating at 65° C. DNA then was extracted and purified for PCR using primers (see Table 6) corresponding to the 3800 to 3584 base pairs upstream of the VASH1 transcription start site.

Real Time Quantitative RT-PCR.

Relative expression of EZH2 and VASH1 mRNA in HUVEC and MOEC cells was determined by real-time quantitative RT-PCR. Cells were seeded at $1.0 \times 10^4$ cells per well in 96-well plates in complete medium and incubated at 37° C. for 24 hours, and then in low-serum medium (0.5% serum) for 18 hours, minus EGF and VEGF supplements where appropriate. After washing with warm PBS, cells were treated in triplicate at 37° C. for 6 hours with EGF (25 ng/mL) and VEGF (50 ng/mL), each in fresh medium (lacking supplemental EGF or VEGF) with no serum, fresh complete medium plus 2% serum, and conditioned media. Relative expression of VASH1 mRNA in MOEC cells was determined by transfecting cells with EZH2 mouse siRNA. Samples were collected after 72 hours of transfection. Expression of E2F transcription factors and levels of EZH2 in E2F transcription factors silenced endothelial cells (MOEC) was determined using specific siRNA for E2F transcriptional factors. Real-time quantitative RT-PCR was performed using 50 ng total RNA isolated from treated cells using the RNeasy Mini Kit (Qiagen). (SiRNA and primer sequences are given in Table 6). Relative expression values were obtained using the average of three reference genes and the $2^{-\Delta\Delta CT}$ method as described previously, and normalized to control for percent fold changes.

SiRNA Constructs and Delivery.

SiRNA nonsilencing control or EZH2 Hs siRNA were purchased from Qiagen and EZH2 Mm siRNA from Dharmacon (Chicago, Ill.). A nonsilencing siRNA that did not share sequence homology with any known human mRNA based on a BLAST search was used as control for target siRNA, and the same sequence with Alexa-555 tag was used to determine the uptake and distribution in tumor and various organs when given in vivo. In vitro transient transfection was performed as described previously and cells were harvested to measure EZH2 protein downregulation by Western blot analysis. (SiRNA sequences are given in Table 6).

DNA Extraction and Methylation Analysis.

DNA was extracted from the EZH2 silencing cells and mock cells using standard phenol-chloroform methods. Methylation analysis was done using a methylation kit (EZ-96 gold; Zymo Research, Orange, Calif.). MethPrimer software was used for the prediction of CpG island of Mm VASH1 (ACCESSION AB284948; VERSION AB284948.1; GI: 118442795) and design of methylation specific primers. The sequence of primers for methylated VASH1 at promoter region was TTAGGGATTTACGTATCGACGT (forward; SEQ ID NO: 44); AAACGACAAACTCCAACCG (reverse; SEQ ID NO: 45); and for unmethylated VASH1 promoter was TTTTTTTTAGGGATTTATGTATTGATGT (forward; SEQ ID NO: 46); CTAAACAACAAACTCCAACCACA (reverse; SEQ ID NO: 47). The PCR conditions were 94° C. for 5 min with hot start, then 94° C. for 45 second, 56° C. for 45 second, and 72° C. for 45 second, repeated for 40 cycles. Image analysis (Scion Image for Windows) was used for semi-quantitative measurement of methylated and unmethylated VASH1. Methylated VASH1 was normalized by unmethylated VASH1. The studies were repeated 3 times.

Cell Proliferation, Migration and Tube Formation Assay:

Cells were seeded in 96-well plates at $1 \times 10^3$ cells/well in replicates of 12. After 48 hours, cell growth was arrested; 36 hours after growth arrest, the specific mediators were added to untreated cells. Proliferation is assessed by the MTT dye technique, as previously described. The Membrane Invasion Culture System (MICS) chamber was used to measure the in vitro migration ability of cells.

Orthotopic In Vivo Model of Ovarian Cancer and Tissue Processing.

Female athymic nude mice (NCr-nu) were purchased from the National Cancer Institute-Frederick Cancer Research and Development Center (Frederick, Md.) and maintained as previously described. Tissue specimens were fixed either with formalin or OCT (optimum cutting temperature; Miles, Inc., Elkhart, Ind.) or were snap frozen.

To assess tumor growth for long-term therapy experiments, treatment began 1 week after intraperitoneal injection of tumor cells. Mice were divided into 4 groups (n=10 mice per group): (a) control siRNA/CH, (b) EZH2 Hs siRNA/CH (c) EZH2 Mm siRNA/CH, and (d) EZH2 Hs siRNA/CH plus EZH2 Mm siRNA/CH. VASH1 gene silencing effects was determined using same cells and mice were divided into 6 groups. (a) Control siRNA/CH, (b) EZH2 Mm siRNA1/CH (c) EZH2 Mm siRNA2/CH, (d) EZH2 Mm siRNA3/CH (e) VASH1 Mm siRNA/CH and (f) VASH1 Mm siRNA/CH plus EZH2 Mm siRNA/CH. Each siRNA was given twice weekly at a dose of 150 µg/kg body weight. Treatment continued until mice became moribund (typically 4 to 5 weeks following tumor-cell injection) in any group. At the time of sacrifice, mouse weight, tumor weight, number of nodules, and distribution of tumors were recorded. The individuals who performed the necropsies, tumor collections, and tissue processing were blinded to the treatment group assignments.

Immunofluorescence and Confocal Microscopy.

Localization of EZH2 and CD31 was performed using frozen tissue. Tumors collected after 48 hours of single injection of control siRNA/CH, or EZH2 Hs siRNA/CH, or EZH2 Mm siRNA/CH, or EZH2 Hs siRNA/CH plus EZH2 Mm siRNA/CH and stained for CD31 and EZH2. Staining for CD31 and desmin was done as described previously. Pericyte coverage was determined by the percent of vessels with 50% or more coverage by the green fluorescence of associated desmin-positive cells in 5 random fields at ×200 magnification for each tumor.

Western Blot Analysis.

Western blot analysis for EZH2 expression, histone3 (Lys27) methylation in vitro and EZH2 expression for in vivo samples was performed as previously reported. Tumors were collected at various time points (after 24, 48, 72 and 96 hours of single injection of control siRNA/CH, or EZH2 Hs siRNA/CH, or EZH2 Mm siRNA/CH, or EZH2 Hs siRNA/CH plus EZH2 Mm siRNA/CH) and lysed to analyze protein levels using Western blotting.

EZH2 Gene Silencing in MOEC.

Relative expression of EZH2 mRNA in MOEC was determined by transfecting cells with control or EZH2 Mm siRNA and harvested after 72 hours of transfection. Real-time quantitative RT-PCR was performed using 50 ng total RNA isolated from treated cells using the RNeasy Mini Kit (Qiagen). Primer sequences are given in the Table 7. Relative expression values were obtained using the average of 3 reference genes and the $2^{-\Delta\Delta CT}$ method as described previously, and normalized to control for percent fold changes.

TABLE 7

Characteristics of tumors after treatment with EZH2 siRNA/CH and VASH1 siRNA/CH.

| Cell line | Treatment | Median no. nodules (range) | p-value (vs. control) |
|---|---|---|---|
| HeyA8 | Control siRNA/CH | 19.0 (9-25) | |
| | EZH2 Mm siRNA1/CH | 2.0 (0-8) | 0.01* |
| | EZH2 Mm siRNA2/CH | 9.0 (0-11) | 0.046* |
| | EZH2 Mm siRNA3/CH | 9.0 (2-19) | ns |
| | VASH1 Mm siRNA/CH | 16.0 (12-21) | 0.01** |
| | EZH2 Mm siRNA1/CH plus VASH1 Mm siRNA/CH | 20.0 (7-32) | 0.02** |

*vs control siRNA/CH;
**vs EZH2siRNA/CH

Immunohistochemical Staining.

Detection of microvessel density was performed using formalin-fixed, paraffin-embedded tumor sections (8 µm thickness) as previously described. To quantify MVD, the number of blood vessels staining positive for CD31 was recorded in 10 random 0.159 mm² fields at ×200 magnification. All staining was quantified by 2 investigators in a blinded fashion. Immunohistochemistry for EZH2 (1:400 dilution, Zymed, San Francisco, Calif.), CD34 (1:20 dilution, BioGenex Laboratories, San Ramon, Calif.), VEGF (1:100 dilution, Santa Cruz Biotechnology, Inc., Santa Cruz, Calif.) was performed, as described previously. A combined score that was based on the staining intensity and the percentage of cells stained was used to assign a final score.

Statistical Analysis.

Differences in continuous variables such as mean body weight, tumor weight, and proliferation (PCNA) were analyzed using the Mann-Whitney rank sum test. Statistical analyses were performed using SPSS 12.0 for Windows® (SPSS Inc., Chicago, Ill.). A 2-tailed p<0.05 was considered statistically significant. Kaplan-Meier survival plots were generated and comparisons between survival curves were made using the log-rank statistic.

Conditioned Media.

Conditioned media were obtained as follows: IOSE120, OVCA420 and SKOV3 cells were grown in 100 mm culture dishes at 37° C. until 80% confluent. Cells were then washed briefly in warm 1×PBS. Then, 5 mL of low-serum, complete HUVEC cell medium (0.5% serum) was added to the dishes and the cells were incubated at 37° C. for 16 hours. Supernatants (conditioned media) were then collected in a syringe and passed through a 0.45 micron filter and stored at −80° C. until needed.

Preparation of siRNA-Incorporated Ch (siRNA/Ch) Nanoparticles.

CH (Molecular weight 50-190 kDa), sodium tripolyphosphate (TPP), and agarose were purchased from Sigma Co. (St. Louis, Mo.). SiRNA/CH nanoparticles were prepared based on ionic gelation of anionic TPP and siRNA with cationic CH. The formulation of the siRNA/CH nanoparticles is shown in FIG. 11A. Briefly, various concentrations of CH solution was obtained by dissolving CH in 0.25% acetic acid and nanoparticles were spontaneously generated by the addition of TPP (0.25% w/v) and siRNA (1 µg/µL) to CH solution under constant stirring at room temperature. After incubating at 4° C. for 40 min, siRNA/CH nanoparticles were collected by centrifugation (Thermo Biofuge, Germany) at 12,000 rpm for 40 minutes at 4° C. The pellet was washed 3 times to remove unbound chemicals or siRNA and siRNA/CH nanoparticles were stored at 4° C. until used.

Characteristics of siRNA/CH Nanoparticles.

The size and zeta potential of the siRNA/CH nanoparticles were measured by light scattering with a particle size analyzer and Zeta Plus (size and zeta potential analyzer, Brookhaven Instrument Co., CA), respectively. To measure the loading efficiency of siRNA into CH nanoparticles, Alexa-555 fluorescent-labeled siRNA was incorporated into CH nanoparticles followed by centrifugation at 12,000 rpm for 40 minutes. The fluorescence intensity in the supernatant was measured at 590 nm using fluorescence spectrophotometer (Fluostar Optima, BMG Labtech Inc., Durham, N.C.). Additionally, the morphology of CH nanoparticles was confirmed by AFM.

Gel Retardation Assay.

The incorporation of siRNA into CH nanoparticles was determined by 4% agarose gel electrophoresis. Electrophoresis was carried out at a constant voltage of 100 V for 1 hour in 0.5% TAE buffer containing 0.5 µg/mL ethidium bromide (EtBr). The siRNA bands were then visualized under a UV transilluminator (Fluor Chem 8900, Alpha Innotech, Madison, Wis.).

Stability Assay.

Stability of the siRNA-CH nanoparticles in 50% serum was characterized using 4% agarose gel electrophoresis. Either naked siRNA or siRNA/CH nanoparticles were mixed in a 1:1 ratio with fresh serum to get the 50% concentration and incubated at 37° C. Aliquots of 20 µL were collected at selected time intervals, loaded onto an agarose gel followed by electrophoresis to visualize intact siRNA.

Results

EZH2 Expression in Human Ovarian Carcinoma

Figure 7:
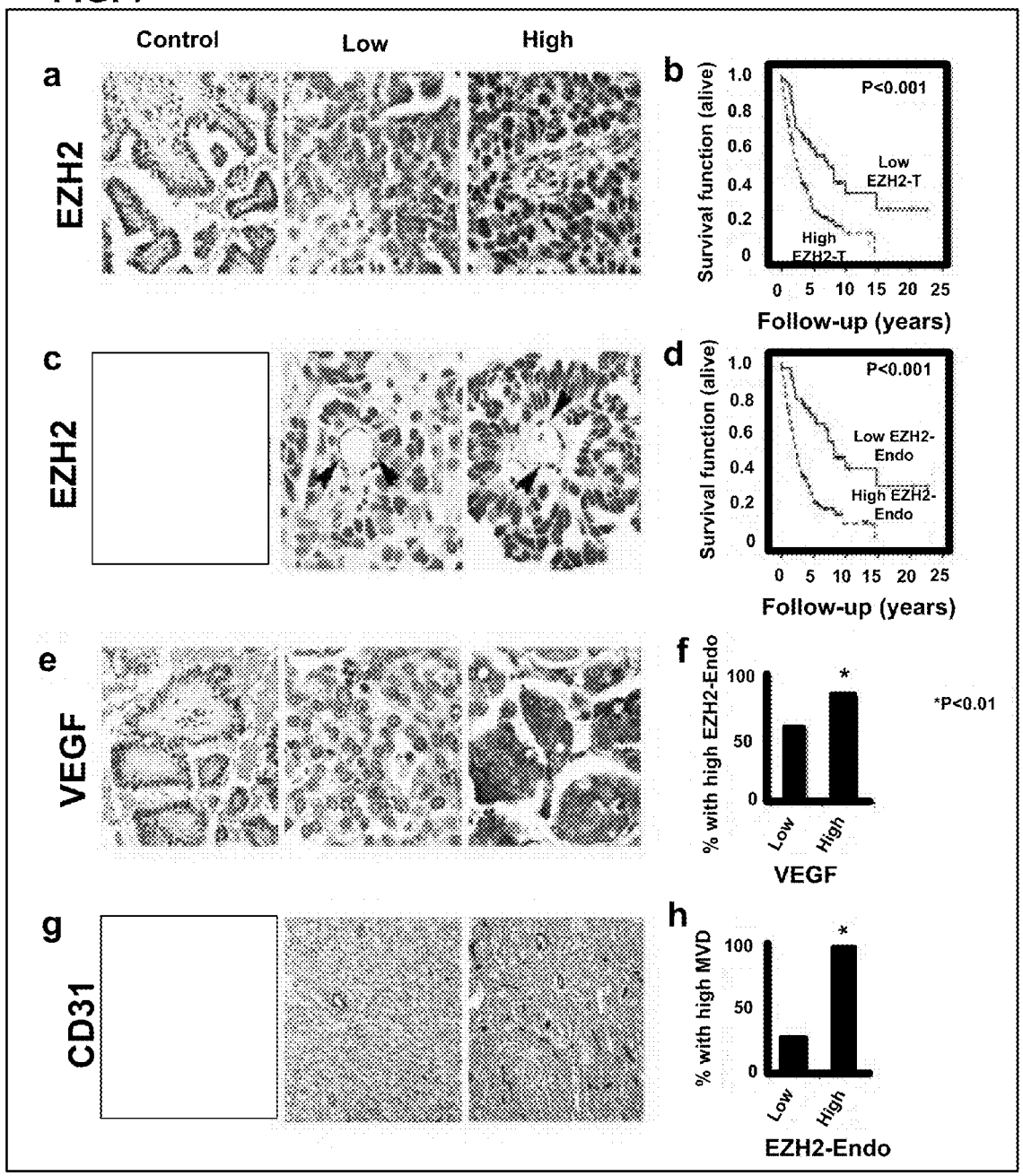
FIGS. 7A-7H illustrate EZH2 expression in human ovarian carcinoma.

The clinical significance of EZH2 was evaluated in 130 epithelial ovarian cancers. Increased tumoral EZH2 (EZH2-T) expression was noted in 66% of samples and increased expression in the vasculature (EZH2-Endo) was noted in 67% of the samples (FIG. 7A). Increased expression of EZH2-T and EZH2-Endo was significantly associated with high-stage (p values<0.001) and high-grade (p values<0.05; see Table 8) disease. Increased EZH2-T was significantly associated with decreased overall survival (median 2.5 years vs. 7.33 years, p values<0.001; FIG. 7B). Similarly, EZH2-Endo was predictive of poor overall survival (2.33 vs. 8.33 years, p<0.001; FIGS. 7C and 7D). On the basis of pathway-analysis predictions from the disclosed genomic profiling data comparing endothelial cells from epithelial ovarian cancer with those from normal ovarian tissues, the potential associations between EZH2 expression, VEGF expression and microvessel density (MVD) was examined. Increased VEGF expression was strongly associated with increased EZH2-Endo expression (p<0.001; FIGS. 7E and 7F). Moreover, increased EZH2-Endo expression was significantly associated with high MVD counts in the tumor (p<0.001; FIGS. 7G and 7H).

TABLE 8

Association of clinical and demographic features with EZH2 in epithelial ovarian carcinoma.

| | EZH2-T overexpression | | | EZH2-Endo overexpression | | |
|---|---|---|---|---|---|---|
| | No | Yes | p-value | No | Yes | p-value |
| Mean age 59.8 yrs (range 37-89 yrs) | | | | | | |
| Stage | | | | | | |
| Low (I/II) | 20 | 9 | <0.001 | 20 | 9 | <0.001 |
| High (III-IV) | 41 | 108 | <0.001 | 37 | 112 | <0.001 |
| Grade | | | | | | |
| Low | 9 | 7 | 0.048 | 10 | 6 | 0.005 |
| High | 52 | 112 | 0.048 | 37 | 112 | 0.005 |
| Histology | | | | | | |
| Serous | 22 | 18 | 0.002 | 22 | 1 | <0.001 |
| Others | 39 | 100 | 0.002 | 35 | 104 | <0.001 |

VEGF Increases EZH2 Levels in Endothelial Cells

Figure 8:
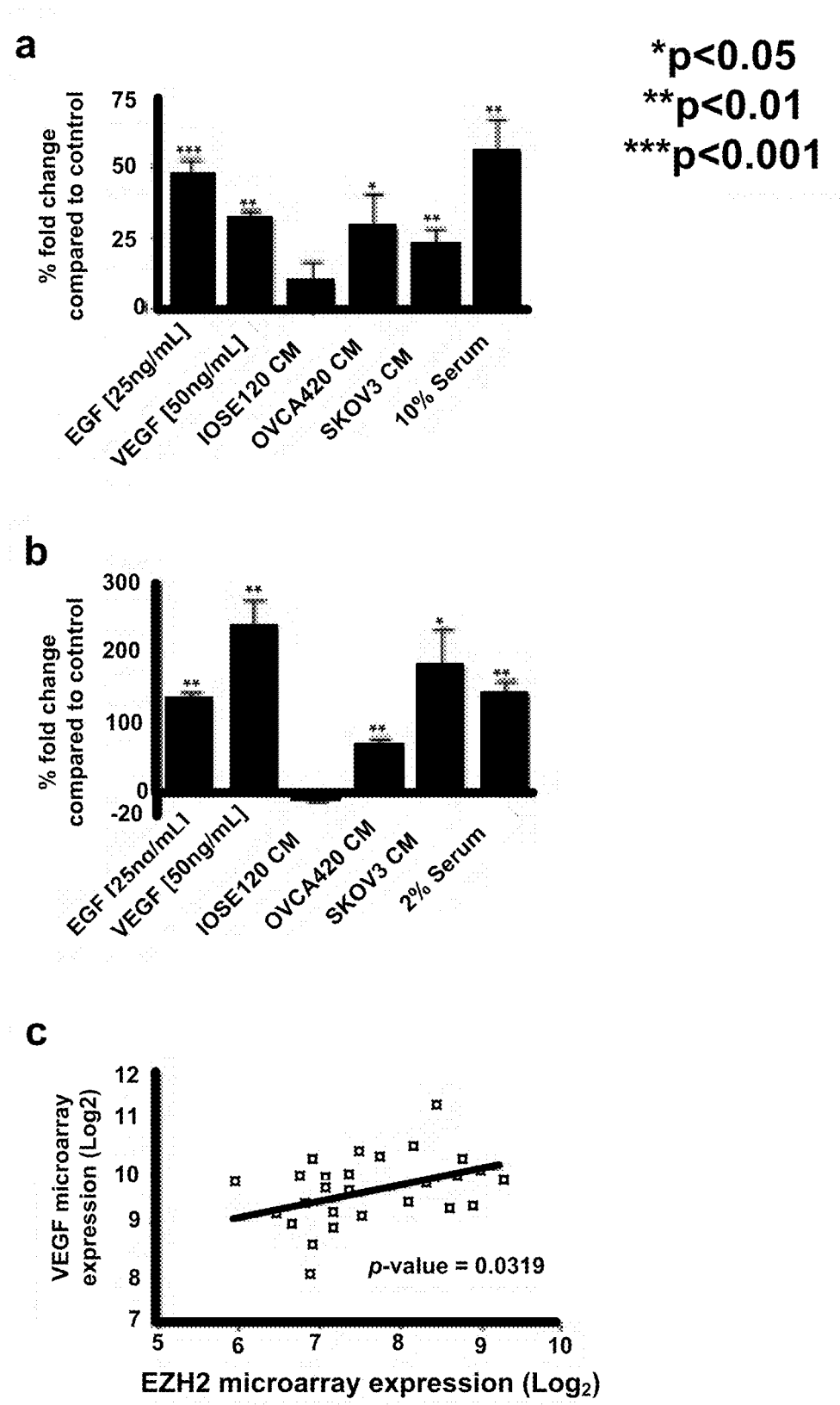
FIGS. 8A-8C are graphs illustrating VEGF-increased EZH2 expression in endothelial cells. Results in FIGS. 8A and 8B are in response to 6-hour treatments with EGF (25 ng/μL), VEGF (50 ng/μL), conditioned medium (CM) from the non-cancerous ovarian epithelial cell line IOSE120, two ovarian cancer cell lines OVCA420 and SKOV3, and complete medium with either 10% serum (A) or 2% serum (B). Percent fold changes represent the mean+/−s.d. of triplicate experiments compared to untreated control cells. *$p<0.05$; $p<0.01$; *$p<0.001$.

EAhy926 hybridoma endothelial cells were co-transfected with the *Renilla* luciferase plasmid and firefly luciferase plasmid either with or without the EZH2 promoter construct. Cells were then treated with VEGF, EGF, or conditioned media from ovarian cancer cell lines. EZH2 promoter activity was determined by the dual-luciferase assay. There was a significant increase in EZH2 promoter activity in endothelial cells in response to VEGF, EGF, and conditioned media (FIG. 8A). In order to examine changes in EZH2 message, HUVECs were treated as indicated above and expression of EZH2 mRNA was examined using quantitative real time RT-PCR. Control values were normalized using 3 housekeeping genes EZH2 mRNA expression levels were induced (by 130-

240% fold change compared to control) in endothelial cells in response to VEGF, EGF, or the conditioned media (FIG. 8B). To examine the relationship between EZH2 and VEGF in human samples, the expression levels of both genes in 29 microdissected high-grade, serous papillary ovarian cancers were determined. Pearson's analysis showed a significant correlation between EZH2 and VEGF levels (p=0.03; FIG. 8C).

EZH2 Silencing Increases VASH1 in Endothelial Cells

Figure 9:
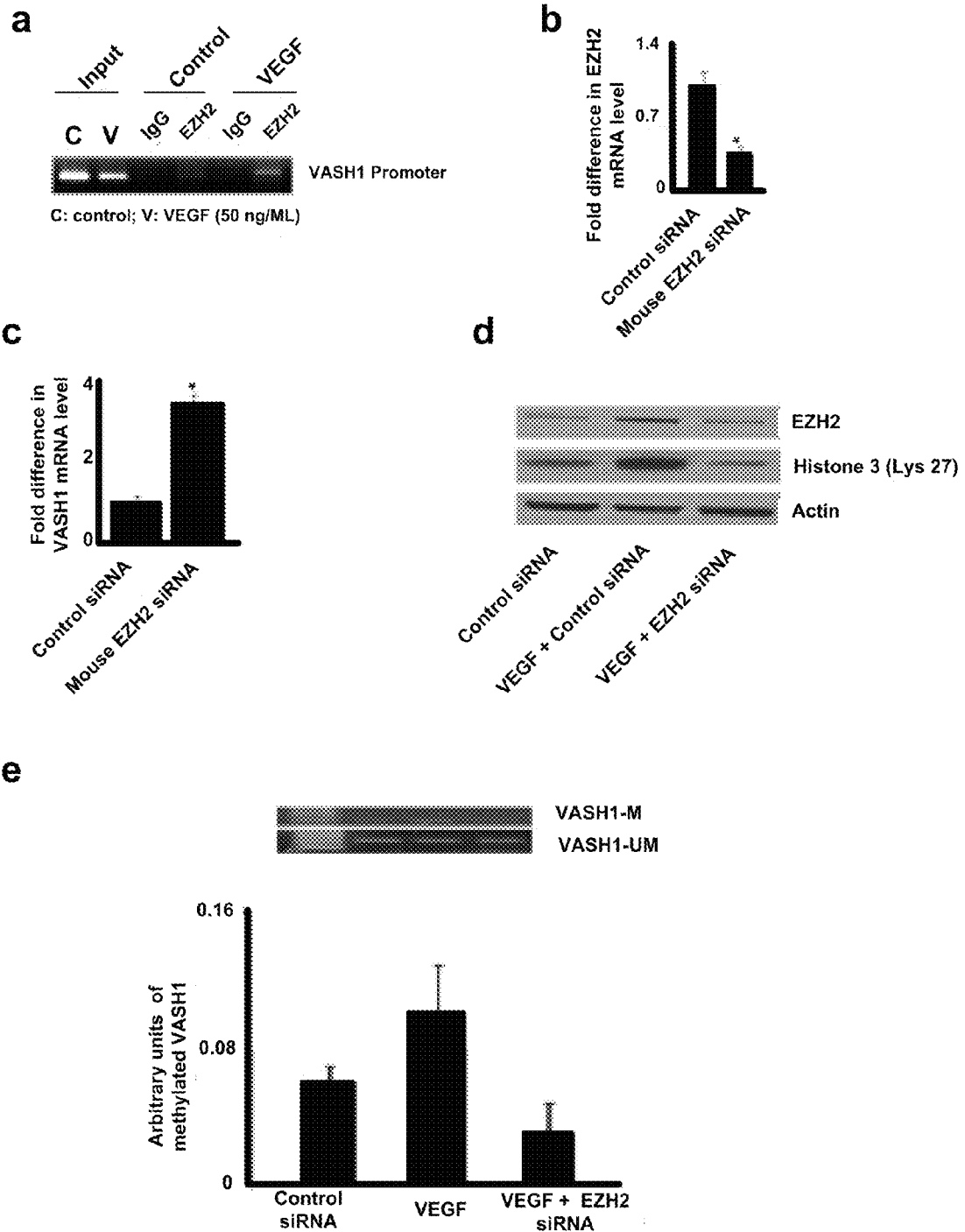
FIGS. 9A-9E show EZH2 gene silencing increases VASH1 mRNA expression in endothelial cells.

To determine the mechanism by which EZH2 silencing could induce anti-angiogenic effects, a whole genome ChIP-on-ChIP analysis was performed. The findings indicate that an anti-angiogenic gene, vasohibin (VASH1) directly binds to EZH2. To validate this finding, a ChIP assay of EZH2 for the VASH1 promoter in endothelial cells in the presence or absence of VEGF was performed (FIG. 9A), which confirmed direct EZH2 binding to the VASH1 promoter. Next, we silenced the EZH2 gene in mouse ovarian endothelial cells (MOEC) using siRNA (FIG. 9B), which resulted in a 2.8 fold increase in VASH1 (FIG. 9C).

To determine the mechanism by which EZH2 regulates VASH1, methylation specific PCR was performed for detecting VASH1 methylation in endothelial cells in the presence of VEGF after silencing EZH2 VEGF treatment resulted in a 1.7 fold increase in VASH1 methylation compared to the controls. However, EZH2 silencing resulted in a 3.3 fold decrease in VASH1 methylation in the VEGF-treated MOEC cells (FIG. 9D). Specifically, EZH2 gene silencing by decreased histone 3 methylation at lysine 27 by 2.5 fold in endothelial cells (FIG. 9E).

E2F Mediated Regulation of EZH2 in Endothelial Cells.

The effect of VEGF on E2F1-5 in MOEC is provided in FIG. 10A. There was a significant increase in E2F1, E2F3 and E2F5 following treatment with VEGF (FIG. 10B). To determine which E2F transcription factors might be responsible for increasing EZH2 levels, the effects of VEGF after silencing either E2F1, 3 or 5 were determined EZH2 levels were significantly decreased in E2F3 and E2F5 silenced cells (FIG. 10B). To validate the binding of EZH2 promoter to E2F3 and E2F5 transcription factors, ChIP assays of EZH2 to these transcription factors were performed. E2F3 and E2F5 were bound to the EZH2 promoters, demonstrating that EZH2 is the direct target of the E2F transcription factors. The studies provide direct explanation for the anti-angiogenesis effects observed in response to EZH2 gene silencing.

VASH1 Gene Silencing Increases the Migration, Tube Formation In Vitro and the Tumor Growth In Vivo To determine the role of VASH1 on angiogenesis, migration and tube formation studies were performed in MOEC and HUVEC by silencing the VASH1 gene in MOEC and HUVEC. MOEC cells were transfected with control and VASH1 siRNA for 48 hours and then resuspended in serum free media. 75,000 cells were plated on pre-gelatin and Matrigel coated Transwell inserts which were placed in the lower chamber of VEGF containing media. Migration and tube formation were significantly increased after VASH1 gene silencing (FIG. 10C); whereas no change in proliferation of cells.

Whether EZH2 silencing in vivo would affect tumor growth and angiogenesis was determined. Before conducting the EZH2 targeted in vivo experiments, CH nanoparticles for systemic delivery of siRNA into both tumor cells and tumor-associated vasculature were developed and characterize. Several formulations of CH with siRNA (siRNA/CH) were tested (FIG. 11A) and optimized (FIGS. 11B-11E; FIGS. 12A-12B; FIGS. 10A-10C) and the 3:1 ratio (CH:TPP) nanoparticles showed the greatest (75%) incorporation efficiency (FIG. 11B). Therefore, for all subsequent studies, siRNA/CH$_3$ nanoparticles were used due to their small size, slight positive charge, and high incorporation efficiency of siRNA.

Figure 13:
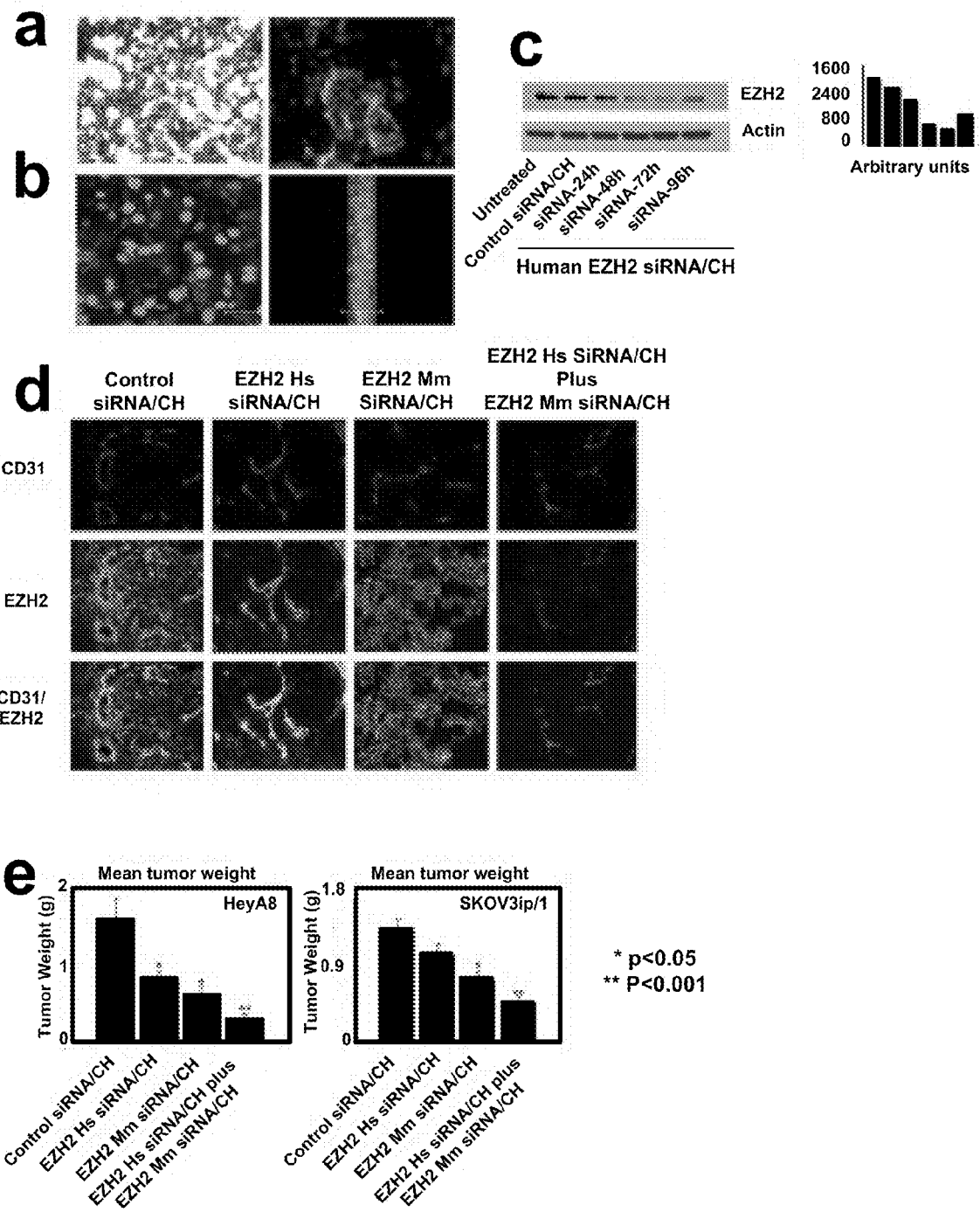
FIGS. 13A-13E illustrate in vivo siRNA delivery using CH nanoparticles and the distribution of siRNA following single intravenous injection of Alexa-555 siRNA/CH nanoparticles in orthotopic HeyA8 tumor bearing nude mice.

Prior to performing proof-of-concept in vivo efficacy studies, the efficiency of siRNA delivery into orthotopic ovarian tumors was tested. Non-silencing siRNA labeled with Alexa-555 was incorporated into CH nanoparticles and injected intravenously (i.v.) into mice bearing HeyA8 orthotopic tumors (17 days after intraperitoneal inoculation of tumor cells). Tumors were harvested at 15 hours and 3, 5 and 7 days (3 mice per time point) following injection and examined for extent of siRNA delivery. At all time points, punctated emissions of the siRNA were noted in the perinuclear regions of individual cells. SiRNA was noted in >80% of fields examined following a single intravenous injection. To confirm delivery of siRNA in the vasculature, slides were also stained for CD31. siRNA was delivered into the tumor-associated endothelial cells, suggesting potential applications for targeting the tumor vasculature. To confirm intracellular delivery of siRNA, 3-dimensional reconstructions of the tumors using confocal microscopy were created. Lateral views of the optical sections clearly demonstrated the presence of siRNA within the tumor cells (FIGS. 13A and 13B). However, very little siRNA was taken up by macrophages as determined by labeling tissues with f4/80. To examine the delivery of siRNA into other organs, sections of liver, lung, kidney, heart, spleen and brain were also examined, and siRNA delivery was detected in most of these organs.

Figure 14:
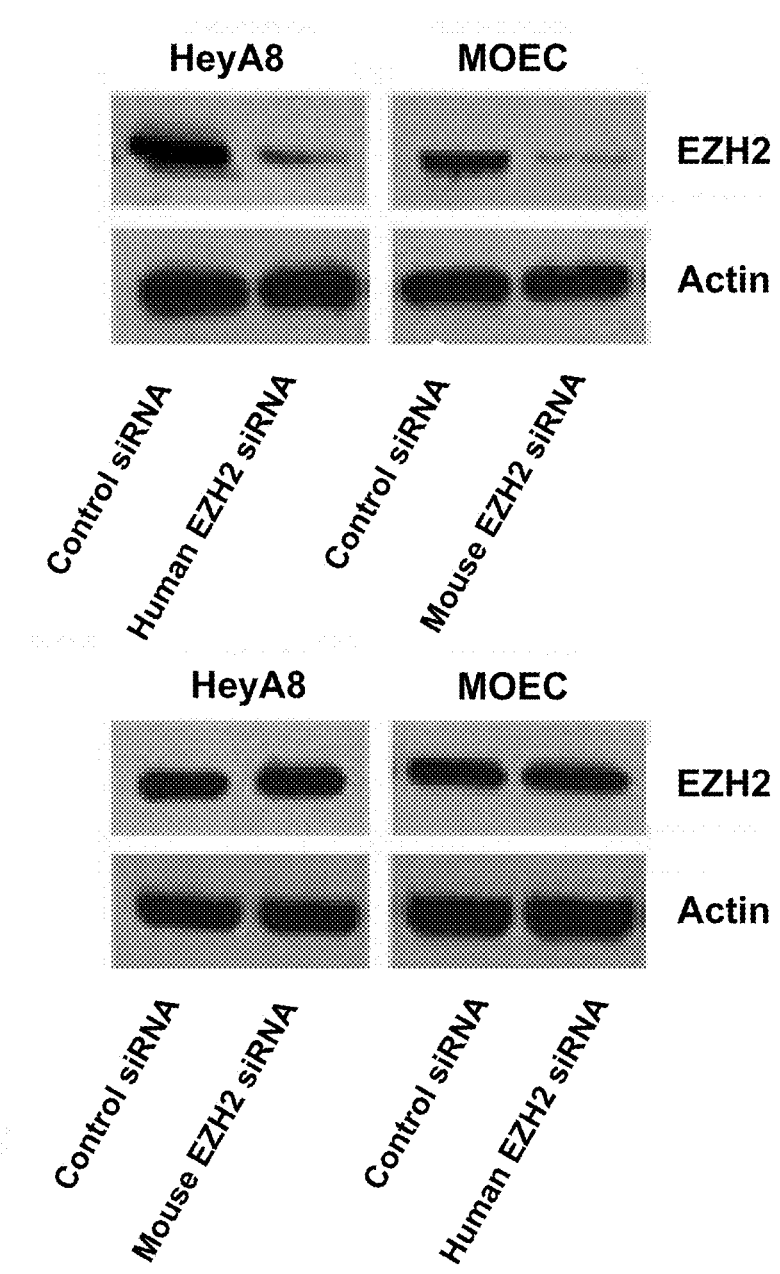
FIG. 14 provides a series of digital images of Western blots of lysate collected 72 hours after transfection of HeyA8 cells or MOEC with control, human EZH2, or mouse EZH2 siRNA.

To examine the in vivo effects of EZH2 gene silencing on tumor growth, EZH2 siRNA directed to either the human (tumor cells; EZH2 Hs siRNA/CH) or mouse (endothelial cells; EZH2 Mm siRNA/CH) sequence were utilized. The specificity of siRNA was confirmed by testing each siRNA in both mouse endothelial (MOEC) and human tumor (HeyA8) cells (FIG. 14). Following intravenous injection of either control siRNA/CH, EZH2 Hs siRNA/CH, EZH2 Mm siRNA/CH, or the combination of EZH2 targeted siRNAs into HeyA8 tumor-bearing mice (n=3 mice per group at each time point), tumors were harvested at different time points and examined for EZH2 protein levels EZH2 levels were decreased by 24 hours following single injection of EZH2 Hs siRNA/CH with return of expression to baseline expression levels after 96 hours (FIG. 13C). To determine the localization of EZH2 silencing following siRNA/CH administration, we performed dual immunofluorescence staining for EZH2 and CD31. This study further demonstrated that EZH2 Hs siRNA/CH resulted in EZH2 silencing in the tumor cells whereas EZH2 Mm siRNA/CH silenced EZH2 only in the tumor endothelial cells (FIG. 13D).

To determine the therapeutic efficacy of EZH2 gene silencing, a well-characterized orthotopic model of ovarian carcinoma was utilized. Seven days following injection tumor cells into the peritoneal cavity, mice were randomly allocated to 1 of 4 groups of 10 mice each: 1) control siRNA/CH, 2) EZH2 Hs siRNA/CH, 3) EZH2 Mm siRNA/CH and 4) combination of EZH2 Hs siRNA/CH plus EZH2 Mm siRNA/CH. Mice were sacrificed when animals appeared moribund due to significant tumor burden (4 to 5 weeks after cell injection depending on the cell line).

Alexa-555 siRNA uptake into macrophages and to various organs was evaluated. Tumor tissues were collected after single injection of untagged control siRNA/CH or Alexa-555 siRNA/CH nanoparticles and stained with anti-f4/80 antibody to detect scavenging macrophages (green; middle or right panels). Macrophages were seen surrounding nests of tumor cells and had minimal siRNA uptake. Left panel demonstrates lack of natural autofluorescence following injection of untagged control siRNA/CH. Images were taken at original magnification ×200 (left and middle) and ×400 (right). Histological sections were made from the liver, kidney, lung, brain, and heart tissues that were collected after intravenous injection of 5 μg Alexa-555 siRNA/CH nanoparticles and exposed to hematoxylin and eosin (H&E) and Hoechst staining. Left panel represents H&E staining, middle panel represents natural auto-fluorescence of each tissue after a single injection of untagged control siRNA/CH and right panel denotes Alexa-555 siRNA/CH (red). All images were taken at original magnification ×200.

Figure 15:
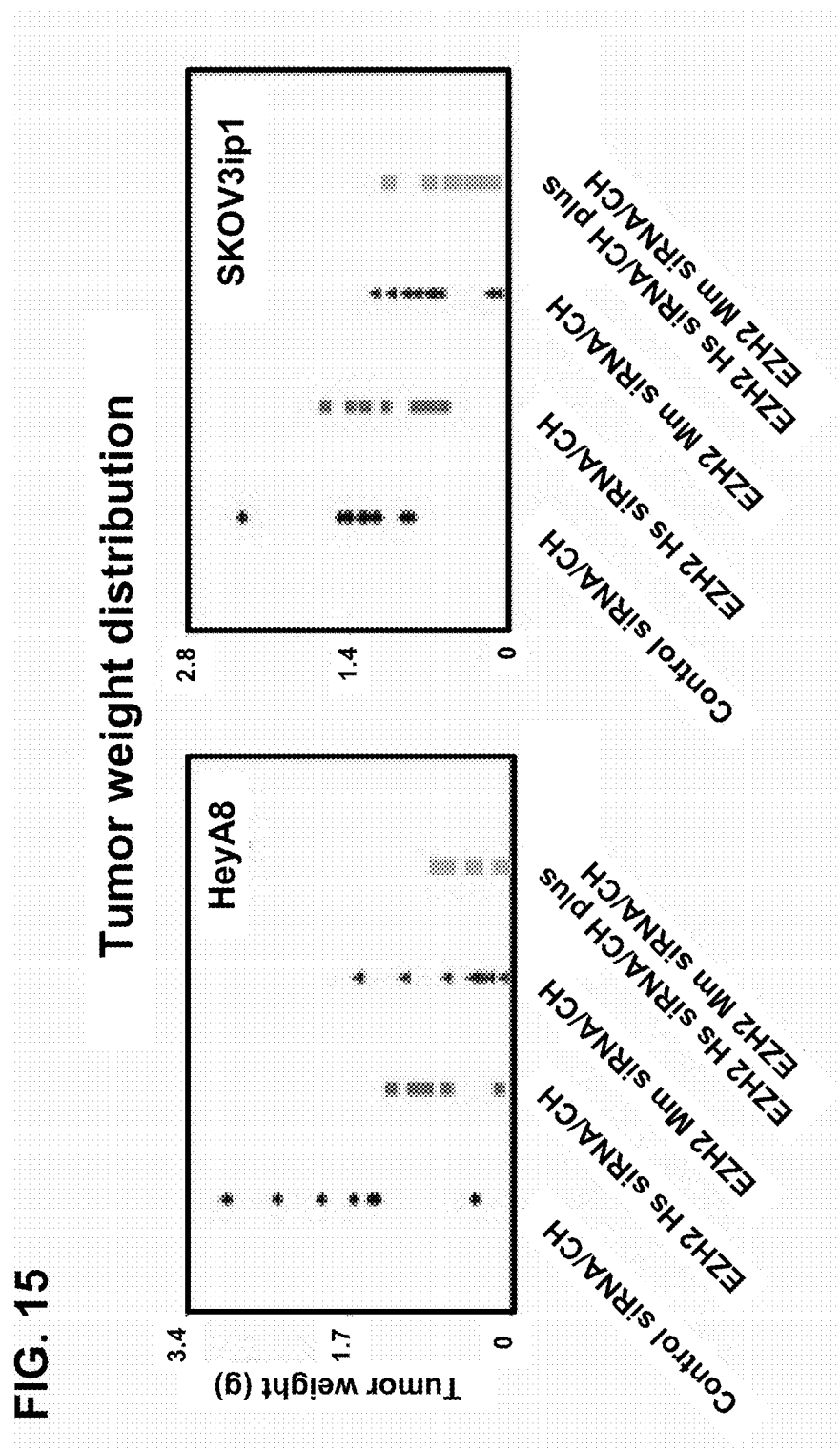
FIG. 15 is a pair of graphs illustrating the weight distribution of HeyA8 and SKOV3ip1 tumors. Seven days following tumor cell injection, mice were randomly divided into 4 groups (10 mice per group) to receive therapy: (1) control siRNA/CH, (2) EZH2 Hs siRNA/CH, (3) EZH2 Mm siRNA/CH, and (4) combination of EZH2 Hs siRNA/CH plus EZH2 Mm siRNA/CH. Mice were sacrificed when any animals in control or a treatment group became moribund (after 3 to 4 weeks of therapy) and tumor weight was recorded.

As shown in FIG. 13E and FIG. 15, treatment with EZH2 Mm siRNA/CH resulted in a significant decrease in tumor burden compared to control siRNA/CH (62% reduction in HeyA8; p<0.02 and 40% reduction in SKOV3ip1, p<0.03) EZH2 Hs siRNA/CH as a single-agent had modest effects on tumor growth (p<0.04 for HeyA8; and p<0.05 for SKOV3ip1) compared with control siRNA/CH. However, the greatest reduction was observed with the combination of EZH2 Hs siRNA/CH plus EZH2 Mm siRNA/CH (83% reduction in HeyA8, p<0.001 and 65% reduction in SKOV3ip1, p<0.001). To test for potential off-target effects, we tested the efficacy of 3 additional mouse EZH2 siRNA sequences with similar effects on tumor growth.

To evaluate the effects of EZH2 on other parameters of tumor growth, we examined tumor incidence and number of nodules (Table 9 below). The combination of EZH2 Hs siRNA/CH plus EZH2 Mm siRNA/CH resulted in a significant reduction in tumor nodules in both HeyA8 (p=0.002 vs. control siRNA treated group) and SKOV3ip1 tumors (p=0.004 vs. control siRNA treated group). The decrease in tumor burden occurred despite having comparable tumor incidence. The mean mouse body weight was similar among the different groups, suggesting that feeding and drinking habits were not affected.

TABLE 9

Characteristics of tumors after treatment with human and mouse EZH2 siRNA/CH

| Cell line | Treatment | Median no. nodules (range) | p-value (vs. control) |
|---|---|---|---|
| HeyA8 | Control siRNA/CH | 6.5 (3-11) | |
| | EZH2 Hs siRNA/CH | 3.5 (1-11) | 0.05 |
| | EZH2 Mm siRNA/CH | 3.0 (1-9) | 0.05 |
| | EZH2 Hs siRNA/CH plus EZH2 Mm siRNA/CH | 1.5 (1-7) | 0.002 |
| SKOV3iP1 | Control siRNA/CH | 16.0 (11-26) | |
| | EZH2 Hs siRNA/CH | 16.0 (8-27) | ns |
| | EZH2 Mm siRNA/CH | 12.0 (1-17) | 0.05 |
| | EZH2 Hs siRNA/CH plus EZH2 Mm siRNA/CH | 7.5 (2-27) | 0.004 |

Effect of EZH2 Targeting on Tumor Vasculature and Proliferation

Figure 16:
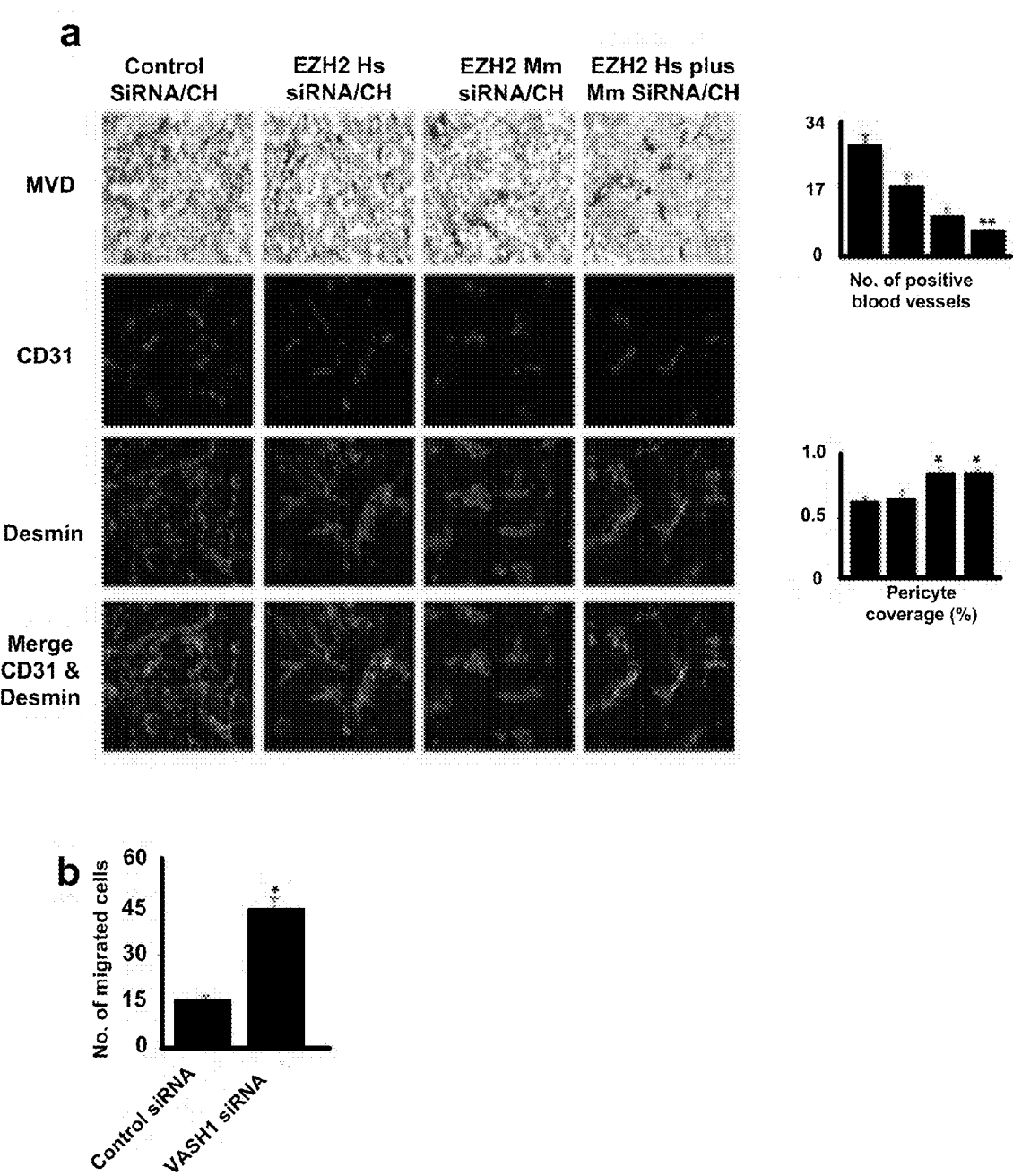
FIGS. 16A-16B (A) Effect of tumor (EZH2 Hs siRNA/CH) or endothelial (EZH2 Mm siRNA/CH) targeted EZH2 siRNA on MVD and pericyte coverage. Tumors harvested following 3 to 4 weeks of therapy were stained for CD31 (MVD; red) and desmin (pericyte coverage; green). All pictures were taken at original magnification ×200. The bars in the graphs correspond sequentially to the labeled columns of images at left. Error bars represent s.e.m. *p<0.05; **p<0.001. (B) Effects of VASH1 gene silencing on tumor growth in vivo. Nude mice were injected with SKOV3ip1 ovarian cancer cells and 1 week later, were randomly divided into 5 groups (10 mice per group): (1) control siRNA/CH, (2) EZH2 Mm siRNA1/CH, (3) EZH2 Mm siRNA2/CH (4) EZH2 Mm siRNA3/CH (5) VASH1 Mm siRNA1/CH and (6) combination of EZH2 Mm siRNA1/CH plus VASH1 Mm siRNA/CH.
Figure 17:
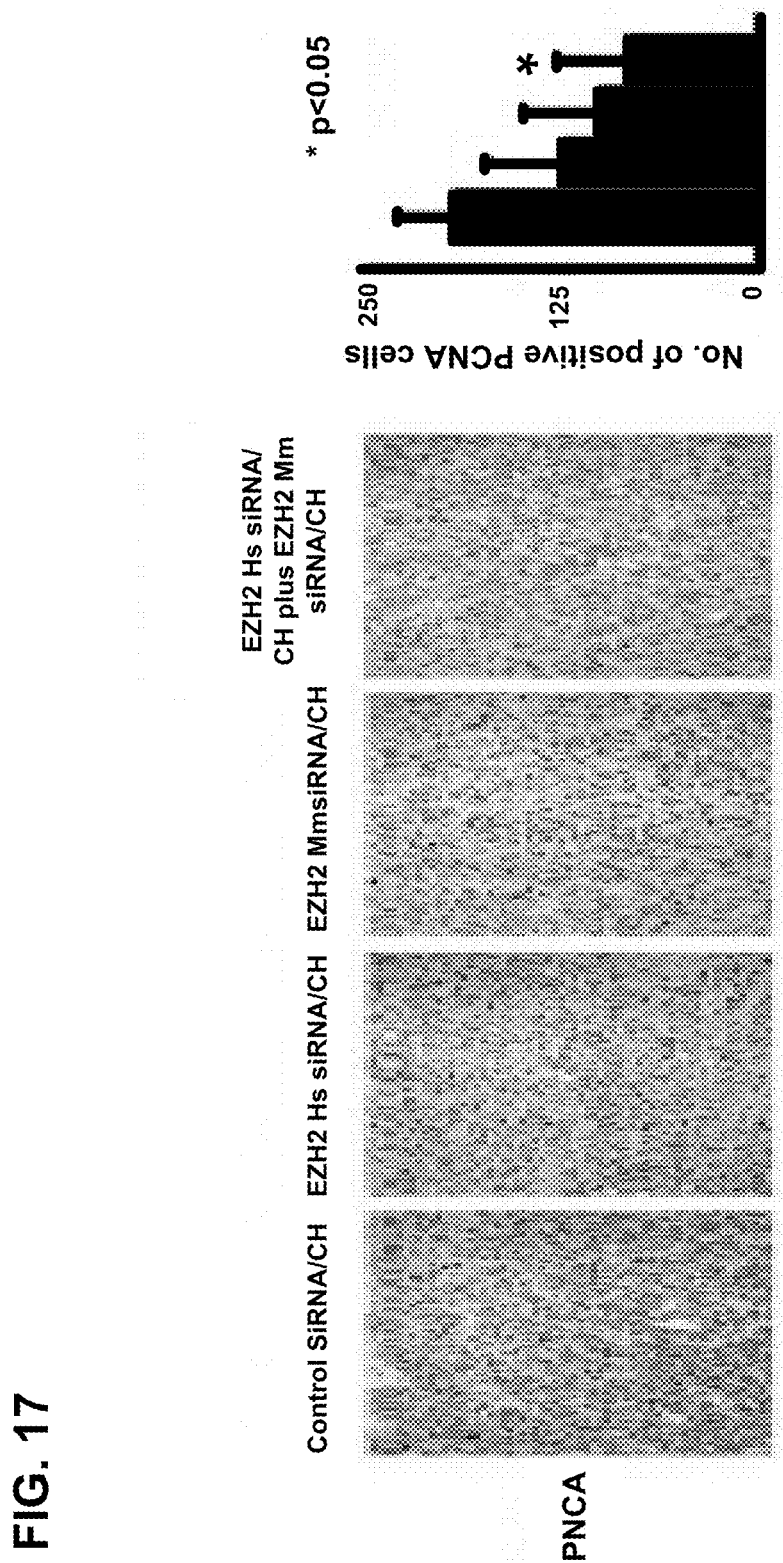
FIG. 17 illustrates the effects of EZH2 Hs siRNA/CH or EZH2 Mm siRNA/CH on proliferation. Tumors were harvested following 3-4 weeks of therapy and then stained for proliferating cell nuclear antigen (PCNA). All images were taken at original magnification ×100. The bars in the graphs correspond sequentially to the labeled columns of images at left. Error bars represent s.e.m. *p<0.05.

To determine the potential mechanisms underlying the efficacy of EZH2 silencing on ovarian tumors, its effects on several biological end points were examined, including MVD, pericyte coverage (desmin) and cell proliferation (PCNA). EZH2 Mm siRNA/CH and the combination therapy groups had significantly lower microvessel density (FIG. 16A) compared to the EZH2 Hs siRNA/CH and control siRNA/CH treated tumors. Pericyte coverage was increased in EZH2 Mm siRNA/CH and the combination groups compared to other 2 groups, suggesting greater vascular maturation (FIG. 16A). Combination treatment with EZH2 Hs siRNA/CH and EZH2 Mm siRNA/CH also resulted in a significant reduction in cell proliferation (FIG. 17).

To determine the requirement for VASH1 in mediating the anti-tumor effects of EZH2 silencing, the effects of VASH1 silencing in combination with EZH2 Mm siRNA/CH was determined. The anti-tumor effect of EZH2 silencing in the tumor vasculature was completely reversed by VASH1 silencing (FIG. 16B and see Table 7) suggesting that VASH1 is required for mediating the anti-tumor effects of EZH2 silencing.

Summary:

The present results provide a new understanding of the regulation of tumor angiogenesis. A novel mechanism by which VEGF increases EZH2 levels in the tumor vasculature was disclosed, which contributes to tumor angiogenesis by inactivating the anti-angiogenic factor, VASH1 via methylation of VASH1 gene and Histone 3 (Lys 27) (H3K27). Moreover, a novel and highly efficient method of gene silencing in the tumor cells as well as in the blood vessels that support their growth was developed and characterized. This approach was highly effective for EZH2 silencing in both compartments.

PcG proteins play a role in determining cell fate during both normal and pathologic processes. Two separate subsets of PcG complexes (PRC1 and PRC2) have been described in humans. PRC1 may be involved in maintenance of repression, whereas PRC2 plays a role in initiating repression. The PRC2 complex includes the EZH2, EED, and SUZ proteins. Altered expression of these proteins has been implicated in cancer pathogenesis. Increased EZH2 levels have been related to cancer cell proliferation and invasion. However, prior to the disclosed work, the role of EZH2 in angiogenesis was not known.

Angiogenesis is regulated by the balance of various pro-angiogenic stimulators, such as VEGF, and several angiogenesis inhibitors, such as angiostatin, endostatin, and antithrombin. On the basis of findings from genomic profiling of endothelial cells from ovarian cancer versus those from normal ovaries, it was discovered that EZH2 expression is significantly increased in tumor-associated endothelial cells. VEGF is well recognized as a pro-angiogenic factor in ovarian and other cancers. In the current study, it was shown for the first time that VEGF can directly increase EZH2 levels in endothelial cells, which in turn inactivating a potent anti-angiogenic factor, VASH1, via methylating VASH1 gene and H3K27. Silencing EZH2 gene resulted in demethylation of VASH1 gene and H3K27 in endothelial cells, which is consistent with other report indicating EZH2 directly controls DNA methylation of EZH2-targeted genes, concomitant with reducing H3K27. Therefore, through this study, a novel mechanism by which tumor angiogenesis is regulated was discovered and a rationale for pursuing EZH2 as a therapeutic target was provided.

While a number of attractive targets in tumor and endothelial cells have been identified, many of these are difficult to target with small molecule inhibitors and monoclonal antibodies. Therefore, RNA interference was employed as a means to target EZH2. Due to limited delivery of siRNA into the tumor-associated endothelial cells with this approach, additional nanoparticles were developed that would allow siRNA delivery into both tumor and tumor-associated endothelial cells. Chitosan (CH) is a naturally occurring polysaccharide with low immunogenicity and low toxicity. Here, CH was used because of its advantageous biological properties such as biodegradability, biocompatibility, and slight positive charge. These properties make use of CH for systemic in vivo siRNA delivery highly attractive. Indeed, the disclosed data demonstrate highly efficient delivery of siRNA incorporated into CH nanoparticles into both tumor and tumor-associated endothelial cells. Therefore, the present work provides an attractive method for systemic delivery of siRNA that could be developed for clinical applications.

Molecular and genetic manipulations have identified EZH2 as a key regulator of tumor angiogenesis here, but these effects do not rule out the possibility that EZH2 has oncogenic functions in the tumor cells. For example, EZH2 has been implicated in cellular transformation, proliferation, and avoidance of apoptosis. Such results imply that multiple signaling pathways likely convey the net effects of EZH2 in promoting tumor growth. However, to the extent that targeting tumor endothelial cells provides therapeutic benefit, interfering with EZH2 in the tumor and endothelial cells represents a novel strategy for treatment of ovarian and other cancers.

In summary, these studies illustrate that increased EZH2 expression in either tumor cells or in tumor vasculature is predictive of poor clinical outcome. The increase in endothelial EZH2 is a direct result of VEGF stimulation and indicates the presence of a paracrine circuit that promotes angiogenesis by methylating (histone H3; lysine 27) and silencing VASH1 EZH2 silencing in tumor cells and in the tumor-associated endothelial cells resulted in inhibition of angiogenesis and ovarian cancer growth. The anti-angiogenic effect was mediated by reactivating VASH1. Thus, these data support the potential for targeting EZH2 as a novel therapeutic approach Example 9

Screening of Agents to Treat an Ovarian Tumor

This example describes methods that can be used to identify agents to treat an ovarian tumor.

According to the teachings herein, one or more agents for the use of treating an ovarian tumor, such as ovarian cancer can be identified by contacting an ovarian tumor endothelial cell with one or more test agents under conditions sufficient for the one or more test agents to alter the activity of at least one ovarian endothelial cell tumor-associated molecule listed in Tables 1, 2, 3, 4 or 5. The method also includes detecting the activity of the at least one ovarian endothelial cell tumor-associated molecule in the presence and absence of the one or more test agents. The activity of the at least one ovarian endothelial cell tumor-associated molecule in the presence of the one or more test agents is then compared to the activity in the absence of such agents to determine if there is differential expression of the at least one ovarian endothelial cell tumor associated molecule. Differential expression of the ovarian endothelial cell tumor-associated molecule indicates that the one or more test agents is of use to treat the ovarian tumor. For example, a test agent that reduces or inhibits the activity or expression of an ovarian endothelial tumor-associated molecule that is upregulated in ovarian tumor endothelial cells indicates that the test agent is of use to treat the ovarian tumor. Differential expression can be detected at the nucleic acid or protein level. An RNA expression product can be detected by a microarray or PCR by methods described above (see, for example, Example 1). A protein expression product can be detected by standard Western blot or immunoassay techniques that are known to one of skill in the art. However, the disclosure is not limited to particular methods of detection.

Example 10

Identification of Ovarian Endothelial Cell Tumor-Associated Molecule Inhibitors to Alter Tumor Growth and/or Vascularization This example describes methods that can be used to identify ovarian endothelial cell tumor-associated molecule inhibitors that can be used to target specific genes involved in ovarian tumor growth and/or vascularization.

Based upon the teaching disclosed herein, iSynthetic siRNA molecules are generated against selected target genes, such as any of the ovarian endothelial cell tumor-associated up-regulated genes identified in Examples 2 through 5. In an example, the siRNA molecules are obtained from commercial sources. Knockdown efficiency of the siRNA molecules is assessed as indicated in Example 1. In an example, a significant knockdown efficiency is approximately 20%. As provided in Example 1, the effects of target gene siRNA's on tumor growth and vascularization can be determined by evaluating the effect of siRNA treatment on cell migration and tube formation in HUVECs.

In additional examples, cells are treated with two or more siRNAs (that target two or more genes). The $IC_{50}$ values are compared (between target gene siRNA individually and in combination) to determine whether the knockdown effect on tumor growth and vascularization is cumulative or additive. siRNAs that reduce or decrease by approximately 20% the activity or expression of the targeted ovarian endothelial cell tumor-associated molecule which is upregulated in ovarian endothelial tumor cells are selected for further study.

Example 11

Effectiveness of an Ovarian Tumor Treatment

This example describes methods that can be used to identify effective ovarian tumor treatments.

Based upon the teachings disclosed herein, the effectiveness of an ovarian tumor treatment can be evaluated by determining the effectiveness of an agent for the treatment of an ovarian tumor in a subject with the ovarian tumor. In an example, the method includes detecting expression of an ovarian endothelial cell tumor-associated molecule in a sample from the subject following treatment with the agent. The expression of the ovarian endothelial cell tumor-associated molecule following treatment is compared to a control (a non-cancerous, ovarian endothelial cell). A reduction or inhibition of the expression or biological activity of the ovarian endothelial cell tumor-associated molecule which is upregulated in ovarian endothelial tumor cells following treatment indicates that the agent is effective for the treatment of an ovarian cancer in the subject. Alternatively, an increase in the expression or biological activity of an ovarian endothelial tumor-associated molecule that is downregulated in ovarian endothelial tumor cells following treatment indicates that the agent is effective for the treatment of the ovarian cancer in the subject. In a specific example, the method includes detecting and comparing the protein expression levels of the ovarian endothelial cell tumor-associated molecules. In other examples, the method includes detecting and comparing the mRNA expression levels of the ovarian endothelial cell tumor-associated molecules.

Example 12

Inhibition of Tumor Growth and/or Vascularization

This example describes methods that can be used to significantly reduce ovarian tumor growth, vascularization in a subject with ovarian cancer.

Based upon the teachings disclosed herein, an ovarian tumor, such as ovarian cancer can be treated by administering a therapeutically effective amount of a composition, wherein the composition comprises a specific binding agent that preferentially binds to one or more ovarian endothelial cell tumor-associated molecules provided in Tables 1 through 5, thereby inhibiting tumor growth and/or vascularization.

In an example, a subject who has been diagnosed with ovarian cancer is identified. In some examples, gene expression is screened to determine which genes are to be targeted. Following subject selection, a therapeutic effective dose of the composition including the specific binding agent is administered to the subject. For example, a therapeutic effective dose of a specific binding agent to one or more of the disclosed ovarian endothelial cell tumor-associated molecules is administered to the subject to reduce or inhibit tumor growth and/or vascularization. In an example, the specific binding agent is a siRNA. In another example, the specific binding agent is an antibody. In a further example, the specific binding agent is conjugated to a therapeutic agent such as a cytotoxin, chemotherapeutic reagent, radionucleotide or a combination thereof.

The amount of the composition administered to prevent, reduce, inhibit, and/or treat ovarian cancer or a condition associated with it depends on the subject being treated, the severity of the disorder, and the manner of administration of the therapeutic composition. Ideally, a therapeutically effective amount of an agent is the amount sufficient to prevent, reduce, and/or inhibit, and/or treat the condition (e.g., ovarian cancer) in a subject without causing a substantial cytotoxic effect in the subject.

In one specific example, siRNAs are incorporated into the neutral liposome DOPC and injected intraperitoneal or intravenously at 150 µg/kg twice weekly for 2 to 3 weeks.

In another specific example, naked antibodies are administered at 5 mg per kg every two weeks or 10 mg per kg every two weeks depending upon the stage of the ovarian cancer. In an example, the antibodies are administered continuously. In another example, antibodies or antibody fragments conjugated to cytotoxic agents (immunotoxins) are administered at 50 µg per kg given twice a week for 2 to 3 weeks.

Example 13

Diagnosis of Metastatic Ovarian Cancer

This example describes particular methods that can be used to diagnose or prognose a metastatic ovarian tumor in a subject, such as metastatic ovarian cancer in a human. However, one skilled in the art will appreciate that similar methods can be used. In some examples, such diagnosis is performed before treating the subject (for example as described in Example 11).

Biological samples are obtained from the subject. If blood or a fraction thereof (such as serum) is used 1-100 µl of blood is collected. Serum can either be used directly or fractionated using filter cut-offs to remove high molecular weight proteins. If desired, the serum can be frozen and thawed before use. If a tissue biopsy sample is used, 1-100 µg of tissue is obtained, for example using a fine needle aspirate RNA or protein is isolated from the tissue using routine methods (for example using a commercial kit).

In one example, pro-angiogenic ovarian endothelial cell tumor-associated nucleic acid expression levels, such as nucleic acid expression levels of EZH2, are determined in a tumor sample obtained from the subject by microarray analysis or real-time quantitative PCR. In an example, the disclosed gene profile is utilized. In other examples, the amount of such molecules is determined at the protein level by methods known to those of ordinary skill in the art, such as Western blot or immunoassay techniques. The relative amount of pro-angiogenic ovarian endothelial cell tumor-associated molecules are compared to a reference value, such as a relative amount of such molecules present in a non-tumor sample from, wherein the presence of significantly greater amounts of pro-angiogenic ovarian endothelial cell tumor-associated molecules listed in Tables 1, 2, 4 and 5 (and indicated to be involved in angiogenesis) in the tumor sample as compared to the non-tumor sample (such as an increase of at least 2-fold, at least 3-fold, or at least 5-fold) indicates that the subject has a metastatic ovarian tumor, has an increased likelihood of an ovarian tumor metastasizing, has a poor prognosis, or combinations thereof. In other examples, a decrease in expression of those molecules listed in Table 3 (and involved in angiogenesis) indicates that the subject has a metastatic ovarian tumor, has an increased likelihood of an ovarian tumor metastasizing, has a poor prognosis, or combinations thereof. In some examples, relative amount of pro-angiogenic ovarian endothelial cell tumor-associated proteins and pro-angiogenic ovarian endothelial cell tumor-associated mRNA expression are determined in the same subject using the methods described above.

While this disclosure has been described with an emphasis upon particular embodiments, it will be obvious to those of ordinary skill in the art that variations of the particular embodiments may be used, and it is intended that the disclosure may be practiced otherwise than as specifically described herein. Features, characteristics, compounds, or examples described in conjunction with a particular aspect, embodiment, or example of the invention are to be understood to be applicable to any other aspect, embodiment, or example of the invention. Accordingly, this disclosure includes all modifications encompassed within the spirit and scope of the disclosure as defined by the following claims. We therefore claim as our invention all that comes within the scope and spirit of these claims.

We claim:

1. A method of diagnosing an epithelial ovarian tumor with a poor prognosis in a subject, comprising:
    contacting a sample containing ovarian tissue, ovarian cells or ovarian endothelial cells obtained from the subject with the epithelial ovarian tumor with a wild-type Zeste homologue 2 (EZH2) nucleic acid molecule or an anti-wild-type EZH2 antibody;
    comparing expression of wild-type EZH2 detected in the sample obtained from the subject with the epithelial ovarian tumor to a control; and
    detecting an at least 2-fold increase in expression of wild-type EZH2 relative to a control indicates the subject has a poor prognosis, thereby diagnosing the epithelial ovarian tumor in a subject with a poor prognosis.

2. The method of claim 1, wherein an at least 2-fold increase in expression of wild-type EZH2 as compared to the control indicates a stage III or stage IV epithelial ovarian tumor.

3. The method of claim 1, wherein an at least 2-fold increase in expression of wild-type EZH2 as compared to the control indicates a high grade epithelial ovarian tumor.

4. The method of claim 1, wherein expression of wild-type EZH2 is determined by polymerase chain reaction.

5. The method of claim 1, further comprising treating the subject with the epithelial ovarian tumor with a poor prognosis by administering to the subject an effective amount of a specific binding agent that preferentially binds to wild-type EZH2 and inhibits epithelial ovarian tumor growth in the subject, wherein the specific binding agent that preferentially binds to wild-type EZH2 is a wild-type EZH2 siRNA.

6. The method of claim 1, wherein the control is a sample obtained from a subject that has a non-metastatic ovarian tumor.

7. The method of claim 1, wherein the wild-type EZH2 nucleic acid molecule or an anti-wild-type EZH2 antibody is positioned on an addressable array.

* * * * *

SEQUENCE LISTING

<160> NUMBER OF SEQ ID NOS: 47

<210> SEQ ID NO 1
<211> LENGTH: 39
<212> TYPE: DNA
<213> ORGANISM: Artificial sequence
<220> FEATURE:
<223> OTHER INFORMATION: Synthetic oligonucleotide primer.

-continued

```
<400> SEQUENCE: 1
ggccagtgaa ttgtaatacg actcactata gggaggcgg                              39

<210> SEQ ID NO 2
<211> LENGTH: 21
<212> TYPE: DNA
<213> ORGANISM: Artificial sequence
<220> FEATURE:
<223> OTHER INFORMATION: Synthetic oligonucleotide siRNA.

<400> SEQUENCE: 2
ctgcatttag ggagtattct a                                                 21

<210> SEQ ID NO 3
<211> LENGTH: 21
<212> TYPE: DNA
<213> ORGANISM: Artificial sequence
<220> FEATURE:
<223> OTHER INFORMATION: Synthetic oligonucleotide siRNA.

<400> SEQUENCE: 3
aaccatgttt acaactatca a                                                 21

<210> SEQ ID NO 4
<211> LENGTH: 21
<212> TYPE: DNA
<213> ORGANISM: Artificial sequence
<220> FEATURE:
<223> OTHER INFORMATION: Synthetic oligonucleotide siRNA.

<400> SEQUENCE: 4
ccauguuuac aacuaucaat t                                                 21

<210> SEQ ID NO 5
<211> LENGTH: 21
<212> TYPE: DNA
<213> ORGANISM: Artificial sequence
<220> FEATURE:
<223> OTHER INFORMATION: Synthetic oligonucleotide siRNA.

<400> SEQUENCE: 5
ttgguacaaa uguugauagu u                                                 21

<210> SEQ ID NO 6
<211> LENGTH: 28
<212> TYPE: DNA
<213> ORGANISM: Artificial sequence
<220> FEATURE:
<223> OTHER INFORMATION: Synthetic oligonucleotide primer.

<400> SEQUENCE: 6
gatactcgag gtcgggagtt cgagacca                                          28

<210> SEQ ID NO 7
<211> LENGTH: 28
<212> TYPE: DNA
<213> ORGANISM: Artificial sequence
<220> FEATURE:
<223> OTHER INFORMATION: Synthetic oligonucleotide primer.

<400> SEQUENCE: 7
gtttaagctt actcgcgttg ttcccgcg                                          28
```

```
<210> SEQ ID NO 8
<211> LENGTH: 21
<212> TYPE: DNA
<213> ORGANISM: Artificial sequence
<220> FEATURE:
<223> OTHER INFORMATION: Synthetic oligonucleotide primer.

<400> SEQUENCE: 8
catgggaggg cttgatgaag g                                                21

<210> SEQ ID NO 9
<211> LENGTH: 21
<212> TYPE: DNA
<213> ORGANISM: Artificial sequence
<220> FEATURE:
<223> OTHER INFORMATION: Synthetic oligonucleotide primer.

<400> SEQUENCE: 9
gcctagtcca tgctgacctt g                                                21

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 10
gctgagcgta taaagacacc                                                  20

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 11
tctacatcct cagtgggaac                                                  20

<210> SEQ ID NO 12
<211> LENGTH: 18
<212> TYPE: DNA
<213> ORGANISM: Artificial sequence
<220> FEATURE:
<223> OTHER INFORMATION: Synthetic oligonucleotide primer.

<400> SEQUENCE: 12
tcatgcaaca cccaacac                                                    18

<210> SEQ ID NO 13
<211> LENGTH: 18
<212> TYPE: DNA
<213> ORGANISM: Artificial sequence
<220> FEATURE:
<223> OTHER INFORMATION: Synthetic oligonucleotide primer.

<400> SEQUENCE: 13
cacaaccggt gtttcctc                                                    18

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide primer.
```

```
<400> SEQUENCE: 14
catcagggag ctgcagtaca                                              20

<210> SEQ ID NO 15
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 15
cccagcttca ccttcttcag                                              20

<210> SEQ ID NO 16
<211> LENGTH: 21
<212> TYPE: DNA
<213> ORGANISM: Artificial sequence
<220> FEATURE:
<223> OTHER INFORMATION: Synthetic oligonucleotide primer.

<400> SEQUENCE: 16
catgggaggg cttgatgaag g                                            21

<210> SEQ ID NO 17
<211> LENGTH: 21
<212> TYPE: DNA
<213> ORGANISM: Artificial sequence
<220> FEATURE:
<223> OTHER INFORMATION: Synthetic oligonucleotide primer.

<400> SEQUENCE: 17
caaggtcagc atggactagg c                                            21

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 18
tggatctgga gactgaccat                                              20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 19
agttgcagct gtgtggtaca                                              20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 20
gctcctgacc aagaagttca                                              20
```

<210> SEQ ID NO 21
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 21
gcaatcactg tctgctcctt                                               20

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 22
tgcagtctgt ctgaggatgg                                               20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 23
gaggccagag gagagaggtt                                               20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 24
aagaactgga ccagcacaag                                               20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 25
actatccagc agtgcagagg                                               20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide primer.

<400> SEQUENCE: 26
agttgtggct acagcaaagc                                               20

<210> SEQ ID NO 27
<211> LENGTH: 20
<212> TYPE: DNA
<213> ORGANISM: Artificial sequence
<220> FEATURE:
<223> OTHER INFORMATION: Synthetic oligonucleotide primer.

```
<400> SEQUENCE: 27
ggagaaagcc gtaaaagagg                                                  20

<210> SEQ ID NO 28
<211> LENGTH: 21
<212> TYPE: DNA
<213> ORGANISM: Artificial sequence
<220> FEATURE:
<223> OTHER INFORMATION: Synthetic oligonucleotide siRNA.

<400> SEQUENCE: 28
ttctccgaac gtgtcacgtt t                                                21

<210> SEQ ID NO 29
<211> LENGTH: 21
<212> TYPE: DNA
<213> ORGANISM: Artificial sequence
<220> FEATURE:
<223> OTHER INFORMATION: Synthetic oligonucleotide siRNA.

<400> SEQUENCE: 29
acgtgacacg ttcggagaat t                                                21

<210> SEQ ID NO 30
<211> LENGTH: 21
<212> TYPE: DNA
<213> ORGANISM: Artificial sequence
<220> FEATURE:
<223> OTHER INFORMATION: Synthetic oligonucleotide siRNA.

<400> SEQUENCE: 30
gctcttactg ctgagcgtat t                                                21

<210> SEQ ID NO 31
<211> LENGTH: 21
<212> TYPE: DNA
<213> ORGANISM: Artificial sequence
<220> FEATURE:
<223> OTHER INFORMATION: Synthetic oligonucleotide siRNA.

<400> SEQUENCE: 31
tacgctcagc agtaagagct t                                                21

<210> SEQ ID NO 32
<211> LENGTH: 21
<212> TYPE: DNA
<213> ORGANISM: Artificial sequence
<220> FEATURE:
<223> OTHER INFORMATION: Synthetic oligonucleotide siRNA.

<400> SEQUENCE: 32
gagcaaagct tgcattcatt t                                                21

<210> SEQ ID NO 33
<211> LENGTH: 21
<212> TYPE: DNA
<213> ORGANISM: Artificial sequence
<220> FEATURE:
<223> OTHER INFORMATION: Synthetic oligonucleotide siRNA.

<400> SEQUENCE: 33
atgaatgcaa gctttgctct t                                                21
```

```
<210> SEQ ID NO 34
<211> LENGTH: 21
<212> TYPE: DNA
<213> ORGANISM: Artificial sequence
<220> FEATURE:
<223> OTHER INFORMATION: Synthetic oligonucleotide siRNA.

<400> SEQUENCE: 34
cattggtact tactacgatt t                                              21

<210> SEQ ID NO 35
<211> LENGTH: 21
<212> TYPE: DNA
<213> ORGANISM: Artificial sequence
<220> FEATURE:
<223> OTHER INFORMATION: Synthetic oligonucleotide siRNA.

<400> SEQUENCE: 35
atcgtagtaa gtaccaatgt t                                              21

<210> SEQ ID NO 36
<211> LENGTH: 21
<212> TYPE: DNA
<213> ORGANISM: Artificial sequence
<220> FEATURE:
<223> OTHER INFORMATION: Synthetic oligonucleotide siRNA.

<400> SEQUENCE: 36
gcgatgactt ccgcaaggat t                                              21

<210> SEQ ID NO 37
<211> LENGTH: 21
<212> TYPE: DNA
<213> ORGANISM: Artificial sequence
<220> FEATURE:
<223> OTHER INFORMATION: Synthetic oligonucleotide siRNA.

<400> SEQUENCE: 37
tccttgcgga agtcatcgct t                                              21

<210> SEQ ID NO 38
<211> LENGTH: 21
<212> TYPE: DNA
<213> ORGANISM: Artificial sequence
<220> FEATURE:
<223> OTHER INFORMATION: Synthetic oligonucleotide siRNA.

<400> SEQUENCE: 38
gtgagctcgt gctggactat t                                              21

<210> SEQ ID NO 39
<211> LENGTH: 21
<212> TYPE: DNA
<213> ORGANISM: Artificial sequence
<220> FEATURE:
<223> OTHER INFORMATION: Synthetic oligonucleotide siRNA.

<400> SEQUENCE: 39
tagtccagca cgagctcact t                                              21

<210> SEQ ID NO 40
<211> LENGTH: 21
<212> TYPE: DNA
<213> ORGANISM: Artificial sequence
<220> FEATURE:
<223> OTHER INFORMATION: Synthetic oligonucleotide siRNA.
```

```
<400> SEQUENCE: 40
gtttctacag caaacctctt t                                              21

<210> SEQ ID NO 41
<211> LENGTH: 21
<212> TYPE: DNA
<213> ORGANISM: Artificial sequence
<220> FEATURE:
<223> OTHER INFORMATION: Synthetic oligonucleotide siRNA.

<400> SEQUENCE: 41
agaggtttgc tgtagaaact t                                              21

<210> SEQ ID NO 42
<211> LENGTH: 21
<212> TYPE: DNA
<213> ORGANISM: Artificial sequence
<220> FEATURE:
<223> OTHER INFORMATION: Synthetic oligonucleotide siRNA.

<400> SEQUENCE: 42
caattgcttt catggtgatt t                                              21

<210> SEQ ID NO 43
<211> LENGTH: 21
<212> TYPE: DNA
<213> ORGANISM: Artificial sequence
<220> FEATURE:
<223> OTHER INFORMATION: Synthetic oligonucleotide siRNA.

<400> SEQUENCE: 43
atcaccatga aagcaattgt t                                              21

<210> SEQ ID NO 44
<211> LENGTH: 22
<212> TYPE: DNA
<213> ORGANISM: Artificial sequence
<220> FEATURE:
<223> OTHER INFORMATION: Synthetic oligonucleotide primer.

<400> SEQUENCE: 44
ttagggattt acgtatcgac gt                                             22

<210> SEQ ID NO 45
<211> LENGTH: 19
<212> TYPE: DNA
<213> ORGANISM: Artificial sequence
<220> FEATURE:
<223> OTHER INFORMATION: Synthetic oligonucleotide primer.

<400> SEQUENCE: 45
aaacgacaaa ctccaaccg                                                 19

<210> SEQ ID NO 46
<211> LENGTH: 28
<212> TYPE: DNA
<213> ORGANISM: Artificial sequence
<220> FEATURE:
<223> OTHER INFORMATION: Synthetic oligonucleotide primer.

<400> SEQUENCE: 46
ttttttttag ggatttatgt attgatgt                                       28
```

-continued

```
<210> SEQ ID NO 47
<211> LENGTH: 23
<212> TYPE: DNA
<213> ORGANISM: Artificial sequence
<220> FEATURE:
<223> OTHER INFORMATION: Synthetic oligonucleotide primer.

<400> SEQUENCE: 47
ctaaacaaca aactccaacc aca                                              23
```